US011834511B2

(12) United States Patent
Press et al.

(10) Patent No.: US 11,834,511 B2
(45) Date of Patent: Dec. 5, 2023

(54) COMPOSITIONS AND METHODS FOR CD20 IMMUNOTHERAPY

(71) Applicant: Fred Hutchinson Cancer Center, Seattle, WA (US)

(72) Inventors: Oliver Press, Seattle, WA (US); Brian Till, Seattle, WA (US)

(73) Assignee: Fred Hutchinson Cancer Center, Seattle, WA (US)

(*) Notice: Subject to any disclaimer, the term of this patent is extended or adjusted under 35 U.S.C. 154(b) by 374 days.

(21) Appl. No.: 17/103,762

(22) Filed: Nov. 24, 2020

(65) Prior Publication Data

US 2021/0147569 A1 May 20, 2021

Related U.S. Application Data

(62) Division of application No. 16/086,290, filed as application No. PCT/US2017/023098 on Mar. 17, 2017, now Pat. No. 10,875,927.

(60) Provisional application No. 62/320,327, filed on Apr. 8, 2016, provisional application No. 62/310,541, filed on Mar. 18, 2016.

(51) Int. Cl.

| | |
|---|---|
| ***A61P 35/00*** | (2006.01) |
| ***A61K 38/00*** | (2006.01) |
| ***A61K 39/395*** | (2006.01) |
| ***A61K 39/00*** | (2006.01) |
| ***C07K 14/725*** | (2006.01) |
| ***C07K 16/28*** | (2006.01) |
| ***C07K 14/705*** | (2006.01) |

(52) U.S. Cl.

CPC .................... *C07K 16/2887* (2013.01); *A61K 39/001124* (2018.08); *A61K 39/39541* (2013.01); *A61K 39/39558* (2013.01); *A61P 35/00* (2018.01); *C07K 14/7051* (2013.01); *C07K 14/70521* (2013.01); *A61K 38/00* (2013.01); *A61K 2039/505* (2013.01); *A61K 2039/507* (2013.01); *A61K 2039/5156* (2013.01); *C07K 2317/24* (2013.01); *C07K 2317/622* (2013.01); *C07K 2317/73* (2013.01); *C07K 2319/03* (2013.01); *C07K 2319/33* (2013.01)

(58) Field of Classification Search

CPC .................... A61P 35/00; A61K 38/00; A61K 39/39558; A61K 2039/505; A61K 2039/507; C07K 14/7051; C07K 2317/24; C07K 2317/622; C07K 2317/73

See application file for complete search history.

(56) References Cited

U.S. PATENT DOCUMENTS

| | | | |
|---|---|---|---|
| 6,410,319 | B1 | 6/2002 | Raubitschek et al. |
| 7,446,191 | B2 | 11/2008 | Jensen |
| 7,514,537 | B2 | 4/2009 | Jensen |
| 8,119,772 | B2 | 2/2012 | Yang et al. |
| 8,679,767 | B2 | 3/2014 | Kaur et al. |
| 8,802,374 | B2 | 8/2014 | Jensen |
| 8,822,647 | B2 | 9/2014 | Jensen |
| 2009/0169550 | A1 | 7/2009 | Dummer |
| 2010/0065818 | A1 | 3/2010 | Kim et al. |
| 2014/0004037 | A1 | 1/2014 | Wilton |
| 2014/0271635 | A1 | 9/2014 | Brogdon et al. |
| 2015/0290317 | A1 | 10/2015 | Weiss et al. |

FOREIGN PATENT DOCUMENTS

| | | | |
|---|---|---|---|
| WO | 00/23573 | A2 | 4/2000 |
| WO | 2006/130458 | A2 | 12/2006 |
| WO | 2012/079000 | A1 | 6/2012 |
| WO | 2012/129514 | A1 | 9/2012 |
| WO | 2014/031687 | A1 | 2/2014 |
| WO | 2015/095895 | A1 | 6/2015 |
| WO | 2016/014576 | A1 | 1/2016 |

OTHER PUBLICATIONS

Becker et al., "Preclinical correction of human Fanconi anemia complementation group A bone marrow cells using a safety-modified lentiviral vector," *Gene Ther. 17*(10):1244-1252, 2010. (22 pages).

Bornstein et al., "Development of a new fully human anti-CD20 monoclonal antibody for the treatment of B-cell malignancies," *Invest New Drugs 28*:561-574, 2010.

Brentjens et al., "CD19-Targeted T Cells Rapidly Induce Molecular Remissions in Adults with Chemotherapy-Refractory Acute Lymphoblastic Leukemia," *Science Translational Medicine 5*(177):177ra38, 2013. (9 pages).

Brentjens et al., "Genetically Targeted T Cells Eradicate Systemic Acute Lymphoblastic Leukemia Xenografts," *Clin. Cancer Res. 13*(18):5426-5435, 2007.

Brentjens et al., "Safety and persistence of adoptively transferred autologous CD19-targeted T cells in patients with relapsed or chemotherapy refractory B-cell leukemias," *Blood 118*(18):4817-4828, 2011. (11 pages).

Budde et al., "Combining a CD20 Chimeric Antigen Receptor and an Inducible Caspase 9 Suicide Switch to Improve the Efficacy and Safety of T Cell Adoptive Immunotherapy for Lymphoma," *PLOS ONE 8*(12):e82742, 2013. (10 pages).

Coiffier et al., "Chop Chemotherapy Plus Rituximab Compared With Chop Alone in Elderly Patients With Diffuse Large B-Cell Lymphoma," *N. Engl. J. Med. 346*(4):235-242, 2002.

(Continued)

*Primary Examiner* — Mark Halvorson
*Assistant Examiner* — Dennis J Sullivan
(74) *Attorney, Agent, or Firm* — Seed IP Law Group LLP

(57) ABSTRACT

The present disclosure provides compositions and uses thereof for treating a disease or disorder associated with CD20 expression. Treatments of this disclosure include use of a host cell expressing a fusion protein, such as an anti-CD20 CAR, optionally in combination with a CD20-specific binding molecule, a chemotherapeutic, an inhibitor of an immunosuppression component, or combinations thereof.

22 Claims, 51 Drawing Sheets

Specification includes a Sequence Listing.

(56) References Cited

OTHER PUBLICATIONS

Czuczman et al., "Acquirement of Rituximab Resistance in Lymphoma Cell Lines Is Associated with Both Global CD20 Gene and Protein Down-Regulation Regulated at the Pretranscriptional and Posttranscriptional Levels," *Clin. Cancer Res. 14*(5):1561-1570, 2008.
Da Silva et al., "Direct Comparison of In Vivo Fate of Second and Third-Generation CD19-Specific Chimeric Antigen Receptor (CAR)-T Cells in Patients with B-Cell Lymphoma: Reversal of Toxicity from Tonic Signaling," *Blood 128*(22):1851, 2016. (Abstract Only, 5 pages).
Du et al., "Structure of the Fab fragment of therapeutic antibody Ofatumumab provides insights into the recognition mechanism with CD20," *Molecular Immunology 46*:2419-2423, 2009.
Engels et al., "Retroviral Vectors for High-Level Transgene Expression in T Lymphocytes," *Human Gene Therapy 14*:1155-1168, 2003.
Examination Report, dated Oct. 24, 2019, for European Patent Application No. 17714373.2, 5 pages.
Examination Report, dated May 25, 2020, for European Patent Application No. 17714373.2, 4 pages.
Fillat et al., "Suicide Gene Therapy Mediated by the Herpes Simplex Virus Thymidine Kinase Gene/Ganciclovir System: Fifteen Years of Application," *Current Gene Therapy 3*:13-26, 2003.
Frecha et al., "Advances in the Field of Lentivector-based Transduction of T and B Lymphocytes for Gene Therapy," *Molecular Therapy 18*(10):1748-1757, 2010.
Gall et al., "T cells armed with anti-CD3 x anti-CD20 bispecific antibody enhance killing of $CD20^+$malignant B cells and bypass complement-mediated rituximab resistance in vitro," *Experimental Hematology 33*:452-459, 2005.
Gargett et al., "The inducible caspase-9 suicide gene system as a "safety switch" to limit on-target, off-tumor toxicities of chimeric antigen receptor T cells," *Frontiers in Pharmacology 5*(235):1-7, 2014.
Gopal et al., "Rituximab blocks binding radiolabeled anti-CD20 antibodies (Ab) but not radiolabeled anti-CD45 Ab," *Blood 112*(3):830-835, 2008.
Grumont et al., "The Mitogen-Induced Increase in T Cell Size Involves PKC and NFAT Activation of Rel/NF-κB-Dependent and c-myc Expression," *Immunity 21*:19-30, 2004.
Grupp et al., "Chimeric Antigen Receptor-Modified T Cells for Actue Lymphoid Leukemia," *The New England Journal of Medicine 368*(16):1509-1518, 2013.
Guest et al., "The Role of Extracellular Spacer Regions in the Optimal Design of Chimeric Immune Receptors: Evaluation of Four Different scFvs and Antigens," *J. Immunother*. 28(3):203-211, 2005.
Haso et al., "Anti-CD22-chimeric antigen receptors targeting B-cell precursor acute lymphoblastic leukemia," *Blood 121*(7):1165-1174, 2013.
Hernandez Ilizaliturri et al., "Neutrophils Contribute to the Biological Antitumor Activity of Rituximab in a Non-Hodgkin's Lymphoma Severe Combined Immunodeficiency Mouse Model," *Clinical Cancer Research 9*:5866-5873, 2003.
Hollyman et al., "Manufacturing validation of biologically functional T cells targeted to CD19 antigen for autologous adoptive cell therapy," *J. Immunother. 32*(2):169-180, 2009. (22 pages).
Hombach et al., "A chimeric receptor that selectively targets membrane-bound carcinoembryonic anitgen (mCEA) in the presence of soluble CEA," *Gene Therapy 6*:300-304, 1999.
Hombach et al., "Adoptive immunotherapy with genetically engineered T cells: modification of the IgG1 Fc 'spacer' domain in the extracellualar moiety of chimeric antigen receptors avoids 'off-target' activation and unintended initiation of an innate immune response," *Gene Therapy 17*:1206-1213, 2010.
Hombach et al., "T cell activation by recombinant FcεRI γ-chain immune receptors: an extracellular spacer domain impairs antigen-dependent T cell activation but not antigen recognition," *Gene Therapy 7*:1067-1075, 2000.
Hudecek et al., "Receptor Affinity and Extracellular Domain Modifications Affect Tumor Recognition by ROR1-Specific Chimeric Antigen Receptor T Cells," *Clinical Cancer Research 19*(12):3153-3164, 2013.
Hudecek et al., "The Nonsignaling Extracellular Spacer Domain of Chimeric Antigen Receptors Is Decisive for In Vivo Antitumor Activity," *Cancer Immunol. Res. 3*(2):125-135, 2015. (12 pages).
International Search Report and Written Opinion, dated Jul. 24, 2017, for International Patent Application No. PCT/US2017/023098, 19 pages.
James et al., "Antibody-mediated B-cell depletion before adoptive immunotherapy with T cells expressing CD20-specific chimeric T-cell receptors facilitates eradication of leukemia in immunocompetent mice," *Blood 114*(27):5454-5463, 2009.
James et al., "Antigen Sensitivity of CD22-Specific Chimeric TCR Is Modulated by Target Epitope Distance from the Cell Membrane," *The Journal of Immunology 180*:7028-7038, 2008.
Jolly, "Emerging Viral Vectors," *The Development of Human Gene Therapy*, pp. 209-240, 1999.
June, "Adoptive T cell therapy for cancer in the clinic," *The Journal of Clinical Investigation 117*(6):1466-1476, 2007.
Kalos et al., "T Cells with Chimeric Antigen Receptors Have Potent Antitumor Effects and Can Establish Memory in Patients with Advanced Leukemia," *Science Translational Medicine 3*(95):95ra73, 2011. (11 pages).
Kochenderfer et al., "Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor," *Journal of Clinical Oncology 33*(6):540-549, 2015. (11 pages).
Krisky et al., "Development of herpes simplex virus replication-defective multigene vectors for combination gene therapy applications," *Gene Therapy 5*:1517-1530, 1998.
Lee et al., "Preclinical optimization of a CD20-specific chimeric antigen receptor vector and culture conditions," *J. Immunother. 41*(1):19-31, 2018. (25 pages).
Lee et al., "T cells expressing CD19 chimeric antigen receptors for acute lymphoblastic leukaemia in children and young adults: a phase 1 dose-escalation trial," *Lancet 385*(9967):517-528, 2015. (12 pages).
Lenz et al., "Immunochemotherapy With Rituximab and Cyclophosphamide, Doxorubicin, Vincristine, and Prednisone Significantly Improves Response and Time to Treatment Failure, But Not Long-Term Outcome in Patients With Previously Untreated Mantle Cell Lymphoma: Results of a Prospective Randomized Trial of the German Low Grade Lymphoma Study Group (GLSG)." *Journal of Clinical Oncology 23*(9):1984-1992, 2005. (15 pages).
Maloney et al., "IDEC-C2B8 (Rituximab) Anti-CD20 Monoclonal Antibody Therapy in Patients With Relapsed Low-Grade Non-Hodgkin's Lymphoma," *Blood 90*(6):2188-2195, 1997.
Marcus et al., "Phase III Study of R-CVP Compared With Cyclophosphamide, Vincristine, and Prednisone Alone in Patients With Previously Untreated Advanced Follicular Lymphoma," *Journal of Clinical Oncology 26*(28):4579-4586, 2008.
Morgan et al., "Cancer Regression in Patients After Transfer of Genetically Engineered Lymphocytes," *Science 314*(5796):126-129, 2006. (5 pages).
Naddafi et al., "Anti-CD19 Monoclonal Antibodies: a New Approach to Lymphoma Therapy," *Int. J. Mol. Cell Med. 4*(3):143-151, 2015. (9 pages).
Nguyen et al., "Identification of a murine CD28 dileucine motif that suppresses single-chain chimeric T-cell receptor expression and function," *Blood 102*:4320-4325, 2003.
Nolan et al., "Bypassing Immunization: Optimized Design of "Designer T Cells" against Carcinoembryonic Antigen (CEA)-expressing Tumors, and Lack of Suppression by Soluble CEA[1]," *Clinical Cancer Research 5*:3928-3941, 1999.
Paszkiewicz et al., "Targeted antibody-mediated depletion of murine CD19 CAR T cells permanently reverses B cell aplasia," *J. Clin. Invest. 126*(11):4262-4272, 2016.
Patel et al., "Impact of chimeric immune receptor extracellular protein domains on T cell function," *Gene Therapy 6*:412-419, 1999.

(56) References Cited

OTHER PUBLICATIONS

Pfreundschuh et al., "CHOP-like chemotherapy with or without rituximab in young patients with good-prognosis diffuse large-B-cell lymphoma: 6-year results of an open-label randomised study of the MabThera International Trial (MInT) Group," *Lancet Oncol. 12*:1013-1022, 2011.
Polyak et al., "Alanine-170 and proline-172 are critical determinants for extracellular CD20 epitopes; heterogeneity in the fine specificity of CD20 monoclonal antibodies is defined by additional requirements imposed by both amino acid sequence and quaternary structure," *Blood 99*(9):3256-3262, 2002.
Porter et al., "Chimeric antigen receptor T cells persist and induce sustained remissions in relapsed refractory chronic lymphocytic leukemia," *Science Translational Medicine 7*(303):303ra139, 2015. (13 pages).
Press et al., "Monoclonal Antibody 1F5 (Anti-CD20) Serotherapy of Human B Cell Lymphomas," *Blood 69*(2):584-591, 1987.
Press et al., "Retention of B-Cell-Specific Monoclonal Antibodies by Human Lymphoma Cells," *Blood 83*(5):1390-1397, 1994.
Pulczynski et al., "Antibody-Induced Modulation and Intracellular Transport of CD10 and CD19 Antigens in Human B-Cell Lines: An Immunofluorescence and Immunoelectron Microscopy Study," *Blood 81*(6):1549-1557, 1993. (10 pages).
Pulczynski et al., "Modulation and Intracellular Transport of CD20 and CD21 Antigens Induced by B1 and B2 Monoclonal Antibodies in Raji and JOK-1 Cells-An Immunofluorescence and Immunoelectron Microscopy Study," *Leukemia Research 18*(7):541-552, 1994.
Rufener et al., "Preservation of CD20-Specific Chimeric Antigen Receptor T Cell Function in the Presence of Residual Rituximab," *Blood 126*(23):4428, 2015. (4 pages).
Rufener et al., "Preserved Activity of CD20-Specific Chimeric Antigen Receptor-Expressing T Cells in the Presence of Rituximab," *Cancer Immunol. Res. 4*(6):509-519, 2016. (12 pages).
Savoldo et al., "CD28 costimulation improves expansion and persistence of chimeric antigen receptor-modified T cells in lymphoma patients," *The Journal of Clinical Investigation 121*(5):1822-1826, 2011.
Schmitt et al., "T Cell Receptor Gene Therapy for Cancer," *Human Gene Therapy 20*:1240-1248, 2009.
Scholten et al., "Codon modification of T cell receptors allows enhanced functional expression in transgenic human T cells," *Clinical Immunology 119*:135-145, 2006.
Shadman et al., "1443 Third Generation CD20 Targeted CAR T-Cell Therapy (MB-106) for Treatment of Patients with Relapsed/Refractory B-Cell Non-Hodgkin Lymphoma," *62nd ASH Annual Meeting and Exposition, Dec. 5-8, 2020*, Dec. 2020. (3 pages).
Shadman et al., "Third Generation CD20 targeted CAR T-Cell therapy (MB-106) for Treatment of Patients with Relapsed/Refractory B-NHL," *62nd ASH Annual Meeting and Exposition, Dec. 5-8, 2020*, Abstract 1143, Dec. 2020. (11 pages).
Sommermeyer et al., "Chimeric antigen receptor-modified T cells derived from defined $CD8^+$and $CD4^+$subsets confer superior antitumor reactivity in vivo," *Leukemia 30*(2):492-500, 2016. (20 pages).
Teeling et al., "Characterization of new human CD20 monoclonal antibodies with potent cytolytic activity against non-Hodgkin lymphomas," *Blood 104*:1793-1800, 2004.
Teeling et al., "The Biological Activity of Human CD20 Monoclonal Antibodies Is Linked to Unique Epitopes on CD20[1]," *The Journal of Immunology 177*:362-371, 2006.
Till et al., "Adoptive immunotherapy for indolent non-Hodgkin lymphoma and mantle cell lymphoma using genetically modified autologous CD20-specific T cells," *Blood 112*(6):2261-2271, 2008.
Till et al., "CD20-specific adoptive immunotherapy for lymphoma using a chimeric antigen receptor with both CD28 and 4-1BB domains: pilot clinical trial results," *Blood 119*(17):3940-3950, 2012.
Till, "Preclinical Optimization of CD20 CAR T cell Adoptive Transfer," *Fred Hutchinson Cancer Research Center, Cellular Immunotherapy Summit at Yale*, Mar. 18, 2016. (42 pages).
Verhoeyen et al., "Lentiviral Vector Gene Transfer into Human T Cells," *Methods in Molecular Biology, Methods and Protocols 506*:97-114, 2009.
Walchli et al., "A Practical Approach to T-Cell Receptor Cloning and Expression," *PLoS One 6*(11):e27930, 2011. (11 pages).
Wang et al., "A transgene-encoded cell surface polypeptide for selection, in vivo tracking, and ablation of engineered cells," *Blood 118*(5):1255-1263, 2011. (10 pages).
Wang et al., "Cellular Immunotherapy for Follicular Lymphoma Using Genetically Modified CD20-Specific $CD8^+$Cytotoxic T Lymphocytes," *Molecular Therapy 9*(4):577-586, 2004.
Wang et al., "Optimizing Adoptive Polyclonal T Cell Immunotherapy of Lymphomas, Using a Chimeric T Cell Receptor Possessing CD28 and CD137 Costimulatory Domains," *Human Gene Therapy 18*:712-725, 2007. (16 pages).
Zhao et al., "Primary Human Lymphocytes Transduced with NY-ESO-1 Antigen-Specific TCR Genes Recognize and Kill Diverse Human Tumor Cell Lines," *The Journal of Immunology 174*:4415-4423, 2005.
Burns et al., "A high molecular weight-melanoma associated antigen-specific chimeric antigen receptor redirects lymphocytes to target human melanomas," *Cancer Res. 70*(8): 3027-3033, Apr. 15, 2010 (NIH Public Access Author Manuscript, available in PMC Dec. 23, 2011) (11 pages).
Chen et al., "Fusion protein linkers: Property, design and functionality," *Advanced Drug Delivery Reviews 65*: 1357-1369, 2013.
Cordoba et al., "The large ectodomains of CD45 and CD148 regulate their segregation from and inhibition of ligated T-cell receptor," *Blood 121*(21): 4295-4302, May 23, 2013. (20 pages).
Gasser et al., "Antibody production with yeasts and filamentous fungi: on the road to large scale?" *Biotechnol Lett 29*: 201-212, 2007.
Kennedy et al., "Incidence and nature of CD20-negative relapses following rituximab therapy in aggressive B-cell non-Hodgkin's lymphoma: a retrospective review," *British Journal of Haematology 119*: 412-416, 2002.
Maeda et al., "Engineering of Functional Chimeric Protein G-Vargula Luciferase," *Analytical Biochemistry 249*: 147-152, 1997.
Muller et al., "Spliceosomal Peptide P140 for Immunotherapy of Systemic Lupus Erythematosus," *Arthritis & Rheumatism 58*(12): 3873-3883, Dec. 2008.
Turtle et al., "CD19 CAR-T cells of defined $CD4^+$:$CD8^+$ composition in adult B cell ALL patients," *J Clin Invest. 126*(6): 2123-2138, Jun. 2016.

SEQUENCE LISTING

```
<160> NUMBER OF SEQ ID NOS: 105

<210> SEQ ID NO 1
<211> LENGTH: 112
<212> TYPE: PRT
<213> ORGANISM: Artificial Sequence
<220> FEATURE:
<223> OTHER INFORMATION: Synthetic sequence

<400> SEQUENCE: 1

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Val Gln Ala
                85                  90                  95

Thr Gln Phe Pro Leu Thr Phe Gly Gly Gly Thr Lys Val Glu Ile Lys
            100                 105                 110


<210> SEQ ID NO 2
<211> LENGTH: 106
<212> TYPE: PRT
<213> ORGANISM: Artificial Sequence
<220> FEATURE:
<223> OTHER INFORMATION: Synthetic sequence

<400> SEQUENCE: 2

Asp Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
            20                  25                  30

Asp Trp Tyr Gln Lys Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80
```

```
Asp Ala Ala Thr Tyr Tyr Cys Gln Gln Trp Ser Phe Asn Pro Pro Thr
                85                  90                  95

Phe Gly Gly Gly Thr Lys Leu Glu Ile Lys
            100                 105


<210> SEQ ID NO 3
<211> LENGTH: 106
<212> TYPE: PRT
<213> ORGANISM: Artificial Sequence
<220> FEATURE:
<223> OTHER INFORMATION: Synthetic sequence

<400> SEQUENCE: 3

Asp Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Leu Ser Phe Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Phe Cys His Gln Trp Ser Ser Asn Pro Leu Thr
                85                  90                  95

Phe Gly Ala Gly Thr Lys Leu Glu Leu Lys
            100                 105


<210> SEQ ID NO 4
<211> LENGTH: 122
<212> TYPE: PRT
<213> ORGANISM: Artificial Sequence
<220> FEATURE:
<223> OTHER INFORMATION: Synthetic sequence

<400> SEQUENCE: 4

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Pro Ser Tyr Gly Ser Gly Ser Pro Asn Phe Asp Tyr Trp
            100                 105                 110

Gly Gln Gly Thr Leu Val Thr Val Ser Ser
        115                 120


<210> SEQ ID NO 5
<211> LENGTH: 128
<212> TYPE: PRT
<213> ORGANISM: Artificial Sequence
<220> FEATURE:
<223> OTHER INFORMATION: Synthetic sequence
```

<400> SEQUENCE: 5

```
Glu Val Gln Leu Gln Gln Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Asp Tyr Tyr Cys
                85                  90                  95

Ala Arg Ser Asn Tyr Tyr Gly Ser Ser Tyr Trp Phe Phe Asp Val Trp
            100                 105                 110

Gly Ala Gly Thr Thr Val Thr Val Ser Ser Leu Asp Glu Ser Lys Tyr
        115                 120                 125
```

<210> SEQ ID NO 6
<211> LENGTH: 128
<212> TYPE: PRT
<213> ORGANISM: Artificial Sequence
<220> FEATURE:
<223> OTHER INFORMATION: Synthetic sequence

<400> SEQUENCE: 6

```
Gln Val Gln Leu Arg Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser His Tyr Gly Ser Asn Tyr Val Asp Tyr Phe Asp Tyr Trp
            100                 105                 110

Gly Gln Gly Thr Thr Leu Thr Val Ser Ser Leu Asp Pro Lys Ser Ser
        115                 120                 125
```

<210> SEQ ID NO 7
<211> LENGTH: 12
<212> TYPE: PRT
<213> ORGANISM: Homo sapiens

<400> SEQUENCE: 7

```
Asp Lys Thr His Thr Cys Pro Pro Cys Pro Ala Pro
1               5                   10
```

<210> SEQ ID NO 8
<211> LENGTH: 8
<212> TYPE: PRT
<213> ORGANISM: Homo sapiens

<400> SEQUENCE: 8

Gly Pro Pro Cys Pro Pro Cys Pro
1 5

<210> SEQ ID NO 9
<211> LENGTH: 6
<212> TYPE: PRT
<213> ORGANISM: Homo sapiens

<400> SEQUENCE: 9

Pro Val Ala Gly Pro Ser
1 5

<210> SEQ ID NO 10
<211> LENGTH: 101
<212> TYPE: PRT
<213> ORGANISM: Artificial Sequence
<220> FEATURE:
<223> OTHER INFORMATION: Synthetic sequence

<400> SEQUENCE: 10

Val Phe Leu Phe Pro Pro Lys Pro Lys Asp Thr Leu Met Ile Ser Arg
1 5 10 15

Thr Pro Glu Val Thr Cys Val Val Val Asp Val Ser His Glu Asp Pro
20 25 30

Glu Val Lys Phe Asn Trp Tyr Val Asp Gly Val Glu Val His Asn Ala
35 40 45

Lys Thr Lys Pro Arg Glu Glu Gln Tyr Gln Ser Thr Tyr Arg Val Val
50 55 60

Ser Val Leu Thr Val Leu His Gln Asp Trp Leu Asn Gly Lys Glu Tyr
65 70 75 80

Lys Cys Lys Val Ser Asn Lys Ala Leu Pro Ala Pro Ile Glu Lys Thr
85 90 95

Ile Ser Lys Ala Lys
100

<210> SEQ ID NO 11
<211> LENGTH: 110
<212> TYPE: PRT
<213> ORGANISM: Homo sapiens

<400> SEQUENCE: 11

Ala Pro Glu Phe Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser Gln Glu Asp Pro Glu Val Gln Phe Asn Trp Tyr
35 40 45

Val Asp Gly Val Glu Val His Asn Ala Lys Thr Lys Pro Arg Glu Glu
50 55 60

Gln Phe Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Gly Leu Pro Ser Ser Ile Glu Lys Thr Ile Ser Lys Ala Lys
100 105 110

<210> SEQ ID NO 12

<211> LENGTH: 105
<212> TYPE: PRT
<213> ORGANISM: Homo sapiens

<400> SEQUENCE: 12

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro
            100                 105

<210> SEQ ID NO 13
<211> LENGTH: 107
<212> TYPE: PRT
<213> ORGANISM: Homo sapiens

<400> SEQUENCE: 13

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 14
<211> LENGTH: 27
<212> TYPE: PRT
<213> ORGANISM: Homo sapiens

<400> SEQUENCE: 14

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 15
<211> LENGTH: 40
<212> TYPE: PRT
<213> ORGANISM: Artificial Sequence
<220> FEATURE:
<223> OTHER INFORMATION: Synthetic sequence

<400> SEQUENCE: 15

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg
        35                  40

<210> SEQ ID NO 16
<211> LENGTH: 42
<212> TYPE: PRT
<213> ORGANISM: Homo sapiens

<400> SEQUENCE: 16

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 17
<211> LENGTH: 112
<212> TYPE: PRT
<213> ORGANISM: Homo sapiens

<400> SEQUENCE: 17

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 18
<211> LENGTH: 22
<212> TYPE: PRT
<213> ORGANISM: Homo sapiens

<400> SEQUENCE: 18

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 19
<211> LENGTH: 20
<212> TYPE: PRT
<213> ORGANISM: Mus musculus

<400> SEQUENCE: 19

Met Glu Thr Asp Thr Leu Leu Leu Trp Val Leu Leu Leu Trp Val Pro
1               5                   10                  15

Gly Ser Thr Gly
            20

<210> SEQ ID NO 20
<211> LENGTH: 15
<212> TYPE: PRT
<213> ORGANISM: Artificial Sequence
<220> FEATURE:
<223> OTHER INFORMATION: Synthetic sequence

<400> SEQUENCE: 20

Gly Gly Gly Gly Ser Gly Gly Gly Gly Ser Gly Gly Gly Gly Ser
1               5                   10                  15

<210> SEQ ID NO 21
<211> LENGTH: 18
<212> TYPE: PRT
<213> ORGANISM: Artificial Sequence
<220> FEATURE:
<223> OTHER INFORMATION: Synthetic sequence

<400> SEQUENCE: 21

Gly Ser Thr Ser Gly Gly Gly Ser Gly Gly Gly Ser Gly Gly Gly Gly
1               5                   10                  15

Ser Ser

<210> SEQ ID NO 22
<211> LENGTH: 20
<212> TYPE: PRT
<213> ORGANISM: Unknown
<220> FEATURE:
<223> OTHER INFORMATION: E2A self-cleaving peptide

<400> SEQUENCE: 22

Gln Cys Thr Asn Tyr Ala Leu Leu Lys Leu Ala Gly Asp Val Glu Ser
1               5                   10                  15

Asn Pro Gly Pro
            20

<210> SEQ ID NO 23
<211> LENGTH: 24
<212> TYPE: PRT
<213> ORGANISM: unknown
<220> FEATURE:
<223> OTHER INFORMATION: T2A self-cleaving peptide

<400> SEQUENCE: 23

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 24
<211> LENGTH: 323
<212> TYPE: PRT
<213> ORGANISM: Artificial Sequence
<220> FEATURE:
<223> OTHER INFORMATION: Synthetic sequence

<400> SEQUENCE: 24

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg

<210> SEQ ID NO 25
<211> LENGTH: 357
<212> TYPE: PRT
<213> ORGANISM: Artificial Sequence
<220> FEATURE:
<223> OTHER INFORMATION: Synthetic sequence

<400> SEQUENCE: 25

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
20 25 30

Glu Phe Lys Asp Ser Leu Ser Ile Asn Ala Thr Asn Ile Lys His Phe
35 40 45

Lys Asn Cys Thr Ser Ile Ser Gly Asp Leu His Ile Leu Pro Val Ala
50 55 60

Phe Arg Gly Asp Ser Phe Thr His Thr Pro Pro Leu Asp Pro Gln Glu
65 70 75 80

Leu Asp Ile Leu Lys Thr Val Lys Glu Ile Thr Gly Phe Leu Leu Ile
85 90 95

Gln Ala Trp Pro Glu Asn Arg Thr Asp Leu His Ala Phe Glu Asn Leu
100 105 110

Glu Ile Ile Arg Gly Arg Thr Lys Gln His Gly Gln Phe Ser Leu Ala
115 120 125

Val Val Ser Leu Asn Ile Thr Ser Leu Gly Leu Arg Ser Leu Lys Glu
130 135 140

Ile Ser Asp Gly Asp Val Ile Ile Ser Gly Asn Lys Asn Leu Cys Tyr
145 150 155 160

Ala Asn Thr Ile Asn Trp Lys Lys Leu Phe Gly Thr Ser Gly Gln Lys
165 170 175

Thr Lys Ile Ile Ser Asn Arg Gly Glu Asn Ser Cys Lys Ala Thr Gly
180 185 190

Gln Val Cys His Ala Leu Cys Ser Pro Glu Gly Cys Trp Gly Pro Glu
195 200 205

Pro Arg Asp Cys Val Ser Cys Arg Asn Val Ser Arg Gly Arg Glu Cys
210 215 220

Val Asp Lys Cys Asn Leu Leu Glu Gly Glu Pro Arg Glu Phe Val Glu
225 230 235 240

Asn Ser Glu Cys Ile Gln Cys His Pro Glu Cys Leu Pro Gln Ala Met
245 250 255

Asn Ile Thr Cys Thr Gly Arg Gly Pro Asp Asn Cys Ile Gln Cys Ala
260 265 270

His Tyr Ile Asp Gly Pro His Cys Val Lys Thr Cys Pro Ala Gly Val
275 280 285

Met Gly Glu Asn Asn Thr Leu Val Trp Lys Tyr Ala Asp Ala Gly His
290 295 300

Val Cys His Leu Cys His Pro Asn Cys Thr Tyr Gly Cys Thr Gly Pro
305 310 315 320

Gly Leu Glu Gly Cys Pro Thr Asn Gly Pro Lys Ile Pro Ser Ile Ala
325 330 335

Thr Gly Met Val Gly Ala Leu Leu Leu Leu Leu Val Val Ala Leu Gly
340 345 350

Ile Gly Leu Phe Met
355

<210> SEQ ID NO 26
<211> LENGTH: 695
<212> TYPE: PRT
<213> ORGANISM: Artificial Sequence
<220> FEATURE:
<223> OTHER INFORMATION: Synthetic sequence

<400> SEQUENCE: 26

Asp Ile Val Met Thr Gln Thr Pro Leu Ser Ser Pro Val Thr Leu Gly
1 5 10 15

-continued

```
Gln Pro Ala Ser Ile Ser Cys Arg Ser Ser Gln Ser Leu Val Tyr Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Val Gln Ala
                85                  90                  95

Thr Gln Phe Pro Leu Thr Phe Gly Gly Gly Thr Lys Val Glu Ile Lys
            100                 105                 110

Gly Gly Gly Gly Ser Gly Gly Gly Gly Ser Gly Gly Gly Gly Ser Glu
        115                 120                 125

Val Gln Leu Val Gln Ser Gly Ala Glu Val Lys Lys Pro Gly Glu Ser
    130                 135                 140

Leu Lys Ile Ser Cys Lys Gly Ser Gly Tyr Ser Phe Thr Ser Tyr Trp
145                 150                 155                 160

Ile Gly Trp Val Arg Gln Met Pro Gly Lys Gly Leu Glu Trp Met Gly
                165                 170                 175

Ile Ile Tyr Pro Gly Asp Ser Asp Thr Arg Tyr Ser Pro Ser Phe Gln
            180                 185                 190

Gly Gln Val Thr Ile Ser Ala Asp Lys Ser Ile Thr Thr Ala Tyr Leu
        195                 200                 205

Gln Trp Ser Ser Leu Lys Ala Ser Asp Thr Ala Met Tyr Tyr Cys Ala
    210                 215                 220

Arg His Pro Ser Tyr Gly Ser Gly Ser Pro Asn Phe Asp Tyr Trp Gly
225                 230                 235                 240

Gln Gly Thr Leu Val Thr Val Ser Ser Asp Lys Thr His Thr Cys Pro
                245                 250                 255

Pro Cys Pro Ala Pro Pro Val Ala Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Gln Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430
```

```
Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Phe Trp Val Leu Val Val Val
465                 470                 475                 480

Gly Gly Val Leu Ala Cys Tyr Ser Leu Leu Val Thr Val Ala Phe Ile
                485                 490                 495

Ile Phe Trp Val Arg Ser Lys Arg Ser Arg Gly Gly His Ser Asp Tyr
            500                 505                 510

Met Asn Met Thr Pro Arg Arg Pro Gly Pro Thr Arg Lys His Tyr Gln
        515                 520                 525

Pro Tyr Ala Pro Pro Arg Asp Phe Ala Ala Tyr Arg Ser Lys Arg Gly
    530                 535                 540

Arg Lys Lys Leu Leu Tyr Ile Phe Lys Gln Pro Phe Met Arg Pro Val
545                 550                 555                 560

Gln Thr Thr Gln Glu Glu Asp Gly Cys Ser Cys Arg Phe Pro Glu Glu
                565                 570                 575

Glu Glu Gly Gly Cys Glu Leu Arg Val Lys Phe Ser Arg Ser Ala Asp
            580                 585                 590

Ala Pro Ala Tyr Gln Gln Gly Gln Asn Gln Leu Tyr Asn Glu Leu Asn
        595                 600                 605

Leu Gly Arg Arg Glu Glu Tyr Asp Val Leu Asp Lys Arg Arg Gly Arg
    610                 615                 620

Asp Pro Glu Met Gly Gly Lys Pro Arg Arg Lys Asn Pro Gln Glu Gly
625                 630                 635                 640

Leu Tyr Asn Glu Leu Gln Lys Asp Lys Met Ala Glu Ala Tyr Ser Glu
                645                 650                 655

Ile Gly Met Lys Gly Glu Arg Arg Arg Gly Lys Gly His Asp Gly Leu
            660                 665                 670

Tyr Gln Gly Leu Ser Thr Ala Thr Lys Asp Thr Tyr Asp Ala Leu His
        675                 680                 685

Met Gln Ala Leu Pro Pro Arg
    690                 695


<210> SEQ ID NO 27
<211> LENGTH: 653
<212> TYPE: PRT
<213> ORGANISM: Artificial Sequence
<220> FEATURE:
<223> OTHER INFORMATION: Synthetic sequence

<400> SEQUENCE: 27

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Val Gln Ala
                85                  90                  95
```

-continued

```
Thr Gln Phe Pro Leu Thr Phe Gly Gly Gly Thr Lys Val Glu Ile Lys
            100                 105                 110

Gly Gly Gly Gly Ser Gly Gly Gly Gly Ser Gly Gly Gly Gly Ser Glu
        115                 120                 125

Val Gln Leu Val Gln Ser Gly Ala Glu Val Lys Lys Pro Gly Glu Ser
    130                 135                 140

Leu Lys Ile Ser Cys Lys Gly Ser Gly Tyr Ser Phe Thr Ser Tyr Trp
145                 150                 155                 160

Ile Gly Trp Val Arg Gln Met Pro Gly Lys Gly Leu Glu Trp Met Gly
                165                 170                 175

Ile Ile Tyr Pro Gly Asp Ser Asp Thr Arg Tyr Ser Pro Ser Phe Gln
            180                 185                 190

Gly Gln Val Thr Ile Ser Ala Asp Lys Ser Ile Thr Thr Ala Tyr Leu
        195                 200                 205

Gln Trp Ser Ser Leu Lys Ala Ser Asp Thr Ala Met Tyr Tyr Cys Ala
    210                 215                 220

Arg His Pro Ser Tyr Gly Ser Gly Ser Pro Asn Phe Asp Tyr Trp Gly
225                 230                 235                 240

Gln Gly Thr Leu Val Thr Val Ser Ser Asp Lys Thr His Thr Cys Pro
                245                 250                 255

Pro Cys Pro Ala Pro Pro Val Ala Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Gln Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Phe Trp Val Leu Val Val Val
465                 470                 475                 480

Gly Gly Val Leu Ala Cys Tyr Ser Leu Leu Val Thr Val Ala Phe Ile
                485                 490                 495

Ile Phe Trp Val Arg Ser Lys Arg Ser Arg Gly Gly His Ser Asp Tyr
            500                 505                 510
```

Met Asn Met Thr Pro Arg Arg Pro Gly Pro Thr Arg Lys His Tyr Gln
515 520 525

Pro Tyr Ala Pro Pro Arg Asp Phe Ala Ala Tyr Arg Ser Arg Val Lys
530 535 540

Phe Ser Arg Ser Ala Asp Ala Pro Ala Tyr Gln Gln Gly Gln Asn Gln
545 550 555 560

Leu Tyr Asn Glu Leu Asn Leu Gly Arg Arg Glu Glu Tyr Asp Val Leu
565 570 575

Asp Lys Arg Arg Gly Arg Asp Pro Glu Met Gly Gly Lys Pro Arg Arg
580 585 590

Lys Asn Pro Gln Glu Gly Leu Tyr Asn Glu Leu Gln Lys Asp Lys Met
595 600 605

Ala Glu Ala Tyr Ser Glu Ile Gly Met Lys Gly Glu Arg Arg Arg Gly
610 615 620

Lys Gly His Asp Gly Leu Tyr Gln Gly Leu Ser Thr Ala Thr Lys Asp
625 630 635 640

Thr Tyr Asp Ala Leu His Met Gln Ala Leu Pro Pro Arg
645 650

<210> SEQ ID NO 28
<211> LENGTH: 654
<212> TYPE: PRT
<213> ORGANISM: Artificial Sequence
<220> FEATURE:
<223> OTHER INFORMATION: Synthetic sequence

<400> SEQUENCE: 28

Asp Ile Val Met Thr Gln Thr Pro Leu Ser Ser Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Ser Trp Leu Gln Gln Arg Pro Gly Gln Pro
35 40 45

Pro Arg Leu Leu Ile Tyr Lys Ile Ser Asn Arg Phe Ser Gly Val Pro
50 55 60

Asp Arg Phe Ser Gly Ser Gly Ala Gly Thr Asp Phe Thr Leu Lys Ile
65 70 75 80

Ser Arg Val Glu Ala Glu Asp Val Gly Val Tyr Tyr Cys Val Gln Ala
85 90 95

Thr Gln Phe Pro Leu Thr Phe Gly Gly Gly Thr Lys Val Glu Ile Lys
100 105 110

Gly Gly Gly Gly Ser Gly Gly Gly Gly Ser Gly Gly Gly Gly Ser Glu
115 120 125

Val Gln Leu Val Gln Ser Gly Ala Glu Val Lys Lys Pro Gly Glu Ser
130 135 140

Leu Lys Ile Ser Cys Lys Gly Ser Gly Tyr Ser Phe Thr Ser Tyr Trp
145 150 155 160

Ile Gly Trp Val Arg Gln Met Pro Gly Lys Gly Leu Glu Trp Met Gly
165 170 175

Ile Ile Tyr Pro Gly Asp Ser Asp Thr Arg Tyr Ser Pro Ser Phe Gln
180 185 190

Gly Gln Val Thr Ile Ser Ala Asp Lys Ser Ile Thr Thr Ala Tyr Leu
195 200 205

Gln Trp Ser Ser Leu Lys Ala Ser Asp Thr Ala Met Tyr Tyr Cys Ala
210 215 220

Arg His Pro Ser Tyr Gly Ser Gly Ser Pro Asn Phe Asp Tyr Trp Gly
225 230 235 240

Gln Gly Thr Leu Val Thr Val Ser Ser Asp Lys Thr His Thr Cys Pro
245 250 255

Pro Cys Pro Ala Pro Pro Val Ala Gly Pro Ser Val Phe Leu Phe Pro
260 265 270

Pro Lys Pro Lys Asp Thr Leu Met Ile Ser Arg Thr Pro Glu Val Thr
275 280 285

Cys Val Val Val Asp Val Ser His Glu Asp Pro Glu Val Lys Phe Asn
290 295 300

Trp Tyr Val Asp Gly Val Glu Val His Asn Ala Lys Thr Lys Pro Arg
305 310 315 320

Glu Glu Gln Tyr Gln Ser Thr Tyr Arg Val Val Ser Val Leu Thr Val
325 330 335

Leu His Gln Asp Trp Leu Asn Gly Lys Glu Tyr Lys Cys Lys Val Ser
340 345 350

Asn Lys Ala Leu Pro Ala Pro Ile Glu Lys Thr Ile Ser Lys Ala Lys
355 360 365

Gly Gln Pro Arg Glu Pro Gln Val Tyr Thr Leu Pro Pro Ser Arg Asp
370 375 380

Glu Leu Thr Lys Asn Gln Val Ser Leu Thr Cys Leu Val Lys Gly Phe
385 390 395 400

Tyr Pro Ser Asp Ile Ala Val Glu Trp Glu Ser Asn Gly Gln Pro Glu
405 410 415

Asn Asn Tyr Lys Thr Thr Pro Pro Val Leu Asp Ser Asp Gly Ser Phe
420 425 430

Phe Leu Tyr Ser Lys Leu Thr Val Asp Lys Ser Arg Trp Gln Gln Gly
435 440 445

Asn Val Phe Ser Cys Ser Val Met His Glu Ala Leu His Asn His Tyr
450 455 460

Thr Gln Lys Ser Leu Ser Leu Ser Pro Phe Trp Val Leu Val Val Val
465 470 475 480

Gly Gly Val Leu Ala Cys Tyr Ser Leu Leu Val Thr Val Ala Phe Ile
485 490 495

Ile Phe Trp Val Lys Arg Gly Arg Lys Lys Leu Leu Tyr Ile Phe Lys
500 505 510

Gln Pro Phe Met Arg Pro Val Gln Thr Thr Gln Glu Glu Asp Gly Cys
515 520 525

Ser Cys Arg Phe Pro Glu Glu Glu Glu Gly Gly Cys Glu Leu Arg Val
530 535 540

Lys Phe Ser Arg Ser Ala Asp Ala Pro Ala Tyr Gln Gln Gly Gln Asn
545 550 555 560

Gln Leu Tyr Asn Glu Leu Asn Leu Gly Arg Arg Glu Glu Tyr Asp Val
565 570 575

Leu Asp Lys Arg Arg Gly Arg Asp Pro Glu Met Gly Gly Lys Pro Arg
580 585 590

Arg Lys Asn Pro Gln Glu Gly Leu Tyr Asn Glu Leu Gln Lys Asp Lys
595 600 605

Met Ala Glu Ala Tyr Ser Glu Ile Gly Met Lys Gly Glu Arg Arg Arg
610 615 620

Gly Lys Gly His Asp Gly Leu Tyr Gln Gly Leu Ser Thr Ala Thr Lys
625 630 635 640

```
Asp Thr Tyr Asp Ala Leu His Met Gln Ala Leu Pro Pro Arg
                645                 650


<210> SEQ ID NO 29
<211> LENGTH: 612
<212> TYPE: PRT
<213> ORGANISM: Artificial Sequence
<220> FEATURE:
<223> OTHER INFORMATION: Synthetic sequence

<400> SEQUENCE: 29

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Val Gln Ala
                85                  90                  95

Thr Gln Phe Pro Leu Thr Phe Gly Gly Gly Thr Lys Val Glu Ile Lys
            100                 105                 110

Gly Gly Gly Gly Ser Gly Gly Gly Gly Ser Gly Gly Gly Gly Ser Glu
        115                 120                 125

Val Gln Leu Val Gln Ser Gly Ala Glu Val Lys Lys Pro Gly Glu Ser
    130                 135                 140

Leu Lys Ile Ser Cys Lys Gly Ser Gly Tyr Ser Phe Thr Ser Tyr Trp
145                 150                 155                 160

Ile Gly Trp Val Arg Gln Met Pro Gly Lys Gly Leu Glu Trp Met Gly
                165                 170                 175

Ile Ile Tyr Pro Gly Asp Ser Asp Thr Arg Tyr Ser Pro Ser Phe Gln
            180                 185                 190

Gly Gln Val Thr Ile Ser Ala Asp Lys Ser Ile Thr Thr Ala Tyr Leu
        195                 200                 205

Gln Trp Ser Ser Leu Lys Ala Ser Asp Thr Ala Met Tyr Tyr Cys Ala
    210                 215                 220

Arg His Pro Ser Tyr Gly Ser Gly Ser Pro Asn Phe Asp Tyr Trp Gly
225                 230                 235                 240

Gln Gly Thr Leu Val Thr Val Ser Ser Asp Lys Thr His Thr Cys Pro
                245                 250                 255

Pro Cys Pro Ala Pro Pro Val Ala Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Gln Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350
```

```
Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Phe Trp Val Leu Val Val Val
465                 470                 475                 480

Gly Gly Val Leu Ala Cys Tyr Ser Leu Leu Val Thr Val Ala Phe Ile
                485                 490                 495

Ile Phe Trp Val Arg Val Lys Phe Ser Arg Ser Ala Asp Ala Pro Ala
            500                 505                 510

Tyr Gln Gln Gly Gln Asn Gln Leu Tyr Asn Glu Leu Asn Leu Gly Arg
        515                 520                 525

Arg Glu Glu Tyr Asp Val Leu Asp Lys Arg Arg Gly Arg Asp Pro Glu
    530                 535                 540

Met Gly Gly Lys Pro Arg Arg Lys Asn Pro Gln Glu Gly Leu Tyr Asn
545                 550                 555                 560

Glu Leu Gln Lys Asp Lys Met Ala Glu Ala Tyr Ser Glu Ile Gly Met
                565                 570                 575

Lys Gly Glu Arg Arg Arg Gly Lys Gly His Asp Gly Leu Tyr Gln Gly
            580                 585                 590

Leu Ser Thr Ala Thr Lys Asp Thr Tyr Asp Ala Leu His Met Gln Ala
        595                 600                 605

Leu Pro Pro Arg
    610


<210> SEQ ID NO 30
<211> LENGTH: 700
<212> TYPE: PRT
<213> ORGANISM: Artificial Sequence
<220> FEATURE:
<223> OTHER INFORMATION: Synthetic sequence

<400> SEQUENCE: 30

Asp Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
            20                  25                  30

Asp Trp Tyr Gln Lys Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95
```

-continued

```
Phe Gly Gly Gly Thr Lys Leu Glu Ile Lys Gly Ser Thr Ser Gly Gly
            100                 105                 110

Gly Ser Gly Gly Gly Ser Gly Gly Gly Gly Ser Ser Glu Val Gln Leu
        115                 120                 125

Gln Gln Ser Gly Ala Glu Leu Val Lys Pro Gly Ala Ser Val Lys Met
    130                 135                 140

Ser Cys Lys Ala Ser Gly Tyr Thr Phe Thr Ser Tyr Asn Met His Trp
145                 150                 155                 160

Val Lys Gln Thr Pro Gly Gln Gly Leu Glu Trp Ile Gly Ala Ile Tyr
                165                 170                 175

Pro Gly Asn Gly Asp Thr Ser Tyr Asn Gln Lys Phe Lys Gly Lys Ala
            180                 185                 190

Thr Leu Thr Ala Asp Lys Ser Ser Ser Thr Ala Tyr Met Gln Leu Ser
        195                 200                 205

Ser Leu Thr Ser Glu Asp Ser Ala Asp Tyr Tyr Cys Ala Arg Ser Asn
    210                 215                 220

Tyr Tyr Gly Ser Ser Tyr Trp Phe Phe Asp Val Trp Gly Ala Gly Thr
225                 230                 235                 240

Thr Val Thr Val Ser Ser Leu Asp Glu Ser Lys Tyr Gly Pro Pro Cys
                245                 250                 255

Pro Pro Cys Pro Ala Pro Glu Phe Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser Gln Glu Asp Pro Glu Val Gln
    290                 295                 300

Phe Asn Trp Tyr Val Asp Gly Val Glu Val His Asn Ala Lys Thr Lys
305                 310                 315                 320

Pro Arg Glu Glu Gln Phe Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Gly Leu Pro Ser Ser Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Gln Glu Glu Met Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Arg Leu Thr Val Asp Lys Ser Arg Trp Gln
        435                 440                 445

Glu Gly Asn Val Phe Ser Cys Ser Val Met His Glu Ala Leu His Asn
    450                 455                 460

His Tyr Thr Gln Lys Ser Leu Ser Leu Ser Leu Gly Lys Met Phe Trp
465                 470                 475                 480

Val Leu Val Val Val Gly Gly Val Leu Ala Cys Tyr Ser Leu Leu Val
                485                 490                 495

Thr Val Ala Phe Ile Ile Phe Trp Val Arg Ser Lys Arg Ser Arg Gly
            500                 505                 510
```

```
Gly His Ser Asp Tyr Met Asn Met Thr Pro Arg Arg Pro Gly Pro Thr
        515                 520                 525

Arg Lys His Tyr Gln Pro Tyr Ala Pro Pro Arg Asp Phe Ala Ala Tyr
    530                 535                 540

Arg Ser Lys Arg Gly Arg Lys Lys Leu Leu Tyr Ile Phe Lys Gln Pro
545                 550                 555                 560

Phe Met Arg Pro Val Gln Thr Thr Gln Glu Glu Asp Gly Cys Ser Cys
                565                 570                 575

Arg Phe Pro Glu Glu Glu Glu Gly Gly Cys Glu Leu Arg Val Lys Phe
            580                 585                 590

Ser Arg Ser Ala Asp Ala Pro Ala Tyr Gln Gln Gly Gln Asn Gln Leu
        595                 600                 605

Tyr Asn Glu Leu Asn Leu Gly Arg Arg Glu Glu Tyr Asp Val Leu Asp
    610                 615                 620

Lys Arg Arg Gly Arg Asp Pro Glu Met Gly Gly Lys Pro Arg Arg Lys
625                 630                 635                 640

Asn Pro Gln Glu Gly Leu Tyr Asn Glu Leu Gln Lys Asp Lys Met Ala
                645                 650                 655

Glu Ala Tyr Ser Glu Ile Gly Met Lys Gly Glu Arg Arg Arg Gly Lys
            660                 665                 670

Gly His Asp Gly Leu Tyr Gln Gly Leu Ser Thr Ala Thr Lys Asp Thr
        675                 680                 685

Tyr Asp Ala Leu His Met Gln Ala Leu Pro Pro Arg
    690                 695                 700


<210> SEQ ID NO 31
<211> LENGTH: 658
<212> TYPE: PRT
<213> ORGANISM: Artificial Sequence
<220> FEATURE:
<223> OTHER INFORMATION: Synthetic sequence

<400> SEQUENCE: 31

Asp Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
            20                  25                  30

Asp Trp Tyr Gln Lys Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Gly Gly Thr Lys Leu Glu Ile Lys Gly Ser Thr Ser Gly Gly
            100                 105                 110

Gly Ser Gly Gly Gly Ser Gly Gly Gly Gly Ser Ser Glu Val Gln Leu
        115                 120                 125

Gln Gln Ser Gly Ala Glu Leu Val Lys Pro Gly Ala Ser Val Lys Met
    130                 135                 140

Ser Cys Lys Ala Ser Gly Tyr Thr Phe Thr Ser Tyr Asn Met His Trp
145                 150                 155                 160

Val Lys Gln Thr Pro Gly Gln Gly Leu Glu Trp Ile Gly Ala Ile Tyr
                165                 170                 175
```

-continued

```
Pro Gly Asn Gly Asp Thr Ser Tyr Asn Gln Lys Phe Lys Gly Lys Ala
            180                 185                 190

Thr Leu Thr Ala Asp Lys Ser Ser Ser Thr Ala Tyr Met Gln Leu Ser
        195                 200                 205

Ser Leu Thr Ser Glu Asp Ser Ala Asp Tyr Tyr Cys Ala Arg Ser Asn
    210                 215                 220

Tyr Tyr Gly Ser Ser Tyr Trp Phe Phe Asp Val Trp Gly Ala Gly Thr
225                 230                 235                 240

Thr Val Thr Val Ser Ser Leu Asp Glu Ser Lys Tyr Gly Pro Pro Cys
                245                 250                 255

Pro Pro Cys Pro Ala Pro Glu Phe Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser Gln Glu Asp Pro Glu Val Gln
    290                 295                 300

Phe Asn Trp Tyr Val Asp Gly Val Glu Val His Asn Ala Lys Thr Lys
305                 310                 315                 320

Pro Arg Glu Glu Gln Phe Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Gly Leu Pro Ser Ser Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Gln Glu Glu Met Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Arg Leu Thr Val Asp Lys Ser Arg Trp Gln
        435                 440                 445

Glu Gly Asn Val Phe Ser Cys Ser Val Met His Glu Ala Leu His Asn
    450                 455                 460

His Tyr Thr Gln Lys Ser Leu Ser Leu Ser Leu Gly Lys Met Phe Trp
465                 470                 475                 480

Val Leu Val Val Val Gly Gly Val Leu Ala Cys Tyr Ser Leu Leu Val
                485                 490                 495

Thr Val Ala Phe Ile Ile Phe Trp Val Arg Ser Lys Arg Ser Arg Gly
            500                 505                 510

Gly His Ser Asp Tyr Met Asn Met Thr Pro Arg Arg Pro Gly Pro Thr
        515                 520                 525

Arg Lys His Tyr Gln Pro Tyr Ala Pro Pro Arg Asp Phe Ala Ala Tyr
    530                 535                 540

Arg Ser Arg Val Lys Phe Ser Arg Ser Ala Asp Ala Pro Ala Tyr Gln
545                 550                 555                 560

Gln Gly Gln Asn Gln Leu Tyr Asn Glu Leu Asn Leu Gly Arg Arg Glu
                565                 570                 575

Glu Tyr Asp Val Leu Asp Lys Arg Arg Gly Arg Asp Pro Glu Met Gly
            580                 585                 590
```

```
Gly Lys Pro Arg Arg Lys Asn Pro Gln Glu Gly Leu Tyr Asn Glu Leu
        595                 600                 605

Gln Lys Asp Lys Met Ala Glu Ala Tyr Ser Glu Ile Gly Met Lys Gly
    610                 615                 620

Glu Arg Arg Arg Gly Lys Gly His Asp Gly Leu Tyr Gln Gly Leu Ser
625                 630                 635                 640

Thr Ala Thr Lys Asp Thr Tyr Asp Ala Leu His Met Gln Ala Leu Pro
                645                 650                 655

Pro Arg


<210> SEQ ID NO 32
<211> LENGTH: 698
<212> TYPE: PRT
<213> ORGANISM: Artificial Sequence
<220> FEATURE:
<223> OTHER INFORMATION: Synthetic sequence

<400> SEQUENCE: 32

Asp Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Leu Ser Phe Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Phe Cys His Gln Trp Ser Ser Asn Pro Leu Thr
                85                  90                  95

Phe Gly Ala Gly Thr Lys Leu Glu Leu Lys Gly Ser Thr Ser Gly Gly
            100                 105                 110

Gly Ser Gly Gly Gly Ser Gly Gly Gly Gly Ser Ser Gln Val Gln Leu
        115                 120                 125

Arg Gln Pro Gly Ala Glu Leu Val Lys Pro Gly Ala Ser Val Lys Met
    130                 135                 140

Ser Cys Lys Ala Ser Gly Tyr Thr Phe Thr Ser Tyr Asn Met His Trp
145                 150                 155                 160

Val Lys Gln Thr Pro Gly Gln Gly Leu Glu Trp Ile Gly Ala Ile Tyr
                165                 170                 175

Pro Gly Asn Gly Asp Thr Ser Tyr Asn Gln Lys Phe Lys Gly Lys Ala
            180                 185                 190

Thr Leu Thr Ala Asp Lys Ser Ser Ser Thr Ala Tyr Met Gln Leu Ser
        195                 200                 205

Ser Leu Thr Ser Glu Asp Ser Ala Val Tyr Tyr Cys Ala Arg Ser His
    210                 215                 220

Tyr Gly Ser Asn Tyr Val Asp Tyr Phe Asp Tyr Trp Gly Gln Gly Thr
225                 230                 235                 240

Thr Leu Thr Val Ser Ser Leu Asp Pro Lys Ser Ser Asp Lys Thr His
                245                 250                 255

Thr Cys Pro Pro Cys Pro Ala Pro Pro Val Ala Gly Pro Ser Val Phe
            260                 265                 270

Leu Phe Pro Pro Lys Pro Lys Asp Thr Leu Met Ile Ser Arg Thr Pro
        275                 280                 285
```

```
Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Gln Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365

Lys Ala Lys Gly Gln Pro Arg Glu Pro Gln Val Tyr Thr Leu Pro Pro
    370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Phe Trp Val Leu
465                 470                 475                 480

Val Val Val Gly Gly Val Leu Ala Cys Tyr Ser Leu Leu Val Thr Val
                485                 490                 495

Ala Phe Ile Ile Phe Trp Val Arg Ser Lys Arg Ser Arg Gly Gly His
            500                 505                 510

Ser Asp Tyr Met Asn Met Thr Pro Arg Arg Pro Gly Pro Thr Arg Lys
        515                 520                 525

His Tyr Gln Pro Tyr Ala Pro Pro Arg Asp Phe Ala Ala Tyr Arg Ser
    530                 535                 540

Lys Arg Gly Arg Lys Lys Leu Leu Tyr Ile Phe Lys Gln Pro Phe Met
545                 550                 555                 560

Arg Pro Val Gln Thr Thr Gln Glu Glu Asp Gly Cys Ser Cys Arg Phe
                565                 570                 575

Pro Glu Glu Glu Glu Gly Gly Cys Glu Leu Arg Val Lys Phe Ser Arg
            580                 585                 590

Ser Ala Asp Ala Pro Ala Tyr Gln Gln Gly Gln Asn Gln Leu Tyr Asn
        595                 600                 605

Glu Leu Asn Leu Gly Arg Arg Glu Glu Tyr Asp Val Leu Asp Lys Arg
    610                 615                 620

Arg Gly Arg Asp Pro Glu Met Gly Gly Lys Pro Arg Arg Lys Asn Pro
625                 630                 635                 640

Gln Glu Gly Leu Tyr Asn Glu Leu Gln Lys Asp Lys Met Ala Glu Ala
                645                 650                 655

Tyr Ser Glu Ile Gly Met Lys Gly Glu Arg Arg Arg Gly Lys Gly His
            660                 665                 670

Asp Gly Leu Tyr Gln Gly Leu Ser Thr Ala Thr Lys Asp Thr Tyr Asp
        675                 680                 685

Ala Leu His Met Gln Ala Leu Pro Pro Arg
    690                 695
```

<210> SEQ ID NO 33
<211> LENGTH: 656
<212> TYPE: PRT
<213> ORGANISM: Artificial Sequence
<220> FEATURE:
<223> OTHER INFORMATION: Synthetic sequence

<400> SEQUENCE: 33

```
Asp Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Leu Ser Phe Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Phe Cys His Gln Trp Ser Ser Asn Pro Leu Thr
                85                  90                  95

Phe Gly Ala Gly Thr Lys Leu Glu Leu Lys Gly Ser Thr Ser Gly Gly
            100                 105                 110

Gly Ser Gly Gly Gly Ser Gly Gly Gly Gly Ser Ser Gln Val Gln Leu
        115                 120                 125

Arg Gln Pro Gly Ala Glu Leu Val Lys Pro Gly Ala Ser Val Lys Met
    130                 135                 140

Ser Cys Lys Ala Ser Gly Tyr Thr Phe Thr Ser Tyr Asn Met His Trp
145                 150                 155                 160

Val Lys Gln Thr Pro Gly Gln Gly Leu Glu Trp Ile Gly Ala Ile Tyr
                165                 170                 175

Pro Gly Asn Gly Asp Thr Ser Tyr Asn Gln Lys Phe Lys Gly Lys Ala
            180                 185                 190

Thr Leu Thr Ala Asp Lys Ser Ser Ser Thr Ala Tyr Met Gln Leu Ser
        195                 200                 205

Ser Leu Thr Ser Glu Asp Ser Ala Val Tyr Tyr Cys Ala Arg Ser His
    210                 215                 220

Tyr Gly Ser Asn Tyr Val Asp Tyr Phe Asp Tyr Trp Gly Gln Gly Thr
225                 230                 235                 240

Thr Leu Thr Val Ser Ser Leu Asp Pro Lys Ser Ser Asp Lys Thr His
                245                 250                 255

Thr Cys Pro Pro Cys Pro Ala Pro Pro Val Ala Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Gln Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365
```

```
Lys Ala Lys Gly Gln Pro Arg Glu Pro Gln Val Tyr Thr Leu Pro Pro
    370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Phe Trp Val Leu
465                 470                 475                 480

Val Val Val Gly Gly Val Leu Ala Cys Tyr Ser Leu Leu Val Thr Val
                485                 490                 495

Ala Phe Ile Ile Phe Trp Val Arg Ser Lys Arg Ser Arg Gly Gly His
            500                 505                 510

Ser Asp Tyr Met Asn Met Thr Pro Arg Arg Pro Gly Pro Thr Arg Lys
        515                 520                 525

His Tyr Gln Pro Tyr Ala Pro Pro Arg Asp Phe Ala Ala Tyr Arg Ser
    530                 535                 540

Arg Val Lys Phe Ser Arg Ser Ala Asp Ala Pro Ala Tyr Gln Gln Gly
545                 550                 555                 560

Gln Asn Gln Leu Tyr Asn Glu Leu Asn Leu Gly Arg Arg Glu Glu Tyr
                565                 570                 575

Asp Val Leu Asp Lys Arg Arg Gly Arg Asp Pro Glu Met Gly Gly Lys
            580                 585                 590

Pro Arg Arg Lys Asn Pro Gln Glu Gly Leu Tyr Asn Glu Leu Gln Lys
        595                 600                 605

Asp Lys Met Ala Glu Ala Tyr Ser Glu Ile Gly Met Lys Gly Glu Arg
    610                 615                 620

Arg Arg Gly Lys Gly His Asp Gly Leu Tyr Gln Gly Leu Ser Thr Ala
625                 630                 635                 640

Thr Lys Asp Thr Tyr Asp Ala Leu His Met Gln Ala Leu Pro Pro Arg
                645                 650                 655


<210> SEQ ID NO 34
<211> LENGTH: 657
<212> TYPE: PRT
<213> ORGANISM: Artificial Sequence
<220> FEATURE:
<223> OTHER INFORMATION: Synthetic sequence

<400> SEQUENCE: 34

Asp Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Leu Ser Phe Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80
```

-continued

```
Asp Ala Ala Thr Tyr Phe Cys His Gln Trp Ser Ser Asn Pro Leu Thr
                85                  90                  95

Phe Gly Ala Gly Thr Lys Leu Glu Leu Lys Gly Ser Thr Ser Gly Gly
            100                 105                 110

Gly Ser Gly Gly Gly Ser Gly Gly Gly Gly Ser Ser Gln Val Gln Leu
        115                 120                 125

Arg Gln Pro Gly Ala Glu Leu Val Lys Pro Gly Ala Ser Val Lys Met
    130                 135                 140

Ser Cys Lys Ala Ser Gly Tyr Thr Phe Thr Ser Tyr Asn Met His Trp
145                 150                 155                 160

Val Lys Gln Thr Pro Gly Gln Gly Leu Glu Trp Ile Gly Ala Ile Tyr
                165                 170                 175

Pro Gly Asn Gly Asp Thr Ser Tyr Asn Gln Lys Phe Lys Gly Lys Ala
            180                 185                 190

Thr Leu Thr Ala Asp Lys Ser Ser Ser Thr Ala Tyr Met Gln Leu Ser
        195                 200                 205

Ser Leu Thr Ser Glu Asp Ser Ala Val Tyr Tyr Cys Ala Arg Ser His
    210                 215                 220

Tyr Gly Ser Asn Tyr Val Asp Tyr Phe Asp Tyr Trp Gly Gln Gly Thr
225                 230                 235                 240

Thr Leu Thr Val Ser Ser Leu Asp Pro Lys Ser Ser Asp Lys Thr His
                245                 250                 255

Thr Cys Pro Pro Cys Pro Ala Pro Pro Val Ala Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Gln Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365

Lys Ala Lys Gly Gln Pro Arg Glu Pro Gln Val Tyr Thr Leu Pro Pro
    370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Phe Trp Val Leu
465                 470                 475                 480

Val Val Val Gly Gly Val Leu Ala Cys Tyr Ser Leu Leu Val Thr Val
                485                 490                 495
```

-continued

Ala Phe Ile Ile Phe Trp Val Lys Arg Gly Arg Lys Lys Leu Leu Tyr
500 505 510

Ile Phe Lys Gln Pro Phe Met Arg Pro Val Gln Thr Thr Gln Glu Glu
515 520 525

Asp Gly Cys Ser Cys Arg Phe Pro Glu Glu Glu Glu Gly Gly Cys Glu
530 535 540

Leu Arg Val Lys Phe Ser Arg Ser Ala Asp Ala Pro Ala Tyr Gln Gln
545 550 555 560

Gly Gln Asn Gln Leu Tyr Asn Glu Leu Asn Leu Gly Arg Arg Glu Glu
565 570 575

Tyr Asp Val Leu Asp Lys Arg Arg Gly Arg Asp Pro Glu Met Gly Gly
580 585 590

Lys Pro Arg Arg Lys Asn Pro Gln Glu Gly Leu Tyr Asn Glu Leu Gln
595 600 605

Lys Asp Lys Met Ala Glu Ala Tyr Ser Glu Ile Gly Met Lys Gly Glu
610 615 620

Arg Arg Arg Gly Lys Gly His Asp Gly Leu Tyr Gln Gly Leu Ser Thr
625 630 635 640

Ala Thr Lys Asp Thr Tyr Asp Ala Leu His Met Gln Ala Leu Pro Pro
645 650 655

Arg

<210> SEQ ID NO 35
<211> LENGTH: 1060
<212> TYPE: PRT
<213> ORGANISM: Artificial Sequence
<220> FEATURE:
<223> OTHER INFORMATION: Synthetic sequence

<400> SEQUENCE: 35

Met Leu Leu Leu Val Thr Ser Leu Leu Leu Cys Glu Leu Pro His Pro
1 5 10 15

Ala Phe Leu Leu Ile Pro Asp Ile Val Met Thr Gln Thr Pro Leu Ser
20 25 30

Ser Pro Val Thr Leu Gly Gln Pro Ala Ser Ile Ser Cys Arg Ser Ser
35 40 45

Gln Ser Leu Val Tyr Ser Asp Gly Asn Thr Tyr Leu Ser Trp Leu Gln
50 55 60

Gln Arg Pro Gly Gln Pro Pro Arg Leu Leu Ile Tyr Lys Ile Ser Asn
65 70 75 80

Arg Phe Ser Gly Val Pro Asp Arg Phe Ser Gly Ser Gly Ala Gly Thr
85 90 95

Asp Phe Thr Leu Lys Ile Ser Arg Val Glu Ala Glu Asp Val Gly Val
100 105 110

Tyr Tyr Cys Val Gln Ala Thr Gln Phe Pro Leu Thr Phe Gly Gly Gly
115 120 125

Thr Lys Val Glu Ile Lys Gly Gly Gly Gly Ser Gly Gly Gly Gly Ser
130 135 140

Gly Gly Gly Gly Ser Glu Val Gln Leu Val Gln Ser Gly Ala Glu Val
145 150 155 160

Lys Lys Pro Gly Glu Ser Leu Lys Ile Ser Cys Lys Gly Ser Gly Tyr
165 170 175

Ser Phe Thr Ser Tyr Trp Ile Gly Trp Val Arg Gln Met Pro Gly Lys
180 185 190

-continued

```
Gly Leu Glu Trp Met Gly Ile Ile Tyr Pro Gly Asp Ser Asp Thr Arg
        195                 200                 205

Tyr Ser Pro Ser Phe Gln Gly Gln Val Thr Ile Ser Ala Asp Lys Ser
    210                 215                 220

Ile Thr Thr Ala Tyr Leu Gln Trp Ser Ser Leu Lys Ala Ser Asp Thr
225                 230                 235                 240

Ala Met Tyr Tyr Cys Ala Arg His Pro Ser Tyr Gly Ser Gly Ser Pro
                245                 250                 255

Asn Phe Asp Tyr Trp Gly Gln Gly Thr Leu Val Thr Val Ser Ser Asp
            260                 265                 270

Lys Thr His Thr Cys Pro Pro Cys Pro Ala Pro Pro Val Ala Gly Pro
        275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Gln Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
    450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Phe
                485                 490                 495

Trp Val Leu Val Val Val Gly Gly Val Leu Ala Cys Tyr Ser Leu Leu
            500                 505                 510

Val Thr Val Ala Phe Ile Ile Phe Trp Val Arg Ser Lys Arg Ser Arg
        515                 520                 525

Gly Gly His Ser Asp Tyr Met Asn Met Thr Pro Arg Arg Pro Gly Pro
    530                 535                 540

Thr Arg Lys His Tyr Gln Pro Tyr Ala Pro Pro Arg Asp Phe Ala Ala
545                 550                 555                 560

Tyr Arg Ser Lys Arg Gly Arg Lys Lys Leu Leu Tyr Ile Phe Lys Gln
                565                 570                 575

Pro Phe Met Arg Pro Val Gln Thr Thr Gln Glu Glu Asp Gly Cys Ser
            580                 585                 590

Cys Arg Phe Pro Glu Glu Glu Glu Gly Gly Cys Glu Leu Arg Val Lys
        595                 600                 605
```

-continued

```
Phe Ser Arg Ser Ala Asp Ala Pro Ala Tyr Gln Gln Gly Gln Asn Gln
    610                 615                 620

Leu Tyr Asn Glu Leu Asn Leu Gly Arg Arg Glu Glu Tyr Asp Val Leu
625                 630                 635                 640

Asp Lys Arg Arg Gly Arg Asp Pro Glu Met Gly Gly Lys Pro Arg Arg
                645                 650                 655

Lys Asn Pro Gln Glu Gly Leu Tyr Asn Glu Leu Gln Lys Asp Lys Met
            660                 665                 670

Ala Glu Ala Tyr Ser Glu Ile Gly Met Lys Gly Glu Arg Arg Arg Gly
        675                 680                 685

Lys Gly His Asp Gly Leu Tyr Gln Gly Leu Ser Thr Ala Thr Lys Asp
    690                 695                 700

Thr Tyr Asp Ala Leu His Met Gln Ala Leu Pro Pro Arg Gln Cys Thr
705                 710                 715                 720

Asn Tyr Ala Leu Leu Lys Leu Ala Gly Asp Val Glu Ser Asn Pro Gly
                725                 730                 735

Pro Met Pro Pro Pro Arg Leu Leu Phe Phe Leu Leu Phe Leu Thr Pro
            740                 745                 750

Met Glu Val Arg Pro Glu Glu Pro Leu Val Val Lys Val Glu Glu Gly
        755                 760                 765

Asp Asn Ala Val Leu Gln Cys Leu Lys Gly Thr Ser Asp Gly Pro Thr
    770                 775                 780

Gln Gln Leu Thr Trp Ser Arg Glu Ser Pro Leu Lys Pro Phe Leu Lys
785                 790                 795                 800

Leu Ser Leu Gly Leu Pro Gly Leu Gly Ile His Met Arg Pro Leu Ala
                805                 810                 815

Ile Trp Leu Phe Ile Phe Asn Val Ser Gln Gln Met Gly Gly Phe Tyr
            820                 825                 830

Leu Cys Gln Pro Gly Pro Pro Ser Glu Lys Ala Trp Gln Pro Gly Trp
        835                 840                 845

Thr Val Asn Val Glu Gly Ser Gly Glu Leu Phe Arg Trp Asn Val Ser
    850                 855                 860

Asp Leu Gly Gly Leu Gly Cys Gly Leu Lys Asn Arg Ser Ser Glu Gly
865                 870                 875                 880

Pro Ser Ser Pro Ser Gly Lys Leu Met Ser Pro Lys Leu Tyr Val Trp
                885                 890                 895

Ala Lys Asp Arg Pro Glu Ile Trp Glu Gly Glu Pro Pro Cys Val Pro
            900                 905                 910

Pro Arg Asp Ser Leu Asn Gln Ser Leu Ser Gln Asp Leu Thr Met Ala
        915                 920                 925

Pro Gly Ser Thr Leu Trp Leu Ser Cys Gly Val Pro Pro Asp Ser Val
    930                 935                 940

Ser Arg Gly Pro Leu Ser Trp Thr His Val His Pro Lys Gly Pro Lys
945                 950                 955                 960

Ser Leu Leu Ser Leu Glu Leu Lys Asp Asp Arg Pro Ala Arg Asp Met
                965                 970                 975

Trp Val Met Glu Thr Gly Leu Leu Leu Pro Arg Ala Thr Ala Gln Asp
            980                 985                 990

Ala Gly Lys Tyr Tyr Cys His Arg Gly Asn Leu Thr Met Ser Phe His
        995                 1000                1005

Leu Glu Ile Thr Ala Arg Pro Val Leu Trp His Trp Leu Leu Arg Thr
    1010                1015                1020
```

```
Gly Gly Trp Lys Val Ser Ala Val Thr Leu Ala Tyr Leu Ile Phe Cys
1025                1030                1035                1040

Leu Cys Ser Leu Val Gly Ile Leu His Leu Gln Arg Ala Leu Val Leu
                1045                1050                1055

Arg Arg Lys Arg
            1060


<210> SEQ ID NO 36
<211> LENGTH: 1018
<212> TYPE: PRT
<213> ORGANISM: Artificial Sequence
<220> FEATURE:
<223> OTHER INFORMATION: Synthetic sequence

<400> SEQUENCE: 36

Met Leu Leu Leu Val Thr Ser Leu Leu Leu Cys Glu Leu Pro His Pro
1               5                   10                  15

Ala Phe Leu Leu Ile Pro Asp Ile Val Met Thr Gln Thr Pro Leu Ser
            20                  25                  30

Ser Pro Val Thr Leu Gly Gln Pro Ala Ser Ile Ser Cys Arg Ser Ser
        35                  40                  45

Gln Ser Leu Val Tyr Ser Asp Gly Asn Thr Tyr Leu Ser Trp Leu Gln
    50                  55                  60

Gln Arg Pro Gly Gln Pro Pro Arg Leu Leu Ile Tyr Lys Ile Ser Asn
65                  70                  75                  80

Arg Phe Ser Gly Val Pro Asp Arg Phe Ser Gly Ser Gly Ala Gly Thr
                85                  90                  95

Asp Phe Thr Leu Lys Ile Ser Arg Val Glu Ala Glu Asp Val Gly Val
            100                 105                 110

Tyr Tyr Cys Val Gln Ala Thr Gln Phe Pro Leu Thr Phe Gly Gly Gly
        115                 120                 125

Thr Lys Val Glu Ile Lys Gly Gly Gly Gly Ser Gly Gly Gly Gly Ser
    130                 135                 140

Gly Gly Gly Gly Ser Glu Val Gln Leu Val Gln Ser Gly Ala Glu Val
145                 150                 155                 160

Lys Lys Pro Gly Glu Ser Leu Lys Ile Ser Cys Lys Gly Ser Gly Tyr
                165                 170                 175

Ser Phe Thr Ser Tyr Trp Ile Gly Trp Val Arg Gln Met Pro Gly Lys
            180                 185                 190

Gly Leu Glu Trp Met Gly Ile Ile Tyr Pro Gly Asp Ser Asp Thr Arg
        195                 200                 205

Tyr Ser Pro Ser Phe Gln Gly Gln Val Thr Ile Ser Ala Asp Lys Ser
    210                 215                 220

Ile Thr Thr Ala Tyr Leu Gln Trp Ser Ser Leu Lys Ala Ser Asp Thr
225                 230                 235                 240

Ala Met Tyr Tyr Cys Ala Arg His Pro Ser Tyr Gly Ser Gly Ser Pro
                245                 250                 255

Asn Phe Asp Tyr Trp Gly Gln Gly Thr Leu Val Thr Val Ser Ser Asp
            260                 265                 270

Lys Thr His Thr Cys Pro Pro Cys Pro Ala Pro Pro Val Ala Gly Pro
        275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser His Glu Asp
305                 310                 315                 320
```

-continued

```
Pro Glu Val Lys Phe Asn Trp Tyr Val Asp Gly Val Glu Val His Asn
                325                 330                 335

Ala Lys Thr Lys Pro Arg Glu Glu Gln Tyr Gln Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
    450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Phe
                485                 490                 495

Trp Val Leu Val Val Val Gly Gly Val Leu Ala Cys Tyr Ser Leu Leu
            500                 505                 510

Val Thr Val Ala Phe Ile Ile Phe Trp Val Arg Ser Lys Arg Ser Arg
        515                 520                 525

Gly Gly His Ser Asp Tyr Met Asn Met Thr Pro Arg Arg Pro Gly Pro
    530                 535                 540

Thr Arg Lys His Tyr Gln Pro Tyr Ala Pro Pro Arg Asp Phe Ala Ala
545                 550                 555                 560

Tyr Arg Ser Arg Val Lys Phe Ser Arg Ser Ala Asp Ala Pro Ala Tyr
                565                 570                 575

Gln Gln Gly Gln Asn Gln Leu Tyr Asn Glu Leu Asn Leu Gly Arg Arg
            580                 585                 590

Glu Glu Tyr Asp Val Leu Asp Lys Arg Arg Gly Arg Asp Pro Glu Met
        595                 600                 605

Gly Gly Lys Pro Arg Arg Lys Asn Pro Gln Glu Gly Leu Tyr Asn Glu
    610                 615                 620

Leu Gln Lys Asp Lys Met Ala Glu Ala Tyr Ser Glu Ile Gly Met Lys
625                 630                 635                 640

Gly Glu Arg Arg Arg Gly Lys Gly His Asp Gly Leu Tyr Gln Gly Leu
                645                 650                 655

Ser Thr Ala Thr Lys Asp Thr Tyr Asp Ala Leu His Met Gln Ala Leu
            660                 665                 670

Pro Pro Arg Gln Cys Thr Asn Tyr Ala Leu Leu Lys Leu Ala Gly Asp
        675                 680                 685

Val Glu Ser Asn Pro Gly Pro Met Pro Pro Pro Arg Leu Leu Phe Phe
    690                 695                 700

Leu Leu Phe Leu Thr Pro Met Glu Val Arg Pro Glu Glu Pro Leu Val
705                 710                 715                 720

Val Lys Val Glu Glu Gly Asp Asn Ala Val Leu Gln Cys Leu Lys Gly
                725                 730                 735
```

```
Thr Ser Asp Gly Pro Thr Gln Gln Leu Thr Trp Ser Arg Glu Ser Pro
            740                 745                 750

Leu Lys Pro Phe Leu Lys Leu Ser Leu Gly Leu Pro Gly Leu Gly Ile
        755                 760                 765

His Met Arg Pro Leu Ala Ile Trp Leu Phe Ile Phe Asn Val Ser Gln
    770                 775                 780

Gln Met Gly Gly Phe Tyr Leu Cys Gln Pro Gly Pro Pro Ser Glu Lys
785                 790                 795                 800

Ala Trp Gln Pro Gly Trp Thr Val Asn Val Glu Gly Ser Gly Glu Leu
                805                 810                 815

Phe Arg Trp Asn Val Ser Asp Leu Gly Gly Leu Gly Cys Gly Leu Lys
            820                 825                 830

Asn Arg Ser Ser Glu Gly Pro Ser Ser Pro Ser Gly Lys Leu Met Ser
        835                 840                 845

Pro Lys Leu Tyr Val Trp Ala Lys Asp Arg Pro Glu Ile Trp Glu Gly
    850                 855                 860

Glu Pro Pro Cys Val Pro Pro Arg Asp Ser Leu Asn Gln Ser Leu Ser
865                 870                 875                 880

Gln Asp Leu Thr Met Ala Pro Gly Ser Thr Leu Trp Leu Ser Cys Gly
                885                 890                 895

Val Pro Pro Asp Ser Val Ser Arg Gly Pro Leu Ser Trp Thr His Val
            900                 905                 910

His Pro Lys Gly Pro Lys Ser Leu Leu Ser Leu Glu Leu Lys Asp Asp
        915                 920                 925

Arg Pro Ala Arg Asp Met Trp Val Met Glu Thr Gly Leu Leu Leu Pro
    930                 935                 940

Arg Ala Thr Ala Gln Asp Ala Gly Lys Tyr Tyr Cys His Arg Gly Asn
945                 950                 955                 960

Leu Thr Met Ser Phe His Leu Glu Ile Thr Ala Arg Pro Val Leu Trp
                965                 970                 975

His Trp Leu Leu Arg Thr Gly Gly Trp Lys Val Ser Ala Val Thr Leu
            980                 985                 990

Ala Tyr Leu Ile Phe Cys Leu Cys Ser Leu Val Gly Ile Leu His Leu
        995                 1000                1005

Gln Arg Ala Leu Val Leu Arg Arg Lys Arg
    1010                1015


<210> SEQ ID NO 37
<211> LENGTH: 1019
<212> TYPE: PRT
<213> ORGANISM: Artificial Sequence
<220> FEATURE:
<223> OTHER INFORMATION: Synthetic sequence

<400> SEQUENCE: 37

Met Leu Leu Leu Val Thr Ser Leu Leu Leu Cys Glu Leu Pro His Pro
1               5                   10                  15

Ala Phe Leu Leu Ile Pro Asp Ile Val Met Thr Gln Thr Pro Leu Ser
            20                  25                  30

Ser Pro Val Thr Leu Gly Gln Pro Ala Ser Ile Ser Cys Arg Ser Ser
        35                  40                  45

Gln Ser Leu Val Tyr Ser Asp Gly Asn Thr Tyr Leu Ser Trp Leu Gln
    50                  55                  60

Gln Arg Pro Gly Gln Pro Pro Arg Leu Leu Ile Tyr Lys Ile Ser Asn
65                  70                  75                  80
```

-continued

```
Arg Phe Ser Gly Val Pro Asp Arg Phe Ser Gly Ser Gly Ala Gly Thr
                85                  90                  95

Asp Phe Thr Leu Lys Ile Ser Arg Val Glu Ala Glu Asp Val Gly Val
            100                 105                 110

Tyr Tyr Cys Val Gln Ala Thr Gln Phe Pro Leu Thr Phe Gly Gly Gly
        115                 120                 125

Thr Lys Val Glu Ile Lys Gly Gly Gly Gly Ser Gly Gly Gly Gly Ser
    130                 135                 140

Gly Gly Gly Gly Ser Glu Val Gln Leu Val Gln Ser Gly Ala Glu Val
145                 150                 155                 160

Lys Lys Pro Gly Glu Ser Leu Lys Ile Ser Cys Lys Gly Ser Gly Tyr
                165                 170                 175

Ser Phe Thr Ser Tyr Trp Ile Gly Trp Val Arg Gln Met Pro Gly Lys
            180                 185                 190

Gly Leu Glu Trp Met Gly Ile Ile Tyr Pro Gly Asp Ser Asp Thr Arg
        195                 200                 205

Tyr Ser Pro Ser Phe Gln Gly Gln Val Thr Ile Ser Ala Asp Lys Ser
    210                 215                 220

Ile Thr Thr Ala Tyr Leu Gln Trp Ser Ser Leu Lys Ala Ser Asp Thr
225                 230                 235                 240

Ala Met Tyr Tyr Cys Ala Arg His Pro Ser Tyr Gly Ser Gly Ser Pro
                245                 250                 255

Asn Phe Asp Tyr Trp Gly Gln Gly Thr Leu Val Thr Val Ser Ser Asp
            260                 265                 270

Lys Thr His Thr Cys Pro Pro Cys Pro Ala Pro Pro Val Ala Gly Pro
        275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Gln Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
    450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Phe
                485                 490                 495
```

```
Trp Val Leu Val Val Val Gly Gly Val Leu Ala Cys Tyr Ser Leu Leu
            500                 505                 510

Val Thr Val Ala Phe Ile Ile Phe Trp Val Lys Arg Gly Arg Lys Lys
        515                 520                 525

Leu Leu Tyr Ile Phe Lys Gln Pro Phe Met Arg Pro Val Gln Thr Thr
    530                 535                 540

Gln Glu Glu Asp Gly Cys Ser Cys Arg Phe Pro Glu Glu Glu Glu Gly
545                 550                 555                 560

Gly Cys Glu Leu Arg Val Lys Phe Ser Arg Ser Ala Asp Ala Pro Ala
                565                 570                 575

Tyr Gln Gln Gly Gln Asn Gln Leu Tyr Asn Glu Leu Asn Leu Gly Arg
            580                 585                 590

Arg Glu Glu Tyr Asp Val Leu Asp Lys Arg Arg Gly Arg Asp Pro Glu
        595                 600                 605

Met Gly Gly Lys Pro Arg Arg Lys Asn Pro Gln Glu Gly Leu Tyr Asn
    610                 615                 620

Glu Leu Gln Lys Asp Lys Met Ala Glu Ala Tyr Ser Glu Ile Gly Met
625                 630                 635                 640

Lys Gly Glu Arg Arg Arg Gly Lys Gly His Asp Gly Leu Tyr Gln Gly
                645                 650                 655

Leu Ser Thr Ala Thr Lys Asp Thr Tyr Asp Ala Leu His Met Gln Ala
            660                 665                 670

Leu Pro Pro Arg Gln Cys Thr Asn Tyr Ala Leu Leu Lys Leu Ala Gly
        675                 680                 685

Asp Val Glu Ser Asn Pro Gly Pro Met Pro Pro Pro Arg Leu Leu Phe
    690                 695                 700

Phe Leu Leu Phe Leu Thr Pro Met Glu Val Arg Pro Glu Glu Pro Leu
705                 710                 715                 720

Val Val Lys Val Glu Glu Gly Asp Asn Ala Val Leu Gln Cys Leu Lys
                725                 730                 735

Gly Thr Ser Asp Gly Pro Thr Gln Gln Leu Thr Trp Ser Arg Glu Ser
            740                 745                 750

Pro Leu Lys Pro Phe Leu Lys Leu Ser Leu Gly Leu Pro Gly Leu Gly
        755                 760                 765

Ile His Met Arg Pro Leu Ala Ile Trp Leu Phe Ile Phe Asn Val Ser
    770                 775                 780

Gln Gln Met Gly Gly Phe Tyr Leu Cys Gln Pro Gly Pro Pro Ser Glu
785                 790                 795                 800

Lys Ala Trp Gln Pro Gly Trp Thr Val Asn Val Glu Gly Ser Gly Glu
                805                 810                 815

Leu Phe Arg Trp Asn Val Ser Asp Leu Gly Gly Leu Gly Cys Gly Leu
            820                 825                 830

Lys Asn Arg Ser Ser Glu Gly Pro Ser Ser Pro Ser Gly Lys Leu Met
        835                 840                 845

Ser Pro Lys Leu Tyr Val Trp Ala Lys Asp Arg Pro Glu Ile Trp Glu
    850                 855                 860

Gly Glu Pro Pro Cys Val Pro Pro Arg Asp Ser Leu Asn Gln Ser Leu
865                 870                 875                 880

Ser Gln Asp Leu Thr Met Ala Pro Gly Ser Thr Leu Trp Leu Ser Cys
                885                 890                 895

Gly Val Pro Pro Asp Ser Val Ser Arg Gly Pro Leu Ser Trp Thr His
            900                 905                 910
```

```
Val His Pro Lys Gly Pro Lys Ser Leu Leu Ser Leu Glu Leu Lys Asp
        915                 920                 925

Asp Arg Pro Ala Arg Asp Met Trp Val Met Glu Thr Gly Leu Leu Leu
    930                 935                 940

Pro Arg Ala Thr Ala Gln Asp Ala Gly Lys Tyr Tyr Cys His Arg Gly
945                 950                 955                 960

Asn Leu Thr Met Ser Phe His Leu Glu Ile Thr Ala Arg Pro Val Leu
                965                 970                 975

Trp His Trp Leu Leu Arg Thr Gly Gly Trp Lys Val Ser Ala Val Thr
            980                 985                 990

Leu Ala Tyr Leu Ile Phe Cys Leu Cys Ser Leu Val Gly Ile Leu His
        995                 1000                1005

Leu Gln Arg Ala Leu Val Leu Arg Arg Lys Arg
    1010                1015


<210> SEQ ID NO 38
<211> LENGTH: 977
<212> TYPE: PRT
<213> ORGANISM: Artificial Sequence
<220> FEATURE:
<223> OTHER INFORMATION: Synthetic sequence

<400> SEQUENCE: 38

Met Leu Leu Leu Val Thr Ser Leu Leu Leu Cys Glu Leu Pro His Pro
1               5                   10                  15

Ala Phe Leu Leu Ile Pro Asp Ile Val Met Thr Gln Thr Pro Leu Ser
            20                  25                  30

Ser Pro Val Thr Leu Gly Gln Pro Ala Ser Ile Ser Cys Arg Ser Ser
        35                  40                  45

Gln Ser Leu Val Tyr Ser Asp Gly Asn Thr Tyr Leu Ser Trp Leu Gln
    50                  55                  60

Gln Arg Pro Gly Gln Pro Pro Arg Leu Leu Ile Tyr Lys Ile Ser Asn
65                  70                  75                  80

Arg Phe Ser Gly Val Pro Asp Arg Phe Ser Gly Ser Gly Ala Gly Thr
                85                  90                  95

Asp Phe Thr Leu Lys Ile Ser Arg Val Glu Ala Glu Asp Val Gly Val
            100                 105                 110

Tyr Tyr Cys Val Gln Ala Thr Gln Phe Pro Leu Thr Phe Gly Gly Gly
        115                 120                 125

Thr Lys Val Glu Ile Lys Gly Gly Gly Gly Ser Gly Gly Gly Gly Ser
    130                 135                 140

Gly Gly Gly Gly Ser Glu Val Gln Leu Val Gln Ser Gly Ala Glu Val
145                 150                 155                 160

Lys Lys Pro Gly Glu Ser Leu Lys Ile Ser Cys Lys Gly Ser Gly Tyr
                165                 170                 175

Ser Phe Thr Ser Tyr Trp Ile Gly Trp Val Arg Gln Met Pro Gly Lys
            180                 185                 190

Gly Leu Glu Trp Met Gly Ile Ile Tyr Pro Gly Asp Ser Asp Thr Arg
        195                 200                 205

Tyr Ser Pro Ser Phe Gln Gly Gln Val Thr Ile Ser Ala Asp Lys Ser
    210                 215                 220

Ile Thr Thr Ala Tyr Leu Gln Trp Ser Ser Leu Lys Ala Ser Asp Thr
225                 230                 235                 240

Ala Met Tyr Tyr Cys Ala Arg His Pro Ser Tyr Gly Ser Gly Ser Pro
                245                 250                 255
```

-continued

```
Asn Phe Asp Tyr Trp Gly Gln Gly Thr Leu Val Thr Val Ser Ser Asp
            260                 265                 270

Lys Thr His Thr Cys Pro Pro Cys Pro Ala Pro Pro Val Ala Gly Pro
        275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Gln Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
    450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Phe
                485                 490                 495

Trp Val Leu Val Val Val Gly Gly Val Leu Ala Cys Tyr Ser Leu Leu
            500                 505                 510

Val Thr Val Ala Phe Ile Ile Phe Trp Val Arg Val Lys Phe Ser Arg
        515                 520                 525

Ser Ala Asp Ala Pro Ala Tyr Gln Gln Gly Gln Asn Gln Leu Tyr Asn
    530                 535                 540

Glu Leu Asn Leu Gly Arg Arg Glu Glu Tyr Asp Val Leu Asp Lys Arg
545                 550                 555                 560

Arg Gly Arg Asp Pro Glu Met Gly Gly Lys Pro Arg Arg Lys Asn Pro
                565                 570                 575

Gln Glu Gly Leu Tyr Asn Glu Leu Gln Lys Asp Lys Met Ala Glu Ala
            580                 585                 590

Tyr Ser Glu Ile Gly Met Lys Gly Glu Arg Arg Arg Gly Lys Gly His
        595                 600                 605

Asp Gly Leu Tyr Gln Gly Leu Ser Thr Ala Thr Lys Asp Thr Tyr Asp
    610                 615                 620

Ala Leu His Met Gln Ala Leu Pro Pro Arg Gln Cys Thr Asn Tyr Ala
625                 630                 635                 640

Leu Leu Lys Leu Ala Gly Asp Val Glu Ser Asn Pro Gly Pro Met Pro
                645                 650                 655

Pro Pro Arg Leu Leu Phe Phe Leu Leu Phe Leu Thr Pro Met Glu Val
            660                 665                 670
```

-continued

```
Arg Pro Glu Glu Pro Leu Val Val Lys Val Glu Glu Gly Asp Asn Ala
        675                 680                 685

Val Leu Gln Cys Leu Lys Gly Thr Ser Asp Gly Pro Thr Gln Gln Leu
    690                 695                 700

Thr Trp Ser Arg Glu Ser Pro Leu Lys Pro Phe Leu Lys Leu Ser Leu
705                 710                 715                 720

Gly Leu Pro Gly Leu Gly Ile His Met Arg Pro Leu Ala Ile Trp Leu
                725                 730                 735

Phe Ile Phe Asn Val Ser Gln Gln Met Gly Gly Phe Tyr Leu Cys Gln
            740                 745                 750

Pro Gly Pro Pro Ser Glu Lys Ala Trp Gln Pro Gly Trp Thr Val Asn
        755                 760                 765

Val Glu Gly Ser Gly Glu Leu Phe Arg Trp Asn Val Ser Asp Leu Gly
    770                 775                 780

Gly Leu Gly Cys Gly Leu Lys Asn Arg Ser Ser Glu Gly Pro Ser Ser
785                 790                 795                 800

Pro Ser Gly Lys Leu Met Ser Pro Lys Leu Tyr Val Trp Ala Lys Asp
                805                 810                 815

Arg Pro Glu Ile Trp Glu Gly Glu Pro Pro Cys Val Pro Pro Arg Asp
            820                 825                 830

Ser Leu Asn Gln Ser Leu Ser Gln Asp Leu Thr Met Ala Pro Gly Ser
        835                 840                 845

Thr Leu Trp Leu Ser Cys Gly Val Pro Pro Asp Ser Val Ser Arg Gly
    850                 855                 860

Pro Leu Ser Trp Thr His Val His Pro Lys Gly Pro Lys Ser Leu Leu
865                 870                 875                 880

Ser Leu Glu Leu Lys Asp Asp Arg Pro Ala Arg Asp Met Trp Val Met
                885                 890                 895

Glu Thr Gly Leu Leu Leu Pro Arg Ala Thr Ala Gln Asp Ala Gly Lys
            900                 905                 910

Tyr Tyr Cys His Arg Gly Asn Leu Thr Met Ser Phe His Leu Glu Ile
        915                 920                 925

Thr Ala Arg Pro Val Leu Trp His Trp Leu Leu Arg Thr Gly Gly Trp
    930                 935                 940

Lys Val Ser Ala Val Thr Leu Ala Tyr Leu Ile Phe Cys Leu Cys Ser
945                 950                 955                 960

Leu Val Gly Ile Leu His Leu Gln Arg Ala Leu Val Leu Arg Arg Lys
                965                 970                 975

Arg


<210> SEQ ID NO 39
<211> LENGTH: 1101
<212> TYPE: PRT
<213> ORGANISM: Artificial Sequence
<220> FEATURE:
<223> OTHER INFORMATION: Synthetic sequence

<400> SEQUENCE: 39

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ile Leu Ser
            20                  25                  30

Ala Ser Pro Gly Glu Lys Val Thr Met Thr Cys Arg Ala Ser Ser Ser
        35                  40                  45
```

```
Val Asn Tyr Met Asp Trp Tyr Gln Lys Lys Pro Gly Ser Ser Pro Lys
    50                  55                  60

Pro Trp Ile Tyr Ala Thr Ser Asn Leu Ala Ser Gly Val Pro Ala Arg
65                  70                  75                  80

Phe Ser Gly Ser Gly Ser Gly Thr Ser Tyr Ser Leu Thr Ile Ser Arg
                85                  90                  95

Val Glu Ala Glu Asp Ala Ala Thr Tyr Tyr Cys Gln Gln Trp Ser Phe
            100                 105                 110

Asn Pro Pro Thr Phe Gly Gly Gly Thr Lys Leu Glu Ile Lys Gly Ser
        115                 120                 125

Thr Ser Gly Gly Gly Ser Gly Gly Gly Ser Gly Gly Gly Gly Ser Ser
    130                 135                 140

Glu Val Gln Leu Gln Gln Ser Gly Ala Glu Leu Val Lys Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Gly Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Ala Asp Lys Ser Ser Ser Thr Ala Tyr
    210                 215                 220

Met Gln Leu Ser Ser Leu Thr Ser Glu Asp Ser Ala Asp Tyr Tyr Cys
225                 230                 235                 240

Ala Arg Ser Asn Tyr Tyr Gly Ser Ser Tyr Trp Phe Phe Asp Val Trp
                245                 250                 255

Gly Ala Gly Thr Thr Val Thr Val Ser Ser Leu Asp Glu Ser Lys Tyr
            260                 265                 270

Gly Pro Pro Cys Pro Pro Cys Pro Ala Pro Glu Phe Leu Gly Gly Pro
        275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser Gln Glu Asp
305                 310                 315                 320

Pro Glu Val Gln Phe Asn Trp Tyr Val Asp Gly Val Glu Val His Asn
                325                 330                 335

Ala Lys Thr Lys Pro Arg Glu Glu Gln Phe Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Gly Leu Pro Ser Ser Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Gln Glu Glu Met Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Arg Leu Thr Val Asp Lys
    450                 455                 460
```

-continued

```
Ser Arg Trp Gln Glu Gly Asn Val Phe Ser Cys Ser Val Met His Glu
465                 470                 475                 480

Ala Leu His Asn His Tyr Thr Gln Lys Ser Leu Ser Leu Ser Leu Gly
                485                 490                 495

Lys Met Phe Trp Val Leu Val Val Val Gly Gly Val Leu Ala Cys Tyr
            500                 505                 510

Ser Leu Leu Val Thr Val Ala Phe Ile Ile Phe Trp Val Arg Ser Lys
        515                 520                 525

Arg Ser Arg Gly Gly His Ser Asp Tyr Met Asn Met Thr Pro Arg Arg
    530                 535                 540

Pro Gly Pro Thr Arg Lys His Tyr Gln Pro Tyr Ala Pro Pro Arg Asp
545                 550                 555                 560

Phe Ala Ala Tyr Arg Ser Lys Arg Gly Arg Lys Lys Leu Leu Tyr Ile
                565                 570                 575

Phe Lys Gln Pro Phe Met Arg Pro Val Gln Thr Thr Gln Glu Glu Asp
            580                 585                 590

Gly Cys Ser Cys Arg Phe Pro Glu Glu Glu Glu Gly Gly Cys Glu Leu
        595                 600                 605

Arg Val Lys Phe Ser Arg Ser Ala Asp Ala Pro Ala Tyr Gln Gln Gly
    610                 615                 620

Gln Asn Gln Leu Tyr Asn Glu Leu Asn Leu Gly Arg Arg Glu Glu Tyr
625                 630                 635                 640

Asp Val Leu Asp Lys Arg Arg Gly Arg Asp Pro Glu Met Gly Gly Lys
                645                 650                 655

Pro Arg Arg Lys Asn Pro Gln Glu Gly Leu Tyr Asn Glu Leu Gln Lys
            660                 665                 670

Asp Lys Met Ala Glu Ala Tyr Ser Glu Ile Gly Met Lys Gly Glu Arg
        675                 680                 685

Arg Arg Gly Lys Gly His Asp Gly Leu Tyr Gln Gly Leu Ser Thr Ala
    690                 695                 700

Thr Lys Asp Thr Tyr Asp Ala Leu His Met Gln Ala Leu Pro Pro Arg
705                 710                 715                 720

Leu Glu Gly Gly Gly Glu Gly Arg Gly Ser Leu Leu Thr Cys Gly Asp
                725                 730                 735

Val Glu Glu Asn Pro Gly Pro Arg Met Leu Leu Leu Val Thr Ser Leu
            740                 745                 750

Leu Leu Cys Glu Leu Pro His Pro Ala Phe Leu Leu Ile Pro Arg Lys
        755                 760                 765

Val Cys Asn Gly Ile Gly Ile Gly Glu Phe Lys Asp Ser Leu Ser Ile
    770                 775                 780

Asn Ala Thr Asn Ile Lys His Phe Lys Asn Cys Thr Ser Ile Ser Gly
785                 790                 795                 800

Asp Leu His Ile Leu Pro Val Ala Phe Arg Gly Asp Ser Phe Thr His
                805                 810                 815

Thr Pro Pro Leu Asp Pro Gln Glu Leu Asp Ile Leu Lys Thr Val Lys
            820                 825                 830

Glu Ile Thr Gly Phe Leu Leu Ile Gln Ala Trp Pro Glu Asn Arg Thr
        835                 840                 845

Asp Leu His Ala Phe Glu Asn Leu Glu Ile Ile Arg Gly Arg Thr Lys
    850                 855                 860

Gln His Gly Gln Phe Ser Leu Ala Val Val Ser Leu Asn Ile Thr Ser
865                 870                 875                 880
```

```
Leu Gly Leu Arg Ser Leu Lys Glu Ile Ser Asp Gly Asp Val Ile Ile
                885                 890                 895

Ser Gly Asn Lys Asn Leu Cys Tyr Ala Asn Thr Ile Asn Trp Lys Lys
            900                 905                 910

Leu Phe Gly Thr Ser Gly Gln Lys Thr Lys Ile Ile Ser Asn Arg Gly
        915                 920                 925

Glu Asn Ser Cys Lys Ala Thr Gly Gln Val Cys His Ala Leu Cys Ser
    930                 935                 940

Pro Glu Gly Cys Trp Gly Pro Glu Pro Arg Asp Cys Val Ser Cys Arg
945                 950                 955                 960

Asn Val Ser Arg Gly Arg Glu Cys Val Asp Lys Cys Asn Leu Leu Glu
                965                 970                 975

Gly Glu Pro Arg Glu Phe Val Glu Asn Ser Glu Cys Ile Gln Cys His
            980                 985                 990

Pro Glu Cys Leu Pro Gln Ala Met Asn Ile Thr Cys Thr Gly Arg Gly
        995                 1000                1005

Pro Asp Asn Cys Ile Gln Cys Ala His Tyr Ile Asp Gly Pro His Cys
    1010                1015                1020

Val Lys Thr Cys Pro Ala Gly Val Met Gly Glu Asn Asn Thr Leu Val
1025                1030                1035                1040

Trp Lys Tyr Ala Asp Ala Gly His Val Cys His Leu Cys His Pro Asn
                1045                1050                1055

Cys Thr Tyr Gly Cys Thr Gly Pro Gly Leu Glu Gly Cys Pro Thr Asn
            1060                1065                1070

Gly Pro Lys Ile Pro Ser Ile Ala Thr Gly Met Val Gly Ala Leu Leu
        1075                1080                1085

Leu Leu Leu Val Val Ala Leu Gly Ile Gly Leu Phe Met
    1090                1095                1100


<210> SEQ ID NO 40
<211> LENGTH: 678
<212> TYPE: PRT
<213> ORGANISM: Artificial Sequence
<220> FEATURE:
<223> OTHER INFORMATION: Synthetic sequence

<400> SEQUENCE: 40

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ile Leu Ser
            20                  25                  30

Ala Ser Pro Gly Glu Lys Val Thr Met Thr Cys Arg Ala Ser Ser Ser
        35                  40                  45

Val Asn Tyr Met Asp Trp Tyr Gln Lys Lys Pro Gly Ser Ser Pro Lys
    50                  55                  60

Pro Trp Ile Tyr Ala Thr Ser Asn Leu Ala Ser Gly Val Pro Ala Arg
65                  70                  75                  80

Phe Ser Gly Ser Gly Ser Gly Thr Ser Tyr Ser Leu Thr Ile Ser Arg
                85                  90                  95

Val Glu Ala Glu Asp Ala Ala Thr Tyr Tyr Cys Gln Gln Trp Ser Phe
            100                 105                 110

Asn Pro Pro Thr Phe Gly Gly Gly Thr Lys Leu Glu Ile Lys Gly Ser
        115                 120                 125

Thr Ser Gly Gly Gly Ser Gly Gly Gly Ser Gly Gly Gly Gly Ser Ser
    130                 135                 140
```

-continued

```
Glu Val Gln Leu Gln Gln Ser Gly Ala Glu Leu Val Lys Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Gly Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Ala Asp Lys Ser Ser Ser Thr Ala Tyr
    210                 215                 220

Met Gln Leu Ser Ser Leu Thr Ser Glu Asp Ser Ala Asp Tyr Tyr Cys
225                 230                 235                 240

Ala Arg Ser Asn Tyr Tyr Gly Ser Ser Tyr Trp Phe Phe Asp Val Trp
                245                 250                 255

Gly Ala Gly Thr Thr Val Thr Val Ser Ser Leu Asp Glu Ser Lys Tyr
            260                 265                 270

Gly Pro Pro Cys Pro Pro Cys Pro Ala Pro Glu Phe Leu Gly Gly Pro
        275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser Gln Glu Asp
305                 310                 315                 320

Pro Glu Val Gln Phe Asn Trp Tyr Val Asp Gly Val Glu Val His Asn
                325                 330                 335

Ala Lys Thr Lys Pro Arg Glu Glu Gln Phe Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Gly Leu Pro Ser Ser Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Gln Glu Glu Met Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Arg Leu Thr Val Asp Lys
    450                 455                 460

Ser Arg Trp Gln Glu Gly Asn Val Phe Ser Cys Ser Val Met His Glu
465                 470                 475                 480

Ala Leu His Asn His Tyr Thr Gln Lys Ser Leu Ser Leu Ser Leu Gly
                485                 490                 495

Lys Met Phe Trp Val Leu Val Val Val Gly Gly Val Leu Ala Cys Tyr
            500                 505                 510

Ser Leu Leu Val Thr Val Ala Phe Ile Ile Phe Trp Val Arg Ser Lys
        515                 520                 525

Arg Ser Arg Gly Gly His Ser Asp Tyr Met Asn Met Thr Pro Arg Arg
    530                 535                 540

Pro Gly Pro Thr Arg Lys His Tyr Gln Pro Tyr Ala Pro Pro Arg Asp
545                 550                 555                 560
```

```
Phe Ala Ala Tyr Arg Ser Arg Val Lys Phe Ser Arg Ser Ala Asp Ala
                565                 570                 575

Pro Ala Tyr Gln Gln Gly Gln Asn Gln Leu Tyr Asn Glu Leu Asn Leu
            580                 585                 590

Gly Arg Arg Glu Glu Tyr Asp Val Leu Asp Lys Arg Arg Gly Arg Asp
        595                 600                 605

Pro Glu Met Gly Gly Lys Pro Arg Arg Lys Asn Pro Gln Glu Gly Leu
    610                 615                 620

Tyr Asn Glu Leu Gln Lys Asp Lys Met Ala Glu Ala Tyr Ser Glu Ile
625                 630                 635                 640

Gly Met Lys Gly Glu Arg Arg Arg Gly Lys Gly His Asp Gly Leu Tyr
                645                 650                 655

Gln Gly Leu Ser Thr Ala Thr Lys Asp Thr Tyr Asp Ala Leu His Met
            660                 665                 670

Gln Ala Leu Pro Pro Arg
        675


<210> SEQ ID NO 41
<211> LENGTH: 1061
<212> TYPE: PRT
<213> ORGANISM: Artificial Sequence
<220> FEATURE:
<223> OTHER INFORMATION: Synthetic sequence

<400> SEQUENCE: 41

Met Glu Thr Asp Thr Leu Leu Leu Trp Val Leu Leu Leu Trp Val Pro
1               5                   10                  15

Gly Ser Thr Gly Asp Ile Val Leu Ser Gln Ser Pro Ala Ile Leu Ser
            20                  25                  30

Ala Ser Pro Gly Glu Lys Val Thr Met Thr Cys Arg Ala Ser Ser Ser
        35                  40                  45

Leu Ser Phe Met His Trp Tyr Gln Gln Lys Pro Gly Ser Ser Pro Lys
    50                  55                  60

Pro Trp Ile Tyr Ala Thr Ser Asn Leu Ala Ser Gly Val Pro Ala Arg
65                  70                  75                  80

Phe Ser Gly Ser Gly Ser Gly Thr Ser Tyr Ser Leu Thr Ile Ser Arg
                85                  90                  95

Val Glu Ala Glu Asp Ala Ala Thr Tyr Phe Cys His Gln Trp Ser Ser
            100                 105                 110

Asn Pro Leu Thr Phe Gly Ala Gly Thr Lys Leu Glu Leu Lys Gly Ser
        115                 120                 125

Thr Ser Gly Gly Gly Ser Gly Gly Gly Ser Gly Gly Gly Gly Ser Ser
    130                 135                 140

Gln Val Gln Leu Arg Gln Pro Gly Ala Glu Leu Val Lys Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Gly Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Ala Asp Lys Ser Ser Ser Thr Ala Tyr
    210                 215                 220

Met Gln Leu Ser Ser Leu Thr Ser Glu Asp Ser Ala Val Tyr Tyr Cys
225                 230                 235                 240
```

-continued

```
Ala Arg Ser His Tyr Gly Ser Asn Tyr Val Asp Tyr Phe Asp Tyr Trp
                245                 250                 255

Gly Gln Gly Thr Thr Leu Thr Val Ser Ser Leu Asp Pro Lys Ser Ser
            260                 265                 270

Asp Lys Thr His Thr Cys Pro Pro Cys Pro Ala Pro Pro Val Ala Gly
        275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

Asn Ala Lys Thr Lys Pro Arg Glu Glu Gln Tyr Gln Ser Thr Tyr Arg
            340                 345                 350

Val Val Ser Val Leu Thr Val Leu His Gln Asp Trp Leu Asn Gly Lys
        355                 360                 365

Glu Tyr Lys Cys Lys Val Ser Asn Lys Ala Leu Pro Ala Pro Ile Glu
    370                 375                 380

Lys Thr Ile Ser Lys Ala Lys Gly Gln Pro Arg Glu Pro Gln Val Tyr
385                 390                 395                 400

Thr Leu Pro Pro Ser Arg Asp Glu Leu Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
        435                 440                 445

Leu Asp Ser Asp Gly Ser Phe Phe Leu Tyr Ser Lys Leu Thr Val Asp
    450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Phe Trp Val Leu Val Val Val Gly Gly Val Leu Ala Cys Tyr Ser Leu
            500                 505                 510

Leu Val Thr Val Ala Phe Ile Ile Phe Trp Val Arg Ser Lys Arg Ser
        515                 520                 525

Arg Gly Gly His Ser Asp Tyr Met Asn Met Thr Pro Arg Arg Pro Gly
    530                 535                 540

Pro Thr Arg Lys His Tyr Gln Pro Tyr Ala Pro Pro Arg Asp Phe Ala
545                 550                 555                 560

Ala Tyr Arg Ser Lys Arg Gly Arg Lys Lys Leu Leu Tyr Ile Phe Lys
                565                 570                 575

Gln Pro Phe Met Arg Pro Val Gln Thr Thr Gln Glu Glu Asp Gly Cys
            580                 585                 590

Ser Cys Arg Phe Pro Glu Glu Glu Glu Gly Gly Cys Glu Leu Arg Val
        595                 600                 605

Lys Phe Ser Arg Ser Ala Asp Ala Pro Ala Tyr Gln Gln Gly Gln Asn
    610                 615                 620

Gln Leu Tyr Asn Glu Leu Asn Leu Gly Arg Arg Glu Glu Tyr Asp Val
625                 630                 635                 640

Leu Asp Lys Arg Arg Gly Arg Asp Pro Glu Met Gly Gly Lys Pro Arg
                645                 650                 655
```

-continued

```
Arg Lys Asn Pro Gln Glu Gly Leu Tyr Asn Glu Leu Gln Lys Asp Lys
            660                 665                 670

Met Ala Glu Ala Tyr Ser Glu Ile Gly Met Lys Gly Glu Arg Arg Arg
        675                 680                 685

Gly Lys Gly His Asp Gly Leu Tyr Gln Gly Leu Ser Thr Ala Thr Lys
    690                 695                 700

Asp Thr Tyr Asp Ala Leu His Met Gln Ala Leu Pro Pro Arg Gln Cys
705                 710                 715                 720

Thr Asn Tyr Ala Leu Leu Lys Leu Ala Gly Asp Val Glu Ser Asn Pro
                725                 730                 735

Gly Pro Met Pro Pro Pro Arg Leu Leu Phe Phe Leu Leu Phe Leu Thr
            740                 745                 750

Pro Met Glu Val Arg Pro Glu Glu Pro Leu Val Val Lys Val Glu Glu
        755                 760                 765

Gly Asp Asn Ala Val Leu Gln Cys Leu Lys Gly Thr Ser Asp Gly Pro
    770                 775                 780

Thr Gln Gln Leu Thr Trp Ser Arg Glu Ser Pro Leu Lys Pro Phe Leu
785                 790                 795                 800

Lys Leu Ser Leu Gly Leu Pro Gly Leu Gly Ile His Met Arg Pro Leu
                805                 810                 815

Ala Ile Trp Leu Phe Ile Phe Asn Val Ser Gln Gln Met Gly Gly Phe
            820                 825                 830

Tyr Leu Cys Gln Pro Gly Pro Pro Ser Glu Lys Ala Trp Gln Pro Gly
        835                 840                 845

Trp Thr Val Asn Val Glu Gly Ser Gly Glu Leu Phe Arg Trp Asn Val
    850                 855                 860

Ser Asp Leu Gly Gly Leu Gly Cys Gly Leu Lys Asn Arg Ser Ser Glu
865                 870                 875                 880

Gly Pro Ser Ser Pro Ser Gly Lys Leu Met Ser Pro Lys Leu Tyr Val
                885                 890                 895

Trp Ala Lys Asp Arg Pro Glu Ile Trp Glu Gly Glu Pro Pro Cys Val
            900                 905                 910

Pro Pro Arg Asp Ser Leu Asn Gln Ser Leu Ser Gln Asp Leu Thr Met
        915                 920                 925

Ala Pro Gly Ser Thr Leu Trp Leu Ser Cys Gly Val Pro Pro Asp Ser
    930                 935                 940

Val Ser Arg Gly Pro Leu Ser Trp Thr His Val His Pro Lys Gly Pro
945                 950                 955                 960

Lys Ser Leu Leu Ser Leu Glu Leu Lys Asp Asp Arg Pro Ala Arg Asp
                965                 970                 975

Met Trp Val Met Glu Thr Gly Leu Leu Leu Pro Arg Ala Thr Ala Gln
            980                 985                 990

Asp Ala Gly Lys Tyr Tyr Cys His Arg Gly Asn Leu Thr Met Ser Phe
        995                 1000                1005

His Leu Glu Ile Thr Ala Arg Pro Val Leu Trp His Trp Leu Leu Arg
    1010                1015                1020

Thr Gly Gly Trp Lys Val Ser Ala Val Thr Leu Ala Tyr Leu Ile Phe
1025                1030                1035                1040

Cys Leu Cys Ser Leu Val Gly Ile Leu His Leu Gln Arg Ala Leu Val
                1045                1050                1055

Leu Arg Arg Lys Arg
            1060
```

<210> SEQ ID NO 42
<211> LENGTH: 1019
<212> TYPE: PRT
<213> ORGANISM: Artificial Sequence
<220> FEATURE:
<223> OTHER INFORMATION: Synthetic sequence

<400> SEQUENCE: 42

```
Met Glu Thr Asp Thr Leu Leu Leu Trp Val Leu Leu Leu Trp Val Pro
1               5                   10                  15

Gly Ser Thr Gly Asp Ile Val Leu Ser Gln Ser Pro Ala Ile Leu Ser
            20                  25                  30

Ala Ser Pro Gly Glu Lys Val Thr Met Thr Cys Arg Ala Ser Ser Ser
        35                  40                  45

Leu Ser Phe Met His Trp Tyr Gln Gln Lys Pro Gly Ser Ser Pro Lys
    50                  55                  60

Pro Trp Ile Tyr Ala Thr Ser Asn Leu Ala Ser Gly Val Pro Ala Arg
65                  70                  75                  80

Phe Ser Gly Ser Gly Ser Gly Thr Ser Tyr Ser Leu Thr Ile Ser Arg
                85                  90                  95

Val Glu Ala Glu Asp Ala Ala Thr Tyr Phe Cys His Gln Trp Ser Ser
            100                 105                 110

Asn Pro Leu Thr Phe Gly Ala Gly Thr Lys Leu Glu Leu Lys Gly Ser
        115                 120                 125

Thr Ser Gly Gly Gly Ser Gly Gly Gly Ser Gly Gly Gly Gly Ser Ser
    130                 135                 140

Gln Val Gln Leu Arg Gln Pro Gly Ala Glu Leu Val Lys Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Gly Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Ala Asp Lys Ser Ser Ser Thr Ala Tyr
    210                 215                 220

Met Gln Leu Ser Ser Leu Thr Ser Glu Asp Ser Ala Val Tyr Tyr Cys
225                 230                 235                 240

Ala Arg Ser His Tyr Gly Ser Asn Tyr Val Asp Tyr Phe Asp Tyr Trp
                245                 250                 255

Gly Gln Gly Thr Thr Leu Thr Val Ser Ser Leu Asp Pro Lys Ser Ser
            260                 265                 270

Asp Lys Thr His Thr Cys Pro Pro Cys Pro Ala Pro Pro Val Ala Gly
        275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

Asn Ala Lys Thr Lys Pro Arg Glu Glu Gln Tyr Gln Ser Thr Tyr Arg
            340                 345                 350

Val Val Ser Val Leu Thr Val Leu His Gln Asp Trp Leu Asn Gly Lys
        355                 360                 365
```

-continued

```
Glu Tyr Lys Cys Lys Val Ser Asn Lys Ala Leu Pro Ala Pro Ile Glu
    370                 375                 380

Lys Thr Ile Ser Lys Ala Lys Gly Gln Pro Arg Glu Pro Gln Val Tyr
385                 390                 395                 400

Thr Leu Pro Pro Ser Arg Asp Glu Leu Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
        435                 440                 445

Leu Asp Ser Asp Gly Ser Phe Phe Leu Tyr Ser Lys Leu Thr Val Asp
    450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Phe Trp Val Leu Val Val Val Gly Gly Val Leu Ala Cys Tyr Ser Leu
            500                 505                 510

Leu Val Thr Val Ala Phe Ile Ile Phe Trp Val Arg Ser Lys Arg Ser
        515                 520                 525

Arg Gly Gly His Ser Asp Tyr Met Asn Met Thr Pro Arg Arg Pro Gly
    530                 535                 540

Pro Thr Arg Lys His Tyr Gln Pro Tyr Ala Pro Pro Arg Asp Phe Ala
545                 550                 555                 560

Ala Tyr Arg Ser Arg Val Lys Phe Ser Arg Ser Ala Asp Ala Pro Ala
                565                 570                 575

Tyr Gln Gln Gly Gln Asn Gln Leu Tyr Asn Glu Leu Asn Leu Gly Arg
            580                 585                 590

Arg Glu Glu Tyr Asp Val Leu Asp Lys Arg Arg Gly Arg Asp Pro Glu
        595                 600                 605

Met Gly Gly Lys Pro Arg Arg Lys Asn Pro Gln Glu Gly Leu Tyr Asn
    610                 615                 620

Glu Leu Gln Lys Asp Lys Met Ala Glu Ala Tyr Ser Glu Ile Gly Met
625                 630                 635                 640

Lys Gly Glu Arg Arg Arg Gly Lys Gly His Asp Gly Leu Tyr Gln Gly
                645                 650                 655

Leu Ser Thr Ala Thr Lys Asp Thr Tyr Asp Ala Leu His Met Gln Ala
            660                 665                 670

Leu Pro Pro Arg Gln Cys Thr Asn Tyr Ala Leu Leu Lys Leu Ala Gly
        675                 680                 685

Asp Val Glu Ser Asn Pro Gly Pro Met Pro Pro Pro Arg Leu Leu Phe
    690                 695                 700

Phe Leu Leu Phe Leu Thr Pro Met Glu Val Arg Pro Glu Glu Pro Leu
705                 710                 715                 720

Val Val Lys Val Glu Glu Gly Asp Asn Ala Val Leu Gln Cys Leu Lys
                725                 730                 735

Gly Thr Ser Asp Gly Pro Thr Gln Gln Leu Thr Trp Ser Arg Glu Ser
            740                 745                 750

Pro Leu Lys Pro Phe Leu Lys Leu Ser Leu Gly Leu Pro Gly Leu Gly
        755                 760                 765

Ile His Met Arg Pro Leu Ala Ile Trp Leu Phe Ile Phe Asn Val Ser
    770                 775                 780
```

```
Gln Gln Met Gly Gly Phe Tyr Leu Cys Gln Pro Gly Pro Pro Ser Glu
785                 790                 795                 800

Lys Ala Trp Gln Pro Gly Trp Thr Val Asn Val Glu Gly Ser Gly Glu
                805                 810                 815

Leu Phe Arg Trp Asn Val Ser Asp Leu Gly Gly Leu Gly Cys Gly Leu
            820                 825                 830

Lys Asn Arg Ser Ser Glu Gly Pro Ser Ser Pro Ser Gly Lys Leu Met
        835                 840                 845

Ser Pro Lys Leu Tyr Val Trp Ala Lys Asp Arg Pro Glu Ile Trp Glu
    850                 855                 860

Gly Glu Pro Pro Cys Val Pro Pro Arg Asp Ser Leu Asn Gln Ser Leu
865                 870                 875                 880

Ser Gln Asp Leu Thr Met Ala Pro Gly Ser Thr Leu Trp Leu Ser Cys
                885                 890                 895

Gly Val Pro Pro Asp Ser Val Ser Arg Gly Pro Leu Ser Trp Thr His
            900                 905                 910

Val His Pro Lys Gly Pro Lys Ser Leu Leu Ser Leu Glu Leu Lys Asp
        915                 920                 925

Asp Arg Pro Ala Arg Asp Met Trp Val Met Glu Thr Gly Leu Leu Leu
    930                 935                 940

Pro Arg Ala Thr Ala Gln Asp Ala Gly Lys Tyr Tyr Cys His Arg Gly
945                 950                 955                 960

Asn Leu Thr Met Ser Phe His Leu Glu Ile Thr Ala Arg Pro Val Leu
                965                 970                 975

Trp His Trp Leu Leu Arg Thr Gly Gly Trp Lys Val Ser Ala Val Thr
            980                 985                 990

Leu Ala Tyr Leu Ile Phe Cys Leu Cys Ser Leu Val Gly Ile Leu His
        995                 1000                1005

Leu Gln Arg Ala Leu Val Leu Arg Arg Lys Arg
    1010                1015


<210> SEQ ID NO 43
<211> LENGTH: 1020
<212> TYPE: PRT
<213> ORGANISM: Artificial Sequence
<220> FEATURE:
<223> OTHER INFORMATION: Synthetic sequence

<400> SEQUENCE: 43

Met Glu Thr Asp Thr Leu Leu Leu Trp Val Leu Leu Leu Trp Val Pro
1               5                   10                  15

Gly Ser Thr Gly Asp Ile Val Leu Ser Gln Ser Pro Ala Ile Leu Ser
            20                  25                  30

Ala Ser Pro Gly Glu Lys Val Thr Met Thr Cys Arg Ala Ser Ser Ser
        35                  40                  45

Leu Ser Phe Met His Trp Tyr Gln Gln Lys Pro Gly Ser Ser Pro Lys
    50                  55                  60

Pro Trp Ile Tyr Ala Thr Ser Asn Leu Ala Ser Gly Val Pro Ala Arg
65                  70                  75                  80

Phe Ser Gly Ser Gly Ser Gly Thr Ser Tyr Ser Leu Thr Ile Ser Arg
                85                  90                  95

Val Glu Ala Glu Asp Ala Ala Thr Tyr Phe Cys His Gln Trp Ser Ser
            100                 105                 110

Asn Pro Leu Thr Phe Gly Ala Gly Thr Lys Leu Glu Leu Lys Gly Ser
        115                 120                 125
```

-continued

```
Thr Ser Gly Gly Gly Ser Gly Gly Gly Ser Gly Gly Gly Gly Ser Ser
    130                 135                 140

Gln Val Gln Leu Arg Gln Pro Gly Ala Glu Leu Val Lys Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Gly Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Ala Asp Lys Ser Ser Ser Thr Ala Tyr
    210                 215                 220

Met Gln Leu Ser Ser Leu Thr Ser Glu Asp Ser Ala Val Tyr Tyr Cys
225                 230                 235                 240

Ala Arg Ser His Tyr Gly Ser Asn Tyr Val Asp Tyr Phe Asp Tyr Trp
                245                 250                 255

Gly Gln Gly Thr Thr Leu Thr Val Ser Ser Leu Asp Pro Lys Ser Ser
            260                 265                 270

Asp Lys Thr His Thr Cys Pro Pro Cys Pro Ala Pro Pro Val Ala Gly
        275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

Asn Ala Lys Thr Lys Pro Arg Glu Glu Gln Tyr Gln Ser Thr Tyr Arg
            340                 345                 350

Val Val Ser Val Leu Thr Val Leu His Gln Asp Trp Leu Asn Gly Lys
        355                 360                 365

Glu Tyr Lys Cys Lys Val Ser Asn Lys Ala Leu Pro Ala Pro Ile Glu
    370                 375                 380

Lys Thr Ile Ser Lys Ala Lys Gly Gln Pro Arg Glu Pro Gln Val Tyr
385                 390                 395                 400

Thr Leu Pro Pro Ser Arg Asp Glu Leu Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
        435                 440                 445

Leu Asp Ser Asp Gly Ser Phe Phe Leu Tyr Ser Lys Leu Thr Val Asp
    450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Phe Trp Val Leu Val Val Val Gly Gly Val Leu Ala Cys Tyr Ser Leu
            500                 505                 510

Leu Val Thr Val Ala Phe Ile Ile Phe Trp Val Lys Arg Gly Arg Lys
        515                 520                 525

Lys Leu Leu Tyr Ile Phe Lys Gln Pro Phe Met Arg Pro Val Gln Thr
    530                 535                 540
```

-continued

```
Thr Gln Glu Glu Asp Gly Cys Ser Cys Arg Phe Pro Glu Glu Glu Glu
545                 550                 555                 560

Gly Gly Cys Glu Leu Arg Val Lys Phe Ser Arg Ser Ala Asp Ala Pro
                565                 570                 575

Ala Tyr Gln Gln Gly Gln Asn Gln Leu Tyr Asn Glu Leu Asn Leu Gly
            580                 585                 590

Arg Arg Glu Glu Tyr Asp Val Leu Asp Lys Arg Arg Gly Arg Asp Pro
        595                 600                 605

Glu Met Gly Gly Lys Pro Arg Arg Lys Asn Pro Gln Glu Gly Leu Tyr
    610                 615                 620

Asn Glu Leu Gln Lys Asp Lys Met Ala Glu Ala Tyr Ser Glu Ile Gly
625                 630                 635                 640

Met Lys Gly Glu Arg Arg Arg Gly Lys Gly His Asp Gly Leu Tyr Gln
                645                 650                 655

Gly Leu Ser Thr Ala Thr Lys Asp Thr Tyr Asp Ala Leu His Met Gln
            660                 665                 670

Ala Leu Pro Pro Arg Gln Cys Thr Asn Tyr Ala Leu Leu Lys Leu Ala
        675                 680                 685

Gly Asp Val Glu Ser Asn Pro Gly Pro Met Pro Pro Pro Arg Leu Leu
    690                 695                 700

Phe Phe Leu Leu Phe Leu Thr Pro Met Glu Val Arg Pro Glu Glu Pro
705                 710                 715                 720

Leu Val Val Lys Val Glu Glu Gly Asp Asn Ala Val Leu Gln Cys Leu
                725                 730                 735

Lys Gly Thr Ser Asp Gly Pro Thr Gln Gln Leu Thr Trp Ser Arg Glu
            740                 745                 750

Ser Pro Leu Lys Pro Phe Leu Lys Leu Ser Leu Gly Leu Pro Gly Leu
        755                 760                 765

Gly Ile His Met Arg Pro Leu Ala Ile Trp Leu Phe Ile Phe Asn Val
    770                 775                 780

Ser Gln Gln Met Gly Gly Phe Tyr Leu Cys Gln Pro Gly Pro Pro Ser
785                 790                 795                 800

Glu Lys Ala Trp Gln Pro Gly Trp Thr Val Asn Val Glu Gly Ser Gly
                805                 810                 815

Glu Leu Phe Arg Trp Asn Val Ser Asp Leu Gly Gly Leu Gly Cys Gly
            820                 825                 830

Leu Lys Asn Arg Ser Ser Glu Gly Pro Ser Ser Pro Ser Gly Lys Leu
        835                 840                 845

Met Ser Pro Lys Leu Tyr Val Trp Ala Lys Asp Arg Pro Glu Ile Trp
    850                 855                 860

Glu Gly Glu Pro Pro Cys Val Pro Pro Arg Asp Ser Leu Asn Gln Ser
865                 870                 875                 880

Leu Ser Gln Asp Leu Thr Met Ala Pro Gly Ser Thr Leu Trp Leu Ser
                885                 890                 895

Cys Gly Val Pro Pro Asp Ser Val Ser Arg Gly Pro Leu Ser Trp Thr
            900                 905                 910

His Val His Pro Lys Gly Pro Lys Ser Leu Leu Ser Leu Glu Leu Lys
        915                 920                 925

Asp Asp Arg Pro Ala Arg Asp Met Trp Val Met Glu Thr Gly Leu Leu
    930                 935                 940

Leu Pro Arg Ala Thr Ala Gln Asp Ala Gly Lys Tyr Tyr Cys His Arg
945                 950                 955                 960
```

```
Gly Asn Leu Thr Met Ser Phe His Leu Glu Ile Thr Ala Arg Pro Val
                965                 970                 975

Leu Trp His Trp Leu Leu Arg Thr Gly Gly Trp Lys Val Ser Ala Val
            980                 985                 990

Thr Leu Ala Tyr Leu Ile Phe Cys Leu Cys Ser Leu Val Gly Ile Leu
        995                 1000                1005

His Leu Gln Arg Ala Leu Val Leu Arg Arg Lys Arg
    1010                1015                1020
```

```
<210> SEQ ID NO 44
<211> LENGTH: 2085
<212> TYPE: DNA
<213> ORGANISM: Artificial Sequence
<220> FEATURE:
<223> OTHER INFORMATION: Synthetic sequence

<400> SEQUENCE: 44

gacattgtga tgactcagac accactgagc tccccagtga ctctgggaca gccagccagt     60

atctcatgca gatctagtca gtcactggtc tacagcgacg gcaacaccta tctgagctgg    120

ctgcagcagc gaccaggaca gccacctaga ctgctgatct acaagatttc caataggttc    180

tctggagtgc ccgaccgctt tagcggatcc ggagctggaa ctgatttcac cctgaaaatc    240

tcccgcgtgg aggctgaaga tgtgggcgtc tactattgcg tccaggcaac ccagttccct    300

ctgacatttg gcgggggaac taaggtggag atcaagggag gaggaggatc tggaggagga    360

ggaagtggag gaggaggatc cgaagtgcag ctggtccagt ctggggccga ggtgaagaaa    420

cctggagaaa gtctgaagat ctcatgtaaa ggctccgggt actctttcac aagttattgg    480

attggctggg tccgacagat gccaggaaag ggcctggagt ggatgggaat catctacccc    540

ggcgacagcg atacccggta ttctcctagt tttcagggcc aggtgacaat cagcgcagac    600

aagtccatta ccacagccta tctgcagtgg tcaagcctga aagcctctga taccgctatg    660

tactattgtg ccaggcaccc tagctacggg tcaggaagcc caaactttga ctattggggc    720

caggggacac tggtgactgt ctcctctgac aaaactcaca catgcccacc gtgcccagca    780

cctcctgtgg caggaccgtc agtcttcctc ttccccccaa aacccaagga caccctcatg    840

atctcccgga cccctgaggt cacatgcgtg gtggtggacg tgagccacga agaccctgag    900

gtcaagttca actggtacgt ggacggcgtg gaggtgcata atgccaagac aaagccgcgg    960

gaggagcagt accagagcac gtaccgtgtg gtcagcgtcc tcaccgtcct gcaccaggac   1020

tggctgaatg gcaaggagta caagtgcaag gtctccaaca aagccctccc agcccccatc   1080

gagaaaacca tctccaaagc caaagggcag ccccgagaac cacaggtgta caccctgcca   1140

ccatcacgag atgagctgac caagaaccag gtcagcctga cctgcctggt caaaggcttc   1200

tatcccagcg acatcgccgt ggagtgggag agcaatgggc agccggagaa caactacaag   1260

accacgcctc ccgtgctgga ctccgacggc tccttcttcc tctacagcaa gctcaccgtg   1320

gacaagagca ggtggcagca ggggaacgtc ttctcatgct ccgtgatgca tgaggctctg   1380

cacaaccact acacgcagaa gagcctctcc ctgtctccct tttgggtgct ggtggtggtt   1440

ggtggagtcc tggcttgcta tagcttgcta gtaacagtgg cctttattat tttctgggtg   1500

aggagtaaga ggagcagggg aggtcacagt gactacatga acatgactcc ccgccgcccc   1560

gggcccaccc gcaagcatta ccagccctat gccccaccac gcgacttcgc agcctatcgc   1620

tccaaacggg gcagaaagaa actcctgtat atattcaaac aaccatttat gagaccagta   1680
```

-continued

```
caaactactc aagaggaaga tggctgtagc tgccgatttc cagaagaaga agaaggagga   1740

tgtgaactga gagtgaagtt cagcaggagc gcagacgccc ccgcgtacca gcagggccag   1800

aaccagctct ataacgagct caatctagga cgaagagagg agtacgatgt tttggacaag   1860

agacgtggcc gggaccctga gatgggggga aagccgagaa ggaagaaccc tcaggaaggc   1920

ctgtacaatg aactgcagaa agataagatg gcggaggcct acagtgagat tgggatgaaa   1980

ggcgagcgcc ggaggggcaa ggggcacgat ggcctttacc agggtctcag tacagccacc   2040

aaggacacct acgacgccct tcacatgcag gccctgcccc ctcgc                   2085
```

<210> SEQ ID NO 45
<211> LENGTH: 1959
<212> TYPE: DNA
<213> ORGANISM: Artificial Sequence
<220> FEATURE:
<223> OTHER INFORMATION: Synthetic sequence

<400> SEQUENCE: 45

```
gacattgtga tgactcagac accactgagc tccccagtga ctctgggaca gccagccagt     60

atctcatgca gatctagtca gtcactggtc tacagcgacg gcaacaccta tctgagctgg    120

ctgcagcagc gaccaggaca gccacctaga ctgctgatct acaagatttc caataggttc    180

tctggagtgc ccgaccgctt tagcggatcc ggagctggaa ctgatttcac cctgaaaatc    240

tcccgcgtgg aggctgaaga tgtgggcgtc tactattgcg tccaggcaac ccagttccct    300

ctgacatttg gcgggggaac taaggtggag atcaagggag gaggaggatc tggaggagga    360

ggaagtggag gaggaggatc cgaagtgcag ctggtccagt ctggggccga ggtgaagaaa    420

cctggagaaa gtctgaagat ctcatgtaaa ggctccgggt actctttcac aagttattgg    480

attggctggg tccgacagat gccaggaaag ggcctggagt ggatgggaat catctacccc    540

ggcgacagcg atacccggta ttctcctagt tttcagggcc aggtgacaat cagcgcagac    600

aagtccatta ccacagccta tctgcagtgg tcaagcctga aagcctctga taccgctatg    660

tactattgtg ccaggcaccc tagctacggg tcaggaagcc caaactttga ctattggggc    720

caggggacac tggtgactgt ctcctctgac aaaactcaca catgcccacc gtgcccagca    780

cctcctgtgg caggaccgtc agtcttcctc ttccccccaa aacccaagga caccctcatg    840

atctcccgga cccctgaggt cacatgcgtg gtggtggacg tgagccacga agaccctgag    900

gtcaagttca actggtacgt ggacggcgtg gaggtgcata atgccaagac aaagccgcgg    960

gaggagcagt accagagcac gtaccgtgtg gtcagcgtcc tcaccgtcct gcaccaggac   1020

tggctgaatg gcaaggagta caagtgcaag gtctccaaca aagccctccc agcccccatc   1080

gagaaaacca tctccaaagc caaagggcag ccccgagaac cacaggtgta caccctgcca   1140

ccatcacgag atgagctgac caagaaccag gtcagcctga cctgcctggt caaaggcttc   1200

tatcccagcg acatcgccgt ggagtgggag agcaatgggc agccggagaa caactacaag   1260

accacgcctc ccgtgctgga ctccgacggc tccttcttcc tctacagcaa gctcaccgtg   1320

gacaagagca ggtggcagca ggggaacgtc ttctcatgct ccgtgatgca tgaggctctg   1380

cacaaccact acacgcagaa gagcctctcc ctgtctccct tttgggtgct ggtggtggtt   1440

ggtggagtcc tggcttgcta tagcttgcta gtaacagtgg cctttattat tttctgggtg   1500

aggagtaaga ggagcagggg aggtcacagt gactacatga acatgactcc ccgccgcccc   1560

gggcccaccc gcaagcatta ccagccctat gccccaccac gcgacttcgc agcctatcgc   1620

tccagagtga agttcagcag gagcgcagac gcccccgcgt accagcaggg ccagaaccag   1680
```

ctctataacg agctcaatct aggacgaaga gaggagtacg atgttttgga caagagacgt 1740
ggccgggacc ctgagatggg gggaaagccg agaaggaaga accctcagga aggcctgtac 1800
aatgaactgc agaaagataa gatggcggag gcctacagtg agattgggat gaaaggcgag 1860
cgccggaggg gcaaggggca cgatggcctt taccagggtc tcagtacagc caccaaggac 1920
acctacgacg cccttcacat gcaggccctg ccccctcgc 1959

<210> SEQ ID NO 46
<211> LENGTH: 1962
<212> TYPE: DNA
<213> ORGANISM: Artificial Sequence
<220> FEATURE:
<223> OTHER INFORMATION: Synthetic sequence

<400> SEQUENCE: 46
gacattgtga tgactcagac accactgagc tccccagtga ctctgggaca gccagccagt 60
atctcatgca gatctagtca gtcactggtc tacagcgacg gcaacaccta tctgagctgg 120
ctgcagcagc gaccaggaca gccacctaga ctgctgatct acaagatttc caataggttc 180
tctggagtgc ccgaccgctt tagcggatcc ggagctggaa ctgatttcac cctgaaaatc 240
tcccgcgtgg aggctgaaga tgtgggcgtc tactattgcg tccaggcaac ccagttccct 300
ctgacatttg gcgggggaac taaggtggag atcaagggag gaggaggatc tggaggagga 360
ggaagtggag gaggaggatc cgaagtgcag ctggtccagt ctggggccga ggtgaagaaa 420
cctggagaaa gtctgaagat ctcatgtaaa ggctccgggt actctttcac aagttattgg 480
attggctggg tccgacagat gccaggaaag ggcctggagt ggatgggaat catctacccc 540
ggcgacagcg atacccggta ttctcctagt tttcagggcc aggtgacaat cagcgcagac 600
aagtccatta ccacagccta tctgcagtgg tcaagcctga aagcctctga taccgctatg 660
tactattgtg ccaggcaccc tagctacggg tcaggaagcc caaactttga ctattggggc 720
caggggacac tggtgactgt ctcctctgac aaaactcaca catgcccacc gtgcccagca 780
cctcctgtgg caggaccgtc agtcttcctc ttccccccaa aacccaagga caccctcatg 840
atctcccgga cccctgaggt cacatgcgtg gtggtggacg tgagccacga agaccctgag 900
gtcaagttca actggtacgt ggacggcgtg gaggtgcata atgccaagac aaagccgcgg 960
gaggagcagt accagagcac gtaccgtgtg gtcagcgtcc tcaccgtcct gcaccaggac 1020
tggctgaatg gcaaggagta caagtgcaag gtctccaaca aagccctccc agcccccatc 1080
gagaaaacca tctccaaagc caaagggcag ccccgagaac cacaggtgta caccctgcca 1140
ccatcacgag atgagctgac caagaaccag gtcagcctga cctgcctggt caaaggcttc 1200
tatcccagcg acatcgccgt ggagtgggag agcaatgggc agccggagaa caactacaag 1260
accacgcctc ccgtgctgga ctccgacggc tccttcttcc tctacagcaa gctcaccgtg 1320
gacaagagca ggtggcagca ggggaacgtc ttctcatgct ccgtgatgca tgaggctctg 1380
cacaaccact acacgcagaa gagcctctcc ctgtctccct tttgggtgct ggtggtggtt 1440
ggtggagtcc tggcttgcta tagcttgcta gtaacagtgg cctttattat tttctgggtg 1500
aaacggggca gaaagaaact cctgtatata ttcaaacaac catttatgag accagtacaa 1560
actactcaag aggaagatgg ctgtagctgc cgatttccag aagaagaaga aggaggatgt 1620
gaactgagag tgaagttcag caggagcgca gacgcccccg cgtaccagca gggccagaac 1680
cagctctata acgagctcaa tctaggacga agagaggagt acgatgtttt ggacaagaga 1740

```
cgtggccggg accctgagat ggggggaaag ccgagaagga agaaccctca ggaaggcctg   1800

tacaatgaac tgcagaaaga taagatggcg gaggcctaca gtgagattgg gatgaaaggc   1860

gagcgccgga ggggcaaggg gcacgatggc ctttaccagg gtctcagtac agccaccaag   1920

gacacctacg acgcccttca catgcaggcc ctgccccctc gc                      1962


<210> SEQ ID NO 47
<211> LENGTH: 1836
<212> TYPE: DNA
<213> ORGANISM: Artificial Sequence
<220> FEATURE:
<223> OTHER INFORMATION: Synthetic sequence

<400> SEQUENCE: 47

gacattgtga tgactcagac accactgagc tccccagtga ctctgggaca gccagccagt     60

atctcatgca gatctagtca gtcactggtc tacagcgacg gcaacaccta tctgagctgg    120

ctgcagcagc gaccaggaca gccacctaga ctgctgatct acaagatttc caataggttc    180

tctggagtgc ccgaccgctt tagcggatcc ggagctggaa ctgatttcac cctgaaaatc    240

tcccgcgtgg aggctgaaga tgtgggcgtc tactattgcg tccaggcaac ccagttccct    300

ctgacatttg gcgggggaac taaggtggag atcaagggag gaggaggatc tggaggagga    360

ggaagtggag gaggaggatc cgaagtgcag ctggtccagt ctggggccga ggtgaagaaa    420

cctggagaaa gtctgaagat ctcatgtaaa ggctccgggt actctttcac aagttattgg    480

attggctggg tccgacagat gccaggaaag ggcctggagt ggatgggaat catctacccc    540

ggcgacagcg atacccggta ttctcctagt tttcagggcc aggtgacaat cagcgcagac    600

aagtccatta ccacagccta tctgcagtgg tcaagcctga aagcctctga taccgctatg    660

tactattgtg ccaggcaccc tagctacggg tcaggaagcc caaactttga ctattggggc    720

caggggacac tggtgactgt ctcctctgac aaaactcaca catgcccacc gtgcccagca    780

cctcctgtgg caggaccgtc agtcttcctc ttccccccaa aacccaagga caccctcatg    840

atctcccgga cccctgaggt cacatgcgtg gtggtggacg tgagccacga agaccctgag    900

gtcaagttca actggtacgt ggacggcgtg gaggtgcata atgccaagac aaagccgcgg    960

gaggagcagt accagagcac gtaccgtgtg gtcagcgtcc tcaccgtcct gcaccaggac   1020

tggctgaatg gcaaggagta caagtgcaag gtctccaaca aagccctccc agcccccatc   1080

gagaaaacca tctccaaagc caaagggcag ccccgagaac cacaggtgta caccctgcca   1140

ccatcacgag atgagctgac caagaaccag gtcagcctga cctgcctggt caaaggcttc   1200

tatcccagcg acatcgccgt ggagtgggag agcaatgggc agccggagaa caactacaag   1260

accacgcctc ccgtgctgga ctccgacggc tccttcttcc tctacagcaa gctcaccgtg   1320

gacaagagca ggtggcagca ggggaacgtc ttctcatgct ccgtgatgca tgaggctctg   1380

cacaaccact acacgcagaa gagcctctcc ctgtctccct ttgggtgct ggtggtggtt    1440

ggtggagtcc tggcttgcta tagcttgcta gtaacagtgg cctttattat tttctgggtg   1500

agagtgaagt tcagcaggag cgcagacgcc cccgcgtacc agcagggcca gaaccagctc   1560

tataacgagc tcaatctagg acgaagagag gagtacgatg ttttggacaa gagacgtggc   1620

cgggaccctg agatgggggg aaagccgaga aggaagaacc ctcaggaagg cctgtacaat   1680

gaactgcaga aagataagat ggcggaggcc tacagtgaga ttgggatgaa aggcgagcgc   1740

cggaggggca aggggcacga tggcctttac cagggtctca gtacagccac caaggacacc   1800

tacgacgccc ttcacatgca ggccctgccc cctcgc                             1836
```

<210> SEQ ID NO 48
<211> LENGTH: 2100
<212> TYPE: DNA
<213> ORGANISM: Artificial Sequence
<220> FEATURE:
<223> OTHER INFORMATION: Synthetic sequence

<400> SEQUENCE: 48
gacattgtgc tgacccaatc tccagctatc ctgtctgcat ctccagggga gaaggtcaca 60
atgacttgca gggccagctc aagtgtaaat tacatggact ggtaccagaa gaagccagga 120
tcctccccca aaccctggat ttatgccaca tccaacctgg cttctggagt ccctgctcgc 180
ttcagtggca gtgggtctgg gacctcttac tctctcacaa tcagcagagt ggaggctgaa 240
gatgctgcca cttattactg ccagcagtgg agttttaatc cacccacgtt cggagggggg 300
accaagctgg aaataaaagg cagtactagc ggtggtggct ccgggggcgg ttccggtggg 360
ggcggcagca gcgaggtgca gctgcagcag tctggggctg agctggtgaa gcctggggcc 420
tcagtgaaga tgtcctgcaa ggcttctggc tacacattta ccagttacaa tatgcactgg 480
gtaaagcaga cacctggaca gggcctggaa tggattggag ctatttatcc aggaaatggt 540
gatacttcct acaatcagaa gttcaaaggc aaggccacat tgactgcaga caaatcctcc 600
agcacagcct acatgcagct cagcagcctg acatctgagg actctgcgga ctattactgt 660
gcaagatcta attattacgg tagtagctac tggttcttcg atgtctgggg cgcagggacc 720
acggtcaccg tctcctcact cgacgaatct aagtacggac cgccctgccc cccttgccct 780
gcccccgagt tcctgggcgg acccagcgtg ttcctgttcc cccccaagcc caaggacacc 840
ctgatgatca gccggacccc cgaggtgacc tgcgtggtgg tggacgtgag ccaggaagat 900
cccgaggtcc agttcaattg gtacgtggac ggcgtggaag tgcacaacgc caagaccaag 960
cccagagagg aacagttcaa cagcacctac cgggtggtgt ctgtgctgac cgtgctgcac 1020
caggactggc tgaacggcaa agaatacaag tgcaaggtgt ccaacaaggg cctgcccagc 1080
agcatcgaaa agaccatcag caaggccaag ggccagcctc gcgagcccca ggtgtacacc 1140
ctgcctccct cccaggaaga gatgaccaag aaccaggtgt ccctgacctg cctggtgaag 1200
ggcttctacc ccagcgacat cgccgtggag tgggagagca acggccagcc tgagaacaac 1260
tacaagacca cccctcccgt gctggacagc gacggcagct tcttcctgta cagccggctg 1320
accgtggaca agagccggtg gcaggaaggc aacgtcttta gctgcagcgt gatgcacgag 1380
gccctgcaca accactacac ccagaagagc ctgagcctgt ccctgggcaa gatgttctgg 1440
gtgctggtgg tggtgggcgg ggtgctggcc tgctacagcc tgctggtgac agtggccttc 1500
atcatctttt gggtgcggag caagcggagc agaggcggcc acagcgacta catgaacatg 1560
acccccagac ggcctggccc cacccggaag cactaccagc cctacgcccc acccagggac 1620
tttgccgcct acagaagcaa acggggcaga aagaaactcc tgtatatatt caaacaacca 1680
tttatgagac cagtacaaac tactcaagag gaagatggct gtagctgccg atttccagaa 1740
gaagaagaag gaggatgtga actgcgggtg aagttcagca gaagcgccga cgcccctgcc 1800
taccagcagg gccagaatca gctgtacaac gagctgaacc tgggcagaag ggaagagtac 1860
gacgtcctgg ataagcggag aggccgggac cctgagatgg gcggcaagcc tcggcggaag 1920
aacccccagg aaggcctgta taacgaactg cagaaagaca agatggccga ggcctacagc 1980

```
gagatcggca tgaagggcga gcggaggcgg ggcaagggcc acgacggcct gtatcagggc   2040

ctgtccaccg ccaccaagga tacctacgac gccctgcaca tgcaggccct gcccccaagg   2100
```

<210> SEQ ID NO 49
<211> LENGTH: 1974
<212> TYPE: DNA
<213> ORGANISM: Artificial Sequence
<220> FEATURE:
<223> OTHER INFORMATION: Synthetic sequence

<400> SEQUENCE: 49

```
gacattgtgc tgacccaatc tccagctatc ctgtctgcat ctccagggga gaaggtcaca     60

atgacttgca gggccagctc aagtgtaaat tacatggact ggtaccagaa gaagccagga    120

tcctccccca aaccctggat ttatgccaca tccaacctgg cttctggagt ccctgctcgc    180

ttcagtggca gtgggtctgg gacctcttac tctctcacaa tcagcagagt ggaggctgaa    240

gatgctgcca cttattactg ccagcagtgg agttttaatc cacccacgtt cggagggggg    300

accaagctgg aaataaaagg cagtactagc ggtggtggct ccgggggcgg ttccggtggg    360

ggcggcagca gcgaggtgca gctgcagcag tctggggctg agctggtgaa gcctggggcc    420

tcagtgaaga tgtcctgcaa ggcttctggc tacacattta ccagttacaa tatgcactgg    480

gtaaagcaga cacctggaca gggcctggaa tggattggag ctatttatcc aggaaatggt    540

gatacttcct acaatcagaa gttcaaaggc aaggccacat tgactgcaga caaatcctcc    600

agcacagcct acatgcagct cagcagcctg acatctgagg actctgcgga ctattactgt    660

gcaagatcta attattacgg tagtagctac tggttcttcg atgtctgggg cgcagggacc    720

acggtcaccg tctcctcact cgacgaatct aagtacggac cgccctgccc cccttgccct    780

gcccccgagt tcctgggcgg acccagcgtg ttcctgttcc cccccaagcc caaggacacc    840

ctgatgatca gccggacccc cgaggtgacc tgcgtggtgg tggacgtgag ccaggaagat    900

cccgaggtcc agttcaattg gtacgtggac ggcgtggaag tgcacaacgc caagaccaag    960

cccagagagg aacagttcaa cagcacctac cgggtggtgt ctgtgctgac cgtgctgcac   1020

caggactggc tgaacggcaa agaatacaag tgcaaggtgt ccaacaaggg cctgcccagc   1080

agcatcgaaa agaccatcag caaggccaag ggccagcctc gcgagcccca ggtgtacacc   1140

ctgcctccct cccaggaaga gatgaccaag aaccaggtgt ccctgacctg cctggtgaag   1200

ggcttctacc ccagcgacat cgccgtggag tgggagagca acggccagcc tgagaacaac   1260

tacaagacca cccctcccgt gctggacagc gacggcagct tcttcctgta cagccggctg   1320

accgtggaca agagccggtg gcaggaaggc aacgtcttta gctgcagcgt gatgcacgag   1380

gccctgcaca accactacac ccagaagagc ctgagcctgt ccctgggcaa gatgttctgg   1440

gtgctggtgg tggtgggcgg ggtgctggcc tgctacagcc tgctggtgac agtggccttc   1500

atcatctttt gggtgcggag caagcggagc agaggcggcc acagcgacta catgaacatg   1560

acccccagac ggcctggccc cacccggaag cactaccagc cctacgcccc acccagggac   1620

tttgccgcct acagaagccg ggtgaagttc agcagaagcg ccgacgcccc tgcctaccag   1680

cagggccaga atcagctgta caacgagctg aacctgggca gaagggaaga gtacgacgtc   1740

ctggataagc ggagaggccg ggaccctgag atgggcggca agcctcggcg gaagaacccc   1800

caggaaggcc tgtataacga actgcagaaa gacaagatgg ccgaggccta cagcgagatc   1860
```

ggcatgaagg gcgagcggag gcggggcaag ggccacgacg gcctgtatca gggcctgtcc 1920
accgccacca aggataccta cgacgccctg cacatgcagg ccctgccccc aagg 1974

<210> SEQ ID NO 50
<211> LENGTH: 2094
<212> TYPE: DNA
<213> ORGANISM: Artificial Sequence
<220> FEATURE:
<223> OTHER INFORMATION: Synthetic sequence

<400> SEQUENCE: 50
gacattgttc tctcccagtc tccagcaatc ctttctgcat ctccagggga gaaggtcaca 60
atgacttgca gggccagctc aagtttaagt ttcatgcact ggtaccagca gaagccagga 120
tcctccccca aaccctggat ttatgccaca tccaacctgg cttctggagt ccctgctcgc 180
ttcagtggca gtgggtctgg gacctcttac tctctcacaa tcagcagagt ggaggctgaa 240
gatgctgcca cttatttctg ccatcagtgg agtagtaacc cgctcacgtt cggtgctggg 300
accaagctgg agctgaaggg cagtactagc ggtggtggct ccgggggcgg ttccggtggg 360
ggcggcagca gccaggtgca actgcggcag cctggggctg agctggtgaa gcctggggcc 420
tcagtgaaga tgtcctgcaa ggcttctggc tacacattta ccagttacaa tatgcactgg 480
gtaaagcaga cacctggaca gggcctggaa tggattggag ctatttatcc aggaaatggt 540
gatacttcct acaatcagaa gttcaaaggc aaggccacat tgactgcaga caaatcctcc 600
agcacagcct acatgcagct cagcagtctg acatctgagg actctgcggt ctattactgt 660
gcaagatcgc actacggtag taactacgta gactactttg actactgggg ccaaggcacc 720
actctcacag tctcctcact cgaccccaaa tcttctgaca aaactcacac atgcccaccg 780
tgcccagcac ctcctgtggc aggaccgtca gtcttcctct tccccccaaa acccaaggac 840
accctcatga tctcccggac ccctgaggtc acatgcgtgg tggtggacgt gagccacgaa 900
gaccctgagg tcaagttcaa ctggtacgtg gacggcgtgg aggtgcataa tgccaagaca 960
aagccgcggg aggagcagta ccagagcacg taccgtgtgg tcagcgtcct caccgtcctg 1020
caccaggact ggctgaatgg caaggagtac aagtgcaagg tctccaacaa agccctccca 1080
gcccccatcg agaaaaccat ctccaaagcc aaagggcagc cccgagaacc acaggtgtac 1140
accctgccac catcacgaga tgagctgacc aagaaccagg tcagcctgac ctgcctggtc 1200
aaaggcttct atcccagcga catcgccgtg gagtgggaga gcaatgggca gccggagaac 1260
aactacaaga ccacgcctcc cgtgctggac tccgacggct ccttcttcct ctacagcaag 1320
ctcaccgtgg acaagagcag gtggcagcag gggaacgtct tctcatgctc cgtgatgcat 1380
gaggctctgc acaaccacta cacgcagaag agcctctccc tgtctccctt ttgggtgctg 1440
gtggtggttg gtggagtcct ggcttgctat agcttgctag taacagtggc ctttattatt 1500
ttctgggtga ggagtaagag gagcagggga ggtcacagtg actacatgaa catgactccc 1560
cgccgccccg ggcccacccg caagcattac cagccctatg ccccaccacg cgacttcgca 1620
gcctatcgct ccaaacgggg cagaaagaaa ctcctgtata tattcaaaca accatttatg 1680
agaccagtac aaactactca agaggaagat ggctgtagct gccgatttcc agaagaagaa 1740
gaaggaggat gtgaactgag agtgaagttc agcaggagcg cagacgcccc cgcgtaccag 1800
cagggccaga accagctcta taacgagctc aatctaggac gaagagagga gtacgatgtt 1860
ttggacaaga gacgtggccg ggaccctgag atggggggaa agccgagaag gaagaaccct 1920
caggaaggcc tgtacaatga actgcagaaa gataagatgg cggaggccta cagtgagatt 1980
gggatgaaag gcgagcgccg gaggggcaag gggcacgatg gcctttacca gggtctcagt 2040
acagccacca aggacaccta cgacgccctt cacatgcagg ccctgccccc tcgc 2094

<210> SEQ ID NO 51
<211> LENGTH: 1968
<212> TYPE: DNA
<213> ORGANISM: Artificial Sequence
<220> FEATURE:
<223> OTHER INFORMATION: Synthetic sequence

<400> SEQUENCE: 51
gacattgttc tctcccagtc tccagcaatc ctttctgcat ctccagggga gaaggtcaca 60
atgacttgca gggccagctc aagtttaagt ttcatgcact ggtaccagca gaagccagga 120
tcctccccca aaccctggat ttatgccaca tccaacctgg cttctggagt ccctgctcgc 180
ttcagtggca gtgggtctgg gacctcttac tctctcacaa tcagcagagt ggaggctgaa 240
gatgctgcca cttatttctg ccatcagtgg agtagtaacc cgctcacgtt cggtgctggg 300
accaagctgg agctgaaggg cagtactagc ggtggtggct ccgggggcgg ttccggtggg 360
ggcggcagca gccaggtgca actgcggcag cctggggctg agctggtgaa gcctggggcc 420
tcagtgaaga tgtcctgcaa ggcttctggc tacacattta ccagttacaa tatgcactgg 480
gtaaagcaga cacctggaca gggcctggaa tggattggag ctatttatcc aggaaatggt 540
gatacttcct acaatcagaa gttcaaaggc aaggccacat tgactgcaga caaatcctcc 600
agcacagcct acatgcagct cagcagtctg acatctgagg actctgcggt ctattactgt 660
gcaagatcgc actacggtag taactacgta gactactttg actactgggg ccaaggcacc 720
actctcacag tctcctcact cgaccccaaa tcttctgaca aaactcacac atgcccaccg 780
tgcccagcac ctcctgtggc aggaccgtca gtcttcctct tccccccaaa acccaaggac 840
accctcatga tctcccggac ccctgaggtc acatgcgtgg tggtggacgt gagccacgaa 900
gaccctgagg tcaagttcaa ctggtacgtg gacggcgtgg aggtgcataa tgccaagaca 960
aagccgcggg aggagcagta ccagagcacg taccgtgtgg tcagcgtcct caccgtcctg 1020
caccaggact ggctgaatgg caaggagtac aagtgcaagg tctccaacaa agccctccca 1080
gcccccatcg agaaaaccat ctccaaagcc aaagggcagc cccgagaacc acaggtgtac 1140
accctgccac catcacgaga tgagctgacc aagaaccagg tcagcctgac ctgcctggtc 1200
aaaggcttct atcccagcga catcgccgtg gagtgggaga gcaatgggca gccggagaac 1260
aactacaaga ccacgcctcc cgtgctggac tccgacggct ccttcttcct ctacagcaag 1320
ctcaccgtgg acaagagcag gtggcagcag gggaacgtct tctcatgctc cgtgatgcat 1380
gaggctctgc acaaccacta cacgcagaag agcctctccc tgtctccctt ttgggtgctg 1440
gtggtggttg gtggagtcct ggcttgctat agcttgctag taacagtggc ctttattatt 1500
ttctgggtga ggagtaagag gagcagggga ggtcacagtg actacatgaa catgactccc 1560
cgccgccccg ggcccacccg caagcattac cagccctatg ccccaccacg cgacttcgca 1620
gcctatcgct ccagagtgaa gttcagcagg agcgcagacg cccccgcgta ccagcagggc 1680
cagaaccagc tctataacga gctcaatcta ggacgaagag aggagtacga tgttttggac 1740
aagagacgtg gccgggaccc tgagatgggg ggaaagccga gaaggaagaa ccctcaggaa 1800
ggcctgtaca atgaactgca gaaagataag atggcggagg cctacagtga gattgggatg 1860
aaaggcgagc gccggagggg caaggggcac gatggccttt accagggtct cagtacagcc 1920
accaaggaca cctacgacgc ccttcacatg caggccctgc cccctcgc 1968

<210> SEQ ID NO 52
<211> LENGTH: 1971
<212> TYPE: DNA
<213> ORGANISM: Artificial Sequence
<220> FEATURE:
<223> OTHER INFORMATION: Synthetic sequence

<400> SEQUENCE: 52
gacattgttc tctcccagtc tccagcaatc ctttctgcat ctccagggga gaaggtcaca 60
atgacttgca gggccagctc aagtttaagt ttcatgcact ggtaccagca gaagccagga 120
tcctccccca aaccctggat ttatgccaca tccaacctgg cttctggagt ccctgctcgc 180
ttcagtggca gtgggtctgg gacctcttac tctctcacaa tcagcagagt ggaggctgaa 240
gatgctgcca cttatttctg ccatcagtgg agtagtaacc cgctcacgtt cggtgctggg 300
accaagctgg agctgaaggg cagtactagc ggtggtggct ccgggggcgg ttccggtggg 360
ggcggcagca gccaggtgca actgcggcag cctggggctg agctggtgaa gcctggggcc 420
tcagtgaaga tgtcctgcaa ggcttctggc tacacattta ccagttacaa tatgcactgg 480
gtaaagcaga cacctggaca gggcctggaa tggattggag ctatttatcc aggaaatggt 540
gatacttcct acaatcagaa gttcaaaggc aaggccacat tgactgcaga caaatcctcc 600
agcacagcct acatgcagct cagcagtctg acatctgagg actctgcggt ctattactgt 660
gcaagatcgc actacggtag taactacgta gactactttg actactgggg ccaaggcacc 720
actctcacag tctcctcact cgaccccaaa tcttctgaca aaactcacac atgcccaccg 780
tgcccagcac ctcctgtggc aggaccgtca gtcttcctct tccccccaaa acccaaggac 840
accctcatga tctcccggac ccctgaggtc acatgcgtgg tggtggacgt gagccacgaa 900
gaccctgagg tcaagttcaa ctggtacgtg gacggcgtgg aggtgcataa tgccaagaca 960
aagccgcggg aggagcagta ccagagcacg taccgtgtgg tcagcgtcct caccgtcctg 1020
caccaggact ggctgaatgg caaggagtac aagtgcaagg tctccaacaa agccctccca 1080
gcccccatcg agaaaaccat ctccaaagcc aaagggcagc cccgagaacc acaggtgtac 1140
accctgccac catcacgaga tgagctgacc aagaaccagg tcagcctgac ctgcctggtc 1200
aaaggcttct atcccagcga catcgccgtg gagtgggaga gcaatgggca gccggagaac 1260
aactacaaga ccacgcctcc cgtgctggac tccgacggct ccttcttcct ctacagcaag 1320
ctcaccgtgg acaagagcag gtggcagcag gggaacgtct tctcatgctc cgtgatgcat 1380
gaggctctgc acaaccacta cacgcagaag agcctctccc tgtctccctt ttgggtgctg 1440
gtggtggttg gtggagtcct ggcttgctat agcttgctag taacagtggc ctttattatt 1500
ttctgggtga aacggggcag aaagaaactc ctgtatatat tcaaacaacc atttatgaga 1560
ccagtacaaa ctactcaaga ggaagatggc tgtagctgcc gatttccaga agaagaagaa 1620
ggaggatgtg aactgagagt gaagttcagc aggagcgcag acgcccccgc gtaccagcag 1680
ggccagaacc agctctataa cgagctcaat ctaggacgaa gagaggagta cgatgttttg 1740
gacaagagac gtggccggga ccctgagatg gggggaaagc cgagaaggaa gaaccctcag 1800
gaaggcctgt acaatgaact gcagaaagat aagatggcgg aggcctacag tgagattggg 1860

-continued atgaaaggcg agcgccggag gggcaagggg cacgatggcc tttaccaggg tctcagtaca 1920
gccaccaagg acacctacga cgcccttcac atgcaggccc tgccccctcg c 1971

<210> SEQ ID NO 53
<211> LENGTH: 3180
<212> TYPE: DNA
<213> ORGANISM: Artificial Sequence
<220> FEATURE:
<223> OTHER INFORMATION: Synthetic sequence

<400> SEQUENCE: 53
atgctgctgc tggtcacctc actgctgctg tgcgaactgc cccaccccgc cttcctgctg 60
attcccgaca ttgtgatgac tcagacacca ctgagctccc cagtgactct gggacagcca 120
gccagtatct catgcagatc tagtcagtca ctggtctaca gcgacggcaa cacctatctg 180
agctggctgc agcagcgacc aggacagcca cctagactgc tgatctacaa gatttccaat 240
aggttctctg gagtgcccga ccgctttagc ggatccggag ctggaactga tttcaccctg 300
aaaatctccc gcgtggaggc tgaagatgtg ggcgtctact attgcgtcca ggcaacccag 360
ttccctctga catttggcgg ggaactaag gtggagatca agggaggagg aggatctgga 420
ggaggaggaa gtggaggagg aggatccgaa gtgcagctgg tccagtctgg ggccgaggtg 480
aagaaacctg gagaaagtct gaagatctca tgtaaaggct ccgggtactc tttcacaagt 540
tattggattg gctgggtccg acagatgcca ggaaagggcc tggagtggat gggaatcatc 600
taccccggcg acagcgatac ccggtattct cctagttttc agggccaggt gacaatcagc 660
gcagacaagt ccattaccac agcctatctg cagtggtcaa gcctgaaagc ctctgatacc 720
gctatgtact attgtgccag gcaccctagc tacgggtcag gaagcccaaa ctttgactat 780
tggggccagg ggacactggt gactgtctcc tctgacaaaa ctcacacatg cccaccgtgc 840
ccagcacctc ctgtggcagg accgtcagtc ttcctcttcc ccccaaaacc caaggacacc 900
ctcatgatct cccggacccc tgaggtcaca tgcgtggtgg tggacgtgag ccacgaagac 960
cctgaggtca agttcaactg gtacgtggac ggcgtggagg tgcataatgc caagacaaag 1020
ccgcgggagg agcagtacca gagcacgtac cgtgtggtca gcgtcctcac cgtcctgcac 1080
caggactggc tgaatggcaa ggagtacaag tgcaaggtct ccaacaaagc cctcccagcc 1140
cccatcgaga aaaccatctc caaagccaaa gggcagcccc gagaaccaca ggtgtacacc 1200
ctgccaccat cacgagatga gctgaccaag aaccaggtca gcctgacctg cctggtcaaa 1260
ggcttctatc ccagcgacat cgccgtggag tgggagagca atgggcagcc ggagaacaac 1320
tacaagacca cgcctcccgt gctggactcc gacggctcct tcttcctcta cagcaagctc 1380
accgtggaca agagcaggtg gcagcagggg aacgtcttct catgctccgt gatgcatgag 1440
gctctgcaca accactacac gcagaagagc ctctccctgt ctccctttttg ggtgctggtg 1500 gtggttggtg gagtcctggc ttgctatagc ttgctagtaa cagtggcctt tattattttc 1560
tgggtgagga gtaagaggag caggggaggt cacagtgact acatgaacat gactccccgc 1620
cgccccgggc ccacccgcaa gcattaccag ccctatgccc caccacgcga cttcgcagcc 1680
tatcgctcca aacggggcag aaagaaactc ctgtatatat tcaaacaacc atttatgaga 1740
ccagtacaaa ctactcaaga ggaagatggc tgtagctgcc gatttccaga agaagaagaa 1800
ggaggatgtg aactgagagt gaagttcagc aggagcgcag acgcccccgc gtaccagcag 1860
ggccagaacc agctctataa cgagctcaat ctaggacgaa gagaggagta cgatgttttg 1920

-continued gacaagagac gtggccggga ccctgagatg gggggaaagc cgagaaggaa gaaccctcag 1980
gaaggcctgt acaatgaact gcagaaagat aagatggcgg aggcctacag tgagattggg 2040
atgaaaggcg agcgccggag gggcaagggg cacgatggcc tttaccaggg tctcagtaca 2100
gccaccaagg acacctacga cgcccttcac atgcaggccc tgccccctcg ccagtgtact 2160
aattatgctc tcttgaaatt ggctggagat gttgagagca accccgggcc gatgccacct 2220
cctcgcctcc tcttcttcct cctcttcctc acccccatgg aagtcaggcc cgaggaacct 2280
ctagtggtga aggtggaaga gggagataac gctgtgctgc agtgcctcaa ggggacctca 2340
gatggcccca ctcagcagct gacctggtct cgggagtccc cgcttaaacc cttcttaaaa 2400
ctcagcctgg ggctgccagg cctgggaatc cacatgaggc ccctggccat ctggcttttc 2460
atcttcaacg tctctcaaca gatggggggc ttctacctgt gccagccggg gcccccctct 2520
gagaaggcct ggcagcctgg ctggacagtc aatgtggagg gcagcgggga gctgttccgg 2580
tggaatgttt cggacctagg tggcctgggc tgtggcctga agaacaggtc ctcagagggc 2640
cccagctccc cttccgggaa gctcatgagc cccaagctgt atgtgtgggc caaagaccgc 2700
cctgagatct gggagggaga gcctccgtgt gtcccaccga gggacagcct gaaccagagc 2760
ctcagccagg acctcaccat ggcccctggc tccacactct ggctgtcctg tggggtaccc 2820
cctgactctg tgtccagggg cccccctctcc tggacccatg tgcaccccaa ggggcctaag 2880
tcattgctga gcctagagct gaaggacgat cgccctgcca gagatatgtg ggtaatggag 2940
acgggtctgt tgttgccccg ggccacagct caagacgctg gaaagtatta ttgtcaccgt 3000
ggcaacctga ccatgtcatt ccacctggag atcactgctc ggccagtact atggcactgg 3060
ctgctgagga ctggtggctg gaaggtctca gctgtgactt tggcttatct gatcttctgc 3120
ctgtgttccc ttgtgggcat tcttcatctt caaagagccc tggtcctgag gaggaaaaga 3180

<210> SEQ ID NO 54
<211> LENGTH: 3054
<212> TYPE: DNA
<213> ORGANISM: Artificial Sequence
<220> FEATURE:
<223> OTHER INFORMATION: Synthetic sequence

<400> SEQUENCE: 54
atgctgctgc tggtcacctc actgctgctg tgcgaactgc cccaccccgc cttcctgctg 60
attcccgaca ttgtgatgac tcagacacca ctgagctccc cagtgactct gggacagcca 120
gccagtatct catgcagatc tagtcagtca ctggtctaca gcgacggcaa cacctatctg 180
agctggctgc agcagcgacc aggacagcca cctagactgc tgatctacaa gatttccaat 240
aggttctctg gagtgcccga ccgctttagc ggatccggag ctggaactga tttcaccctg 300
aaaatctccc gcgtggaggc tgaagatgtg ggcgtctact attgcgtcca ggcaacccag 360
ttccctctga catttggcgg gggaactaag gtggagatca agggaggagg aggatctgga 420
ggaggaggaa gtggaggagg aggatccgaa gtgcagctgg tccagtctgg ggccgaggtg 480
aagaaacctg gagaaagtct gaagatctca tgtaaaggct ccgggtactc tttcacaagt 540
tattggattg gctgggtccg acagatgcca ggaaagggcc tggagtggat gggaatcatc 600
taccccggcg acagcgatac ccggtattct cctagttttc agggccaggt gacaatcagc 660
gcagacaagt ccattaccac agcctatctg cagtggtcaa gcctgaaagc ctctgatacc 720
gctatgtact attgtgccag gcaccctagc tacgggtcag gaagcccaaa ctttgactat 780
tggggccagg ggacactggt gactgtctcc tctgacaaaa ctcacacatg cccaccgtgc 840

```
ccagcacctc ctgtggcagg accgtcagtc ttcctcttcc ccccaaaacc caaggacacc     900
ctcatgatct cccggacccc tgaggtcaca tgcgtggtgg tggacgtgag ccacgaagac     960
cctgaggtca agttcaactg gtacgtggac ggcgtggagg tgcataatgc caagacaaag    1020
ccgcgggagg agcagtacca gagcacgtac cgtgtggtca gcgtcctcac cgtcctgcac    1080
caggactggc tgaatggcaa ggagtacaag tgcaaggtct ccaacaaagc cctcccagcc    1140
cccatcgaga aaaccatctc caaagccaaa gggcagcccc gagaaccaca ggtgtacacc    1200
ctgccaccat cacgagatga gctgaccaag aaccaggtca gcctgacctg cctggtcaaa    1260
ggcttctatc ccagcgacat cgccgtggag tgggagagca atgggcagcc ggagaacaac    1320
tacaagacca cgcctcccgt gctggactcc gacggctcct tcttcctcta cagcaagctc    1380
accgtggaca agagcaggtg gcagcagggg aacgtcttct catgctccgt gatgcatgag    1440
gctctgcaca accactacac gcagaagagc ctctccctgt ctcccttttg ggtgctggtg    1500
gtggttggtg gagtcctggc ttgctatagc ttgctagtaa cagtggcctt tattattttc    1560
tgggtgagga gtaagaggag caggggaggt cacagtgact acatgaacat gactccccgc    1620
cgccccgggc ccacccgcaa gcattaccag ccctatgccc caccacgcga cttcgcagcc    1680
tatcgctcca gagtgaagtt cagcaggagc gcagacgccc ccgcgtacca gcagggccag    1740
aaccagctct ataacgagct caatctagga cgaagagagg agtacgatgt tttggacaag    1800
agacgtggcc gggaccctga gatgggggga aagccgagaa ggaagaaccc tcaggaaggc    1860
ctgtacaatg aactgcagaa agataagatg gcggaggcct acagtgagat tgggatgaaa    1920
ggcgagcgcc ggaggggcaa ggggcacgat ggcctttacc agggtctcag tacagccacc    1980
aaggacacct acgacgccct tcacatgcag gccctgcccc ctcgccagtg tactaattat    2040
gctctcttga aattggctgg agatgttgag agcaaccccg ggccgatgcc acctcctcgc    2100
ctcctcttct tcctcctctt cctcaccccc atggaagtca ggcccgagga acctctagtg    2160
gtgaaggtgg aagagggaga taacgctgtg ctgcagtgcc tcaaggggac ctcagatggc    2220
cccactcagc agctgacctg gtctcgggag tccccgctta aacccttctt aaaactcagc    2280
ctggggctgc caggcctggg aatccacatg aggcccctgg ccatctggct tttcatcttc    2340
aacgtctctc aacagatggg gggcttctac ctgtgccagc cggggccccc ctctgagaag    2400
gcctggcagc ctggctggac agtcaatgtg gagggcagcg gggagctgtt ccggtggaat    2460
gtttcggacc taggtggcct gggctgtggc ctgaagaaca ggtcctcaga gggccccagc    2520
tccccttccg ggaagctcat gagccccaag ctgtatgtgt gggccaaaga ccgccctgag    2580
atctgggagg gagagcctcc gtgtgtccca ccgagggaca gcctgaacca gagcctcagc    2640
caggacctca ccatggcccc tggctccaca ctctggctgt cctgtggggt accccctgac    2700
tctgtgtcca ggggccccct ctcctggacc catgtgcacc ccaaggggcc taagtcattg    2760
ctgagcctag agctgaagga cgatcgcccg gccagagata tgtgggtaat ggagacgggt    2820
ctgttgttgc ccgggccac agctcaagac gctggaaagt attattgtca ccgtggcaac    2880
ctgaccatgt cattccacct ggagatcact gctcggccag tactatggca ctggctgctg    2940
aggactggtg gctggaaggt ctcagctgtg actttggctt atctgatctt ctgcctgtgt    3000
tcccttgtgg gcattcttca tcttcaaaga gccctggtcc tgaggaggaa aaga          3054
```

<210> SEQ ID NO 55
<211> LENGTH: 3057
<212> TYPE: DNA

<213> ORGANISM: Artificial Sequence
<220> FEATURE:
<223> OTHER INFORMATION: Synthetic sequence

<400> SEQUENCE: 55
atgctgctgc tggtcacctc actgctgctg tgcgaactgc cccaccccgc cttcctgctg 60
attcccgaca ttgtgatgac tcagacacca ctgagctccc cagtgactct gggacagcca 120
gccagtatct catgcagatc tagtcagtca ctggtctaca gcgacggcaa cacctatctg 180
agctggctgc agcagcgacc aggacagcca cctagactgc tgatctacaa gatttccaat 240
aggttctctg gagtgcccga ccgctttagc ggatccggag ctggaactga tttcaccctg 300
aaaatctccc gcgtggaggc tgaagatgtg ggcgtctact attgcgtcca ggcaacccag 360
ttccctctga catttggcgg gggaactaag gtggagatca agggaggagg aggatctgga 420
ggaggaggaa gtggaggagg aggatccgaa gtgcagctgg tccagtctgg ggccgaggtg 480
aagaaacctg gagaaagtct gaagatctca tgtaaaggct ccgggtactc tttcacaagt 540
tattggattg gctgggtccg acagatgcca ggaaagggcc tggagtggat gggaatcatc 600
taccccggcg acagcgatac ccggtattct cctagttttc agggccaggt gacaatcagc 660
gcagacaagt ccattaccac agcctatctg cagtggtcaa gcctgaaagc ctctgatacc 720
gctatgtact attgtgccag gcaccctagc tacgggtcag gaagcccaaa ctttgactat 780
tggggccagg ggacactggt gactgtctcc tctgacaaaa ctcacacatg cccaccgtgc 840
ccagcacctc ctgtggcagg accgtcagtc ttcctcttcc ccccaaaacc caaggacacc 900
ctcatgatct cccggacccc tgaggtcaca tgcgtggtgg tggacgtgag ccacgaagac 960
cctgaggtca agttcaactg gtacgtggac ggcgtggagg tgcataatgc caagacaaag 1020
ccgcgggagg agcagtacca gagcacgtac cgtgtggtca gcgtcctcac cgtcctgcac 1080
caggactggc tgaatggcaa ggagtacaag tgcaaggtct ccaacaaagc cctcccagcc 1140
cccatcgaga aaaccatctc caaagccaaa gggcagcccc gagaaccaca ggtgtacacc 1200
ctgccaccat cacgagatga gctgaccaag aaccaggtca gcctgacctg cctggtcaaa 1260
ggcttctatc ccagcgacat cgccgtggag tgggagagca atgggcagcc ggagaacaac 1320
tacaagacca cgcctcccgt gctggactcc gacggctcct tcttcctcta cagcaagctc 1380
accgtggaca agagcaggtg gcagcagggg aacgtcttct catgctccgt gatgcatgag 1440
gctctgcaca accactacac gcagaagagc ctctccctgt ctcccttttg ggtgctggtg 1500
gtggttggtg gagtcctggc ttgctatagc ttgctagtaa cagtggcctt tattattttc 1560
tgggtgaaac ggggcagaaa gaaactcctg tatatattca aacaaccatt tatgagacca 1620
gtacaaacta ctcaagagga agatggctgt agctgccgat ttccagaaga agaagaagga 1680
ggatgtgaac tgagagtgaa gttcagcagg agcgcagacg cccccgcgta ccagcagggc 1740
cagaaccagc tctataacga gctcaatcta ggacgaagag aggagtacga tgttttggac 1800
aagagacgtg gccgggaccc tgagatgggg ggaaagccga gaaggaagaa ccctcaggaa 1860
ggcctgtaca atgaactgca gaaagataag atggcggagg cctacagtga gattgggatg 1920
aaaggcgagc gccggagggg caaggggcac gatggccttt accagggtct cagtacagcc 1980
accaaggaca cctacgacgc ccttcacatg caggccctgc cccctcgcca gtgtactaat 2040
tatgctctct tgaaattggc tggagatgtt gagagcaacc ccgggccgat gccacctcct 2100
cgcctcctct tcttcctcct cttcctcacc cccatggaag tcaggcccga ggaacctcta 2160
gtggtgaagg tggaagaggg agataacgct gtgctgcagt gcctcaaggg gacctcagat 2220

```
ggccccactc agcagctgac ctggtctcgg gagtccccgc ttaaaccctt cttaaaactc   2280

agcctggggc tgccaggcct gggaatccac atgaggcccc tggccatctg gcttttcatc   2340

ttcaacgtct ctcaacagat ggggggcttc tacctgtgcc agccggggcc cccctctgag   2400

aaggcctggc agcctggctg gacagtcaat gtggagggca gcggggagct gttccggtgg   2460

aatgtttcgg acctaggtgg cctgggctgt ggcctgaaga acaggtcctc agagggcccc   2520

agctcccctt ccgggaagct catgagcccc aagctgtatg tgtgggccaa agaccgccct   2580

gagatctggg agggagagcc tccgtgtgtc ccaccgaggg acagcctgaa ccagagcctc   2640

agccaggacc tcaccatggc cctggctcc acactctggc tgtcctgtgg ggtacccct   2700

gactctgtgt ccaggggccc cctctcctgg acccatgtgc accccaaggg gcctaagtca   2760

ttgctgagcc tagagctgaa ggacgatcgc cctgccagag atatgtgggt aatggagacg   2820

ggtctgttgt tgccccgggc cacagctcaa gacgctggaa agtattattg tcaccgtggc   2880

aacctgacca tgtcattcca cctggagatc actgctcggc cagtactatg gcactggctg   2940

ctgaggactg gtggctggaa ggtctcagct gtgactttgg cttatctgat cttctgcctg   3000

tgttcccttg tgggcattct tcatcttcaa agagccctgg tcctgaggag gaaaaga      3057
```

<210> SEQ ID NO 56
<211> LENGTH: 2931
<212> TYPE: DNA
<213> ORGANISM: Artificial Sequence
<220> FEATURE:
<223> OTHER INFORMATION: Synthetic sequence

<400> SEQUENCE: 56

```
atgctgctgc tggtcacctc actgctgctg tgcgaactgc cccaccccgc cttcctgctg     60

attcccgaca ttgtgatgac tcagacacca ctgagctccc cagtgactct gggacagcca    120

gccagtatct catgcagatc tagtcagtca ctggtctaca gcgacggcaa cacctatctg    180

agctggctgc agcagcgacc aggacagcca cctagactgc tgatctacaa gatttccaat    240

aggttctctg gagtgcccga ccgctttagc ggatccggag ctggaactga tttcaccctg    300

aaaatctccc gcgtggaggc tgaagatgtg ggcgtctact attgcgtcca ggcaacccag    360

ttccctctga catttggcgg ggaactaag gtggagatca agggaggagg aggatctgga    420

ggaggaggaa gtggaggagg aggatccgaa gtgcagctgg tccagtctgg ggccgaggtg    480

aagaaacctg gagaaagtct gaagatctca tgtaaaggct ccgggtactc tttcacaagt    540

tattggattg gctgggtccg acagatgcca ggaaagggcc tggagtggat gggaatcatc    600

taccccggcg acagcgatac ccggtattct cctagttttc agggccaggt gacaatcagc    660

gcagacaagt ccattaccac agcctatctg cagtggtcaa gcctgaaagc ctctgatacc    720

gctatgtact attgtgccag gcaccctagc tacgggtcag gaagcccaaa ctttgactat    780

tggggccagg ggacactggt gactgtctcc tctgacaaaa ctcacacatg cccaccgtgc    840

ccagcacctc ctgtggcagg accgtcagtc ttcctcttcc ccccaaaacc caaggacacc    900

ctcatgatct cccggacccc tgaggtcaca tgcgtggtgg tggacgtgag ccacgaagac    960

cctgaggtca agttcaactg gtacgtggac ggcgtggagg tgcataatgc caagacaaag   1020

ccgcgggagg agcagtacca gagcacgtac cgtgtggtca gcgtcctcac cgtcctgcac   1080

caggactggc tgaatggcaa ggagtacaag tgcaaggtct ccaacaaagc cctcccagcc   1140

cccatcgaga aaaccatctc caaagccaaa gggcagcccc gagaaccaca ggtgtacacc   1200
```

```
ctgccaccat cacgagatga gctgaccaag aaccaggtca gcctgacctg cctggtcaaa   1260

ggcttctatc ccagcgacat cgccgtggag tgggagagca atgggcagcc ggagaacaac   1320

tacaagacca cgcctcccgt gctggactcc gacggctcct tcttcctcta cagcaagctc   1380

accgtggaca agagcaggtg gcagcagggg aacgtcttct catgctccgt gatgcatgag   1440

gctctgcaca accactacac gcagaagagc ctctccctgt ctcccttttg ggtgctggtg   1500

gtggttggtg gagtcctggc ttgctatagc ttgctagtaa cagtggcctt tattattttc   1560

tgggtgagag tgaagttcag caggagcgca gacgcccccg cgtaccagca gggccagaac   1620

cagctctata acgagctcaa tctaggacga agagaggagt acgatgtttt ggacaagaga   1680

cgtggccggg accctgagat gggggggaaag ccgagaagga agaaccctca ggaaggcctg   1740

tacaatgaac tgcagaaaga taagatggcg gaggcctaca gtgagattgg gatgaaaggc   1800

gagcgccgga ggggcaaggg gcacgatggc ctttaccagg gtctcagtac agccaccaag   1860

gacacctacg acgcccttca catgcaggcc ctgccccctc gccagtgtac taattatgct   1920

ctcttgaaat tggctggaga tgttgagagc aaccccgggc cgatgccacc tcctcgcctc   1980

ctcttcttcc tcctcttcct cacccccatg gaagtcaggc ccgaggaacc tctagtggtg   2040

aaggtggaag agggagataa cgctgtgctg cagtgcctca aggggacctc agatggcccc   2100

actcagcagc tgacctggtc tcgggagtcc ccgcttaaac ccttcttaaa actcagcctg   2160

gggctgccag gcctgggaat ccacatgagg cccctggcca tctggctttt catcttcaac   2220

gtctctcaac agatgggggg cttctacctg tgccagccgg ggcccccctc tgagaaggcc   2280

tggcagcctg gctggacagt caatgtggag ggcagcgggg agctgttccg gtggaatgtt   2340

tcggacctag gtggcctggg ctgtggcctg aagaacaggt cctcagaggg ccccagctcc   2400

ccttccggga agctcatgag ccccaagctg tatgtgtggg ccaaagaccg ccctgagatc   2460

tgggagggag agcctccgtg tgtcccaccg agggacagcc tgaaccagag cctcagccag   2520

gacctcacca tggcccctgg ctccacactc tggctgtcct gtggggtacc ccctgactct   2580

gtgtccaggg gcccccctctc ctggacccat gtgcacccca aggggcctaa gtcattgctg   2640

agcctagagc tgaaggacga tcgccctgcc agagatatgt gggtaatgga gacgggtctg   2700

ttgttgcccc gggccacagc tcaagacgct ggaaagtatt attgtcaccg tggcaacctg   2760

accatgtcat tccacctgga gatcactgct cggccagtac tatggcactg gctgctgagg   2820

actggtggct ggaaggtctc agctgtgact ttggcttatc tgatcttctg cctgtgttcc   2880

cttgtgggca ttcttcatct tcaaagagcc ctggtcctga ggaggaaaag a            2931
```

```
<210> SEQ ID NO 57
<211> LENGTH: 3306
<212> TYPE: DNA
<213> ORGANISM: Artificial Sequence
<220> FEATURE:
<223> OTHER INFORMATION: Synthetic sequence

<400> SEQUENCE: 57

atggagacag acacactcct gctatgggtg ctgctgctct gggttccagg ttccacaggt     60

gacattgtgc tgacccaatc tccagctatc ctgtctgcat ctccagggga gaaggtcaca    120

atgacttgca gggccagctc aagtgtaaat tacatggact ggtaccagaa gaagccagga    180

tcctccccca aaccctggat ttatgccaca tccaacctgg cttctggagt ccctgctcgc    240

ttcagtggca gtgggtctgg gacctcttac tctctcacaa tcagcagagt ggaggctgaa    300

gatgctgcca cttattactg ccagcagtgg agttttaatc cacccacgtt cggagggggg    360
```

-continued

```
accaagctgg aaataaaagg cagtactagc ggtggtggct ccgggggcgg ttccggtggg    420
ggcggcagca gcgaggtgca gctgcagcag tctggggctg agctggtgaa gcctggggcc    480
tcagtgaaga tgtcctgcaa ggcttctggc tacacattta ccagttacaa tatgcactgg    540
gtaaagcaga cacctggaca gggcctggaa tggattggag ctatttatcc aggaaatggt    600
gatacttcct acaatcagaa gttcaaaggc aaggccacat tgactgcaga caaatcctcc    660
agcacagcct acatgcagct cagcagcctg acatctgagg actctgcgga ctattactgt    720
gcaagatcta attattacgg tagtagctac tggttcttcg atgtctgggg cgcagggacc    780
acggtcaccg tctcctcact cgacgaatct aagtacggac cgccctgccc cccttgccct    840
gcccccgagt tcctgggcgg acccagcgtg ttcctgttcc cccccaagcc caaggacacc    900
ctgatgatca gccggacccc cgaggtgacc tgcgtggtgg tggacgtgag ccaggaagat    960
cccgaggtcc agttcaattg gtacgtggac ggcgtggaag tgcacaacgc caagaccaag   1020
cccagagagg aacagttcaa cagcacctac cgggtggtgt ctgtgctgac cgtgctgcac   1080
caggactggc tgaacggcaa agaatacaag tgcaaggtgt ccaacaaggg cctgcccagc   1140
agcatcgaaa agaccatcag caaggccaag ggccagcctc gcgagcccca ggtgtacacc   1200
ctgcctccct cccaggaaga gatgaccaag aaccaggtgt ccctgacctg cctggtgaag   1260
ggcttctacc ccagcgacat cgccgtggag tgggagagca acggccagcc tgagaacaac   1320
tacaagacca cccctcccgt gctggacagc gacggcagct tcttcctgta cagccggctg   1380
accgtggaca agagccggtg gcaggaaggc aacgtcttta gctgcagcgt gatgcacgag   1440
gccctgcaca accactacac ccagaagagc ctgagcctgt ccctgggcaa gatgttctgg   1500
gtgctggtgg tggtgggcgg ggtgctggcc tgctacagcc tgctggtgac agtggccttc   1560
atcatctttt gggtgcggag caagcggagc agaggcggcc acagcgacta catgaacatg   1620
acccccagac ggcctggccc cacccggaag cactaccagc cctacgcccc acccagggac   1680
tttgccgcct acagaagcaa acggggcaga aagaaactcc tgtatatatt caaacaacca   1740
tttatgagac cagtacaaac tactcaagag gaagatggct gtagctgccg atttccagaa   1800
gaagaagaag gaggatgtga actgcgggtg aagttcagca gaagcgccga cgcccctgcc   1860
taccagcagg gccagaatca gctgtacaac gagctgaacc tgggcagaag ggaagagtac   1920
gacgtcctgg ataagcggag aggccgggac cctgagatgg gcggcaagcc tcggcggaag   1980
aacccccagg aaggcctgta taacgaactg cagaaagaca agatggccga ggcctacagc   2040
gagatcggca tgaagggcga gcggaggcgg ggcaagggcc acgacggcct gtatcagggc   2100
ctgtccaccg ccaccaagga tacctacgac gccctgcaca tgcaggccct gcccccaagg   2160
ctcgagggcg gcggagaggg cagaggaagt cttctaacat gcggtgacgt ggaggagaat   2220
cccggcccta ggatgcttct cctggtgaca agccttctgc tctgtgagtt accacaccca   2280
gcattcctcc tgatcccacg caaagtgtgt aacggaatag gtattggtga atttaaagac   2340
tcactctcca taaatgctac gaatattaaa cacttcaaaa actgcacctc catcagtggc   2400
gatctccaca tcctgccggt ggcatttagg ggtgactcct tcacacatac tcctcctctg   2460
gatccacagg aactggatat tctgaaaacc gtaaaggaaa tcacagggtt tttgctgatt   2520
caggcttggc ctgaaaacag gacggacctc catgcctttg agaacctaga aatcatacgc   2580
ggcaggacca agcaacatgg tcagttttct cttgcagtcg tcagcctgaa cataacatcc   2640
ttgggattac gctccctcaa ggagataagt gatggagatg tgataatttc aggaaacaaa   2700
```

-continued aatttgtgct atgcaaatac aataaactgg aaaaaactgt ttgggacctc cggtcagaaa 2760
accaaaatta taagcaacag aggtgaaaac agctgcaagg ccacaggcca ggtctgccat 2820
gccttgtgct cccccgaggg ctgctggggc ccggagccca gggactgcgt ctcttgccgg 2880
aatgtcagcc gaggcaggga atgcgtggac aagtgcaacc ttctggaggg tgagccaagg 2940
gagtttgtgg agaactctga gtgcatacag tgccacccag agtgcctgcc tcaggccatg 3000
aacatcacct gcacaggacg gggaccagac aactgtatcc agtgtgccca ctacattgac 3060
ggcccccact gcgtcaagac ctgcccggca ggagtcatgg gagaaaacaa caccctggtc 3120
tggaagtacg cagacgccgg ccatgtgtgc cacctgtgcc atccaaactg cacctacgga 3180
tgcactgggc caggtcttga aggctgtcca acgaatgggc ctaagatccc gtccatcgcc 3240
actgggatgg tgggggccct cctcttgctg ctggtggtgg ccctggggat cggcctcttc 3300
atgtga 3306

<210> SEQ ID NO 58
<211> LENGTH: 2034
<212> TYPE: DNA
<213> ORGANISM: Artificial Sequence
<220> FEATURE:
<223> OTHER INFORMATION: Synthetic sequence

<400> SEQUENCE: 58
atggagacag acacactcct gctatgggtg ctgctgctct gggttccagg ttccacaggt 60
gacattgtgc tgacccaatc tccagctatc ctgtctgcat ctccagggga gaaggtcaca 120
atgacttgca gggccagctc aagtgtaaat tacatggact ggtaccagaa gaagccagga 180
tcctccccca aaccctggat ttatgccaca tccaacctgg cttctggagt ccctgctcgc 240
ttcagtggca gtgggtctgg gacctcttac tctctcacaa tcagcagagt ggaggctgaa 300
gatgctgcca cttattactg ccagcagtgg agttttaatc cacccacgtt cggagggggg 360
accaagctgg aaataaaagg cagtactagc ggtggtggct ccgggggcgg ttccggtggg 420
ggcggcagca gcgaggtgca gctgcagcag tctggggctg agctggtgaa gcctggggcc 480
tcagtgaaga tgtcctgcaa ggcttctggc tacacattta ccagttacaa tatgcactgg 540
gtaaagcaga cacctggaca gggcctggaa tggattggag ctatttatcc aggaaatggt 600
gatacttcct acaatcagaa gttcaaaggc aaggccacat tgactgcaga caaatcctcc 660
agcacagcct acatgcagct cagcagcctg acatctgagg actctgcgga ctattactgt 720
gcaagatcta attattacgg tagtagctac tggttcttcg atgtctgggg cgcagggacc 780
acggtcaccg tctcctcact cgacgaatct aagtacggac cgccctgccc cccttgccct 840
gcccccgagt tcctgggcgg acccagcgtg ttcctgttcc cccccaagcc caaggacacc 900
ctgatgatca gccggacccc cgaggtgacc tgcgtggtgg tggacgtgag ccaggaagat 960
cccgaggtcc agttcaattg gtacgtggac ggcgtggaag tgcacaacgc caagaccaag 1020
cccagagagg aacagttcaa cagcacctac cgggtggtgt ctgtgctgac cgtgctgcac 1080
caggactggc tgaacggcaa agaatacaag tgcaaggtgt ccaacaaggg cctgcccagc 1140
agcatcgaaa agaccatcag caaggccaag ggccagcctc gcgagcccca ggtgtacacc 1200
ctgcctccct cccaggaaga gatgaccaag aaccaggtgt ccctgacctg cctggtgaag 1260
ggcttctacc ccagcgacat cgccgtggag tgggagagca acggccagcc tgagaacaac 1320
tacaagacca cccctcccgt gctggacagc gacggcagct tcttcctgta cagccggctg 1380
accgtggaca agagccggtg gcaggaaggc aacgtcttta gctgcagcgt gatgcacgag 1440

-continued

```
gccctgcaca accactacac ccagaagagc ctgagcctgt ccctgggcaa gatgttctgg   1500

gtgctggtgg tggtgggcgg ggtgctggcc tgctacagcc tgctggtgac agtggccttc   1560

atcatctttt gggtgcggag caagcggagc agaggcggcc acagcgacta catgaacatg   1620

acccccagac ggcctggccc cacccggaag cactaccagc cctacgcccc acccagggac   1680

tttgccgcct acagaagccg ggtgaagttc agcagaagcg ccgacgcccc tgcctaccag   1740

cagggccaga atcagctgta caacgagctg aacctgggca gaagggaaga gtacgacgtc   1800

ctggataagc ggagaggccg ggaccctgag atgggcggca agcctcggcg gaagaacccc   1860

caggaaggcc tgtataacga actgcagaaa gacaagatgg ccgaggccta cagcgagatc   1920

ggcatgaagg gcgagcggag gcggggcaag ggccacgacg gcctgtatca gggcctgtcc   1980

accgccacca aggataccta cgacgccctg cacatgcagg ccctgccccc aagg         2034
```

<210> SEQ ID NO 59
<211> LENGTH: 3183
<212> TYPE: DNA
<213> ORGANISM: Artificial Sequence
<220> FEATURE:
<223> OTHER INFORMATION: Synthetic sequence

<400> SEQUENCE: 59

```
atggagacag acacactcct gctatgggtg ctgctgctct gggttccagg ttccacaggt     60

gacattgttc tctcccagtc tccagcaatc ctttctgcat ctccagggga gaaggtcaca    120

atgacttgca gggccagctc aagtttaagt ttcatgcact ggtaccagca gaagccagga    180

tcctccccca aaccctggat ttatgccaca tccaacctgg cttctggagt ccctgctcgc    240

ttcagtggca gtgggtctgg gacctcttac tctctcacaa tcagcagagt ggaggctgaa    300

gatgctgcca cttatttctg ccatcagtgg agtagtaacc cgctcacgtt cggtgctggg    360

accaagctgg agctgaaggg cagtactagc ggtggtggct ccgggggcgg ttccggtggg    420

ggcggcagca gccaggtgca actgcggcag cctggggctg agctggtgaa gcctggggcc    480

tcagtgaaga tgtcctgcaa ggcttctggc tacacattta ccagttacaa tatgcactgg    540

gtaaagcaga cacctggaca gggcctggaa tggattggag ctatttatcc aggaaatggt    600

gatacttcct acaatcagaa gttcaaaggc aaggccacat tgactgcaga caaatcctcc    660

agcacagcct acatgcagct cagcagtctg acatctgagg actctgcggt ctattactgt    720

gcaagatcgc actacggtag taactacgta gactactttg actactgggg ccaaggcacc    780

actctcacag tctcctcact cgaccccaaa tcttctgaca aaactcacac atgcccaccg    840

tgcccagcac ctcctgtggc aggaccgtca gtcttcctct tcccccaaa acccaaggac     900

accctcatga tctcccggac ccctgaggtc acatgcgtgg tggtggacgt gagccacgaa    960

gaccctgagg tcaagttcaa ctggtacgtg gacggcgtgg aggtgcataa tgccaagaca   1020

aagccgcggg aggagcagta ccagagcacg taccgtgtgg tcagcgtcct caccgtcctg   1080

caccaggact ggctgaatgg caaggagtac aagtgcaagg tctccaacaa agccctccca   1140

gcccccatcg agaaaaccat ctccaaagcc aaagggcagc cccgagaacc acaggtgtac   1200

accctgccac catcacgaga tgagctgacc aagaaccagg tcagcctgac ctgcctggtc   1260

aaaggcttct atcccagcga catcgccgtg gagtgggaga gcaatgggca gccggagaac   1320

aactacaaga ccacgcctcc cgtgctggac tccgacggct ccttcttcct ctacagcaag   1380

ctcaccgtgg acaagagcag gtggcagcag gggaacgtct tctcatgctc cgtgatgcat   1440
```

gaggctctgc acaaccacta cacgcagaag agcctctccc tgtctccctt ttgggtgctg 1500
gtggtggttg gtggagtcct ggcttgctat agcttgctag taacagtggc ctttattatt 1560
ttctgggtga ggagtaagag gagcagggga ggtcacagtg actacatgaa catgactccc 1620
cgccgccccg ggcccacccg caagcattac cagccctatg ccccaccacg cgacttcgca 1680
gcctatcgct ccaaacgggg cagaaagaaa ctcctgtata tattcaaaca accatttatg 1740
agaccagtac aaactactca agaggaagat ggctgtagct gccgatttcc agaagaagaa 1800
gaaggaggat gtgaactgag agtgaagttc agcaggagcg cagacgcccc cgcgtaccag 1860
cagggccaga accagctcta taacgagctc aatctaggac gaagagagga gtacgatgtt 1920
ttggacaaga gacgtggccg ggaccctgag atgggggga agccgagaag gaagaaccct 1980
caggaaggcc tgtacaatga actgcagaaa gataagatgg cggaggccta cagtgagatt 2040
gggatgaaag gcgagcgccg gaggggcaag gggcacgatg gcctttacca gggtctcagt 2100
acagccacca aggacaccta cgacgccctt cacatgcagg ccctgccccc tcgccagtgt 2160
actaattatg ctctcttgaa attggctgga gatgttgaga gcaaccccgg gccgatgcca 2220
cctcctcgcc tcctcttctt cctcctcttc ctcaccccca tggaagtcag gcccgaggaa 2280
cctctagtgg tgaaggtgga agagggagat aacgctgtgc tgcagtgcct caaggggacc 2340
tcagatggcc ccactcagca gctgacctgg tctcgggagt ccccgcttaa acccttctta 2400
aaactcagcc tggggctgcc aggcctggga atccacatga ggcccctggc catctggctt 2460
ttcatcttca acgtctctca acagatgggg ggcttctacc tgtgccagcc ggggcccccc 2520
tctgagaagg cctggcagcc tggctggaca gtcaatgtgg agggcagcgg ggagctgttc 2580
cggtggaatg tttcggacct aggtggcctg ggctgtggcc tgaagaacag gtcctcagag 2640
ggccccagct ccccttccgg gaagctcatg agccccaagc tgtatgtgtg ggccaaagac 2700
cgccctgaga tctgggaggg agagcctccg tgtgtcccac cgagggacag cctgaaccag 2760
agcctcagcc aggacctcac catggcccct ggctccacac tctggctgtc ctgtggggta 2820
ccccctgact ctgtgtccag gggcccccctc tcctggaccc atgtgcaccc caaggggcct 2880
aagtcattgc tgagcctaga gctgaaggac gatcgcccgg ccagagatat gtgggtaatg 2940
gagacgggtc tgttgttgcc ccgggccaca gctcaagacg ctggaaagta ttattgtcac 3000
cgtggcaacc tgaccatgtc attccacctg gagatcactg ctcggccagt actatggcac 3060
tggctgctga ggactggtgg ctggaaggtc tcagctgtga ctttggctta tctgatcttc 3120
tgcctgtgtt cccttgtggg cattcttcat cttcaaagag ccctggtcct gaggaggaaa 3180
aga 3183

<210> SEQ ID NO 60
<211> LENGTH: 3057
<212> TYPE: DNA
<213> ORGANISM: Artificial Sequence
<220> FEATURE:
<223> OTHER INFORMATION: Synthetic sequence

<400> SEQUENCE: 60
atggagacag acacactcct gctatgggtg ctgctgctct gggttccagg ttccacaggt 60
gacattgttc tctcccagtc tccagcaatc ctttctgcat ctccagggga gaaggtcaca 120
atgacttgca gggccagctc aagtttaagt ttcatgcact ggtaccagca gaagccagga 180
tcctccccca aaccctggat ttatgccaca tccaacctgg cttctggagt ccctgctcgc 240
ttcagtggca gtgggtctgg gacctcttac tctctcacaa tcagcagagt ggaggctgaa 300

```
gatgctgcca cttatttctg ccatcagtgg agtagtaacc cgctcacgtt cggtgctggg    360
accaagctgg agctgaaggg cagtactagc ggtggtggct ccgggggcgg ttccggtggg    420
ggcggcagca gccaggtgca actgcggcag cctggggctg agctggtgaa gcctggggcc    480
tcagtgaaga tgtcctgcaa ggcttctggc tacacattta ccagttacaa tatgcactgg    540
gtaaagcaga cacctggaca gggcctggaa tggattggag ctatttatcc aggaaatggt    600
gatacttcct acaatcagaa gttcaaaggc aaggccacat tgactgcaga caaatcctcc    660
agcacagcct acatgcagct cagcagtctg acatctgagg actctgcggt ctattactgt    720
gcaagatcgc actacggtag taactacgta gactactttg actactgggg ccaaggcacc    780
actctcacag tctcctcact cgaccccaaa tcttctgaca aaactcacac atgcccaccg    840
tgcccagcac ctcctgtggc aggaccgtca gtcttcctct tccccccaaa acccaaggac    900
accctcatga tctcccggac ccctgaggtc acatgcgtgg tggtggacgt gagccacgaa    960
gaccctgagg tcaagttcaa ctggtacgtg gacggcgtgg aggtgcataa tgccaagaca   1020
aagccgcggg aggagcagta ccagagcacg taccgtgtgg tcagcgtcct caccgtcctg   1080
caccaggact ggctgaatgg caaggagtac aagtgcaagg tctccaacaa agccctccca   1140
gcccccatcg agaaaaccat ctccaaagcc aaagggcagc cccgagaacc acaggtgtac   1200
accctgccac catcacgaga tgagctgacc aagaaccagg tcagcctgac ctgcctggtc   1260
aaaggcttct atcccagcga catcgccgtg gagtgggaga gcaatgggca gccggagaac   1320
aactacaaga ccacgcctcc cgtgctggac tccgacggct ccttcttcct ctacagcaag   1380
ctcaccgtgg acaagagcag gtggcagcag gggaacgtct tctcatgctc cgtgatgcat   1440
gaggctctgc acaaccacta cacgcagaag agcctctccc tgtctccctt ttgggtgctg   1500
gtggtggttg gtggagtcct ggcttgctat agcttgctag taacagtggc ctttattatt   1560
ttctgggtga ggagtaagag gagcagggga ggtcacagtg actacatgaa catgactccc   1620
cgccgccccg ggcccacccg caagcattac cagccctatg ccccaccacg cgacttcgca   1680
gcctatcgct ccagagtgaa gttcagcagg agcgcagacg cccccgcgta ccagcagggc   1740
cagaaccagc tctataacga gctcaatcta ggacgaagag aggagtacga tgttttggac   1800
aagagacgtg gccgggaccc tgagatgggg ggaaagccga gaaggaagaa ccctcaggaa   1860
ggcctgtaca atgaactgca gaaagataag atggcggagg cctacagtga gattgggatg   1920
aaaggcgagc gccggagggg caaggggcac gatggccttt accagggtct cagtacagcc   1980
accaaggaca cctacgacgc ccttcacatg caggccctgc cccctcgcca gtgtactaat   2040
tatgctctct tgaaattggc tggagatgtt gagagcaacc ccgggccgat gccacctcct   2100
cgcctcctct tcttcctcct cttcctcacc cccatggaag tcaggcccga ggaacctcta   2160
gtggtgaagg tggaagaggg agataacgct gtgctgcagt gcctcaaggg gacctcagat   2220
ggccccactc agcagctgac ctggtctcgg gagtccccgc ttaaaccctt cttaaaactc   2280
agcctggggc tgccaggcct gggaatccac atgaggcccc tggccatctg gcttttcatc   2340
ttcaacgtct ctcaacagat gggggcttc tacctgtgcc agccggggcc cccctctgag   2400
aaggcctggc agcctggctg gacagtcaat gtggagggca gcggggagct gttccggtgg   2460
aatgtttcgg acctaggtgg cctgggctgt ggcctgaaga acaggtcctc agagggcccc   2520
agctcccctt ccgggaagct catgagcccc aagctgtatg tgtgggccaa agaccgccct   2580
gagatctggg agggagagcc tccgtgtgtc ccaccgaggg acagcctgaa ccagagcctc   2640
```

-continued

```
agccaggacc tcaccatggc ccctggctcc acactctggc tgtcctgtgg ggtacccccct   2700

gactctgtgt ccaggggccc cctctcctgg acccatgtgc accccaaggg gcctaagtca   2760

ttgctgagcc tagagctgaa ggacgatcgc ccggccagag atatgtgggt aatggagacg   2820

ggtctgttgt tgccccgggc cacagctcaa gacgctggaa agtattattg tcaccgtggc   2880

aacctgacca tgtcattcca cctggagatc actgctcggc cagtactatg gcactggctg   2940

ctgaggactg gtggctggaa ggtctcagct gtgactttgg cttatctgat cttctgcctg   3000

tgttcccttg tgggcattct tcatcttcaa agagccctgg tcctgaggag gaaaaga      3057
```

<210> SEQ ID NO 61
<211> LENGTH: 3060
<212> TYPE: DNA
<213> ORGANISM: Artificial Sequence
<220> FEATURE:
<223> OTHER INFORMATION: Synthetic sequence

<400> SEQUENCE: 61

```
atggagacag acacactcct gctatgggtg ctgctgctct gggttccagg ttccacaggt     60

gacattgttc tctcccagtc tccagcaatc ctttctgcat ctccagggga gaaggtcaca    120

atgacttgca gggccagctc aagtttaagt ttcatgcact ggtaccagca gaagccagga    180

tcctccccca aaccctggat ttatgccaca tccaacctgg cttctggagt ccctgctcgc    240

ttcagtggca gtgggtctgg gacctcttac tctctcacaa tcagcagagt ggaggctgaa    300

gatgctgcca cttatttctg ccatcagtgg agtagtaacc cgctcacgtt cggtgctggg    360

accaagctgg agctgaaggg cagtactagc ggtggtggct ccgggggcgg ttccggtggg    420

ggcggcagca gccaggtgca actgcggcag cctggggctg agctggtgaa gcctggggcc    480

tcagtgaaga tgtcctgcaa ggcttctggc tacacattta ccagttacaa tatgcactgg    540

gtaaagcaga cacctggaca gggcctggaa tggattggag ctatttatcc aggaaatggt    600

gatacttcct acaatcagaa gttcaaaggc aaggccacat tgactgcaga caaatcctcc    660

agcacagcct acatgcagct cagcagtctg acatctgagg actctgcggt ctattactgt    720

gcaagatcgc actacggtag taactacgta gactactttg actactgggg ccaaggcacc    780

actctcacag tctcctcact cgaccccaaa tcttctgaca aaactcacac atgcccaccg    840

tgcccagcac ctcctgtggc aggaccgtca gtcttcctct tcccccccaaa acccaaggac    900

accctcatga tctcccggac ccctgaggtc acatgcgtgg tggtggacgt gagccacgaa    960

gaccctgagg tcaagttcaa ctggtacgtg gacggcgtgg aggtgcataa tgccaagaca   1020

aagccgcggg aggagcagta ccagagcacg taccgtgtgg tcagcgtcct caccgtcctg   1080

caccaggact ggctgaatgg caaggagtac aagtgcaagg tctccaacaa agccctccca   1140

gcccccatcg agaaaaccat ctccaaagcc aaagggcagc cccgagaacc acaggtgtac   1200

accctgccac catcacgaga tgagctgacc aagaaccagg tcagcctgac ctgcctggtc   1260

aaaggcttct atcccagcga catcgccgtg gagtgggaga gcaatgggca gccggagaac   1320

aactacaaga ccacgcctcc cgtgctggac tccgacggct ccttcttcct ctacagcaag   1380

ctcaccgtgg acaagagcag gtggcagcag gggaacgtct tctcatgctc cgtgatgcat   1440

gaggctctgc acaaccacta cacgcagaag agcctctccc tgtctccctt ttgggtgctg   1500

gtggtggttg gtggagtcct ggcttgctat agcttgctag taacagtggc ctttattatt   1560

ttctgggtga aacggggcag aaagaaactc ctgtatatat tcaaacaacc atttatgaga   1620

ccagtacaaa ctactcaaga ggaagatggc tgtagctgcc gatttccaga agaagaagaa   1680
```

```
ggaggatgtg aactgagagt gaagttcagc aggagcgcag acgcccccgc gtaccagcag   1740

ggccagaacc agctctataa cgagctcaat ctaggacgaa gagaggagta cgatgttttg   1800

gacaagagac gtggccggga ccctgagatg gggggaaagc cgagaaggaa gaaccctcag   1860

gaaggcctgt acaatgaact gcagaaagat aagatggcgg aggcctacag tgagattggg   1920

atgaaaggcg agcgccggag gggcaagggg cacgatggcc tttaccaggg tctcagtaca   1980

gccaccaagg acacctacga cgcccttcac atgcaggccc tgccccctcg ccagtgtact   2040

aattatgctc tcttgaaatt ggctggagat gttgagagca accccgggcc gatgccacct   2100

cctcgcctcc tcttcttcct cctcttcctc acccccatgg aagtcaggcc cgaggaacct   2160

ctagtggtga aggtggaaga gggagataac gctgtgctgc agtgcctcaa ggggacctca   2220

gatggcccca ctcagcagct gacctggtct cgggagtccc cgcttaaacc cttcttaaaa   2280

ctcagcctgg ggctgccagg cctgggaatc cacatgaggc ccctggccat ctggcttttc   2340

atcttcaacg tctctcaaca gatggggggc ttctacctgt gccagccggg gccccccctct   2400

gagaaggcct ggcagcctgg ctggacagtc aatgtggagg gcagcgggga gctgttccgg   2460

tggaatgttt cggacctagg tggcctgggc tgtggcctga agaacaggtc ctcagagggc   2520

cccagctccc cttccgggaa gctcatgagc cccaagctgt atgtgtgggc caaagaccgc   2580

cctgagatct gggagggaga gcctccgtgt gtcccaccga gggacagcct gaaccagagc   2640

ctcagccagg acctcaccat ggcccctggc tccacactct ggctgtcctg tggggtaccc   2700

cctgactctg tgtccagggg cccccctctcc tggacccatg tgcaccccaa ggggcctaag   2760

tcattgctga gcctagagct gaaggacgat cgcccggcca gagatatgtg ggtaatggag   2820

acgggtctgt tgttgccccg ggccacagct caagacgctg gaaagtatta ttgtcaccgt   2880

ggcaacctga ccatgtcatt ccacctggag atcactgctc ggccagtact atggcactgg   2940

ctgctgagga ctggtggctg gaaggtctca gctgtgactt tggcttatct gatcttctgc   3000

ctgtgttccc ttgtgggcat tcttcatctt caaagagccc tggtcctgag gaggaaaaga   3060
```

<210> SEQ ID NO 62
<211> LENGTH: 8
<212> TYPE: PRT
<213> ORGANISM: Artificial Sequence
<220> FEATURE:
<223> OTHER INFORMATION: Synthetic sequence

<400> SEQUENCE: 62

```
Trp Ser His Pro Gln Phe Glu Lys
1               5
```

<210> SEQ ID NO 63
<211> LENGTH: 8
<212> TYPE: PRT
<213> ORGANISM: Artificial Sequence
<220> FEATURE:
<223> OTHER INFORMATION: Synthetic sequence

<400> SEQUENCE: 63

```
Trp Arg His Pro Gln Phe Gly Gly
1               5
```

<210> SEQ ID NO 64
<211> LENGTH: 249
<212> TYPE: PRT
<213> ORGANISM: Artificial Sequence
<220> FEATURE:

<223> OTHER INFORMATION: Synthetic sequence

<400> SEQUENCE: 64

Asp Ile Val Met Thr Gln Thr Pro Leu Ser Ser Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Ser Trp Leu Gln Gln Arg Pro Gly Gln Pro
35 40 45

Pro Arg Leu Leu Ile Tyr Lys Ile Ser Asn Arg Phe Ser Gly Val Pro
50 55 60

Asp Arg Phe Ser Gly Ser Gly Ala Gly Thr Asp Phe Thr Leu Lys Ile
65 70 75 80

Ser Arg Val Glu Ala Glu Asp Val Gly Val Tyr Tyr Cys Val Gln Ala
85 90 95

Thr Gln Phe Pro Leu Thr Phe Gly Gly Gly Thr Lys Val Glu Ile Lys
100 105 110

Gly Gly Gly Gly Ser Gly Gly Gly Gly Ser Gly Gly Gly Gly Ser Glu
115 120 125

Val Gln Leu Val Gln Ser Gly Ala Glu Val Lys Lys Pro Gly Glu Ser
130 135 140

Leu Lys Ile Ser Cys Lys Gly Ser Gly Tyr Ser Phe Thr Ser Tyr Trp
145 150 155 160

Ile Gly Trp Val Arg Gln Met Pro Gly Lys Gly Leu Glu Trp Met Gly
165 170 175

Ile Ile Tyr Pro Gly Asp Ser Asp Thr Arg Tyr Ser Pro Ser Phe Gln
180 185 190

Gly Gln Val Thr Ile Ser Ala Asp Lys Ser Ile Thr Thr Ala Tyr Leu
195 200 205

Gln Trp Ser Ser Leu Lys Ala Ser Asp Thr Ala Met Tyr Tyr Cys Ala
210 215 220

Arg His Pro Ser Tyr Gly Ser Gly Ser Pro Asn Phe Asp Tyr Trp Gly
225 230 235 240

Gln Gly Thr Leu Val Thr Val Ser Ser
245

<210> SEQ ID NO 65
<211> LENGTH: 252
<212> TYPE: PRT
<213> ORGANISM: Artificial Sequence
<220> FEATURE:
<223> OTHER INFORMATION: Synthetic sequence

<400> SEQUENCE: 65

Asp Ile Val Leu Thr Gln Ser Pro Ala Ile Leu Ser Ala Ser Pro Gly
1 5 10 15

Glu Lys Val Thr Met Thr Cys Arg Ala Ser Ser Ser Val Asn Tyr Met
20 25 30

Asp Trp Tyr Gln Lys Lys Pro Gly Ser Ser Pro Lys Pro Trp Ile Tyr
35 40 45

Ala Thr Ser Asn Leu Ala Ser Gly Val Pro Ala Arg Phe Ser Gly Ser
50 55 60

Gly Ser Gly Thr Ser Tyr Ser Leu Thr Ile Ser Arg Val Glu Ala Glu
65 70 75 80

Asp Ala Ala Thr Tyr Tyr Cys Gln Gln Trp Ser Phe Asn Pro Pro Thr
85 90 95

```
Phe Gly Gly Gly Thr Lys Leu Glu Ile Lys Gly Ser Thr Ser Gly Gly
            100                 105                 110

Gly Ser Gly Gly Gly Ser Gly Gly Gly Gly Ser Ser Glu Val Gln Leu
        115                 120                 125

Gln Gln Ser Gly Ala Glu Leu Val Lys Pro Gly Ala Ser Val Lys Met
    130                 135                 140

Ser Cys Lys Ala Ser Gly Tyr Thr Phe Thr Ser Tyr Asn Met His Trp
145                 150                 155                 160

Val Lys Gln Thr Pro Gly Gln Gly Leu Glu Trp Ile Gly Ala Ile Tyr
                165                 170                 175

Pro Gly Asn Gly Asp Thr Ser Tyr Asn Gln Lys Phe Lys Gly Lys Ala
            180                 185                 190

Thr Leu Thr Ala Asp Lys Ser Ser Ser Thr Ala Tyr Met Gln Leu Ser
        195                 200                 205

Ser Leu Thr Ser Glu Asp Ser Ala Asp Tyr Tyr Cys Ala Arg Ser Asn
    210                 215                 220

Tyr Tyr Gly Ser Ser Tyr Trp Phe Phe Asp Val Trp Gly Ala Gly Thr
225                 230                 235                 240

Thr Val Thr Val Ser Ser Leu Asp Glu Ser Lys Tyr
                245                 250


<210> SEQ ID NO 66
<211> LENGTH: 252
<212> TYPE: PRT
<213> ORGANISM: Artificial Sequence
<220> FEATURE:
<223> OTHER INFORMATION: Synthetic sequence

<400> SEQUENCE: 66

Asp Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Leu Ser Phe Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Phe Cys His Gln Trp Ser Ser Asn Pro Leu Thr
                85                  90                  95

Phe Gly Ala Gly Thr Lys Leu Glu Leu Lys Gly Ser Thr Ser Gly Gly
            100                 105                 110

Gly Ser Gly Gly Gly Ser Gly Gly Gly Gly Ser Ser Gln Val Gln Leu
        115                 120                 125

Arg Gln Pro Gly Ala Glu Leu Val Lys Pro Gly Ala Ser Val Lys Met
    130                 135                 140

Ser Cys Lys Ala Ser Gly Tyr Thr Phe Thr Ser Tyr Asn Met His Trp
145                 150                 155                 160

Val Lys Gln Thr Pro Gly Gln Gly Leu Glu Trp Ile Gly Ala Ile Tyr
                165                 170                 175

Pro Gly Asn Gly Asp Thr Ser Tyr Asn Gln Lys Phe Lys Gly Lys Ala
            180                 185                 190

Thr Leu Thr Ala Asp Lys Ser Ser Ser Thr Ala Tyr Met Gln Leu Ser
        195                 200                 205
```

Ser Leu Thr Ser Glu Asp Ser Ala Val Tyr Tyr Cys Ala Arg Ser His
    210                 215                 220

Tyr Gly Ser Asn Tyr Val Asp Tyr Phe Asp Tyr Trp Gly Gln Gly Thr
225                 230                 235                 240

Thr Leu Thr Val Ser Ser Leu Asp Pro Lys Ser Ser
                245                 250

<210> SEQ ID NO 67
<211> LENGTH: 747
<212> TYPE: DNA
<213> ORGANISM: Artificial Sequence
<220> FEATURE:
<223> OTHER INFORMATION: Synthetic sequence

<400> SEQUENCE: 67
gacattgtga tgactcagac accactgagc tccccagtga ctctgggaca gccagccagt 60
atctcatgca gatctagtca gtcactggtc tacagcgacg gcaacaccta tctgagctgg 120
ctgcagcagc gaccaggaca gccacctaga ctgctgatct acaagatttc caataggttc 180
tctggagtgc ccgaccgctt tagcggatcc ggagctggaa ctgatttcac cctgaaaatc 240
tcccgcgtgg aggctgaaga tgtgggcgtc tactattgcg tccaggcaac ccagttccct 300
ctgacatttg gcgggggaac taaggtggag atcaagggag gaggaggatc tggaggagga 360
ggaagtggag gaggaggatc cgaagtgcag ctggtccagt ctggggccga ggtgaagaaa 420
cctggagaaa gtctgaagat ctcatgtaaa ggctccgggt actctttcac aagttattgg 480
attggctggg tccgacagat gccaggaaag ggcctggagt ggatgggaat catctacccc 540
ggcgacagcg atacccggta ttctcctagt tttcagggcc aggtgacaat cagcgcagac 600
aagtccatta ccacagccta tctgcagtgg tcaagcctga aagcctctga taccgctatg 660
tactattgtg ccaggcaccc tagctacggg tcaggaagcc caaactttga ctattggggc 720
caggggacac tggtgactgt ctcctct 747

<210> SEQ ID NO 68
<211> LENGTH: 756
<212> TYPE: DNA
<213> ORGANISM: Artificial Sequence
<220> FEATURE:
<223> OTHER INFORMATION: Synthetic sequence

<400> SEQUENCE: 68
gacattgtgc tgacccaatc tccagctatc ctgtctgcat ctccagggga gaaggtcaca 60
atgacttgca gggccagctc aagtgtaaat tacatggact ggtaccagaa gaagccagga 120
tcctccccca aaccctggat ttatgccaca tccaacctgg cttctggagt ccctgctcgc 180
ttcagtggca gtgggtctgg gacctcttac tctctcacaa tcagcagagt ggaggctgaa 240
gatgctgcca cttattactg ccagcagtgg agttttaatc cacccacgtt cggagggggg 300
accaagctgg aaataaaagg cagtactagc ggtggtggct ccgggggcgg ttccggtggg 360
ggcggcagca gcgaggtgca gctgcagcag tctggggctg agctggtgaa gcctggggcc 420
tcagtgaaga tgtcctgcaa ggcttctggc tacacattta ccagttacaa tatgcactgg 480
gtaaagcaga cacctggaca gggcctggaa tggattggag ctatttatcc aggaaatggt 540
gatacttcct acaatcagaa gttcaaaggc aaggccacat tgactgcaga caaatcctcc 600
agcacagcct acatgcagct cagcagcctg acatctgagg actctgcgga ctattactgt 660
gcaagatcta attattacgg tagtagctac tggttcttcg atgtctgggg cgcagggacc 720
acggtcaccg tctcctcact cgacgaatct aagtac 756

<210> SEQ ID NO 69
<211> LENGTH: 738
<212> TYPE: DNA
<213> ORGANISM: Artificial Sequence
<220> FEATURE:
<223> OTHER INFORMATION: Synthetic sequence

<400> SEQUENCE: 69
gacattgttc tctcccagtc tccagcaatc ctttctgcat ctccagggga gaaggtcaca 60
atgacttgca gggccagctc aagtttaagt ttcatgcact ggtaccagca gaagccagga 120
tcctccccca aaccctggat ttatgccaca tccaacctgg cttctggagt ccctgctcgc 180
ttcagtggca gtgggtctgg gacctcttac tctctcacaa tcagcagagt ggaggctgaa 240
gatgctgcca cttatttctg ccatcagtgg agtagtaacc cgctcacgtt cggtgctggg 300
accaagctgg agctgaaggg cagtactagc ggtggtggct ccgggggcgg ttccggtggg 360
ggcggcagca gccaggtgca actgcggcag cctggggctg agctggtgaa gcctggggcc 420
tcagtgaaga tgtcctgcaa ggcttctggc tacacattta ccagttacaa tatgcactgg 480
gtaaagcaga cacctggaca gggcctggaa tggattggag ctatttatcc aggaaatggt 540
gatacttcct acaatcagaa gttcaaaggc aaggccacat tgactgcaga caaatcctcc 600
agcacagcct acatgcagct cagcagtctg acatctgagg actctgcggt ctattactgt 660
gcaagatcgc actacggtag taactacgta gactactttg actactgggg ccaaggcacc 720
actctcacag tctcctca 738

<210> SEQ ID NO 70
<211> LENGTH: 336
<212> TYPE: DNA
<213> ORGANISM: Artificial Sequence
<220> FEATURE:
<223> OTHER INFORMATION: Synthetic sequence

<400> SEQUENCE: 70
gacattgtga tgactcagac accactgagc tccccagtga ctctgggaca gccagccagt 60
atctcatgca gatctagtca gtcactggtc tacagcgacg gcaacaccta tctgagctgg 120
ctgcagcagc gaccaggaca gccacctaga ctgctgatct acaagatttc caataggttc 180
tctggagtgc ccgaccgctt tagcggatcc ggagctggaa ctgatttcac cctgaaaatc 240
tcccgcgtgg aggctgaaga tgtgggcgtc tactattgcg tccaggcaac ccagttccct 300
ctgacatttg gcgggggaac taaggtggag atcaag 336

<210> SEQ ID NO 71
<211> LENGTH: 318
<212> TYPE: DNA
<213> ORGANISM: Artificial Sequence
<220> FEATURE:
<223> OTHER INFORMATION: Synthetic sequence

<400> SEQUENCE: 71
gacattgtgc tgacccaatc tccagctatc ctgtctgcat ctccagggga gaaggtcaca 60
atgacttgca gggccagctc aagtgtaaat tacatggact ggtaccagaa gaagccagga 120
tcctccccca aaccctggat ttatgccaca tccaacctgg cttctggagt ccctgctcgc 180

-continued

```
ttcagtggca gtgggtctgg gacctcttac tctctcacaa tcagcagagt ggaggctgaa    240

gatgctgcca cttattactg ccagcagtgg agttttaatc cacccacgtt cggagggggg    300

accaagctgg aaataaaa                                                  318
```

<210> SEQ ID NO 72
<211> LENGTH: 318
<212> TYPE: DNA
<213> ORGANISM: Artificial Sequence
<220> FEATURE:
<223> OTHER INFORMATION: Synthetic sequence

<400> SEQUENCE: 72

```
gacattgttc tctcccagtc tccagcaatc ctttctgcat ctccagggga gaaggtcaca     60

atgacttgca gggccagctc aagtttaagt ttcatgcact ggtaccagca gaagccagga    120

tcctccccca aaccctggat ttatgccaca tccaacctgg cttctggagt ccctgctcgc    180

ttcagtggca gtgggtctgg gacctcttac tctctcacaa tcagcagagt ggaggctgaa    240

gatgctgcca cttatttctg ccatcagtgg agtagtaacc cgctcacgtt cggtgctggg    300

accaagctgg agctgaag                                                  318
```

<210> SEQ ID NO 73
<211> LENGTH: 366
<212> TYPE: DNA
<213> ORGANISM: Artificial Sequence
<220> FEATURE:
<223> OTHER INFORMATION: Synthetic sequence

<400> SEQUENCE: 73

```
gaagtgcagc tggtccagtc tggggccgag gtgaagaaac ctggagaaag tctgaagatc     60

tcatgtaaag gctccgggta ctctttcaca agttattgga ttggctgggt ccgacagatg    120

ccaggaaagg gcctggagtg gatgggaatc atctaccccg gcgacagcga tacccggtat    180

tctcctagtt ttcagggcca ggtgacaatc agcgcagaca agtccattac cacagcctat    240

ctgcagtggt caagcctgaa agcctctgat accgctatgt actattgtgc caggcaccct    300

agctacgggt caggaagccc aaactttgac tattggggcc aggggacact ggtgactgtc    360

tcctct                                                               366
```

<210> SEQ ID NO 74
<211> LENGTH: 384
<212> TYPE: DNA
<213> ORGANISM: Artificial Sequence
<220> FEATURE:
<223> OTHER INFORMATION: Synthetic sequence

<400> SEQUENCE: 74

```
gaggtgcagc tgcagcagtc tggggctgag ctggtgaagc ctggggcctc agtgaagatg     60

tcctgcaagg cttctggcta cacatttacc agttacaata tgcactgggt aaagcagaca    120

cctggacagg gcctggaatg gattggagct atttatccag gaaatggtga tacttcctac    180

aatcagaagt tcaaaggcaa ggccacattg actgcagaca aatcctccag cacagcctac    240

atgcagctca gcagcctgac atctgaggac tctgcggact attactgtgc aagatctaat    300

tattacggta gtagctactg gttcttcgat gtctggggcg cagggaccac ggtcaccgtc    360

tcctcactcg acgaatctaa gtac                                           384
```

<210> SEQ ID NO 75
<211> LENGTH: 366

<212> TYPE: DNA
<213> ORGANISM: Artificial Sequence
<220> FEATURE:
<223> OTHER INFORMATION: Synthetic sequence

<400> SEQUENCE: 75
caggtgcaac tgcggcagcc tggggctgag ctggtgaagc ctggggcctc agtgaagatg 60
tcctgcaagg cttctggcta cacatttacc agttacaata tgcactgggt aaagcagaca 120
cctggacagg gcctggaatg gattggagct atttatccag gaaatggtga tacttcctac 180
aatcagaagt tcaaaggcaa ggccacattg actgcagaca aatcctccag cacagcctac 240
atgcagctca gcagtctgac atctgaggac tctgcggtct attactgtgc aagatcgcac 300
tacggtagta actacgtaga ctactttgac tactggggcc aaggcaccac tctcacagtc 360
tcctca 366

<210> SEQ ID NO 76
<211> LENGTH: 36
<212> TYPE: DNA
<213> ORGANISM: Homo sapiens

<400> SEQUENCE: 76
gacaaaactc acacatgccc accgtgccca gcacct 36

<210> SEQ ID NO 77
<211> LENGTH: 24
<212> TYPE: DNA
<213> ORGANISM: Homo sapiens

<400> SEQUENCE: 77
ggaccgccct gcccccccttg ccct 24

<210> SEQ ID NO 78
<211> LENGTH: 18
<212> TYPE: DNA
<213> ORGANISM: Homo sapiens

<400> SEQUENCE: 78
cctgtggcag gaccgtca 18

<210> SEQ ID NO 79
<211> LENGTH: 303
<212> TYPE: DNA
<213> ORGANISM: Artificial Sequence
<220> FEATURE:
<223> OTHER INFORMATION: Synthetic sequence

<400> SEQUENCE: 79
gtcttcctct tcccccccaaa acccaaggac accctcatga tctcccggac ccctgaggtc 60
acatgcgtgg tggtggacgt gagccacgaa gaccctgagg tcaagttcaa ctggtacgtg 120
gacggcgtgg aggtgcataa tgccaagaca aagccgcggg aggagcagta ccagagcacg 180
taccgtgtgg tcagcgtcct caccgtcctg caccaggact ggctgaatgg caaggagtac 240
aagtgcaagg tctccaacaa agccctccca gcccccatcg agaaaaccat ctccaaagcc 300
aaa 303

<210> SEQ ID NO 80
<211> LENGTH: 330
<212> TYPE: DNA
<213> ORGANISM: Homo sapiens

<400> SEQUENCE: 80
gcccccgagt tcctgggcgg acccagcgtg ttcctgttcc cccccaagcc caaggacacc 60
ctgatgatca gccggacccc cgaggtgacc tgcgtggtgg tggacgtgag ccaggaagat 120
cccgaggtcc agttcaattg gtacgtggac ggcgtggaag tgcacaacgc caagaccaag 180
cccagagagg aacagttcaa cagcacctac cgggtggtgt ctgtgctgac cgtgctgcac 240
caggactggc tgaacggcaa agaatacaag tgcaaggtgt ccaacaaggg cctgcccagc 300
agcatcgaaa agaccatcag caaggccaag 330

<210> SEQ ID NO 81
<211> LENGTH: 315
<212> TYPE: DNA
<213> ORGANISM: Homo sapiens

<400> SEQUENCE: 81
gggcagcccc gagaaccaca ggtgtacacc ctgccaccat cacgagatga gctgaccaag 60
aaccaggtca gcctgacctg cctggtcaaa ggcttctatc ccagcgacat cgccgtggag 120
tgggagagca atgggcagcc ggagaacaac tacaagacca cgcctcccgt gctggactcc 180
gacggctcct tcttcctcta cagcaagctc accgtggaca agagcaggtg gcagcagggg 240
aacgtcttct catgctccgt gatgcatgag gctctgcaca accactacac gcagaagagc 300
ctctccctgt ctccc 315

<210> SEQ ID NO 82
<211> LENGTH: 321
<212> TYPE: DNA
<213> ORGANISM: Homo sapiens

<400> SEQUENCE: 82
ggccagcctc gcgagcccca ggtgtacacc ctgcctccct cccaggaaga gatgaccaag 60
aaccaggtgt ccctgacctg cctggtgaag ggcttctacc ccagcgacat cgccgtggag 120
tgggagagca acggccagcc tgagaacaac tacaagacca cccctcccgt gctggacagc 180
gacggcagct tcttcctgta cagccggctg accgtggaca agagccggtg gcaggaaggc 240
aacgtcttta gctgcagcgt gatgcacgag gccctgcaca accactacac ccagaagagc 300
ctgagcctgt ccctgggcaa g 321

<210> SEQ ID NO 83
<211> LENGTH: 84
<212> TYPE: DNA
<213> ORGANISM: Homo sapiens

<400> SEQUENCE: 83
atgttctggg tgctggtggt ggtgggcggg gtgctggcct gctacagcct gctggtgaca 60
gtggccttca tcatcttttg ggtg 84

<210> SEQ ID NO 84
<211> LENGTH: 123
<212> TYPE: DNA
<213> ORGANISM: Artificial Sequence
<220> FEATURE:
<223> OTHER INFORMATION: Synthetic sequence -continued

<400> SEQUENCE: 84
cggagcaagc ggagcagagg cggccacagc gactacatga acatgacccc cagacggcct 60
ggccccaccc ggaagcacta ccagccctac gccccaccca gggactttgc cgcctacaga 120
agc 123

<210> SEQ ID NO 85
<211> LENGTH: 126
<212> TYPE: DNA
<213> ORGANISM: Homo sapiens

<400> SEQUENCE: 85
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 86
<211> LENGTH: 336
<212> TYPE: DNA
<213> ORGANISM: Homo sapiens

<400> SEQUENCE: 86
cgggtgaagt tcagcagaag cgccgacgcc cctgcctacc agcagggcca gaatcagctg 60
tacaacgagc tgaacctggg cagaagggaa gagtacgacg tcctggataa gcggagaggc 120
cgggaccctg agatgggcgg caagcctcgg cggaagaacc cccaggaagg cctgtataac 180
gaactgcaga aagacaagat ggccgaggcc tacagcgaga tcggcatgaa gggcgagcgg 240
aggcggggca agggccacga cggcctgtat cagggcctgt ccaccgccac caaggatacc 300
tacgacgccc tgcacatgca ggccctgccc ccaagg 336

<210> SEQ ID NO 87
<211> LENGTH: 66
<212> TYPE: DNA
<213> ORGANISM: Homo sapiens

<400> SEQUENCE: 87
atgctgctgc tggtcacctc actgctgctg tgcgaactgc cccaccccgc cttcctgctg 60
attccc 66

<210> SEQ ID NO 88
<211> LENGTH: 60
<212> TYPE: DNA
<213> ORGANISM: Mus musculus

<400> SEQUENCE: 88
atggagacag acacactcct gctatgggtg ctgctgctct gggttccagg ttccacaggt 60

<210> SEQ ID NO 89
<211> LENGTH: 45
<212> TYPE: DNA
<213> ORGANISM: Artificial Sequence
<220> FEATURE:
<223> OTHER INFORMATION: Synthetic sequence

<400> SEQUENCE: 89
ggaggaggag gatctggagg aggaggaagt ggaggaggag gatcc 45

<210> SEQ ID NO 90

<211> LENGTH: 54
<212> TYPE: DNA
<213> ORGANISM: Artificial Sequence
<220> FEATURE:
<223> OTHER INFORMATION: Synthetic sequence

<400> SEQUENCE: 90
ggcagtacta gcggtggtgg ctccgggggc ggttccggtg gggcggcag cagc 54

<210> SEQ ID NO 91
<211> LENGTH: 60
<212> TYPE: DNA
<213> ORGANISM: unknown
<220> FEATURE:
<223> OTHER INFORMATION: E2A self-cleaving peptide

<400> SEQUENCE: 91
cagtgtacta attatgctct cttgaaattg gctggagatg ttgagagcaa ccccgggccg 60

<210> SEQ ID NO 92
<211> LENGTH: 71
<212> TYPE: DNA
<213> ORGANISM: unknown
<220> FEATURE:
<223> OTHER INFORMATION: T2A self-cleaving peptide

<400> SEQUENCE: 92
tcgagggcgg cggagagggc agaggaagtc ttctaacatg cggtgacgtg gaggagaatc 60
ccggccctag g 71

<210> SEQ ID NO 93
<211> LENGTH: 969
<212> TYPE: DNA
<213> ORGANISM: Artificial Sequence
<220> FEATURE:
<223> OTHER INFORMATION: Synthetic sequence

<400> SEQUENCE: 93
atgccacctc ctcgcctcct cttcttcctc ctcttcctca cccccatgga agtcaggccc 60
gaggaacctc tagtggtgaa ggtggaagag ggagataacg ctgtgctgca gtgcctcaag 120
gggacctcag atggccccac tcagcagctg acctggtctc gggagtcccc gcttaaaccc 180
ttcttaaaac tcagcctggg gctgccaggc ctgggaatcc acatgaggcc cctggccatc 240
tggcttttca tcttcaacgt ctctcaacag atgggggggct tctacctgtg ccagccgggg 300 ccccctctg agaaggcctg gcagcctggc tggacagtca atgtggaggg cagcggggag 360
ctgttccggt ggaatgtttc ggacctaggt ggcctgggct gtggcctgaa gaacaggtcc 420
tcagagggcc ccagctcccc ttccgggaag ctcatgagcc ccaagctgta tgtgtgggcc 480
aaagaccgcc ctgagatctg ggagggagag cctccgtgtg tcccaccgag ggacagcctg 540
aaccagagcc tcagccagga cctcaccatg gcccctggct ccacactctg gctgtcctgt 600
ggggtacccc ctgactctgt gtccaggggc cccctctcct ggacccatgt gcaccccaag 660
gggcctaagt cattgctgag cctagagctg aaggacgatc gcccggccag agatatgtgg 720
gtaatggaga cgggtctgtt gttgccccgg gccacagctc aagacgctgg aaagtattat 780
tgtcaccgtg gcaacctgac catgtcattc cacctggaga tcactgctcg gccagtacta 840
tggcactggc tgctgaggac tggtggctgg aaggtctcag ctgtgacttt ggcttatctg 900
atcttctgcc tgtgttccct tgtgggcatt cttcatcttc aaagagccct ggtcctgagg 960
aggaaaaga 969

<210> SEQ ID NO 94
<211> LENGTH: 1074
<212> TYPE: DNA
<213> ORGANISM: Artificial Sequence
<220> FEATURE:
<223> OTHER INFORMATION: Synthetic sequence

<400> SEQUENCE: 94

```
atgcttctcc tggtgacaag ccttctgctc tgtgagttac cacacccagc attcctcctg     60

atcccacgca aagtgtgtaa cggaataggt attggtgaat ttaaagactc actctccata    120

aatgctacga atattaaaca cttcaaaaac tgcacctcca tcagtggcga tctccacatc    180

ctgccggtgg catttagggg tgactccttc acacatactc ctcctctgga tccacaggaa    240

ctggatattc tgaaaaccgt aaaggaaatc acagggtttt tgctgattca ggcttggcct    300

gaaaacagga cggacctcca tgcctttgag aacctagaaa tcatacgcgg caggaccaag    360

caacatggtc agttttctct tgcagtcgtc agcctgaaca taacatcctt gggattacgc    420

tccctcaagg agataagtga tggagatgtg ataatttcag gaaacaaaaa tttgtgctat    480

gcaaatacaa taaactggaa aaaactgttt gggacctccg gtcagaaaac caaaattata    540

agcaacagag gtgaaaacag ctgcaaggcc acaggccagg tctgccatgc cttgtgctcc    600

cccgagggct gctggggccc ggagcccagg gactgcgtct cttgccggaa tgtcagccga    660

ggcagggaat gcgtggacaa gtgcaacctt ctggagggtg agccaaggga gtttgtggag    720

aactctgagt gcatacagtg ccacccagag tgcctgcctc aggccatgaa catcacctgc    780

acaggacggg gaccagacaa ctgtatccag tgtgcccact acattgacgg cccccactgc    840

gtcaagacct gcccggcagg agtcatggga gaaaacaaca ccctggtctg gaagtacgca    900

gacgccggcc atgtgtgcca cctgtgccat ccaaactgca cctacggatg cactgggcca    960

ggtcttgaag gctgtccaac gaatgggcct aagatcccgt ccatcgccac tgggatggtg   1020

ggggccctcc tcttgctgct ggtggtggcc ctggggatcg gcctcttcat gtga         1074
```

<210> SEQ ID NO 95
<211> LENGTH: 22
<212> TYPE: PRT
<213> ORGANISM: Artificial Sequence
<220> FEATURE:
<223> OTHER INFORMATION: Synthetic sequence

<400> SEQUENCE: 95

```
Gly Ser Gly Ala Thr Asn Phe Ser Leu Leu Lys Gln Ala Gly Asp Val
1               5                   10                  15

Glu Glu Asn Pro Gly Pro
            20
```

<210> SEQ ID NO 96
<211> LENGTH: 25
<212> TYPE: PRT
<213> ORGANISM: Artificial Sequence
<220> FEATURE:
<223> OTHER INFORMATION: Synthetic sequence

<400> SEQUENCE: 96

```
Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25
```

<210> SEQ ID NO 97
<211> LENGTH: 66
<212> TYPE: DNA
<213> ORGANISM: Artificial Sequence
<220> FEATURE:
<223> OTHER INFORMATION: Synthetic sequence

<400> SEQUENCE: 97
ggaagcggag ctactaactt cagcctgctg aagcaggctg gagacgtgga ggagaaccct 60
ggacct 66

<210> SEQ ID NO 98
<211> LENGTH: 75
<212> TYPE: DNA
<213> ORGANISM: Artificial Sequence
<220> FEATURE:
<223> OTHER INFORMATION: Synthetic sequence

<400> SEQUENCE: 98
ggaagcggag tgaaacagac tttgaatttt gaccttctca agttggcggg agacgtggag 60
tccaaccctg gacct 75

<210> SEQ ID NO 99
<211> LENGTH: 20
<212> TYPE: PRT
<213> ORGANISM: Artificial Sequence
<220> FEATURE:
<223> OTHER INFORMATION: Variable region linker
<220> FEATURE:
<221> NAME/KEY: VARIANT
<222> LOCATION: (2)...(10)
<223> OTHER INFORMATION: any one or all of amino acids 2-10 can either
be present or absent
<220> FEATURE:
<221> NAME/KEY: VARIANT
<222> LOCATION: (12)...(20)
<223> OTHER INFORMATION: any one or all of amino acids 12-20 can either
be present or absent

<400> SEQUENCE: 99

Gly Gly Gly Gly Gly Gly Gly Gly Gly Gly Ser Ser Ser Ser Ser Ser
1 5 10 15

Ser Ser Ser Ser
20

<210> SEQ ID NO 100
<211> LENGTH: 5
<212> TYPE: PRT
<213> ORGANISM: Artificial Sequence
<220> FEATURE:
<223> OTHER INFORMATION: Variable region linker

<400> SEQUENCE: 100

Gly Gly Gly Gly Ser
1 5

<210> SEQ ID NO 101
<211> LENGTH: 4
<212> TYPE: PRT
<213> ORGANISM: Artificial Sequence
<220> FEATURE:
<223> OTHER INFORMATION: Variable region linker

<400> SEQUENCE: 101

Gly Gly Gly Ser
1

<210> SEQ ID NO 102
<211> LENGTH: 29
<212> TYPE: PRT
<213> ORGANISM: Artificial Sequence
<220> FEATURE:
<223> OTHER INFORMATION: Variable region linker
<220> FEATURE:
<221> NAME/KEY: VARIANT
<222> LOCATION: (5)...(24)
<223> OTHER INFORMATION: any one or all of amino acids 5-24 can either be present or absent.

<400> SEQUENCE: 102

```
Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Gly Ser
            20                  25
```

<210> SEQ ID NO 103
<211> LENGTH: 42
<212> TYPE: PRT
<213> ORGANISM: Artificial Sequence
<220> FEATURE:
<223> OTHER INFORMATION: Variable region linker
<220> FEATURE:
<221> NAME/KEY: VARIANT
<222> LOCATION: (5)...(24)
<223> OTHER INFORMATION: any one or all of amino acids 5-24 can either be present or absent.
<220> FEATURE:
<221> NAME/KEY: VARIANT
<222> LOCATION: (28)...(42)
<223> OTHER INFORMATION: any one or all of amino acids 28-42 can either be present or absent.

<400> SEQUENCE: 103

```
Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Ser Gly Gly Ser Gly Gly
            20                  25                  30

Ser Gly Gly Ser Gly Gly Ser Gly Gly Ser
        35                  40
```

<210> SEQ ID NO 104
<211> LENGTH: 54
<212> TYPE: PRT
<213> ORGANISM: Artificial Sequence
<220> FEATURE:
<223> OTHER INFORMATION: Variable region linker
<220> FEATURE:
<221> NAME/KEY: VARIANT
<222> LOCATION: (5)...(24)
<223> OTHER INFORMATION: any one or all of amino acids 5-24 can either be present or absent.
<220> FEATURE:
<221> NAME/KEY: VARIANT
<222> LOCATION: (30)...(54)
<223> OTHER INFORMATION: any one or all of amino acids 30-54 can either be present or absent.

<400> SEQUENCE: 104

```
Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Gly Ser Gly Gly Gly
            20                  25                  30

Gly Ser Gly Gly Gly Gly Ser Gly Gly Gly Gly Ser Gly Gly Gly Gly
        35                  40                  45
```

-continued

```
Ser Gly Gly Gly Gly Ser
    50


<210> SEQ ID NO 105
<211> LENGTH: 30
<212> TYPE: PRT
<213> ORGANISM: Artificial Sequence
<220> FEATURE:
<223> OTHER INFORMATION: Variable region linker
<220> FEATURE:
<221> NAME/KEY: VARIANT
<222> LOCATION: (6)...(30)
<223> OTHER INFORMATION: any one or all of amino acids 6-30 can either
      be present or absent.

<400> SEQUENCE: 105

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

COMPOSITIONS AND METHODS FOR CD20 IMMUNOTHERAPY

CROSS-REFERENCE TO RELATED APPLICATIONS

This application is a divisional application of U.S. patent application Ser. No. 16/086,290, filed Sep. 18, 2018 (now allowed), which is a 371 national stage application of International Patent Application No. PCT/US2017/023098, filed Mar. 17, 2017, which claims the benefit of U.S. Provisional Application No. 62/320,327, filed Apr. 8, 2016, and U.S. Provisional Application No. 62/310,541, filed Mar. 18, 2016, which applications are incorporated herein by reference in their entirety.

STATEMENT OF GOVERNMENT INTEREST

This invention was made with government support under CA154874 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_441D1_SEQUENCE_LISTING.txt. The text file is 213 KB, was created on Nov. 24, 2020, and is being submitted electronically via EFS-Web.

BACKGROUND

Adoptive transfer of genetically modified T cells has emerged as a potent therapy for various malignancies. The most widely employed strategy has been infusion of patient-derived T cells expressing chimeric antigen receptors (CARs) targeting tumor-associated antigens. This approach has numerous theoretical advantages, including the ability to target T cells to any cell surface antigen, circumvent loss of major histocompatibility complex as a tumor escape mechanism, and employ a single vector construct to treat any patient, regardless of human leukocyte antigen haplotype. For example, CAR clinical trials for B-cell non-Hodgkin's lymphoma (NHL) have, to date, targeted CD19, CD20, or CD22 antigens that are expressed on malignant lymphoid cells as well as on normal B cells (Brentjens et al., *Sci Transl Med* 2013; 5(177):177ra38; Haso et al., *Blood* 2013; 121 (7):1165-74; James et al., *J Immunol* 2008; 180(10):7028-38; Kalos et al., *Sci Transl Med* 2011; 3(95):95ra73; Kochenderfer et al., *J Clin Oncol* 2015; 33(6):540-9; Lee et al., *Lancet* 2015; 385(9967):517-28; Porter et al., *Sci Transl Med* 2015; 7(303):303ra139; Savoldo et al., *J Clin Invest* 2011; 121(5):1822-6; Till et al., *Blood* 2008; 112(6):2261-71; Till et al., *Blood* 2012; 119(17):3940-50; Coiffier et al., *N Engl J Med* 2002; 346(4):235-42). Most investigators studying therapies for lymphoid malignancies have chosen to target CD19 since this molecule is expressed from earlier stages of B-cell differentiation than CD20 or CD22. CAR T cells targeting CD19 can therefore be used to treat a slightly wider range of B-cell malignancies, including acute lymphoblastic leukemia, which arises at the pro- or pre-B cell stage of differentiation.

CD20 remains an appealing antigen, however, due to its extensive clinical record as a successful immunotherapy target, as demonstrated in trials using rituximab, a monoclonal antibody targeting CD20 (Coiffier et al., *N Engl J Med* 2002; 346(4):235-42; Lenz et al., *J Clin Oncol* 2005; 23(9): 1984-92; Marcus R, et al., *J Clin Oncol* 2008; 26(28):4579-86; Pfreundschuh et al., *Lancet Oncol* 2011; 12(11):1013-22). In contrast to CD19, which is readily internalized upon antibody binding (Pulczynski et al., *Blood* 1993; 81(6): 1549-57), CD20 undergoes endocytosis much more slowly after antibody binding (Press et al., *Blood* 1994; 83(5):1390-7; Pulczynski et al., *Leuk Res* 1994; 18(7):541-52). This stability could theoretically impact the quality of the immunological synapse and subsequent CAR triggering and T cell activation. Loss of CD19 expression on tumor cells has been described as an escape mechanism in patients treated with CD19-targeted T cells (Grupp et al., *N Engl J Med* 2013; 368(16):1509-18). Although CD20 loss has also been described following anti-CD20 antibody therapy, CD20-specific CAR T cells provide an alternative target that would allow sequential therapy, or could be used in concert with CD19 CART cells to target multiple antigens simultaneously, reducing the risk of immune escape by antigen loss.

One potential limitation of CD20 as a target antigen for CARs is that patients with relapsed or refractory lymphoma who are likely to be candidates for CAR T cell therapy trials will often have been treated recently with rituximab-containing regimens. Since antibody can persist in the serum for months, residual rituximab could theoretically block the binding of CARs to CD20 and prevent or weaken T-cell activation, potentially rendering therapy ineffective. In previous CD20 CAR T cell trials (Till et al., *Blood* 112:2261-71, 2008; Till et al., *Blood* 119:3940-50, 2012), eligibility criteria excluded patients recently treated with rituximab. However, this approach significantly impacts accrual and would ultimately limit the availability of this therapy for patients most in need of novel treatment options.

Currently, there remains a need in the immunotherapy field for compositions and methods for additional or alternative immunotherapies directed against various diseases, including cancer (e.g., leukemia, lymphoma). Presently disclosed embodiments address this need and provide other related advantages.

BRIEF DESCRIPTION OF THE DRAWINGS

(FIG. 5B) cytokine secretion of the Leu16-28-z CAR-transduced T cells at 24 hours from (FIG. 5A) above, measured by Luminex assay; and (FIG. 5C) cytotoxicity using Leu16-28-z CAR-transduced $CD8^+$ T cells by $^{51}$Cr-release assay as described in FIG. 4. Data are representative of three independent experiments. Absolute values for cytokine secretion are shown in FIG. 11.

(FIG. 21A) tCD19$^+$ T cells at 3 post-infusion time points as a percentage of total nucleated cells in the blood are shown (n=9 initially in CAR T cell group). Truncated CD19$^+$ cells from an empty vector mouse are shown for reference. (FIG. 21B) In a separate experiment, the tCD19$^+$ cells from 2 mice in each group (empty vector vs CAR T cells) are shown longitudinally with weekly measurements.

DETAILED DESCRIPTION

Figure 1A:
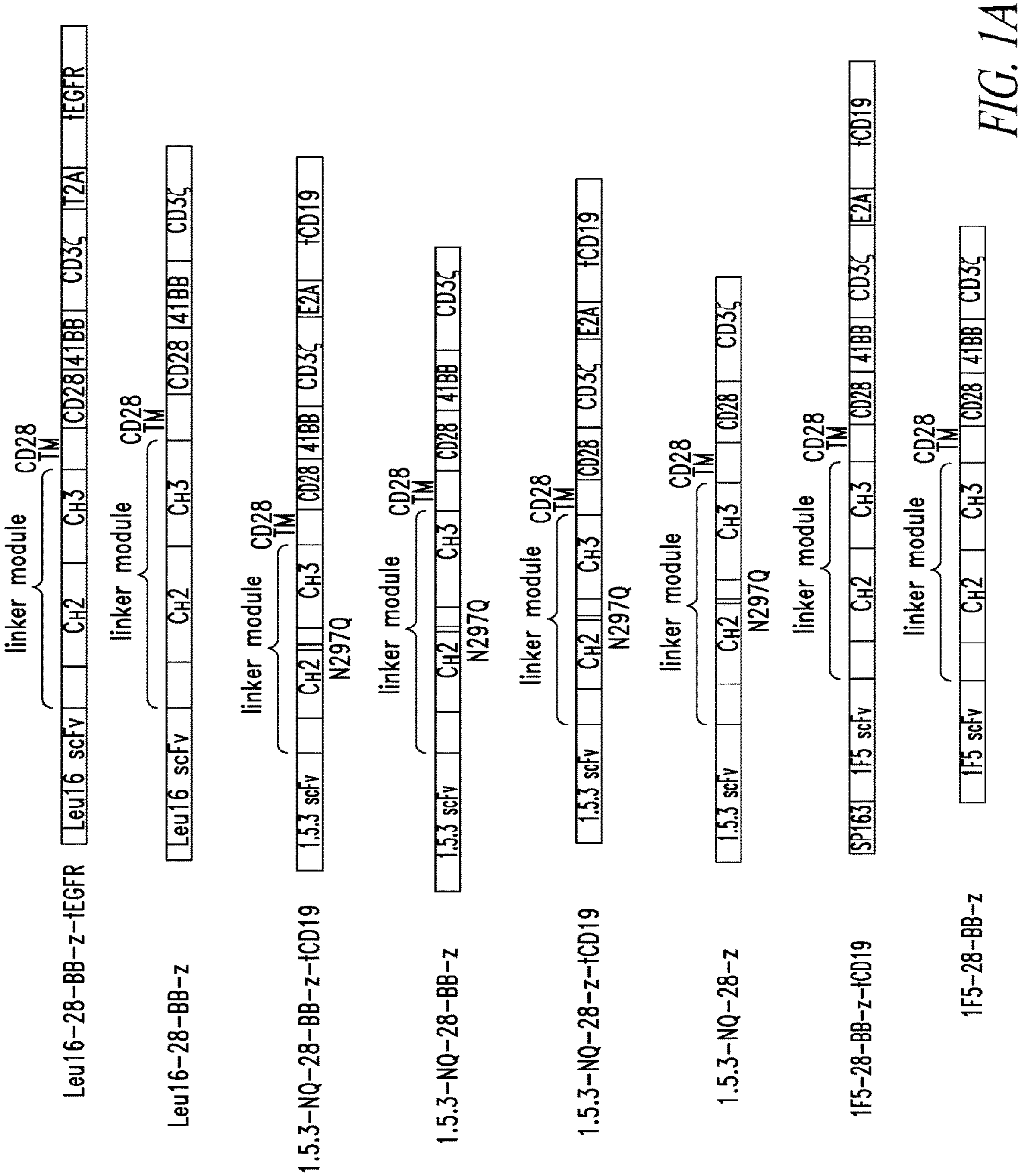
FIGS. 1A and 1B show schematic diagrams of CD20-specific CAR constructs containing scFvs from different anti-CD20 antibodies (Leu16, 1F5, and 1.5.3). (A) Shows CD20-specific CAR constructs and their respective mature CAR proteins. (B) Shows additional mature CD20-specific CAR proteins.

The instant disclosure provides compositions and methods for reducing the number of CD20-expressing cells or treating a disease or disorder associated with CD20 expression (e.g., reducing the number of B-cells or treating a disease or disorder associated with aberrant B cell activity), comprising treating a subject with a therapeutically effective amount of a host cell comprising a heterologous nucleic acid molecule encoding a fusion protein, the fusion protein comprising an extracellular component and an intracellular component connected to the extracellular component by a hydrophobic portion, wherein the extracellular component comprises a binding domain that specifically binds CD20 and the intracellular component comprises an effector domain. Optionally, the method may further comprise a therapeutically effective amount of a CD20-specific binding molecule in combination with the host cell expressing the fusion protein specific for CD20. In certain embodiments, the fusion protein is a chimeric antigen receptor (CAR). In still further embodiments, the CAR comprises a scFv from an anti-CD20 antibody or a scTCR from a TCR specific for a CD20 antigen.

By way of background, it is generally believed that residual anti-CD20 antibody levels might represent a major constraint for CD20-targeted CAR T cells. For example, previous studies with other targets have demonstrated that cytokine secretion and cytotoxicity of CAR T cells targeting carcinoembryonic antigen, Lewis-Y antigen, or CD30 are largely unimpaired in the presence of levels of soluble cognate antigen of up to 10 μg/ml (Hombach et al., *Gene Ther* 2000; 7(12):1067-75; Hombach et al., *Gene Ther* 1999; 6(2):300-4; Nolan et al., *Clin Cancer Res* 1999; 5(12):3928-41; Westwood et al., *J Immunother* 2009; 32(3):292-301); it was observed that levels higher than this are potentially inhibitory (Hombach et al., *Gene Ther* 2000; 7(12):1067-75). In this disclosure, it was surprisingly found that various anti-CD20 antibodies (e.g., rituximab) in clinically relevant concentrations largely did not affect the activity of T cells expressing anti-CD20 CARs either in vitro or in vivo (see, also, Gall et al., *Exp. Hematol.* 33:452, 2005). Moreover, mouse experiments of this disclosure demonstrate groups receiving a combination therapy had outcomes as good as or better than mice treated with CAR T cells alone.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means ±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

"Optional" or "optionally" means that the subsequently described element, component, event, or circumstance may or may not occur, and that the description includes instances in which the element, component, event, or circumstance occurs and instances in which they do not.

In addition, it should be understood that the individual constructs, or groups of constructs, derived from the various combinations of the structures and subunits described herein, are disclosed by the present application to the same extent as if each construct or group of constructs was set forth individually. Thus, selection of particular structures or particular subunit is within the scope of the present disclosure.

The term "consisting essentially of" limits the scope of a claim to the specified materials or steps, or to those that do not materially affect the basic characteristics of a claimed invention. For example, a protein domain, region, module, or fragment (e.g., a binding domain, hinge region, linker module, or tag) or a protein (which may have one or more domains, regions, or modules) "consists essentially of" a particular amino acid sequence when the amino acid sequence of a domain, region, module, fragment, or protein includes insertions, deletions, substitutions, or a combination thereof (e.g., addition of amino acids at the amino- or carboxy-terminus, or between domains) that, in combination, contribute to at most 20% (e.g., at most 15%, 10%, 8%, 6%, 5%, 4%, 3%, 2% or 1%) of the length of a domain, region, module, cassette or protein and do not substantially affect (i.e., do not reduce the activity by more than 50%, such as no more than 40%, 30%, 25%, 20%, 15%, 10%, 5%, or 1%) the activity of the domain(s), region(s), module(s), cassette(s), or protein (e.g., the target binding affinity of a binding domain).

As used herein, “amino acid” refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that functions in a manner similar to a naturally occurring amino acid.

A “conservative substitution” refers to amino acid substitutions that do not significantly affect or alter binding characteristics of a particular protein. Generally, conservative substitutions are ones in which a substituted amino acid residue is replaced with an amino acid residue having a similar side chain. Conservative substitutions include a substitution found in one of the following groups: Group 1: Alanine (Ala or A), Glycine (Gly or G), Serine (Ser or S), Threonine (Thr or T); Group 2: Aspartic acid (Asp or D), Glutamic acid (Glu or Z); Group 3: Asparagine (Asn or N), Glutamine (Gln or Q); Group 4: Arginine (Arg or R), Lysine (Lys or K), Histidine (His or H); Group 5: Isoleucine (Ile or I), Leucine (Leu or L), Methionine (Met or M), Valine (Val or V); and Group 6: Phenylalanine (Phe or F), Tyrosine (Tyr or Y), Tryptophan (Trp or W). Additionally or alternatively, amino acids can be grouped into conservative substitution groups by similar function, chemical structure, or composition (e.g., acidic, basic, aliphatic, aromatic, or sulfur-containing). For example, an aliphatic grouping may include, for purposes of substitution, Gly, Ala, Val, Leu, and Ile. Other conservative substitutions groups include: sulfur-containing: Met and Cysteine (Cys or C); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information can be found in Creighton (1984) Proteins, W.H. Freeman and Company.

As used herein, “protein” or “polypeptide refers to a polymer of amino acid residues. Proteins apply to naturally occurring amino acid polymers, as well as to amino acid polymers in which one or more amino acid residue is an artificial chemical mimetic of a corresponding naturally occurring amino acid and non-naturally occurring amino acid polymers.

“Percent sequence identity” refers to a relationship between two or more sequences, as determined by comparing the sequences. Preferred methods to determine sequence identity are designed to give the best match between the sequences being compared. For example, the sequences are aligned for optimal comparison purposes (e.g., gaps can be introduced in one or both of a first and a second amino acid or nucleic acid sequence for optimal alignment). Further, non-homologous sequences may be disregarded for comparison purposes. The percent sequence identity referenced herein is calculated over the length of the reference sequence, unless indicated otherwise. Methods to determine sequence identity and similarity can be found in publicly available computer programs. Sequence alignments and percent identity calculations may be performed using a BLAST program (e.g., BLAST 2.0, BLASTP, BLASTN, or BLASTX). The mathematical algorithm used in the BLAST programs can be found in Altschul et al., Nucleic Acids Res. 25:3389-3402, 1997. Within the context of this disclosure, it will be understood that where sequence analysis software is used for analysis, the results of the analysis are based on the “default values” of the program referenced. “Default values” mean any set of values or parameters which originally load with the software when first initialized.

“Nucleic acid molecule” or “polynucleotide” refers to a polymeric compound including covalently linked nucleotides, which can be made up of natural subunits (e.g., purine or pyrimidine bases) or non-natural subunits (e.g., morpholine ring). Purine bases include adenine, guanine, hypoxanthine, and xanthine, and pyrimidine bases include uracil, thymine, and cytosine. Nucleic acid molecules include polyribonucleic acid (RNA), polydeoxyribonucleic acid (DNA), which includes cDNA, genomic DNA, and synthetic DNA, either of which may be single or double stranded. If single stranded, the nucleic acid molecule may be the coding strand or non-coding (anti-sense strand). A nucleic acid molecule encoding an amino acid sequence includes all nucleotide sequences that encode the same amino acid sequence. Some versions of the nucleotide sequences may also include intron(s) to the extent that the intron(s) would be removed through co- or post-transcriptional mechanisms. In other words, different nucleotide sequences may encode the same amino acid sequence as the result of the redundancy or degeneracy of the genetic code, or by splicing.

Variants of nucleic acid molecules of this disclosure are also contemplated. Variant nucleic acid molecules are at least 70%, 75%, 80%, 85%, 90%, and preferably 95%, 96%, 97%, 98%, 99%, or 99.9% identical a nucleic acid molecule of a defined or reference polynucleotide as described herein, or that hybridizes to a polynucleotide under stringent hybridization conditions of 0.015M sodium chloride, 0.0015M sodium citrate at about 65-68° C. or 0.015M sodium chloride, 0.0015M sodium citrate, and 50% formamide at about 42° C. Nucleic acid molecule variants retain the capacity to encode a fusion protein or a binding domain thereof having a functionality described herein, such as specifically binding a target molecule (e.g., CD20).

A “functional variant” refers to a polypeptide or polynucleotide that is structurally similar or substantially structurally similar to a parent or reference compound of this disclosure, but differs slightly in composition (e.g., one base, atom or functional group is different, added, or removed), such that the polypeptide or encoded polypeptide is capable of performing at least one function of the encoded parent polypeptide with at least 50% efficiency, preferably at least 55%, 60%, 70%, 75%, 80%, 85%, 90%, 95% or 100% level of activity of the parent polypeptide. In other words, a functional variant of a polypeptide or encoded polypeptide of this disclosure has "similar binding," "similar affinity" or "similar activity" when the functional variant displays no more than a 50% reduction in performance in a selected assay as compared to the parent or reference polypeptide, such as an assay for measuring binding affinity (e.g., Biacore® or tetramer staining measuring an association ($K_a$) or a dissociation ($K_D$) constant).

As used herein, a "functional portion" or "functional fragment" refers to a polypeptide or polynucleotide that comprises only a domain, portion or fragment of a parent or reference compound, and the polypeptide or encoded polypeptide retains at least 50% activity associated with the domain, portion or fragment of the parent or reference compound, preferably at least 55%, 60%, 70%, 75%, 80%, 85%, 90%, 95% or 100% level of activity of the parent polypeptide, or provides a biological benefit (e.g., effector function). A "functional portion" or "functional fragment" of a polypeptide or encoded polypeptide of this disclosure has "similar binding" or "similar activity" when the functional portion or fragment displays no more than a 50% reduction in performance in a selected assay as compared to the parent or reference polypeptide (preferably no more than 20% or 10%, or no more than a log difference as compared to the parent or reference with regard to affinity), such as an assay for measuring binding affinity or measuring effector function (e.g., cytokine release).

As used herein, "heterologous" or "non-endogenous" or "exogenous" refers to any gene, protein, compound, nucleic acid molecule, or activity that is not native to a host cell or a subject, or any gene, protein, compound, nucleic acid molecule, or activity native to a host cell or a subject that has been altered. Heterologous, non-endogenous, or exogenous includes genes, proteins, compounds, or nucleic acid molecules that have been mutated or otherwise altered such that the structure, activity, or both is different as between the native and altered genes, proteins, compounds, or nucleic acid molecules. In certain embodiments, heterologous, non-endogenous, or exogenous genes, proteins, or nucleic acid molecules (e.g., receptors, ligands, etc.) may not be endogenous to a host cell or a subject, but instead nucleic acids encoding such genes, proteins, or nucleic acid molecules may have been added to a host cell by conjugation, transformation, transfection, electroporation, or the like, wherein the added nucleic acid molecule may integrate into a host cell genome or can exist as extra-chromosomal genetic material (e.g., as a plasmid or other self-replicating vector). The term "homologous" or "homolog" refers to a gene, protein, compound, nucleic acid molecule, or activity found in or derived from a host cell, species, or strain. For example, a heterologous or exogenous polynucleotide or gene encoding a polypeptide may be homologous to a native polynucleotide or gene and encode a homologous polypeptide or activity, but the polynucleotide or polypeptide may have an altered structure, sequence, expression level, or any combination thereof. A non-endogenous polynucleotide or gene, as well as the encoded polypeptide or activity, may be from the same species, a different species, or a combination thereof.

As used herein, the term "endogenous" or "native" refers to a polynucleotide, gene, protein, compound, molecule, or activity that is normally present in a host cell or a subject.

"Expression" refers to transcription or translation of a nucleic acid molecule that is operably linked to an expression control sequence (e.g., promoter).

As used herein, the term "engineered," "recombinant" or "non-natural" refers to an organism, microorganism, cell, nucleic acid molecule, or vector that includes at least one genetic alteration or has been modified by introduction of an exogenous nucleic acid molecule, wherein such alterations or modifications are introduced by genetic engineering (i.e., human intervention). Genetic alterations include, for example, modifications introducing expressible nucleic acid molecules encoding proteins, fusion proteins or enzymes, or other nucleic acid molecule additions, deletions, substitutions or other functional disruption of a cell's genetic material. Additional modifications include, for example, non-coding regulatory regions in which the modifications alter expression of a polynucleotide, gene or operon.

As used herein, a "fusion protein" refers to a protein that, in a single chain, has at least two distinct domains, wherein the domains are not naturally found together in a protein. A polynucleotide encoding a fusion protein may be constructed using PCR, recombinantly engineered, or the like, or such fusion proteins can be synthesized. A fusion protein may further contain other components, such as a tag, a linker module or a transduction marker. In certain embodiments, a fusion protein expressed or produced by a host cell (e.g., a T cell) locates to a cell surface, where the fusion protein is anchored to the cell membrane (e.g., via a transmembrane domain) and comprises an extracellular portion (e.g., containing a binding domain) and an intracellular portion (e.g., containing a signaling domain, effector domain, co-stimulatory domain or combinations thereof).

Terms understood by those in the art of antibody technology are each given the meaning acquired in the art, unless expressly defined differently herein. The term "antibody" refers to an intact antibody comprising at least two heavy (H) chains and two light (L) chains inter-connected by disulfide bonds, as well as an antigen-binding portion of an intact antibody that has or retains the capacity to bind a target molecule. Antibodies include polyclonal and monoclonal antibodies. An antibody may be naturally occurring, recombinantly produced, genetically engineered, or modified, and includes modified forms of immunoglobulins, such as, for example intrabodies, peptibodies, nanobodies, single domain antibodies, multispecific antibodies (e.g., bispecific antibodies, diabodies, triabodies, tetrabodies, tandem di-scFV, tandem tri-scFv). "Antigen-binding portion," "antigen-binding fragment" or "antigen-binding domain" from an antibody refers to an "antibody fragment" that comprises a portion of an intact antibody and contains the antigenic determining variable regions or complementary determining regions of an antibody. Examples of antibody fragments include Fab, Fab', F(ab')2, and Fv fragments, Fab'-SH, $F(ab')_2$, diabodies, linear antibodies, single chain antibodies, scFv (i.e., a fusion protein of the variable heavy (VH) and variable light (VL) regions of an Ig molecule, connected with a short linked peptide of generally about 10 to about 25 amino acids), single domain antibodies (e.g., sdAb, sdFv, nanobody), and multispecific antibodies comprising antibody fragments. A monoclonal antibody or antigen-binding portion thereof may be non-human, chimeric, humanized, or human, preferably humanized or human. Immunoglobulin structure and function are reviewed, for example, in Harlow et al., Eds., Antibodies: A Laboratory Manual, Chapter 14 (Cold Spring Harbor Laboratory, Cold Spring Harbor, 1988). An antibody may be of any class or subclass, including IgG and subclasses thereof ($IgG_1$, $IgG_2$, $IgG_3$, $IgG_4$), IgM, IgE, IgA, and IgD.

The terms "$V_L$" and "$V_H$" refer to the variable binding region from an antibody light and heavy chain, respectively. The variable binding regions are made up of discrete, well-defined sub-regions known as "complementarity determining regions" (CDRs) and "framework regions" (FRs).

The terms "complementarity determining region" (CDR) or "hypervariable region" (HVR) are known in the art to refer to non-contiguous sequences of amino acids within antibody variable regions, which confer antigen specificity or binding affinity. In general, there are three CDRs in each heavy chain variable region (HCDR1, HCDR2, and HCDR3) and three CDRs in each light chain variable region (LCDR1, LCDR2, and LCDR3).

"Framework regions" (FR) as used herein refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The term "CL" refers to an "immunoglobulin light chain constant region" or a "light chain constant region," i.e., a constant region from an antibody light chain. The term "CH" refers to an "immunoglobulin heavy chain constant region" or a "heavy chain constant region," which is further divisible, depending on the antibody isotype into CH1, CH2, and CH3 (IgA, IgD, IgG), or CH1, CH2, CH3, and CH4 domains (IgE, IgM).

A "fragment antigen binding" (Fab) region is a part of an antibody that binds to antigens, and includes the variable region and CH1 of the heavy chain linked to the light chain via an inter-chain disulfide bond. A "fragment crystallizable" (Fc) region is a part of an antibody that is not a Fab region, and includes the CH regions other than CH1 (e.g., CH2 and CH3 of an IgG, IgA, or IgD antibody, or CH2, CH3, and CH4 of an IgE antibody). By way of background, an Fc region is responsible for the effector functions of an immunoglobulin, such as antibody-dependent cell-mediated cytotoxicity (ADCC), complement-dependent cytotoxicity (CDC) and complement fixation, binding to Fc receptors (e.g., CD16, CD32, FcRn), greater half-life in vivo relative to a polypeptide lacking an Fc region, protein A binding, and perhaps even placental transfer (see Capon et al., *Nature* 337:525, 1989).

As used herein, "Fc region portion" refers to the heavy chain constant region segment of an Fc fragment from an antibody, which can include one or more constant domains, such as CH2, CH3, CH4, or any combination thereof. In certain embodiments, an Fc region portion includes the CH2 and CH3 domains of an IgG, IgA, or IgD antibody or any combination thereof, or the CH2, CH3, and CH4 domains of an IgM or IgE antibody and any combination thereof. In other embodiments, a CH2CH3 or a CH3CH4 structure has sub-region domains from the same antibody isotype and are human, such as human IgG1, IgG2, IgG3, IgG4, IgA1, IgA2, IgD, IgE, or IgM (e.g., CH2CH3 from human IgG1 or IgG4). In certain embodiments, an Fc region portion found in fusion proteins of the present disclosure will be capable of mediating one or more of effector functions of an immunoglobulin, will be capable of mediating one or more enhanced effector functions, or will lack one or more or all of these activities by way of, for example, one or more mutations known in the art.

In addition, antibodies have a hinge sequence that is typically situated between the Fab and Fc region (but a lower section of the hinge may include an amino-terminal portion of the Fc region). By way of background, an immunoglobulin hinge acts as a flexible spacer to allow the Fab region to move freely in space. In contrast to the constant regions, hinges are structurally diverse, varying in both sequence and length between immunoglobulin classes and even among subclasses. For example, a human IgG1 hinge region is freely flexible, which allows the Fab regions to rotate about their axes of symmetry and move within a sphere centered at the first of two inter-heavy chain disulfide bridges. By comparison, a human IgG2 hinge is relatively short and contains a rigid poly-proline double helix stabilized by four inter-heavy chain disulfide bridges, which restricts the flexibility. A human IgG3 hinge differs from the other subclasses by its unique extended hinge region (about four times as long as the IgG1 hinge), containing 62 amino acids (including 21 prolines and 11 cysteines), forming an inflexible poly-proline double helix and providing greater flexibility because the Fab regions are relatively far away from the Fc region. A human IgG4 hinge is shorter than IgG1 but has the same length as IgG2, and its flexibility is intermediate between that of IgG1 and IgG2.

A "T cell" is an immune system cell that matures in the thymus and produces T cell receptors (TCRs). T cells can be naïve (not exposed to antigen; increased expression of CD62L, CCR7, CD28, CD3, CD127, and CD45RA, and decreased expression of CD45RO as compared to $T_{CM}$), memory T cells ($T_M$) (antigen-experienced and long-lived), and effector cells (antigen-experienced, cytotoxic). $T_M$ can be further divided into subsets of central memory T cells ($T_{CM}$, increased expression of CD62L, CCR7, CD28, CD127, CD45RO, and CD95, and decreased expression of CD54RA as compared to naïve T cells) and effector memory T cells ($T_{EM}$, decreased expression of CD62L, CCR7, CD28, CD45RA, and increased expression of CD127 as compared to naïve T cells or $T_{CM}$). Effector T cells ($T_E$) refers to antigen-experienced $CD8^+$ cytotoxic T lymphocytes that have decreased expression of CD62L, CCR7, CD28, and are positive for granzyme and perforin as compared to $T_{CM}$. T helper cells ($T_H$) release cytokines to aid in antigen signaling and, when mature, express the surface protein CD4 (are $CD4^+$)As used herein, "T cells" or "T lymphocytes" are from any mammal, including primates, dogs, or horses, preferably humans. In some embodiments, T cells are autologous, allogeneic, or syngeneic.

"T cell receptor" (TCR) refers to a molecule found on the surface of T cells (or T lymphocytes) that, in association with CD3, is generally responsible for recognizing antigens bound to major histocompatibility complex (MHC) molecules. The TCR has a disulfide-linked heterodimer of the highly variable α and β chains (also known as TCRα and TCRβ, respectively) in most T cells. In a small subset of T cells, the TCR is made up of a heterodimer of variable γ and δ chains (also known as TCRγ and TCRδ, respectively). Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see, Janeway et al., *Immunobiology: The Immune System in Health and Disease,* 3rd Ed., Current Biology Publications, p. 4:33, 1997). TCR, as used in the present disclosure, may be from various animal species, including human, mouse, rat, cat, dog, goat, horse, or other mammals. TCRs may be cell-bound (i.e., have a transmembrane region or domain) or in soluble form. As discussed herein, a binding domain according to the present disclosure may comprise a single-chain TCR (scTCR), which is analogous to an scFv derived from an immunoglobulin and comprises the variable domains from TCRα and TCRβ chains linked together using, e.g., a peptide or non-peptide linker and optionally through disulfide bonding.

"Major histocompatibility complex molecules" (MHC molecules) refer to glycoproteins that deliver peptide antigens to a cell surface. MHC class I molecules are heterodimers consisting of a membrane spanning α chain (with three a domains) and a non-covalently associated β2 microglobulin. MHC class II molecules are composed of two transmembrane glycoproteins, α and β, both of which span the membrane. Each chain has two domains. MHC class I molecules deliver peptides originating in the cytosol to the cell surface, where a peptide:MHC complex is recognized by $CD8^+$ T cells. MHC class II molecules deliver peptides originating in the vesicular system to the cell surface, where they are recognized by $CD4^+$ T cells. An MHC molecule may be from various animal species, including human, mouse, rat, cat, dog, goat, horse, or other mammals.

"Cells of T cell lineage" refer to cells that show at least one phenotypic characteristic of a T cell, or a precursor or progenitor thereof that distinguishes the cells from other lymphoid cells, and cells of the erythroid or myeloid lineages. Such phenotypic characteristics can include expression of one or more proteins specific for T cells (e.g., $CD3^+$, $CD4^+$, $CD8^+$), or a physiological, morphological, functional, or immunological feature specific for a T cell. For example, cells of the T cell lineage may be progenitor or precursor cells committed to the T cell lineage; $CD25^+$ immature and inactivated T cells; cells that have undergone CD4 or CD8 linage commitment; thymocyte progenitor cells that are $CD4^+CD8^+$ double positive; single positive $CD4^+$ or $CD8^+$; TCRαβ or TCR γδ; or mature and functional or activated T cells.

As used herein, "enriched" or "depleted" with respect to amounts of cell types in a mixture refers to an increase in the number of the "enriched" type, a decrease in the number of the "depleted" cells, or both, in a mixture of cells resulting from one or more enriching or depleting processes or steps. Thus, depending upon the source of an original population of cells subjected to an enriching process, a mixture or composition may contain 30%, 35%, 40%, 45%, 50%, 55%, 60%, 65%, 70%, 75%, 80%, 85%, 90%, 91%, 92%, 93%, 94%, 95%, 96%, 97%, 98%, or 99% or more (in number or count) of the "enriched" cells. Cells subjected to a depleting process can result in a mixture or composition containing 50%, 45%, 40%, 35%, 30%, 25%, 20%, 15%, 10%, 9%, 8%, 7%, 6%, 5%, 4%, 3%, 2%, or 1% percent or less (in number or count) of the "depleted" cells. In certain embodiments, amounts of a certain cell type in a mixture will be enriched and amounts of a different cell type will be depleted, such as enriching for $CD4^+$ cells while depleting $CD8^+$ cells, or enriching for $CD62L^+$ cells while depleting $CD62L^-$ cells, or combinations thereof.

"Treat" or "treatment" or "ameliorate" refers to medical management of a disease, disorder, or condition of a subject (e.g., a human or non-human mammal, such as a primate, horse, cat, dog, goat, mouse, or rat). In general, an appropriate dose or treatment regimen comprising a host cell expressing a fusion protein, the fusion protein comprising an extracellular component and an intracellular component connected by a hydrophobic portion, wherein the extracellular component comprises a binding domain that specifically binds CD20 and the intracellular component comprises an effector domain of this disclosure, and optionally an adjuvant, is administered in an amount sufficient to elicit a therapeutic or prophylactic benefit. Therapeutic or prophylactic/preventive benefit includes improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; prolonged survival; or any combination thereof. As further described herein, a treatment regimen may comprise a combination therapy in which one or more CD20-specific binding molecules, such as, for example, anti-CD20 antibodies are administered prior to, simultaneous with, contemporaneous with, or subsequent to administration of one or more second or adjunctive therapeutic. Exemplary anti-CD20 antibodies suitable for use in the therapeutic methods described herein include 1.5.3, 1F5, Leu16, rituximab, ofatumumab, veltuzumab, ublituximab, and ocrelizumab.

A "therapeutically effective amount" or "effective amount" of a CD20-specific binding molecule, a fusion protein, or host cell expressing a fusion protein of this disclosure (e.g., CD20 CAR) refers to an amount of CD20-specific binding molecules, fusion proteins, or host cells sufficient to result in a therapeutic effect, including improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; or prolonged survival in a statistically significant manner. When referring to an individual active ingredient or a cell expressing a single active ingredient, administered alone, a therapeutically effective amount refers to the effects of that ingredient or cell expressing that ingredient alone. When referring to a combination, a therapeutically effective amount refers to the combined amounts of active ingredients or combined adjunctive active ingredient with a cell expressing an active ingredient that results in a therapeutic effect, whether administered serially or simultaneously. A combination may also be a cell expressing more than one active ingredient, such as two different CD20 CARs, or one CD20 CAR and CD20 TCR, or CD20 CAR and another relevant therapeutic.

The term "pharmaceutically acceptable excipient or carrier" or "physiologically acceptable excipient or carrier" refer to biologically compatible vehicles, e.g., physiological saline, which are described in greater detail herein, that are suitable for administration to a human or other non-human mammalian subject and generally recognized as safe or not causing a serious adverse event.

As used herein, "statistically significant" refers to a p value of 0.050 or less when calculated using the Students t-test and indicates that it is unlikely that a particular event or result being measured has arisen by chance.

As used herein, the term "adoptive immune therapy" or "adoptive immunotherapy" refers to administration of naturally occurring or genetically engineered, disease antigen-specific immune cells (e.g., T cells). Adoptive cellular immunotherapy may be autologous (immune cells are from the recipient), allogeneic (immune cells are from a donor of the same species) or syngeneic (immune cells are from a donor genetically identical to the recipient).

Fusion Proteins

In certain aspects, the present disclosure provides fusion proteins comprising an extracellular component and an intracellular component connected by a hydrophobic portion.

An "extracellular component" comprises a binding domain that specifically binds CD20. A "binding domain" (also referred to as a "binding region" or "binding moiety"), as used herein, refers to a molecule, such as a peptide, oligopeptide, polypeptide, or protein that possesses the ability to specifically and non-covalently associate, unite, or combine with a target molecule (e.g., CD20). A binding domain includes any naturally occurring, synthetic, semi-synthetic, or recombinantly produced binding partner for a biological molecule or other target of interest. In some embodiments, a binding domain is an antigen-binding domain, such as an antibody or TCR, or functional binding domain or antigen-binding fragment thereof.

In certain embodiments, a binding domain comprises a variable region linker (e.g., scFv). A "variable region linker" specifically refers to a five amino acid to about 35 amino acid sequence that connects a heavy chain immunoglobulin variable region (VH) to a light chain immunoglobulin variable region (VL), or connects TCR $V_{\alpha/\beta}$ and $C_{\alpha/\beta}$ chains (e.g., $V_\alpha$-$C_\alpha$, $V_\beta$-$C_\beta$, $V_\alpha$-$V_\beta$) or connects each $V_\alpha$-$C_\alpha$, $V_\beta$-$C_\beta$, or $V_\alpha$-$V_\beta$ pair to a hinge or hydrophobic domain, which provides a spacer function and flexibility sufficient for interaction of the two sub-binding domains so that the resulting single chain polypeptide retains a specific binding affinity to the same target molecule as an antibody or TCR.

In certain embodiments, a variable region linker comprises from about ten amino acids to about 30 amino acids or from about 15 amino acids to about 25 amino acids. In particular embodiments, a variable region linker peptide comprises from one to ten repeats of $Gly_xSer_y$ (SEQ ID NO: 99), wherein x and y are independently an integer from 0 to 10, provided that x and y are not both 0 (e.g., $Gly_4Ser$ (SEQ ID NO: 100)), $Gly_3Ser$ (SEQ ID NO: 101), $Gly_2Ser$, or $(Gly_3Ser)_n(Gly_4Ser)_n$ (SEQ ID NO: 102), $(Gly_3Ser)_n(Gly_2Ser)_n$ (SEQ ID NO: 103), $(Gly_3Ser)_n(Gly_4Ser)_n$ (SEQ ID NO: 104), or $(Gly_4Ser)_n$ (SEQ ID NO: 105), wherein n is an integer of 1, 2, 3, 4, 5, or 6) and wherein linked variable regions form a functional immunoglobulin-like binding domain (e.g., scFv or scTCR).

Exemplary binding domains include single chain antibody variable regions (e.g., domain antibodies, sFv, scFv, or Fab), antigen-binding regions of TCRs, such as single chain TCRs (scTCRs), or synthetic polypeptides selected for the specific ability to bind to a biological molecule.

As used herein, "specifically binds" refers to an association or union of a binding domain, or a fusion protein thereof, to a target molecule with an affinity or $K_a$ (i.e., an equilibrium association constant of a particular binding interaction with units of 1/M) equal to or greater than $10^5 M^{-1}$, while not significantly associating or uniting with any other molecules or components in a sample. Binding domains (or fusion proteins thereof) may be classified as "high affinity" binding domains (or fusion proteins thereof) or "low affinity" binding domains (or fusion proteins thereof). "High affinity" binding domains (or fusion proteins thereof) refer to those binding domains (or fusion proteins thereof) with a $K_a$ of at least $10^7 M^{-1}$, at least $10^8 M^{-1}$, at least $10^9 M^{-1}$, at least $10^{10} M^{-1}$, at least $10^{11} M^{-1}$, at least $10^{12} M^{-1}$, or at least $10^{13} M^{-1}$. "Low affinity" binding domains (or fusion proteins thereof) refer to those binding domains (or fusion proteins thereof) with a $K_a$ of up to $10^7 M^{-1}$, up to $10^6 M^{-1}$, up to $10^5 M^{-1}$.

Alternatively, affinity may be defined as an equilibrium dissociation constant ($K_d$) of a particular binding interaction with units of M (e.g., $10^{-5}$ M to $10^{-13}$ M). In certain embodiments, a binding domain may have "enhanced affinity," which refers to a selected or engineered binding domain with stronger binding to a target antigen than a wild type (or parent) binding domain. For example, enhanced affinity may be due to a $K_a$ (equilibrium association constant) for the target antigen that is greater than the wild type binding domain, due to a $K_d$ (dissociation constant) for the target antigen that is less than that of the wild type binding domain, or due to an off-rate ($K_{off}$) for the target antigen that is less than that of the wild type binding domain. A variety of assays are known for identifying binding domains of the present disclosure that specifically bind a particular target, as well as determining binding domain or fusion protein affinities, such as Western blot, ELISA, and Biacore® analysis (see also, e.g., Scatchard et al., *Ann. N.Y. Acad. Sci.* 51:660, 1949; and U.S. Pat. Nos. 5,283,173, 5,468,614, or an equivalent).

Analysis or computer modeling of the primary and secondary amino acid structure of a binding domain to analyze the tertiary structure of a protein may aid in identifying specific amino acid residues that can be substituted, added, or deleted without significantly altering the structure and as a consequence, potentially significantly reducing the binding specificity and affinity of a binding domain.

In certain embodiments, a binding domain comprises a $V_H$ region. For example, a $V_H$ region in a binding domain of the present disclosure can be derived from or based on a $V_H$ of a known monoclonal antibody and may contain one or more (e.g., 2, 3, 4, 5, 6, 7, 8, 9, or 10) insertions, one or more (e.g., 2, 3, 4, 5, 6, 7, 8, 9, or 10) deletions, one or more (e.g., 2, 3, 4, 5, 6, 7, 8, 9, or 10) amino acid substitutions (e.g., conservative amino acid substitutions or non-conservative amino acid substitutions), or a combination of the above-noted changes, when compared with the $V_H$ of a known monoclonal antibody. An insertion, deletion, or substitution may be anywhere in the $V_H$ region, including at the amino-terminus, carboxy-terminus, or both ends of the region, provided that each CDR comprises zero changes or at most one, two, three or four changes from a CDR of the $V_H$ region of a known monoclonal antibody, and provided a binding domain containing the modified $V_H$ region specifically binds its target with an affinity similar to the wild type binding domain.

In certain embodiments, a binding domain comprises a $V_L$ region. For example, a $V_L$ region in a binding domain of the present disclosure is derived from or based on a $V_L$ of a known monoclonal antibody and may contain one or more (e.g., 2, 3, 4, 5, 6, 7, 8, 9, or 10) insertions, one or more (e.g., 2, 3, 4, 5, 6, 7, 8, 9, or 10) deletions, one or more (e.g., 2, 3, 4, 5, 6, 7, 8, 9, or 10) amino acid substitutions (e.g., conservative amino acid substitutions), or a combination of the above-noted changes, when compared with the $V_L$ of a known monoclonal antibody. An insertion, deletion, or substitution may be anywhere in the $V_L$ region, including at the amino-terminus, carboxy-terminus, or both ends of the region, provided that each CDR comprises zero changes or at most one, two, three or four changes from a CDR of the $V_L$ region of a known monoclonal antibody, and provided a binding domain containing the modified $V_L$ region specifically binds its target with an affinity similar to the wild type binding domain.

In certain embodiments, a binding domain comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a light chain variable region ($V_L$); e.g., to a $V_L$ from 1.5.3 (SEQ ID NO.:1), 1F5 (SEQ ID NO.:3), Leu16 (SEQ ID NO.:2), rituximab, ofatumumab, veltuzumab, ublituximab, or ocrelizumab.

In further embodiments, a binding domain comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a heavy chain variable region ($V_H$); e.g., to a $V_H$ from 1.5.3 (SEQ ID NO.:4), 1F5 (SEQ ID NO.:6), Leu16 (SEQ ID NO.:5), rituximab, ofatumumab, veltuzumab, ublituximab, or ocrelizumab.

In still further embodiments, a binding domain comprises (a) an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a $V_L$; e.g., to a $V_L$ from 1.5.3 (SEQ ID NO.:1), 1F5 (SEQ ID NO.:3), Leu16 (SEQ ID NO.:2), rituximab, ofatumumab, veltuzumab, ublituximab, or ocrelizumab; and (b) an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a $V_H$; e.g., to a $V_H$ from 1.5.3 (SEQ ID NO.:4), 1F5 (SEQ ID NO.:6), Leu16 (SEQ ID NO.:5), rituximab, ofatumumab, veltuzumab, ublituximab, or ocrelizumab. In any of the aforementioned embodiments, each CDR of the $V_L$, $V_H$, or both comprises zero changes or at most one, two, three, four, five or six changes, as compared to a parent monoclonal antibody or fragment or derivative thereof that specifically binds to CD20, provided that a binding domain containing the modified $V_L$, $V_H$, or both region specifically binds CD20 with an affinity similar to the wild type binding domain.

In certain embodiments, a binding domain comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a scFv, e.g., a scFv from an antibody of 1.5.3 (SEQ ID NO.:64), 1F5 (SEQ ID NO.:66), Leu16 (SEQ ID NO.:65), rituximab, ofatumumab, veltuzumab, ublituximab, or ocrelizumab, wherein each CDR of the scFv comprises zero changes or at most one, two, three, four, five or six changes, as compared to the corresponding CDR of a parent monoclonal antibody or fragment or derivative thereof that specifically binds to CD20, provided that scFv containing one or more modified CDRs specifically binds CD20 with an affinity similar to the wild type scFv or corresponding antibody.

In certain embodiments, a binding domain is encoded by a polynucleotide that is at least 60%, at least 70%, at least 75%, at least 80%, at least 85%, at least 90%, at least 95%, or 100% identical to a polynucleotide sequence encoding a light chain variable region ($V_L$); e.g., to a $V_L$-encoding polynucleotide from 1.5.3 (SEQ ID NO.:70), 1F5 (SEQ ID NO.:72), Leu16 (SEQ ID NO.:71), rituximab, ofatumumab, veltuzumab, ublituximab, or ocrelizumab.

In further embodiments, a binding domain comprises a polynucleotide that is at least 60%, at least 70%, at least 75%, at least 80%, at least 85%, at least 90%, at least 95%, or 100% identical to a polynucleotide sequence encoding a heavy chain variable region ($V_H$); e.g., to a $V_H$-encoding polynucleotide from 1.5.3 (SEQ ID NO.:73), 1F5 (SEQ ID NO.:75), Leu16 (SEQ ID NO.:74), rituximab, ofatumumab, veltuzumab, ublituximab, or ocrelizumab.

In still further embodiments, a binding domain comprises (a) a polynucleotide that is at least 60%, at least 70%, at least 75%, at least 80%, at least 85%, at least 90%, at least 95%, or 100% identical to a polynucleotide sequence encoding a $V_L$; e.g., to a $V_L$-encoding polynucleotide from 1.5.3 (SEQ ID NO.:70), 1F5 (SEQ ID NO.:72), Leu16 (SEQ ID NO.: 71), rituximab, ofatumumab, veltuzumab, ublituximab, or ocrelizumab; and (b) a polynucleotide that is at least 60%, at least 70%, at least 75%, at least 80%, at least 85%, at least 90%, at least 95%, or 100% identical to a polynucleotide sequence encoding a $V_H$; e.g., to a $V_H$-encoding polynucleotide from 1.5.3 (SEQ ID NO.:73), 1F5 (SEQ ID NO.:75), Leu16 (SEQ ID NO.:74), rituximab, ofatumumab, veltuzumab, ublituximab, or ocrelizumab. In any of the aforementioned embodiments, polynucleotides encoding each CDR of the $V_L$, $V_H$, or both comprises zero changes or at most one to six nucleotide changes, as compared to a polynucleotide encoding a parent monoclonal antibody or fragment or derivative thereof that specifically binds to CD20, provided that a binding domain containing the modified $V_L$, $V_H$, or both regions specifically binds CD20 with an affinity similar to the wild type binding domain.

In certain embodiments, a binding domain comprises a polynucleotide that is at least 60%, at least 70%, at least 75%, at least 80%, at least 85%, at least 90%, at least 95%, or 100% identical to a polynucleotide sequence encoding a scFv, e.g., an encoded scFv comprising variable domains from an antibody of 1.5.3 (SEQ ID NO.:67), 1F5 (SEQ ID NO.:69), Leu16 (SEQ ID NO.:68), rituximab, ofatumumab, veltuzumab, ublituximab, or ocrelizumab. In each of the aforementioned embodiments, polynucleotide sequences encoding each CDR of a scFv comprises zero changes or at most one to six nucleotide changes, as compared to a polynucleotide encoding a parent scFv from a monoclonal antibody that specifically binds to CD20, provided that scFv containing one or more modified CDRs specifically binds CD20 with an affinity similar to the wild type scFv or corresponding antibody.

In any of the embodiments described herein, a binding domain may consist, comprise, be based on or be derived from a $V_H$, a $V_L$, or both, from ublituximab (see, e.g., US 2015/0290317), rituximab (see, e.g., US 2014/0004037), ocrelizumab (see, e.g., U.S. Pat. No. 8,679,767), ofatumumab (see, e.g., US 2009/0169550), or veltuzumab (see, e.g., US 2009/0169550), the nucleotide and amino acid sequences of which are herein incorporated by reference in their entirety. Additionally, in any of the methods described herein, a CD20 binding molecule may comprise rituximab, ofatumumab, veltuzumab, or ocrelizumab, ublituximab, or any combination thereof.

A fusion protein of the present disclosure comprises an intracellular component that comprises an effector domain. As used herein, an "effector domain" is an intracellular portion or domain of a fusion protein or receptor that can directly or indirectly promote a biological or physiological response in a cell when receiving an appropriate signal. In certain embodiments, an effector domain is from or a portion of a protein or protein complex that receives a signal when bound, or when the protein or portion thereof or protein complex binds directly to a target molecule, and triggers a signal from the effector domain. An effector domain may directly promote a cellular response when it contains one or more signaling domains or motifs, such as an immunoreceptor tyrosine-based activation motif (ITAM), as found in costimulatory molecules. A costimulatory molecule or portion thereof comprising ITAMs are generally known to be capable of initiating T cell activation signaling following ligand engagement. In further embodiments, an effector domain will indirectly promote a cellular response by associating with one or more other proteins that directly promote a cellular response.

In certain embodiments, an effector domain comprises a lymphocyte receptor signaling domain (e.g., CD3ζ), comprises a polypeptide having one or more ITAMs from a costimulatory molecule (e.g., CD28, 4-1BB (CD137), OX40 (CD134)), or combinations thereof. In still further embodiments, an effector domain comprises a cytoplasmic portion that associates with a cytoplasmic signaling protein, wherein the cytoplasmic signaling protein is a lymphocyte receptor or signaling domain thereof, a protein comprising a plurality of ITAMs, a costimulatory factor, or any combination thereof.

Exemplary effector domains include those from 4-1BB (CD137), CD3ε, CD3δ, CD3ζ, CD25, CD27, CD28, CD79A, CD79B, CARD11, DAP10, FcRα, FcRβ, FcRγ, Fyn, HVEM, ICOS, Lck, LAG3, LAT, LRP, NKG2D, NOTCH1, NOTCH2, NOTCH3, NOTCH4, Wnt, OX40 (CD134), ROR2, Ryk, SLAMF1, Slp76, pTα, TCRα, TCRβ, TRIM, Zap70, PTCH2, or any combination thereof.

In certain embodiments, an effector domain comprises a portion or domain from costimulatory molecule CD28, which may optionally include a LL→GG mutation at positions 186-187 of the native CD28 protein (SEQ ID NO.:15; see Nguyen et al., *Blood* 102:4320, 2003). In further embodiments, an effector domain comprises CD3ζ or a functional portion thereof (SEQ ID NO.:17) and one or more portions or domains from a costimulatory molecule, such as CD28 (SEQ ID NO.:15), 4-1BB (SEQ ID NO.:16), CD27, or OX40. In particular embodiments, an effector domain of a fusion protein of the instant disclosure comprises an effector domains or a functional portion thereof from CD3ζ (SEQ ID NO.:17) and CD28 (SEQ ID NO.:15); CD3ζ (SEQ ID NO.:17) and 4-1BB (SEQ ID NO.:16); or CD3ζ (SEQ ID NO.:17), CD28 (SEQ ID NO.:15), and 4-1BB (SEQ ID NO.:16).

In certain embodiments, an effector domain comprises CD3ζ or a functional portion thereof, which is encoded by a polynucleotide having at least 60%, at least 70%, at least 75%, at least 80%, at least 85%, at least 90%, at least 95%, or 100% sequence identity with SEQ ID NO.:86. In further embodiments, an effector domain comprises a portion or a domain from costimulatory molecule CD28, which is encoded by a polynucleotide having at least 60%, at least 70%, at least 75%, at least 80%, at least 85%, at least 90%, at least 95%, or 100% sequence identity to SEQ ID NO.:84. In still further embodiments, an effector domain comprises a portion or a domain from costimulatory molecule 4-1BB, which is encoded by a polynucleotide having at least 60%, at least 70%, at least 75%, at least 80%, at least 85%, at least 90%, at least 95%, or 100% sequence identity to SEQ ID NO.:85.

An extracellular domain and an intracellular domain of the present disclosure are connected by a hydrophobic portion. A "hydrophobic portion," as used herein, means any amino acid sequence having a three-dimensional structure that is thermodynamically stable in a cell membrane, and generally ranges in length from about 15 amino acids to about 30 amino acids. The structure of a hydrophobic portion may comprise an alpha helix, a beta barrel, a beta sheet, a beta helix, or any combination thereof. In certain embodiments, a hydrophobic portion is comprised of a "transmembrane domain" from a known transmembrane protein, which is a portion of the transmembrane protein that can insert into or span a cell membrane. In some embodiments, a hydrophobic portion is a transmembrane domain, such as a CD4 transmembrane domain, CD8 transmembrane domain, CD28 (e.g., SEQ ID NO.:14), CD27 transmembrane domain, and 4-1BB transmembrane domain. In certain embodiments, a hydrophobic portion is a CD28 transmembrane domain (SEQ ID NO.:14). In further embodiments, a hydrophobic portion is a CD28 transmembrane domain, which is encoded by a polynucleotide having at least 60%, at least 70%, at least 75%, at least 80%, at least 85%, at least 90%, at least 95%, or 100% sequence identity to SEQ ID NO.:83.

A fusion protein of the present disclosure may further comprise a linker module. A "linker module" may be an amino acid sequence having from about two amino acids to about 500 amino acids, which can provide flexibility and room for conformational movement between two regions, domains, motifs, fragments, or modules connected by a linker. In certain embodiments, a linker module may be located between a binding domain and a hydrophobic region. In such embodiments, a linker module can position a binding domain away from the cell surface to enable proper cell/cell contact, antigen binding, and activation (Patel et al., *Gene Therapy* 6: 412-419, 1999). Linker module length may be varied to maximize tumor recognition based on the selected target molecule, selected binding epitope, or antigen binding domain size and affinity (see, e.g., Guest et al., *J. Immunother.* 28:203-11, 2005; PCT Publication No. WO 2014/031687). Exemplary linker modules include those having a glycine-serine (Gly-Ser) linker having from one to about ten repeats of $Gly_xSer_y$, wherein x and y are independently an integer from 0 to 10, provided that x and y are not both 0 (e.g., $(Gly_4Ser)_2$, $(Gly_3Ser)_2$, $Gly_2Ser$, or a combination thereof, such as $(Gly_3Ser)_2$ $Gly_2Ser$). In certain embodiments, a linker module comprises one or more immunoglobulin heavy chain constant regions, such as a CH3 alone, or a CH2CH3 structure, a CH3CH4 structure, an immunoglobulin hinge, or any combination thereof (e.g., a CH2CH3 structure together with a hinge). In further embodiments, a linker module comprises all or a portion of an Fc domain selected from: a CH1 domain, a CH2 domain, a CH3 domain, or combinations thereof (see, e.g., PCT Publication WO 2014/031687).

Exemplary linker modules can vary in length, for instance, from about five amino acids to about 500 amino acids, from about ten amino acids to about 350 amino acids, from about 15 amino acids to about 100 amino acids, from about 20 amino acids to about 75 amino acids, or from about 25 amino acids to about 35 amino acids. In further embodiments, a linker module may further comprise a hinge region, a tag or both. Each such component of the linker module is not mutually exclusive.

In certain embodiments, a linker module of a fusion protein of this disclosure may include an IgG1 CH2 region with a N297Q mutation (SEQ ID NO.:10); an IgG4 CH2 region (SEQ ID NO.:11); an IgG1 CH3 region (SEQ ID NO.:12); or an IgG4 CH3 region (SEQ ID NO.:13). In certain embodiments, a linker module may include a glycine-serine linker (SEQ ID NO.:20, which may be encoded by SEQ ID NO.:89, or SEQ ID NO.:21, which may be encoded by SEQ ID NO.:90).

In further embodiments, a linker module of a fusion protein of this disclosure may include an IgG1 CH2 region with a N297Q mutation, which is encoded by a polynucleotide having at least 60%, at least 70%, at least 75%, at least 80%, at least 85%, at least 90%, at least 95%, or 100% sequence identity with SEQ ID NO.:79. In other embodiments, a linker module of a fusion protein of this disclosure may include an IgG4 CH2 region, which is encoded by a polynucleotide having at least 60%, at least 70%, at least 75%, at least 80%, at least 85%, at least 90%, at least 95%, or 100% sequence identity with SEQ ID NO.:80. In still other embodiments, a linker module of a fusion protein of this disclosure may include an IgG1 CH3 region, which is encoded by a polynucleotide having at least 60%, at least 70%, at least 75%, at least 80%, at least 85%, at least 90%, at least 95%, or 100% sequence identity with SEQ ID NO.:81. In yet other embodiments, a linker module of a fusion protein of this disclosure may include an IgG4 CH3 region, which is encoded by a polynucleotide having at least 60%, at least 70%, at least 75%, at least 80%, at least 85%, at least 90%, at least 95%, or 100% sequence identity with SEQ ID NO.:82.

In certain embodiments, a linker module further comprises a hinge region. As used herein, a "hinge region" or a "hinge" refers to (a) an immunoglobulin hinge sequence (made up of, for example, upper and core regions), or a functional fragment or variant thereof, (b) a type II C-lectin interdomain (stalk) region, or a functional fragment or variant thereof, or (c) a cluster of differentiation (CD) molecule stalk region, or a functional variant thereof. As used herein, a "wild type immunoglobulin hinge region" refers to naturally occurring upper and middle hinge amino acid sequences interposed between and connecting the CH1 and CH2 domains found in the heavy chain of an antibody. In certain embodiments, a hinge region is human, and in particular embodiments, comprises a human IgG hinge region. In further embodiments, a hinge region is an altered IgG4 hinge region as described in PCT Publication No. WO 2014/031687. In particular embodiments, a hinge region of a fusion protein of this disclosure may be an IgG1 hinge (SEQ ID NO.:7). In related embodiments, a hinge region of a fusion protein of this disclosure may be an IgG1 hinge, which is encoded by a polynucleotide as set forth in SEQ ID NO.:76.

A fusion protein of the present disclosure may further comprise junction amino acids. "Junction amino acids" or "junction amino acid residues" refer to one or more (e.g., about 2-20) amino acid residues between two adjacent domains, motifs, regions, modules, or fragments of a protein, such as between a binding domain and an adjacent linker module, between a hydrophobic domain and an adjacent effector domain, or on one or both ends of a linker module that links two domains, motifs, regions, modules, or fragments (e.g., between a linker module and an adjacent binding domain or between a linker module and an adjacent hinge). Junction amino acids may result from the construct design of a fusion protein (e.g., amino acid residues resulting from the use of a restriction enzyme site during the construction of a nucleic acid molecule encoding a fusion protein). For example, a hydrophobic portion of a fusion protein may have one or more junction amino acids at the amino-terminal end, carboxy-terminal end, or both. Examples of junction amino acids include junction amino acids from IgG2 (e.g., SEQ ID NO.:9, which may be encoded by SEQ ID NO.:78). In some embodiments where a hinge region is from IgG4, the hinge region can include junction amino acids (e.g., SEQ ID NO.:8, which may be encoded by SEQ ID NO.:77). In certain embodiments, a hydrophobic portion is a CD28 transmembrane domain having an amino acid of SEQ ID NO.:14 wherein the CD28 transmembrane domain comprises an amino-terminal junction amino acid of, for example, methionine (see, e.g., fusion proteins of SEQ ID NO.:30, 31, 39, and 40). Thus, in certain embodiments, a linker module comprises an IgG4 hinge, IgG4 junction amino acids, and IgG4 CH2-CH3. In certain other embodiments, a linker module comprises an IgG1 hinge, IgG2 junction amino acids, and IgG1 CH2-CH3.

In some embodiments, a fusion protein of the present disclosure may further comprise a tag. As used herein, "tag" refers to a unique peptide sequence affixed to, fused to, or that is part of a protein of interest, to which a heterologous or non-endogenous cognate binding molecule (e.g., receptor, ligand, antibody, or other binding partner) is capable of specifically binding, where the binding property can be used to detect, identify, isolate or purify, track, enrich for, or target a tagged protein or cells expressing a tagged protein, particularly when a tagged protein is part of a heterogeneous population of proteins or other material, or when cells expressing a tagged protein are part of a heterogeneous population of cells (e.g., a biological sample like peripheral blood). (See, e.g., WO 2015/095895.) In the provided fusion proteins, the ability of the tag(s) to be specifically bound by the cognate binding molecule(s) is distinct from, or in addition to, the ability of the binding domain(s) to specifically bind to the target molecule(s). A tag generally is not an antigen-binding molecule, for example, is not an antibody or TCR or an antigen-binding portion thereof. Examples of tags include Strep tag, His tag, Flag tag, Xpress tag, Avi tag, Calmodulin tag, Polyglutamate tag, HA tag, Myc tag, Nus tag, S tag, X tag, SBP tag, Softag, V5 tag, CBP, GST, MBP, GFP, Thioredoxin tag. In particular embodiments, a Strep tag has an amino acid sequence of SEQ ID NO.:62 or SEQ ID NO.:63.

A fusion protein of the present disclosure may comprise a signal peptide. A "signal peptide" is a short (e.g., 5-30 amino acids) sequence that is used to target the fusion protein for cell surface expression. Exemplary signal peptides include Granulocyte-macrophage colony-stimulating factor (GM-CSF) signaling peptide (SEQ ID NO.:18, which may be encoded by SEQ ID NO.:87) and murine kappa signal peptide (SEQ ID NO.:19, which may be encoded by SEQ ID NO.:88).

In certain embodiments, a fusion protein is a chimeric antigen receptor. "Chimeric antigen receptor" (CAR) refers to a fusion protein of the present disclosure engineered to contain two or more naturally-occurring amino acid sequences linked together in a way that does not occur naturally or does not occur naturally in a host cell, which fusion protein can function as a receptor when present on a surface of a cell.

In some embodiments, a CAR is fully human or humanized. In certain embodiments, a CAR has a scFv from an anti-CD20 antibody or a scTCR from a TCR specific for a CD20 antigen. In particular embodiments, a CAR comprises a scFv from 1.5.3, 1F5, Leu16, rituximab, ofatumumab, veltuzumab, ocrelizumab, ublituximab, or any combination thereof. In particular embodiments, a CAR comprises a linker module comprising an IgG1 hinge, an IgG4 hinge, or any combination thereof. In further embodiments, a CAR comprises a linker module comprising an IgG1 CH2 region with a N297Q mutation, an IgG4 CH2 region, an IgG1 CH3 region, an IgG4 CH3 region, or any combination thereof. In still further embodiments, a hydrophobic portion of a CAR comprises a CD28 transmembrane domain. In some embodiments, a CAR comprises an intracellular domain comprising a portion or domain from CD3, 4-1BB, CD28, or any combination thereof. In any of the above embodiments, a CAR comprises junction amino acids between two adjacent domains, motifs, regions, modules, or fragments.

In certain embodiments, a CAR may be at least 90%, at least 91%, at least 92%, at least 93%, at least 94%, at least 95%, at least 96%, at least 97%, at least 98%, at least 99%, at least 99.5%, or 100% identical to 1.5.3-NQ-28-BB-z (SEQ ID NO.:26); 1.5.3-NQ-28-z (SEQ ID NO.:27); 1.5.3-NQ-BB-z (SEQ ID NO.:28); 1.5.3-NQ-z (SEQ ID NO.:29); Leu16-28-BB-z (SEQ ID NO.:30); Leu16-28-z (SEQ ID NO.:31); 1F5-NQ-28-BB-z (SEQ ID NO.:32); 1F5-NQ-28-z (SEQ ID NO.:33); or 1F5-NQ-BB-z (SEQ ID NO.:34). In particular embodiments, a CAR comprise or consists of an amino acid sequence of any one of SEQ ID NOS.:26-34.

In certain embodiments, a CAR may be at least 60%, at least 70%, at least 75%, at least 80%, at least 85%, at least 90%, at least 95%, or 100% identical to a nucleic acid molecule sequence of any one of SEQ ID NOS.:44-52. In particular embodiments, a CAR is encoded by a polynucleotide comprising or consisting of a sequence of any one of SEQ ID NOS.:44-52.

Methods of making fusion proteins, including CARs, are well known in the art and are described, for example, in U.S. Pat. Nos. 6,410,319; 7,446,191; U.S. Patent Publication No. 2010/065818; U.S. Pat. No. 8,822,647; PCT Publication No. WO 2014/031687; U.S. Pat. No. 7,514,537; and Brentjens et al., 2007, *Clin. Cancer Res.* 13:5426.

Host Cells, Nucleic Acids and Vectors

In certain aspects, the present disclosure provides nucleic acid molecules that encode any one or more of the fusion proteins described herein. A polynucleotide encoding a desired fusion protein can be obtained or produced using recombinant methods known in the art using standard techniques, such as screening libraries from cells expressing a desired sequence or a portion thereof, by deriving a sequence from a vector known to include the same, or by isolating a sequence or a portion thereof directly from cells or tissues containing the same. Alternatively, a sequence of interest can be produced synthetically. Such nucleic acid molecules can be inserted into an appropriate vector (e.g., viral vector or non-viral plasmid vector) for introduction into a host cell of interest (e.g., an immune cell, such as a T cell).

A "vector" is a nucleic acid molecule that is capable of transporting another nucleic acid. In some embodiments, vectors contain transcription or translation terminators, initiation sequences, or promoters for regulation of expression of a desired nucleic acid sequence. Vectors may be, for example, plasmids, cosmids, viruses, or phage, or a transposon system (e.g., Sleeping Beauty, see, e.g., Geurts et al., *Mol. Ther.* 8:108, 2003; Mátés et al., *Nat. Genet.* 41:753, 2009). An "expression vector" is a vector that is capable of directing expression of a protein encoded by one or more genes carried by a vector when it is present in the appropriate environment.

A vector that encodes a core virus is referred to herein as a "viral vector." There are a large number of available viral vectors suitable for use with compositions of the instant disclosure, including those identified for human gene therapy applications (see Pfeifer and Verma, *Ann. Rev. Genomics Hum. Genet.* 2:177, 2001). Suitable viral vectors include vectors based on RNA viruses, such as retrovirus-derived vectors.

"Retroviruses" are viruses having an RNA genome, which is reverse-transcribed into DNA using a reverse transcriptase enzyme, the reverse-transcribed DNA is then incorporated into the host cell genome. "Gammaretrovirus" refers to a genus of the retroviridae family. Examples of gammaretroviruses include mouse stem cell virus, murine leukemia virus, feline leukemia virus, feline sarcoma virus, and avian reticuloendotheliosis viruses. "Lentivirus" refers to another genus of retroviruses that are capable of infecting dividing and non-dividing cells. Several examples of lentiviruses include human immunodeficiency virus (HIV; including HIV type 1, and HIV type 2); equine infectious anemia virus; feline immunodeficiency virus (M); bovine immune deficiency virus (BIV); and simian immunodeficiency virus (SIV).

In certain embodiments, the viral vector can be a gammaretrovirus, e.g., Moloney murine leukemia virus (MLV)-derived vectors. In other embodiments, the viral vector can be a more complex retrovirus-derived vector, e.g., a lentivirus-derived vector. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing CAR transgenes are known in the art and have been previous described, for example, in U.S. Pat. No. 8,119,772; Walchli et al., *PLoS One* 6:327930, 2011; Zhao et al., *J. Immunol.* 174:4415, 2005; Engels et al., *Hum. Gene Ther.* 14:1155, 2003; Frecha et al., *Mol. Ther.* 18:1748, 2010; Verhoeyen et al., *Methods Mot Biol.* 506:97, 2009. Retroviral and lentiviral vector constructs and expression systems are also commercially available. Other viral vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., *Gene Ther.* 5: 1517, 1998).

Other vectors recently developed for gene therapy uses can also be used with the compositions and methods of this disclosure. Such vectors include those derived from baculoviruses and α-viruses. (Jolly, D J. 1999. Emerging Viral Vectors. pp 209-40 in Friedmann T. ed. The Development of Human Gene Therapy. New York: Cold Spring Harbor Lab), or plasmid vectors (such as sleeping beauty or other transposon vectors).

In certain embodiments, a viral vector is used to introduce a non-endogenous polynucleotide encoding a fusion protein specific for a target, such as CD20. In such embodiments, a viral vector may be a retroviral vector or a lentiviral vector. A viral vector may also include nucleic acid sequences encoding a marker for transduction. Transduction markers for viral vectors are known in the art and include selection markers, which may confer drug resistance, detectable markers, such as fluorescent markers or cell surface proteins that can be detected by methods such as flow cytometry.

In certain embodiments, a viral vector comprises a transduction marker. As used herein, a "transduction marker" can be included in any of the constructs as a way to monitor transfection efficiency or to detect cells expressing a fusion protein of interest. Exemplary transduction markers green fluorescent protein, an extracellular domain of human CD2, a truncated human EGFR (huEGFRt; SEQ ID NO.:25, which may be encoded by SEQ ID NO.:94; see Wang et al., *Blood* 118:1255, 2011), or a truncated CD19 (SEQ ID NO.:24, which may be encoded by SEQ ID NO.:93). In certain embodiments, a viral vector comprises a suicide gene, such as iCasp9 (see, e.g., Gargett and Brown, *Front. Pharmacol.* 5:235, 2104), or HSV-TK (see, e.g., Fillat et al., *Curr. Gene Ther.* 3:13, 2003).

When a viral vector genome comprises a plurality of polynucleotides to be expressed in a host cell as separate transcripts, the viral vector may also comprise additional sequences between the two (or more) transcripts allowing for bicistronic or multicistronic expression. Examples of such sequences used in viral vectors include internal ribosome entry sites (IRES), furin cleavage sites, viral 2A peptide, or any combination thereof. In certain embodiments, a vector construct may comprise a polynucleotide encoding a self-cleaving peptide (e.g., E2A (SEQ ID NO.:22, which may be encoded by SEQ ID NO.:91), T2A (SEQ ID NO.:23, which may be encoded by SEQ ID NO.:92), P2A (SEQ ID NO.:95, which may be encoded by SEQ ID NO.:97), or F2A (SEQ ID NO.:96, which may be encoded by SEQ ID NO.:98)) such that the mature fusion protein does not contain a transduction marker or a suicide gene. In certain embodiments, a nucleic acid vector may encode a fusion peptide of the present disclosure, optionally containing a transduction marker (such as tCD19 or tEGFR). In further embodiments, nucleic acid molecules encoding a fusion protein of this disclosure may be codon optimized to enhance or maximize expression in certain types of cells, such as T cells (Scholten et al., *Clin. Immunol.* 119: 135-145, 2006), and may optionally contain a transduction marker (such as tCD19 or tEGFR).

In any of the embodiments described herein, a vector containing a polynucleotide encoding a fusion protein of this disclosure may also contain a polynucleotide encoding a transduction marker, which may be used to target a host cell expressing the transduction marker for ablation or death. It has been shown that the persistence of functional antigen-targeting CAR T cells may cause sustained depletion of healthy cells that endogenously express the antigen (see, e.g., Paskiewicz et al., *J. Clin. Invest.,* 126(11):4262-4272 (2016). Thus, control mechanisms that permit regulation (e.g., ablation, killing, or producing another cytotoxic effect) of the transferred T cells after a achieving a desired antitumor affect are desirable. As used herein, the term "cytotoxic effect" encompasses ablating, killing, or otherwise impairing or reducing the ability of a cell to grow, divide, or survive. Non-limiting examples of cytotoxic effects include necrosis, lysis, apoptosis, swelling, loss of membrane integrity, reduced levels or rates of transcription, reduced levels or rates of translation, reduced levels or rates of ATP production, increased levels or rates of reactive oxygen species, reduced mitochondrial function, nuclear condensation, increased cleavage of the cell's DNA, reduced rates of division or proliferation, and reduction or loss of specific cell function (e.g., the ability of a B lymphocyte to produce immunoglobulins). One exemplary approach is to use a marker (e.g., tEGFR) recognizable by an antibody (e.g., cetuximab) or antibody-drug conjugate that, upon binding the marker, facilitates antibody-dependent cell-mediated cytotoxic (ADCC) or complement-dependent cytotoxic (CDC) responses, or delivers a cytotoxic molecule, to ablate, kill, or otherwise cause a cytotoxic effect on the transferred T cells. Thus, in certain embodiments, a vector comprises a polynucleotide encoding a fusion protein and comprises a polynucleotide encoding a transduction marker. A transduction marker that can be specifically bound by a cytotoxic antibody, antibody-drug conjugate or other cytotoxic agent is referred to herein as "a suicide transduction marker." In certain embodiments, a method of treating a disease or disorder associated with CD20 expression comprises administering a therapeutically effective amount of a transformed host cell to a subject according to the present disclosure, wherein the transformed host cell comprises a heterologous polynucleotide encoding a fusion protein and a heterologous polynucleotide encoding a suicide transduction marker, wherein the method optionally comprises administering a cytotoxic antibody, antibody-drug conjugate or other cytotoxic agent that specifically associates with, binds to or forms a complex with the suicide transduction marker. In some embodiments, a suicide transduction marker comprises or consists of a truncated EGFR (e.g., SEQ ID NO.: 25), which is specifically bound by an anti-EGFR antibody, such as, for example, cetuximab. In further embodiments, a suicide transduction marker comprises or consists of a truncated CD19 (e.g., SEQ ID NO.: 24), which is specifically bound by a cytotoxic anti-CD19 antibody or antibody-drug conjugate, such as, for example, blinatumomab, coltuximabravtansine, MOR208, MEDI-551, denintuzumabmafodotin, Merck patent anti-CD19, taplutumomabpaptox, XmAb 5871, MDX-1342, SAR3419, SGN-19A, or AFM11 (see, e.g., Naddafi and Davami, *Int. J. Mol. Cell. Med.,* 4(3):143-151 (2015)).

In any of the embodiments described herein, an encoded fusion protein of this disclosure may be a CAR, such as a CD20 specific CAR. In certain embodiments, a CAR or binding domain thereof encoded by a polynucleotide contained in a vector of this disclosure is fully human or humanized. In further embodiments, a CAR encoded by a vector of this disclosure has a scFv from an anti-CD20 antibody or a scTCR from a TCR specific for a CD20 antigen. In still further embodiments, a CAR encoded by a vector of this disclosure comprises a scFv from 1.5.3, 1F5, Leu16, rituximab, ofatumumab, veltuzumab, ocrelizumab, ublituximab, or any combination thereof. In particular embodiments, a CAR encoded by a polynucleotide contained in a vector of this disclosure comprises a linker module comprising an IgG1 hinge, an IgG4 hinge, or any combination thereof. In further embodiments, a CAR encoded by a polynucleotide contained in a vector of this disclosure comprises a linker module comprising an IgG1 CH2 region with a N297Q mutation, an IgG4 CH2 region, an IgG1 CH3 region, an IgG4 CH3 region, or any combination thereof. In particular embodiments, a linker module or a variable region linker of a CAR encoded by a vector of this disclosure comprises a glycine-serine linker. In still further embodiments, a hydrophobic portion of a CAR encoded by a polynucleotide contained in a vector of this disclosure comprises a CD28 transmembrane domain. In some embodiments, a CAR encoded by a polynucleotide contained in a vector of this disclosure comprises an intracellular domain comprising a portion or domain from CD3ζ, 4-1BB, CD28, or any combination thereof. In any of the embodiments described herein, a CAR encoded by a polynucleotide contained in a vector of this disclosure comprises junction amino acids between adjacent domains, motifs, regions, modules, or fragments.

In any of the embodiments described herein, a vector may comprise a polynucleotide that encodes a CAR that is at least 90%, at least 91%, at least 92%, at least 93%, at least 94%, at least 95%, at least 96%, at least 97%, at least 98%, at least 99%, at least 99.5%, or 100% identical to 1.5.3-NQ-28-BB-z (SEQ ID NO.:26); 1.5.3-NQ-28-z (SEQ ID NO.:27); 1.5.3-NQ-BB-z (SEQ ID NO.:28); 1.5.3-NQ-z (SEQ ID NO.:29); Leu16-28-BB-z (SEQ ID NO.:30); Leu16-28-z (SEQ ID NO.:31); 1F5-NQ-28-BB-z (SEQ ID NO.:32); 1F5-NQ-28-z (SEQ ID NO.:33); or 1F5-NQ-BB-z (SEQ ID NO.:34). In further embodiments, a vector may comprise a polynucleotide that encodes a CAR that is comprised of or consists of an amino acid sequence of any one of SEQ ID NOS.:26-34.

In still further embodiments, a CD20-specific CAR is encoded by a polynucleotide contained in a vector, wherein the polynucleotide has at least 60%, at least 70%, at least 75%, at least 80%, at least 85%, at least 90%, at least 95%, or 100% identity to a nucleic acid molecule sequence of any one of SEQ ID NOS.:44-52. In related embodiments, a CD20-specific CAR is encoded by a polynucleotide contained in a vector, wherein the polynucleotide comprises or consists of a sequence of any one of SEQ ID NOS.:44-52.

Optionally, any vector of this disclosure containing a polynucleotide that encodes a CAR of this disclosure can also encode a transduction marker (e.g., tCD19), which may also include a self-cleaving peptide so that the transduction marker and CAR are separated into separate molecules—a CAR and a transduction marker. In certain embodiments, a vector may comprise a polynucleotide encodes a self-cleaving peptide disposed between a CD20-specific CAR and a tCD19 transduction marker, which polynucleotide is at least 60%, at least 70%, at least 75%, at least 80%, at least 85%, at least 90%, at least 95%, or 100% identical to a nucleic acid molecule sequence of any one of SEQ ID NOS.:53-61. In further embodiments, a vector may comprise a polynucleotide encoding a self-cleaving peptide disposed between a CD20-specific CAR and a tCD19 transduction marker and that comprises or consists of a nucleic acid molecule sequence of any one of SEQ ID NOS.:53-61.

In any of the embodiments disclosed herein, an isolated polynucleotide encodes a fusion protein capable of specifically binding CD20, wherein the polynucleotide: (a) is at least 80% identical to a polynucleotide sequence of any one of SEQ ID NOS.:53-56; (b) is at least 80% identical to a polynucleotide sequence of any one of SEQ ID NOS.:44-47; (c) comprises a polynucleotide sequence of any one of SEQ ID NOS.:53-56; (d) comprises a polynucleotide sequence of any one of SEQ ID NOS.:44-47; (e) consists of a polynucleotide sequence of any one of SEQ ID NOS.:53-56; or (f) consists of a polynucleotide sequence of any one of SEQ ID NOS.:44-47.

In any of the embodiments disclosed herein, a fusion protein is encoded by an isolated polynucleotide as disclosed herein. In certain embodiments, the fusion protein consists of or comprises an amino acid sequence wherein the fusion protein: (a) is at least 90% identical to a mature fusion protein, wherein the mature fusion protein comprises an amino acid sequence of any one of SEQ ID NOS.:26-29 and 35-38 and 32-34 with the tCD19 transduction marker removed; (b) is comprised of a mature fusion protein, wherein the mature fusion protein comprises an amino acid sequence of any one of SEQ ID NOS.: 35-38 with the tCD19 transduction marker removed; (c) consists of a mature fusion protein, wherein the mature fusion protein comprises an amino acid sequence of any one of SEQ ID NOS.: 35-38 with the tCD19 transduction marker removed; (d) is at least 90% identical to an amino acid sequence of any one of SEQ ID NOS.:26 29; (e) is comprised of an amino acid sequence of any one of SEQ ID NOS.:26 29; (f) consists of an amino acid sequence of any one of SEQ ID NOS.:26 29.

In certain embodiments, a host cell is provided that comprises a heterologous polynucleotide as disclosed herein and is capable of expressing the fusion protein encoded by the heterologous polynucleotide.

In any of the embodiments disclosed herein, a host cell comprises an isolated polynucleotide encoding a fusion protein capable of specifically binding CD20, wherein the polynucleotide: (a) is at least 80% identical to a polynucleotide sequence of any one of SEQ ID NOS.:53-56; (b) is at least 80% identical to a polynucleotide sequence of any one of SEQ ID NOS.:44-47; (c) comprises a polynucleotide sequence of any one of SEQ ID NOS.:53-56; (d) comprises a polynucleotide sequence of any one of SEQ ID NOS.:44-47; (e) consists of a polynucleotide sequence of any one of SEQ ID NOS.:53-56; or (f) consists of a polynucleotide sequence of any one of SEQ ID NOS.:44-47.

In certain embodiments, a host cell comprises a fusion protein that consists of or comprises an amino acid sequence wherein the fusion protein: (a) is at least 90% identical to a mature fusion protein, wherein the mature fusion protein comprises an amino acid sequence of any one of SEQ ID NOS.:26-29 and 35-38 and 32-34 with the tCD19 transduction marker removed; (b) is comprised of a mature fusion protein, wherein the mature fusion protein comprises an amino acid sequence of any one of SEQ ID NOS.: 35-38 with the tCD19 transduction marker removed; (c) consists of a mature fusion protein, wherein the mature fusion protein comprises an amino acid sequence of any one of SEQ ID NOS.: 35-38 with the tCD19 transduction marker removed; (d) is at least 90% identical to an amino acid sequence of any one of SEQ ID NOS.:26 29; (e) is comprised of an amino acid sequence of any one of SEQ ID NOS.:26 29; (f) consists of an amino acid sequence of any one of SEQ ID NOS.:26 29.

In certain embodiments, a host cell comprises a heterologous polynucleotide as disclosed herein and is capable of expressing the fusion protein encoded by the heterologous polynucleotide.

In certain embodiments, a host cell comprises a heterologous polynucleotide encoding a fusion protein comprising a binding domain, wherein the binding domain is: (a) a 1.5.3 scFv comprising an amino acid sequence that is at least 90% identical to an amino acid sequence of SEQ ID NO.:64, wherein each CDR of the scFv comprises zero changes or at most one, two, three, four, five or six changes as compared to the corresponding CDR of a parent monoclonal antibody or fragment or derivative thereof that specifically binds to CD20, provided that scFv containing one or more modified CDRs specifically binds CD20 with an affinity similar to the wild type scFv or corresponding antibody; (b) a 1.5.3 scFv comprising or consisting of an amino acid sequence of SEQ ID NO.:64; (c) a 1F5 scFv comprising an amino acid sequence that is at least 90% identical to an amino acid sequence of SEQ ID NO.:66, wherein each CDR of the scFv comprises zero changes or at most one, two, three, four, five or six changes as compared to the corresponding CDR of a parent monoclonal antibody or fragment or derivative thereof that specifically binds to CD20, provided that scFv containing one or more modified CDRs specifically binds CD20 with an affinity similar to the wild type scFv or corresponding antibody; (d) a 1F5 scFv comprising or consisting of an amino acid sequence of SEQ ID NO.:66; (e) a Leu16 scFv comprising an amino acid sequence that is at least 90% identical to an amino acid sequence of SEQ ID NO.:65, wherein each CDR of the scFv comprises zero changes or at most one, two, three, four, five or six changes as compared to the corresponding CDR of a parent monoclonal antibody or fragment or derivative thereof that specifically binds to CD20, provided that scFv containing one or more modified CDRs specifically binds CD20 with an affinity similar to the wild type scFv or corresponding antibody; or (f) a Leu16 scFv comprising or consisting of an amino acid sequence of SEQ ID NO.:65.

In certain embodiments, a host cell comprises a heterologous polynucleotide encoding a fusion protein comprising an scFv, wherein the scFv is encoded by: (a) a polynucleotide having at least 80% identity to a nucleic acid molecule sequence of SEQ ID NO.:67, wherein polynucleotide sequences encoding each CDR of a scFv comprises zero changes or at most one to six nucleotide changes, as compared to a polynucleotide encoding a parent scFv from a monoclonal antibody that specifically binds to CD20, provided that scFv containing one or more modified CDRs specifically binds CD20 with an affinity similar to the wild type scFv or corresponding antibody; (b) a polynucleotide comprising or consisting of a nucleic acid molecule sequence of SEQ ID NO.:67; (c) a polynucleotide having at least 80% identity to a nucleic acid molecule sequence of SEQ ID NO.:69, wherein polynucleotide sequences encoding each CDR of a scFv comprises zero changes or at most one to six nucleotide changes, as compared to a polynucleotide encoding a parent scFv from a monoclonal antibody that specifically binds to CD20, provided that scFv containing one or more modified CDRs specifically binds CD20 with an affinity similar to the wild type scFv or corresponding antibody; (d) a polynucleotide comprising or consisting of a nucleic acid molecule sequence of SEQ ID NO.:69; (e) a polynucleotide having at least 80% identity to a nucleic acid molecule sequence of SEQ ID NO.:68, wherein polynucleotide sequences encoding each CDR of a scFv comprises zero changes or at most one to six nucleotide changes, as compared to a polynucleotide encoding a parent scFv from a monoclonal antibody that specifically binds to CD20, provided that scFv containing one or more modified CDRs specifically binds CD20 with an affinity similar to the wild type scFv or corresponding antibody; or (f) a polynucleotide comprising or consisting of a nucleic acid molecule sequence of SEQ ID NO.:68.

In certain embodiments, a host cell comprises a heterologous polynucleotide encoding a fusion protein, wherein the fusion protein is a chimeric antigen receptor and comprises or consists of an amino acid sequence that is at least 90% identical to an amino acid sequence of any one of SEQ ID NOS.:26-3443.

In certain embodiments, a host cell comprises a heterologous polynucleotide encoding a fusion protein comprising a hydrophobic portion, wherein the hydrophobic portion is a transmembrane domain. In certain embodiments, the hydrophobic portion is a CD4, CD8, CD28 or CD27 transmembrane domain.

In certain embodiments, a host cell comprises a heterologous polynucleotide encoding a fusion protein comprising an effector domain or functional portion thereof, wherein the effector domain or functional portion thereof is a 4-1BB (CD137), CD3ε, CD3δ, CD3ζ, CD25, CD27, CD28, CD79A, CD79B, CARD11, DAP10, FcRα, FCRβ, FcRγ, Fyn, HVEM, ICOS, Lck, LAG3, LAT, LRP, NKG2D, NOTCH1, NOTCH2, NOTCH3, NOTCH4, OX40 (CD134), ROR2, Ryk, SLAMF1, Slp76, pTα, TCRα, TCRβ, TRIM, Zap70, PTCH2, or any combination thereof.

In certain embodiments, a host cell comprises a heterologous polynucleotide encoding a fusion protein comprising an intracellular component, wherein the intracellular component comprises: (a) a CD3ζ effector domain or functional portion thereof, a CD28 costimulatory domain or functional portion thereof and a 4-1BB (CD137) costimulatory domain or portion thereof; (b) a CD3ζ effector domain or functional portion thereof, a CD28 costimulatory domain or functional portion thereof and a OX40 (CD134) costimulatory domain or portion thereof; (c) a CD3ζ effector domain or functional portion thereof, a CD27 costimulatory domain or functional portion thereof and a 4-1BB (CD137) costimulatory domain or portion thereof; (d) a CD3ζ effector domain or functional portion thereof, a CD27 costimulatory domain or functional portion thereof and a OX40 (CD134) costimulatory domain or portion thereof; (e) a CD3ζ effector domain or functional portion thereof, a CD27 costimulatory domain or functional portion thereof and a CD28 costimulatory domain or portion thereof; or (f) a CD3ζ effector domain or functional portion thereof, a 4-1BB (CD137) costimulatory domain or functional portion thereof and a OX40 (CD134) costimulatory domain or portion thereof.

In any of the embodiments described herein, a vector containing a fusion protein of this disclosure is transduced into a host cell. "Transduction" refers to introduction of a nucleic acid molecule (e.g., a vector encoding a fusion protein of the present disclosure) into a host cell. After transduction, a host cell may carry a vector extra-chromosomally or integrated into a chromosome. Integration into a host cell genome or self-replicating vectors generally result in genetically stable inheritance of a transformed vector. Any suitable transduction method can be utilized. A vector can be transferred into a host cell by physical, chemical, or biological means. A host cell containing a transformed nucleic acid molecule is referred to as "engineered," "recombinant," or "non-natural."

In certain embodiments, a cell, such as a T cell, obtained from a subject may be converted into an engineered, non-natural, or recombinant cell (e.g., an engineered, non-natural, or recombinant T cell) by introducing a nucleic acid molecule encoding a cell surface located fusion protein as described herein, where the cell expresses the fusion protein.

In certain embodiments, a host cell transfected to express a fusion protein of this disclosure is a functional T cell, such as a virus-specific T cell, a tumor antigen specific cytotoxic T cell, a naïve T cell, a memory stem T cell, a central or effector memory T cell, γδ T cells, or a CD4+ CD25+ regulatory T cell. In further embodiments, a nucleic acid molecule encoding a fusion protein of this disclosure is introduced into bulk CD8+ T cells, naïve CD8+ T cells, CD8+ $T_{CM}$ cells, CD8+ $T_{EM}$ cells, or any combination thereof. In still further embodiments, a nucleic acid molecule encoding a fusion protein of this disclosure is introduced into bulk CD4+ T cells, naïve CD4+ T cells, CD4+ $T_{CM}$ cells, CD4+ $T_{EM}$ cells, or any combination thereof. In other embodiments, a nucleic acid molecule encoding a fusion protein of this disclosure is introduced into a population of T cells enriched for naïve CD8+ T cells and CD8+ $T_{CM}$ cells. In still other embodiments, a nucleic acid molecule encoding a fusion protein of this disclosure is introduced into a population of T cells enriched for naïve CD4+ T cells and CD4+ $T_{CM}$ cells. In any of the aforementioned embodiments, the T cells further contain a nucleic acid molecule encoding an engineered CD20-specific TCR, an engineered CD20-specific high affinity TCR, a CD20-specific CAR, or any combination thereof.

In certain embodiments, prior to expansion and genetic modification of the T cells with a fusion protein construct of this disclosure, a source of T cells is obtained from a subject (e.g., peripheral blood mononuclear cells (PBMCs), bone marrow, lymph node tissue, cord blood, thymus tissue, tissue from a site of infection, ascites, pleural effusion, or spleen tissue), from which T cells are isolated using methods known in the art. Specific T cell subsets can be collected in accordance with known techniques and enriched or depleted by known techniques, such as affinity binding to antibodies, flow cytometry, or immunomagnetic selection. After enrichment or depletion steps and introduction of a fusion protein, in vitro expansion of the desired modified T cells can be carried out in accordance with known techniques (including those described in U.S. Pat. No. 6,040,177), or variations thereof that will be apparent to those skilled in the art.

For example, a desired T cell population or subpopulation may be expanded by adding an initial T cell population to a culture medium in vitro, and then adding feeder cells, such as non-dividing PBMCs to the culture medium, (e.g., such that the resulting population of cells contains at least about 5, 10, 20, or 40 or more PBMC feeder cells for each T cell in the initial population to be expanded); and incubating the culture (e.g. for a time sufficient to expand the numbers of T cells). Non-dividing feeder cells can comprise gamma-irradiated PBMC feeder cells. In some embodiments, PBMCs are irradiated with gamma rays in the range of about 3000 to 3600 rads. The order of addition of T cells and feeder cells to the culture media can be reversed if desired. A culture can typically be incubated under conditions of temperature and the like that are suitable for the growth of T cells. For the growth of human T lymphocytes, for example, the temperature will generally be at least about 25° C., preferably at least about 30° C., more preferably about 37° C.

Optionally, expansion methods may further comprise adding non-dividing Epstein-Barr Virus (EBV)-transformed lymphoblastoid cells (LCL) as feeder cells. LCL can be irradiated with gamma rays in the range of about 6000 to 10,000 rads. The LCL feeder cells may be provided in any suitable amount, such as a ratio of LCL feeder cells to initial T lymphocytes of at least about 10:1.

After isolation of T lymphocytes, both CD8+ cytotoxic and CD4+ helper T lymphocytes can be sorted into naïve, memory, and effector T cell subpopulations before genetically modifying with a fusion protein and expanding. In certain embodiments, T cells that are modified to express fusion proteins of this disclosure are bulk T cells (e.g., bulk CD4+ T cells or bulk CD8+ T cells), or are a subpopulation of T cells, such as central memory T cells (e.g., CD8+ central memory T cells) or a combination of central memory ($T_{CM}$) and naïve ($T_N$) T cells (e.g., CD4+ $T_{CM}$+ $T_N$ cells).

In any of the embodiments described herein, a host cell (e.g., T cell) comprises a vector that contains a polynucleotide that encodes a CAR that is at least 90%, at least 91%, at least 92%, at least 93%, at least 94%, at least 95%, at least 96%, at least 97%, at least 98%, at least 99%, at least 99.5%, or 100% identical to 1.5.3-NQ-28-BB-z (SEQ ID NO.:26); 1.5.3-NQ-28-z (SEQ ID NO.:27); 1.5.3-NQ-BB-z (SEQ ID NO.:28); 1.5.3-NQ-z (SEQ ID NO.:29); Leu16-28-BB-z (SEQ ID NO.:30); Leu16-28-z (SEQ ID NO.:31); 1F5-NQ-28-BB-z (SEQ ID NO.:32); 1F5-NQ-28-z (SEQ ID NO.:33); or 1F5-NQ-BB-z (SEQ ID NO.:34). In further embodiments, a host cell (e.g., T cell) comprises a vector that contains a polynucleotide that encodes a CAR that is comprised of or consists of an amino acid sequence of any one of SEQ ID NOS.:26-34. In any of these embodiments, the host cell is a T cell, wherein the T cells bulk CD4+ T cells, bulk CD8+ T cells, CD4+ central memory T cells, CD8+ central memory T cells or a combination of CD4+ central memory ($T_{CM}$) and CD4+ naïve ($T_N$) T cells. The CAR-modified CD4+ T cells and CAR-modified CD8+ T cells can be mixed in a ratio of 3:1 to 1:1 to 1:3 before administration to a subject, or can be administered to a subject separately at the same or similar ratios.

In still further embodiments, a host cell (e.g., T cell) comprises a vector that contains a polynucleotide that encodes a CD20-specific CAR, wherein the polynucleotide has at least 60%, at least 70%, at least 75%, at least 80%, at least 85%, at least 90%, at least 95%, or 100% identity to a nucleic acid molecule sequence of any one of SEQ ID NOS.:44-52. In related embodiments, a host cell (e.g., T cell) comprises a vector that contains a polynucleotide that encodes a CD20-specific CAR, wherein the polynucleotide comprises or consists of a sequence of any one of SEQ ID NOS.:44-52. In any of these embodiments, the host cell is a T cell, wherein the T cells bulk CD4+ T cells, bulk CD8+ T cells, CD4+ central memory T cells, CD8+ central memory T cells or a combination of CD4+ central memory ($T_{CM}$) and CD4+ naïve ($T_N$) T cells. The CAR-modified CD4+ T cells and CAR-modified CD8+ T cells can be mixed in a ratio of 3:1 to 1:1 to 1:3 before administration to a subject, or can be administered to a subject separately at the same or similar ratios.

Optionally, a host cell comprising any vector of this disclosure that contains a polynucleotide that encodes a CAR of this disclosure can also encode a transduction marker (e.g., tCD19), which may also include a self-cleaving peptide so that the transduction marker and CAR are separated into separate molecules—a CAR and a transduction marker. In certain embodiments, a host cell (e.g., T cell) comprises a vector that contains a polynucleotide encoding a self-cleaving peptide disposed between a CD20-specific CAR and a tCD19 transduction marker, which polynucleotide is at least 60%, at least 70%, at least 75%, at least 80%, at least 85%, at least 90%, at least 95%, or 100% identical to a nucleic acid molecule sequence of any one of SEQ ID NOS.:53-61. In further embodiments, a host cell (e.g., T cell) comprises a vector that contains a polynucleotide encoding a self-cleaving peptide disposed between a CD20-specific CAR and a tCD19 transduction marker and comprises or consists of a nucleic acid molecule sequence of any one of SEQ ID NOS.:53-61.

Whether a T cell or T cell population is positive for a particular cell surface marker can be determined by flow cytometry using staining with a specific antibody for the surface marker and an isotype matched control antibody. A cell population being "negative" for a marker refers to the absence of significant staining of the cell population with a specific antibody above an isotype control, and "positive" refers to uniform staining of the cell population above the levels found on an isotype control. In some embodiments, a decrease in expression of one or more markers refers to a loss of 1 log 10 in the MFI or a percentage decrease of T cells that exhibit the marker of at least 20% of the cells, 25% of the cells, 30% of the cells, 35% of the cells, 40% of the cells, 45% of the cells, 50% of the cells, 55% of the cells, 60% of the cells, 65% of the cells, 70% of the cells, 75% of the cells, 80% of the cells, 85% of the cells, 90% of the cell, 95% of the cells, or 100% of the cells, or any percentage between 20% and 100% when compared to a reference T cell population. In some embodiments, a T cell population positive for a marker refers to a percentage of cells that exhibit the marker, which may be at least 50% of the cells, 55% of the cells, 60% of the cells, 65% of the cells, 70% of the cells, 75% of the cells, 80% of the cells, 85% of the cells, 90% of the cell, 95% of the cells, or 100% of the cells, or any percentage between 50% and 100% when compared to a reference T cell population.

Immunomagnetic selection methods may also be used to purify T cell subpopulations using commercially available clinical grade antibody bead conjugates using a CliniMACS device (see, e.g., Terakura et al., 2012, *Blood* 119:72-82; Wang et al., 2012, *J. Immunother.* 35:689-701). For example, to isolate human CD8+ $T_{CM}$ cells, CD4+, CD14+, and CD45RA+ cells are removed from peripheral blood mononuclear cells by depletion with antibody conjugated paramagnetic beads, and then the CD62L+ fraction from the remaining cells is positively selected with an anti-CD62L labeled bead to enrich for the CD45RO+, CD62L+, CD8+ $T_{CM}$ subpopulation. The enriched CD8+ $T_{CM}$ subpopulation can be activated with anti-CD3/CD28 beads or with antigen, modified with tumor-specific CAR using retroviral or lentiviral vectors, and expanded for use in cellular immunotherapy (see, e.g., Terakura et al., supra; Wang et al., supra).

Alternatively, T cell subsets may be selected using low-affinity Fab fragments fused to Strep-tag II. A Fab monomers do not have sufficient binding affinity for stable binding to a target antigen on the cell surface. However, when multimerized on a StrepTactin bead, these reagents stably bind a target cell and enable selection based on cell surface marker specificity. A Fab multimer binding can be rapidly reversed by the addition of excess D-biotin, which has a higher affinity for StrepTactin and disrupts the binding between a Strep-tag on a Fab-fragment and a Strep-Tactin "backbone."

Fab monomers cannot maintain stable binding a the cell. This "Fab-Streptamers" technology allows for serial positive enrichment of T cells based on multiple cell surface markers and can be used to select any desired T cell subset (see, e.g., Stemberger et al., *PluS One* 7:e35793, 2012).

Bulk CD8+ T cells can be obtained by using standard methods. In some embodiments, bulk CD8+ T cells are further sorted into naïve, central memory, and effector T cells by identifying certain cell surface markers that are associated with each of those types of CD8+ T cells. In certain embodiments, memory T cells are present in both CD62L+ and CD62L− subsets of CD8+ peripheral blood lymphocytes. For example, PBMCs can be sorted into CD62L−CD8+ and CD62L+CD8+ fractions after staining with anti-CD8 and anti-CD62L antibodies. In some embodiments, expression of phenotypic markers of CD8+ central memory T cells include CD45RO, CD62L, CCR7, CD28, CD3, or CD127 or are negative for granzyme B. In some embodiments, central memory T cells are CD45RO+, CD62L+, CD8+ T cells. In some embodiments, CD8+ effector T cells are negative for or have reduced expression of CD62L, CCR7, CD28, or CD127, or are positive for or have increased expression of granzyme B or perforin, as compared to CD8+ central memory T cells. In some embodiments, naïve CD8+ T cells are characterized by the expression of phenotypic markers of naïve T cells including CD62L, CCR7, CD28, CD3, CD127, or CD45RA.

Bulk CD4+ lymphocytes can be obtained by standard methods. In some embodiments, bulk CD4+ T cells are further sorted into naïve, central memory, and effector cells by identifying cell populations that have certain cell surface markers. In some embodiments, naïve CD4+ T lymphocytes are CD45RO−, CD45RA+, CD62L+, CD4+ T cell. In some embodiments, central memory CD4+ cells are CD62L positive and CD45RO positive. In some embodiments, effector CD4+ cells are CD62L or CD45RO negative or have reduced expression of CD62L or CD45RO as compared to central memory CD4+ cells.

Populations of CD4+ and CD8+ having TCRs that are antigen specific can be obtained by stimulating naïve or antigen-specific T lymphocytes with antigen. For example, T cell clones having antigen-specific TCRs can be generated against, for example, Cytomegalovirus antigens by isolating T cells from infected subjects and stimulating the cells in vitro with the same antigen. Naïve T cells may also be used by exposing them to peptide antigens presented in the context of an antigen presenting cell or a peptide-MHC complex. Any number of antigens from tumor cells, cancer cells, or pathogenic agents may be utilized. Examples of such antigens include HIV antigens, Hepatitis C Virus (HCV) antigens, Hepatitis B Virus (HBV) antigens, Cytomegalovirus (CMV) antigens, EBV antigens, parasitic antigens, and tumor antigens, such as orphan tyrosine kinase receptor ROR1, EGFR, EGFRvIII, GD2, GD3, HPV E6, HPV E7, Her2, L1-CAM, Lewis A, Lewis Y, MUC1, MUC16, PSMA, CD19, CD20, CD22, CD56, CD23, CD24, CD37, CD30, CD33, CD38, CD56, CD123, CA125, c-MET, FcRH5, WT1, folate receptor α, VEGF-α, VEGFR1, VEGFR2, IL-13Rα2, IL-11Rα, MAGE-A1, PSA, ephrin A2, ephrin B2, NKG2D ligands, NY-ESO-1, TAG-72, mesothelin, CEA, or the like. Such T cells having antigen-specific TCRs may be further modified to contain a fusion protein as described herein, wherein the fusion protein is specific for the same antigen, specific for a different epitope on the same antigen, or specific for a different antigen. In any of these embodiments, the CD4+ T cells and the CD8+ T cells will contain different CARs, and in particular the intracellular signaling components of the CARs will be distinct.

Methods of preparing and modifying T cells to express fusion proteins of this disclosure, confirming fusion protein modified T cell activity, expanding fusion protein modified T cell populations are known in the art and are described, for example, in Hollyman et al., 2009, *J. Immunother.* 32:169-180; PCT Publication No. WO 2012/079000; U.S. Pat. No. 8,802,374; Brentjens et al., *Blood* 118:4817-4828; 2011; U.S. Patent Publication No. US 2014/0271635.

Uses

The present disclosure provides methods of treating a disease, condition, or disorder in a subject comprising: administering any of the fusion proteins described herein to the subject. In embodiments, methods of the present disclosure include methods of reducing the number of B-cells or treating a disease or disorder associated with aberrant B-cell activity in a subject. Another embodiment provides a method of treating a disease, condition, or disorder a subject comprising analyzing a biological sample of the subject for the presence of an antigen associated with the disease, condition, or disorder and administering a fusion protein described herein, wherein the fusion protein specifically binds to the antigen. In some embodiments, the antigen associated with the disease, condition, or disorder is a tumor associated antigen.

Diseases, conditions, or disorders that may be treated with compositions and methods as described in the present disclosure include cancer and immune diseases (e.g., autoimmune). For example, in certain embodiments, a CD20-expressing cell comprises B-cells. In further embodiments, the disease or disorder associated with CD20 expression is in B-cells or aberrant B cell activity, such as B-cell-related cancers. Adoptive immune and gene therapy are promising treatments for various types of cancer (Morgan et al., *Science* 314:126, 2006; Schmitt et al., *Hum. Gene Ther.* 20:1240, 2009; *June, J. Clin. Invest.* 117:1466, 2007).

A wide variety of cancers, including solid tumors and leukemias are amenable to the compositions and methods disclosed herein. Exemplary types of cancer that may be treated include adenocarcinoma of the breast, prostate, and colon; all forms of bronchogenic carcinoma of the lung; myeloid leukemia; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, Merkel cell, mucinous, non-small cell lung, oat cell, papillary, scirrhous, bronchiolar, bronchogenic, squamous cell, and transitional cell). Additional types of cancers that may be treated include histiocytic disorders; malignant histiocytosis; leukemia; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Exemplifying the variety of hyperproliferative disorders amenable to the compositions and methods disclosed herein described herein are disorders or diseases associated with CD20 expression, such as aberrant B-cell activity, including B-cell cancers, such as B-cell lymphomas (such as various forms of Hodgkin's disease, non-Hodgkins lymphoma (NHL) or central nervous system lymphomas), leukemias (such as acute lymphoblastic leukemia (ALL), chronic lymphocytic leukemia (CLL), hairy cell leukemia, B cell blast transformation of chronic myeloid leukemia) and myelomas (such as multiple myeloma). Additional B cell cancers include small lymphocytic lymphoma (SLL), Waldenström's macroglobulinemia, CD37+ dendritic cell lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, precursor B-lymphoblastic lymphoma, immunoblastic large cell lymphoma, intravascular large B-cell lymphoma, primary effusion lymphoma, Burkitt's lymphoma/leukemia, B-cell proliferations of uncertain malignant potential, lymphomatoid granulomatosis, and post-transplant lymphoproliferative disorder. In certain embodiments, the compositions and methods of this disclosure can be used treat non-B-cell disorders or diseases associated with CD20 expression, including multiple myeloma, melanoma, multiple myeloma of stem cells and melanoma of stem cells.

Inflammatory and autoimmune diseases amenable to the compositions and methods disclosed herein include arthritis, rheumatoid arthritis, juvenile rheumatoid arthritis, osteoarthritis, polychondritis, psoriatic arthritis, psoriasis, dermatitis, idiopathic inflammatory myopathy, polymyositis/dermatomyositis, inclusion body myositis, inflammatory myositis, toxic epidermal necrolysis, systemic scleroderma and sclerosis, CREST syndrome, inflammatory bowel disease, Crohn's disease, Grave's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), subacute cutaneous lupus erythematosus, discoid lupus, lupus myelitis, lupus cerebritis, juvenile onset diabetes, multiple sclerosis, allergic encephalomyelitis, neuromyelitis optica, rheumatic fever, Sydenham's chorea, immune responses associated with acute and delayed hypersensitivity mediated by cytokines and T-lymphocytes, tuberculosis, sarcoidosis, granulomatosis including Wegener's granulomatosis and Churg-Strauss disease, agranulocytosis, vasculitis (including hypersensitivity vasculitis/angiitis, ANCA and rheumatoid vasculitis), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, myasthenia gravis, antigen-antibody complex mediated diseases, anti-glomerular basement membrane disease, anti-phospholipid antibody syndrome, allergic neuritis, Behcet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), bullous pemphigoid, pemphigus, autoimmune polyendocrinopathies, seronegative spondyloarthropathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), Henoch-Schonlein purpura, autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes mellitus, also referred to as insulin-dependent diabetes mellitus (IDDM), and Sheehan's syndrome; autoimmune hepatitis, lymphoid interstitial pneumonitis (HIV), bronchiolitis obliterans (non-transplant), non-specific interstitial pneumonia (NSIP), Guillain-Barré Syndrome, large vessel vasculitis (including polymyalgia rheumatica and giant cell (Takayasu's) arteritis), medium vessel vasculitis (including Kawasaki's disease and polyarteritis nodosa), polyarteritis nodosa (PAN) ankylosing spondylitis, Berger's disease (IgA nephropathy), rapidly progressive glomerulonephritis, primary biliary cirrhosis, Celiac sprue (gluten enteropathy), cryoglobulinemia, cryoglobulinemia associated with hepatitis, amyotrophic lateral sclerosis (ALS), coronary artery disease, familial Mediterranean fever, microscopic polyangiitis, Cogan's syndrome, Whiskott-Aldrich syndrome and thromboangiitis obliterans.

Subjects that can be treated by the present invention are, in general, human and other primate subjects, such as monkeys and apes for veterinary medicine purposes. The subjects can be male or female and can be any suitable age, including infant, juvenile, adolescent, adult, and geriatric subjects.

Fusion proteins of the present disclosure may be formulated for administration in any suitable manner, as understood by persons skilled in the art. A CD20-specific fusion protein (e.g., a CAR) of this disclosure (or fusion protein specific for a different target) may be administered to a subject in cell-bound form (e.g., ex vivo modification of a target cell population (mature T cells (e.g., $CD8^+$ or $CD4^+$ T cells) or other cells of T cell lineage)). In a particular embodiment, cells of T cell lineage expressing CD20-specific fusion proteins of this disclosure (or fusion protein specific for a different target) administered to a subject are syngeneic, allogeneic, or autologous cells to the subject. In some embodiments, cells comprising fusion proteins of this disclosure are prepared by harvesting cells (from a biological sample, tissue, or culture medium), washing, concentrating, and formulating in a medium and container system suitable for administration.

The present disclosure provides compositions comprising cells expressing fusion proteins as disclosed herein and a pharmaceutically acceptable carrier, diluents, or excipient. Suitable excipients include water, saline, dextrose, glycerol, or the like and combinations thereof. In embodiments, compositions comprising cells expressing fusion proteins as disclosed herein further comprise a suitable infusion media. Suitable infusion media can be any isotonic medium formulation, typically normal saline, Normosol R (Abbott) or Plasma-Lyte A (Baxter), 5% dextrose in water, Ringer's lactate can be utilized. An infusion medium can be supplemented with human serum albumin or other human serum components.

In other embodiments, CD20-specific fusion proteins of this disclosure (or fusion protein specific for a different target) may be administered to a subject in soluble form. For example, soluble TCRs are known in the art (see, e.g., Molloy et al., *Curr. Opin. Pharmacol.* 5:438, 2005; U.S. Pat. No. 6,759,243).

Fusion proteins of this disclosure, or cells including the same, may be administered in a manner appropriate to the disease, condition, or disorder to be treated as determined by persons skilled in the medical art. In any of the above embodiments, a cell comprising a fusion protein as described herein is administered intravenously, intraperitoneally, intratumorly, into the bone marrow, into a lymph node, or into cerebrospinal fluid. In some embodiments, cells comprising a fusion protein of the present disclosure are delivered to the site of a tumor.

An appropriate dose, suitable duration, and frequency of administration of the compositions will be determined by such factors as a condition of the patient; size, type, and severity of the disease, condition, or disorder; particular form of the active ingredient; and the method of administration.

In any of the above embodiments, methods of the present disclosure comprise administering a therapeutically effective amount of a host cell expressing a fusion protein of the present disclosure or a host cell expressing a fusion of this disclosure. A therapeutically effective amount of cells in a composition is at least one cell (for example, one fusion protein modified CD8+ T cell subpopulation; one fusion protein modified CD4+ T cell subpopulation) or is more typically greater than $10^2$ cells, for example, up to $10^6$, up to $10^7$, up to $10^8$ cells, up to $10^9$ cells, or more than $10^{10}$ cells. In certain embodiments, the cells are administered in a range from about $10^6$ to about $10^{10}$ cells/$m^2$, preferably in a range of about $10^5$ to about $10^9$ cells/$m^2$. The number of cells will depend upon the ultimate use for which the composition is intended as well the type of cells included therein. For example, cells modified to contain a fusion protein specific for a particular antigen will comprise a cell population containing at least 30%, 35%, 40%, 45%, 50%, 55%, 60%, 65%, 70%, 75%, 80%, 85%, 90%, 95% or more of such cells. For uses provided herein, cells are generally in a volume of a liter or less, 500 mls or less, 250 mls or less, or 100 mls or less. In embodiments, the density of the desired cells is typically greater than $10^4$ cells/ml and generally is greater than $10^7$ cells/ml, generally $10^8$ cells/ml or greater. The cells may be administered as a single infusion or in multiple infusions over a range of time. A clinically relevant number of immune cells can be apportioned into multiple infusions that cumulatively equal or exceed $10^6$, $10^7$, $10^8$, $10^9$, $10^{10}$, or $10^{11}$ cells.

In some embodiments, methods of the present disclosure comprise administering a host cell expressing a CAR of this disclosure that is fully human or humanized. In any of the embodiments described herein, methods of the present disclosure comprise administering a host cell expressing a CAR that has a scFv from an anti-CD20 antibody or a scTCR from a TCR specific for a CD20 antigen. In any of the embodiments described herein, methods of the present disclosure comprise administering a host cell expressing a CAR that comprises a scFv from 1.5.3, 1F5, Leu16, rituximab, ofatumumab, veltuzumab, ocrelizumab, ublituximab, or any combination thereof. In any of the above embodiments, methods of the present disclosure comprise administering a host cell expressing a CAR that comprises a linker module comprising an IgG1 hinge, an IgG4 hinge, or any combination thereof. In any of the embodiments described herein, methods of the present disclosure comprise administering a host cell expressing a CAR that comprises a linker module comprising an IgG1 CH2 region with a N297Q mutation, an IgG4 CH2 region, an IgG1 CH3 region, an IgG4 CH3 region, or any combination thereof. In any of the embodiments of this disclosure, methods of the present disclosure comprise administering a host cell expressing a CAR that comprises a glycine-serine linker module or glycine-serine variable region linker. In any of the embodiments described herein, methods of the present disclosure comprise administering a host cell expressing a CAR that comprises a hydrophobic portion comprised of a CD28 transmembrane domain. In any of the embodiments described herein, methods of the present disclosure comprise administering a host cell expressing a CAR that comprises an intracellular domain comprising a domain from CD3ζ, 4-1BB, CD28, or any combination thereof. In any of the above embodiments, methods of the present disclosure comprise administering a CAR that comprises junction amino acids between adjacent domains, motifs, regions, modules, or fragments.

In any of the embodiments described herein, methods of this disclosure comprise administering to a subject a host cell comprising a heterologous nucleic acid molecule encoding a fusion protein, the fusion protein comprising an extracellular component and an intracellular component connected by a hydrophobic portion, wherein the extracellular component comprises a binding domain that specifically binds CD20 and the intracellular component comprises an effector domain, wherein the encoded fusion protein (e.g., CAR) is at least 90%, at least 91%, at least 92%, at least 93%, at least 94%, at least 95%, at least 96%, at least 97%, at least 98%, at least 99%, at least 99.5%, or 100% identical to 1.5.3-NQ-28-BB-z (SEQ ID NO.:26); 1.5.3-NQ-28-z (SEQ ID NO.:27); 1.5.3-NQ-BB-z (SEQ ID NO.:28); 1.5.3-NQ-z (SEQ ID NO.:29); Leu16-28-BB-z (SEQ ID NO.:30); Leu16-28-z (SEQ ID NO.:31); 1F5-NQ-28-BB-z (SEQ ID NO.:32); 1F5-NQ-28-z (SEQ ID NO.:33); or 1F5-NQ-BB-z (SEQ ID NO.:34). In further embodiments, methods of the present disclosure comprise administering to a subject a host cell comprising a heterologous nucleic acid molecule encoding a fusion protein, the fusion protein comprising an extracellular component and an intracellular component connected by a hydrophobic portion, wherein the extracellular component comprises a binding domain that specifically binds CD20 and the intracellular component comprises an effector domain, wherein the encoded fusion protein (e.g., CAR) comprises or consists of an amino acid sequence of any one of SEQ ID NOS.:26-34. In any of these embodiments, the host cell is a T cell, wherein the T cells bulk CD4+ T cells, bulk CD8+ T cells, CD4+ central memory T cells, CD8+ central memory T cells or a combination of CD4+ central memory ($T_{CM}$) and CD4+ naïve ($T_N$) T cells. The CAR-modified CD4+ T cells and CAR-modified CD8+ T cells can be mixed in a ratio of 3:1 to 1:1 to 1:3 before administration to a subject, or can be administered to a subject separately at the same or similar ratios.

In still further embodiments, methods of this disclosure comprise administering to a subject a host cell comprising a heterologous nucleic acid molecule encoding a fusion protein, the fusion protein comprising an extracellular component and an intracellular component connected by a hydrophobic portion, wherein the extracellular component comprises a binding domain that specifically binds CD20 and the intracellular component comprises an effector domain, wherein the fusion protein (e.g., CAR) is encoded by a polynucleotide having at least 60%, at least 70%, at least 75%, at least 80%, at least 85%, at least 90%, at least 95%, or 100% identity to a nucleic acid molecule sequence of any one of SEQ ID NOS.:44-52. In related embodiments, methods comprise administering to a subject a host cell comprising a heterologous nucleic acid molecule encoding a fusion protein, the fusion protein comprising an extracellular component and an intracellular component connected by a hydrophobic portion, wherein the extracellular component comprises a binding domain that specifically binds CD20 and the intracellular component comprises an effector domain, wherein the fusion protein (e.g., CAR) is encoded by a polynucleotide comprising or consisting of a sequence of any one of SEQ ID NOS.:44-52. In any of these embodiments, the host cell is a T cell, wherein the T cells bulk CD4+ T cells, bulk CD8+ T cells, CD4+ central memory T cells, CD8+ central memory T cells or a combination of CD4+ central memory ($T_{CM}$) and CD4+ naïve ($T_N$) T cells. The CAR-modified CD4+ T cells and CAR-modified CD8+ T cells can be mixed in a ratio of 3:1 to 1:1 to 1:3 before administration to a subject, or can be administered to a subject separately at the same or similar ratios.

Optionally, a host cell comprising any vector of this disclosure that contains a polynucleotide that encodes a fusion protein of this disclosure, for use in the methods described herein, can also encode a transduction marker (e.g., tCD19), which may also include a self-cleaving peptide so that the transduction marker and CAR are separated into separate molecules—a CAR and a transduction marker. In certain embodiments, a host cell (e.g., T cell) comprises a vector that contains a polynucleotide encoding a self-cleaving peptide disposed between a CD20-specific CAR and a tCD19 transduction marker, which polynucleotide is at least 60%, at least 70%, at least 75%, at least 80%, at least 85%, at least 90%, at least 95%, or 100% identical to a nucleic acid molecule sequence of any one of SEQ ID NOS.:53-61. In further embodiments, a host cell (e.g., T cell) comprises a vector that contains a polynucleotide encoding a self-cleaving peptide disposed between a CD20-specific CAR and a tCD19 transduction marker and comprises or consists of a nucleic acid molecule sequence of any one of SEQ ID NOS.:53-61.

Accordingly, in any of the methods disclosed herein a host cell comprises an isolated polynucleotide encoding a fusion protein capable of specifically binding CD20, wherein the polynucleotide: (a) is at least 80% identical to a polynucleotide sequence of any one of SEQ ID NOS.:53-56; (b) is at least 80% identical to a polynucleotide sequence of any one of SEQ ID NOS.:44-47; (c) comprises a polynucleotide sequence of any one of SEQ ID NOS.:53-56; (d) comprises a polynucleotide sequence of any one of SEQ ID NOS.:44-47; (e) consists of a polynucleotide sequence of any one of SEQ ID NOS.:53-56; or (f) consists of a polynucleotide sequence of any one of SEQ ID NOS.:44-47.

In certain embodiments, the host cell used in the methods comprises a fusion protein that consists of or comprises an amino acid sequence wherein the fusion protein: (a) is at least 90% identical to a mature fusion protein, wherein the mature fusion protein comprises an amino acid sequence of any one of SEQ ID NOS.:26-29 and 35-38 and 32-34 with the tCD19 transduction marker removed; (b) is comprised of a mature fusion protein, wherein the mature fusion protein comprises an amino acid sequence of any one of SEQ ID NOS.: 35-38 with the tCD19 transduction marker removed; (c) consists of a mature fusion protein, wherein the mature fusion protein comprises an amino acid sequence of any one of SEQ ID NOS.: 35-38 with the tCD19 transduction marker removed; (d) is at least 90% identical to an amino acid sequence of any one of SEQ ID NOS.:26 29; (e) is comprised of an amino acid sequence of any one of SEQ ID NOS.:26 29; (f) consists of an amino acid sequence of any one of SEQ ID NOS.:26 29.

In certain embodiments, a host cell used in the methods comprises a heterologous polynucleotide as disclosed herein and is capable of expressing the fusion protein.

In certain embodiments, a host cell used in the methods comprises a heterologous polynucleotide encoding a fusion protein comprising a binding domain, wherein the binding domain is: (a) a 1.5.3 scFv comprising an amino acid sequence that is at least 90% identical to an amino acid sequence of SEQ ID NO.:64, wherein each CDR of the scFv comprises zero changes or at most one, two, three, four, five or six changes as compared to the corresponding CDR of a parent monoclonal antibody or fragment or derivative thereof that specifically binds to CD20, provided that scFv containing one or more modified CDRs specifically binds CD20 with an affinity similar to the wild type scFv or corresponding antibody; (b) a 1.5.3 scFv comprising or consisting of an amino acid sequence of SEQ ID NO.:64; (c) a 1F5 scFv comprising an amino acid sequence that is at least 90% identical to an amino acid sequence of SEQ ID NO.:66, wherein each CDR of the scFv comprises zero changes or at most one, two, three, four, five or six changes as compared to the corresponding CDR of a parent monoclonal antibody or fragment or derivative thereof that specifically binds to CD20, provided that scFv containing one or more modified CDRs specifically binds CD20 with an affinity similar to the wild type scFv or corresponding antibody; (d) a 1F5 scFv comprising or consisting of an amino acid sequence of SEQ ID NO.:66; (e) a Leu16 scFv comprising an amino acid sequence that is at least 90% identical to an amino acid sequence of SEQ ID NO.:65, wherein each CDR of the scFv comprises zero changes or at most one, two, three, four, five or six changes as compared to the corresponding CDR of a parent monoclonal antibody or fragment or derivative thereof that specifically binds to CD20, provided that scFv containing one or more modified CDRs specifically binds CD20 with an affinity similar to the wild type scFv or corresponding antibody; or (f) a Leu16 scFv comprising or consisting of an amino acid sequence of SEQ ID NO.:65.

In certain embodiments, a host cell used in the methods comprises a heterologous polynucleotide encoding a fusion protein comprising an scFv, wherein the scFv is encoded by: (a) a polynucleotide having at least 80% identity to a nucleic acid molecule sequence of SEQ ID NO.:67, wherein polynucleotide sequences encoding each CDR of a scFv comprises zero changes or at most one to six nucleotide changes, as compared to a polynucleotide encoding a parent scFv from a monoclonal antibody that specifically binds to CD20, provided that scFv containing one or more modified CDRs specifically binds CD20 with an affinity similar to the wild type scFv or corresponding antibody; (b) a polynucleotide comprising or consisting of a nucleic acid molecule sequence of SEQ ID NO.:67; (c) a polynucleotide having at least 80% identity to a nucleic acid molecule sequence of SEQ ID NO.:69, wherein polynucleotide sequences encoding each CDR of a scFv comprises zero changes or at most one to six nucleotide changes, as compared to a polynucleotide encoding a parent scFv from a monoclonal antibody that specifically binds to CD20, provided that scFv containing one or more modified CDRs specifically binds CD20 with an affinity similar to the wild type scFv or corresponding antibody; (d) a polynucleotide comprising or consisting of a nucleic acid molecule sequence of SEQ ID NO.:69; (e) a polynucleotide having at least 80% identity to a nucleic acid molecule sequence of SEQ ID NO.:68, wherein polynucleotide sequences encoding each CDR of a scFv comprises zero changes or at most one to six nucleotide changes, as compared to a polynucleotide encoding a parent scFv from a monoclonal antibody that specifically binds to CD20, provided that scFv containing one or more modified CDRs specifically binds CD20 with an affinity similar to the wild type scFv or corresponding antibody; or (f) a polynucleotide comprising or consisting of a nucleic acid molecule sequence of SEQ ID NO.:68.

In certain embodiments, a host cell used in the methods comprises a heterologous polynucleotide encoding a fusion protein, wherein the fusion protein is a chimeric antigen receptor and comprises or consists of an amino acid sequence that is at least 90% identical to an amino acid sequence of any one of SEQ ID NOS.:26-43.

In certain embodiments, a host cell used in the methods comprises a heterologous polynucleotide encoding a fusion protein comprising a hydrophobic portion, wherein the hydrophobic portion is a transmembrane domain. In certain embodiments, the hydrophobic portion is a CD4, CD8, CD28 or CD27 transmembrane domain.

In certain embodiments, a host cell used in the methods comprises a heterologous polynucleotide encoding a fusion protein comprising an effector domain or functional portion thereof, wherein the effector domain or functional portion thereof is a 4-1BB (CD137), CD3ε, CD3δ, CD3ζ, CD25, CD27, CD28, CD79A, CD79B, CARD11, DAP10, FcRα, FcRβ, FcRγ, Fyn, HVEM, ICOS, Lck, LAG3, LAT, LRP, NKG2D, NOTCH1, NOTCH2, NOTCH3, NOTCH4, OX40 (CD134), ROR2, Ryk, SLAMF1, Slp76, pTα, TCRα, TCRβ, TRIM, Zap70, PTCH2, or any combination thereof.

In certain embodiments, a host cell used in the methods comprises a heterologous polynucleotide encoding a fusion protein comprising an intracellular component, wherein the intracellular component comprises: (a) a CD3ζ effector domain or functional portion thereof, a CD28 costimulatory domain or functional portion thereof and a 4-1BB (CD137) costimulatory domain or portion thereof; (b) a CD3ζ effector domain or functional portion thereof, a CD28 costimulatory domain or functional portion thereof and a OX40 (CD134) costimulatory domain or portion thereof; (c) a CD3ζ effector domain or functional portion thereof, a CD27 costimulatory domain or functional portion thereof and a 4-1BB (CD137) costimulatory domain or portion thereof; (d) a CD3ζ effector domain or functional portion thereof, a CD27 costimulatory domain or functional portion thereof and a OX40 (CD134) costimulatory domain or portion thereof; (e) a CD3ζ effector domain or functional portion thereof, a CD27 costimulatory domain or functional portion thereof and a CD28 costimulatory domain or portion thereof; or (f) a CD3ζ effector domain or functional portion thereof, a 4-1BB (CD137) costimulatory domain or functional portion thereof and a OX40 (CD134) costimulatory domain or portion thereof.

Compositions of this disclosure may also be administered simultaneously with, prior to, or after administration of one or more other therapeutic agents. Such combination therapy includes administration of a single dosage formulation which contains a fusion protein of this disclosure and one or more additional active agents, as well as administration of a fusion protein of this disclosure and each active agent in its own separate dosage formulation. For example, a fusion protein of this disclosure and another active agent can be administered to a subject together in a single infusion dosage composition, or each agent can be administered in separate infusion dosage formulations. Where separate dosage formulations are used, a fusion protein of this disclosure and one or more additional active agents can be administered at the same time, i.e., simultaneously, at essentially the same time, i.e., concurrently, or at separately staggered times, i.e., sequentially; combination therapy is understood to include all these regimens.

The present disclosure provides pharmaceutical compositions comprising CD20-specific binding molecules, cells expressing fusion proteins as disclosed herein or both, and a pharmaceutically acceptable carrier, diluents, or excipient. In certain embodiments, the CD20-specific binding molecule is an antibody. In such embodiments, a CD20-specific antibody can be rituximab, ofatumumab, ocrelizumab, obinutuzumab, ublituximab, veltuzumab, ibritumomab tiuxetan, tositumomab, or any combination thereof.

In certain embodiments, a method of treating a disease or disorder associated with CD20 expression comprises administering to a subject having or suspected of having a disease or disorder associated with CD20 expression a therapeutically effective amount of a host cell comprising a heterologous nucleic acid molecule encoding a fusion protein, the fusion protein comprising an extracellular component and an intracellular component connected by a hydrophobic portion, wherein the extracellular component comprises a binding domain that specifically binds CD20 and the intracellular component comprises an effector domain, and optionally administering a therapeutically effective amount of a CD20-specific binding molecule, chemotherapeutic or inhibitor of an immunosuppression component. In further embodiments, the method reduces the number of B-cells or treats a disease or disorder associated with aberrant B-cell activity.

Thus, in certain embodiments, provided are methods of treating a disease or disorder associated with CD20 expression, comprising administering to a subject having or suspected of having a disease or disorder associated with CD20 expression a therapeutically effective amount of a host cell comprising a heterologous nucleic acid molecule encoding a fusion protein comprised of an amino acid sequence that is at least 90% identical to an amino acid sequence of any one of SEQ ID NOS.: 26-29 and 32-38, and 41-43, and optionally administering a CD20-specific binding molecule, a chemotherapeutic, an inhibitor of an immunosuppression component, or combinations thereof. In further embodiments, the method reduces the number of B-cells or treats a disease or disorder associated with aberrant B-cell activity.

In some embodiments, compositions as described herein are administered with chemotherapeutic agents or immune modulators (e.g., immunosuppressants, or inhibitors of immunosuppression components, such as immune checkpoint inhibitors). Immune checkpoint inhibitors include inhibitors of CTLA-4, A2AR, B7-H3, B7-H4, BTLA, HVEM, GALS, IDO, KIR, LAG-3, PD-1, PD-L1, PD-L2, Tim-3, VISTA, TIGIT, LAIR1, CD160, 2B4, TGFR beta, CEACAM-1, CEACAM-3, CEACAM-5, CD244, or any combination thereof. An inhibitor of an immune checkpoint molecule can be an antibody or antigen binding fragment thereof, a fusion protein, a small molecule, an RNAi molecule, (e.g., siRNA, shRNA, or miRNA), a ribozyme, an aptamer, or an antisense oligonucleotide. A chemotherapeutic can be a B-Raf inhibitor, a MEK inhibitor, a VEGF inhibitor, a VEGFR inhibitor, a tyrosine kinase inhibitor, an anti-mitotic agent, or any combination thereof.

In any of the embodiments herein, a method of treating a disease or disorder associated with CD20 expression comprises administering to a subject having or suspected of having a disease or disorder associated with CD20 expression a therapeutically effective amount of a host cell comprising a heterologous nucleic acid molecule encoding a fusion protein as disclosed herein, and a therapeutically effective amount of an inhibitor of an immunosuppression component, such as an immune checkpoint inhibitor. In some embodiments, an immune checkpoint inhibitor is an inhibitor of CTLA-4, A2AR, B7-H3, B7-H4, BTLA, HVEM, GAL9, IDO, KIR, LAG-3, PD-1, PD-L1, PD-L2, Tim-3, VISTA, TIGIT, LAIR1, CD160, 2B4, TGFR beta, CEACAM-1, CEACAM-3, CEACAM-5, CD244, or any combination thereof.

Accordingly, in certain embodiments, this disclosure provides methods of treating a disease or disorder associated with CD20 expression, comprising administering to a subject having or suspected of having a disease or disorder associated with CD20 expression a therapeutically effective amount of a host cell comprising a heterologous nucleic acid molecule encoding a fusion protein having an amino acid sequence that is at least 90% identical to an amino acid sequence of any one of SEQ ID NOS.: 26-29 and 32-38, and 41-43, and a therapeutically effective amount of an inhibitor of an immunosuppression component, such as an immune checkpoint inhibitor. In some embodiments, an immune checkpoint inhibitor is an inhibitor of CTLA-4, A2AR, B7-H3, B7-H4, BTLA, HVEM, GAL9, IDO, KIR, LAG-3, PD-1, PD-L1, PD-L2, Tim-3, VISTA, TIGIT, LAIR1, CD160, 2B4, TGFR beta, CEACAM-1, CEACAM-3, CEACAM-5, CD244, or any combination thereof. In some embodiments, an immune checkpoint inhibitor is selected from (a) an antibody specific for PD-1, such as pidilizumab, nivolumab, or pembrolizumab; (b) an antibody specific for PD-L1, such as MDX-1105, BMS-936559, MEDI4736, MPDL3280A, or MSB0010718C; or (c) an antibody specific for CTLA4, such as tremelimumab or ipilimumab.

In further embodiments, this disclosure provides methods of treating a disease or disorder associated with CD20 expression, comprising administering to a subject having or suspected of having a disease or disorder associated with CD20 expression a therapeutically effective amount of a host cell comprising a heterologous nucleic acid molecule encoding a fusion protein that comprises or consists of an amino acid sequence of any one of SEQ ID NOS.:26-29, 32-38, and 41-43, and a therapeutically effective amount of an immune checkpoint inhibitor, optionally wherein the immune checkpoint inhibitor is selected from (a) an antibody specific for PD-1, such as pidilizumab, nivolumab, or pembrolizumab; (b) an antibody specific for PD-L1, such as MDX-1105, BMS-936559, MEDI4736, MPDL3280A, or MSB0010718C; or (c) an antibody specific for CTLA4, such as tremelimumab or ipilimumab.

Exemplary chemotherapeutic agents include alkylating agents (e.g., cisplatin, oxaliplatin, carboplatin, busulfan, nitrosoureas, nitrogen mustards such as bendamustine, uramustine, temozolomide), antimetabolites (e.g., aminopterin, methotrexate, mercaptopurine, fluorouracil, cytarabine, gemcitabine), taxanes (e.g., paclitaxel, nab-paclitaxel, docetaxel), anthracyclines (e.g., doxorubicin, daunorubicin, epirubicin, idaruicin, mitoxantrone, valrubicin), bleomycin, mytomycin, actinomycin, hydroxyurea, topoisomerase inhibitors (e.g., camptothecin, topotecan, irinotecan, etoposide, teniposide), monoclonal antibodies (e.g., ipilimumab, pembrolizumab, nivolumab, avelumab, alemtuzumab, bevacizumab, cetuximab, gemtuzumab, panitumumab, rituximab, tositumomab, trastuzumab), vinca alkaloids (e.g., vincristine, vinblastine, vindesine, vinorelbine), cyclophosphamide, prednisone, leucovorin, oxaliplatin, hyalurodinases, or any combination thereof. In certain embodiments, a chemotherapeutic is vemurafenib, dabrafenib, trametinib, cobimetinib, sunitinib, erlotinib, paclitaxel, docetaxel, or any combination thereof. In some embodiments, a patient is first treated with a chemotherapeutic agent that inhibits or destroys other immune cells followed by a pharmaceutical composition described herein. In some cases, chemotherapy may be avoided entirely.

In any of the embodiments described herein, the methods of this disclosure are applied to a subject that has been pre-treated with a CD20-specific binding molecule, optionally wherein the CD20-specific binding molecule is rituximab, ofatumumab, ocrelizumab, ublituximab, veltuzumab, or any combination thereof; or a chemotherapeutic (e.g., a CHOP [cyclophosphamide-Hydroxydaunorubicin-Oncovin-Prednisone], CHOP-R [R is rituximab], or CHOEP or CHOEP-R [E is etoposide] regimen); or an inhibitor of an immune suppression component (e.g., an antibody against PD-1, PD-L1, CTLA4, or the like).

Administration of certain compounds of this disclosure (e.g. antibodies, chemotherapeutic agents or immune modulators), or their pharmaceutically acceptable salts, in pure form or in an appropriate pharmaceutical composition, can be carried out using any mode of administration for agents serving similar utilities. The pharmaceutical compositions of this disclosure can be prepared by combining a compound of this disclosure with an appropriate pharmaceutically acceptable carrier, diluent or excipient, and may be formulated into preparations in solid, semi solid, liquid or gaseous forms, such as tablets, capsules, powders, granules, ointments, solutions, suppositories, injections, inhalants, gels, microspheres, and aerosols. Exemplary routes of administering such pharmaceutical compositions include oral, topical, transdermal, inhalation, parenteral, sublingual, buccal, rectal, vaginal, and intranasal.

The term "parenteral" as used herein includes subcutaneous injections, intravenous, intramuscular, intrasternal injection or infusion techniques. Pharmaceutical compositions of this disclosure (e.g., chemotherapeutic agents or immune modulators) are formulated to allow the active ingredients contained therein to be bioavailable upon administration of the composition to a patient. Compositions that will be administered to a subject or patient take the form of one or more dosage units, where for example, a tablet may be a single dosage unit, and a container of a compound of this disclosure in aerosol form may hold a plurality of dosage units. Actual methods of preparing such dosage forms are known, or will be apparent, to those skilled in this art (see, e.g., Remington: *The Science and Practice of Pharmacy*, 22nd Edition (Pharmaceutical Press, 2012). The composition to be administered will, in any event, contain a therapeutically effective amount of a compound of this disclosure, or a pharmaceutically acceptable salt thereof, for therapeutic methods in accordance with the teachings of this disclosure.

As a solid composition for oral administration, the pharmaceutical composition may be formulated into a powder, granule, compressed tablet, pill, capsule, chewing gum, wafer or the like form. Exemplary solid compositions can contain one or more inert diluents or edible carriers. In addition, one or more additives may be present, including binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; or a coloring agent. When a pharmaceutical composition is in the form of a capsule, such as a gelatin capsule, it may contain, in addition to materials of the above type, a liquid carrier such as polyethylene glycol or oil or combinations thereof.

The pharmaceutical composition may be in the form of a liquid, such as an elixir, syrup, solution, emulsion, or suspension. In certain embodiments, a liquid composition may be formulated for oral administration or for delivery by injection, as two examples. When intended for oral administration, exemplary compositions may further contain, in addition to one or more compounds of this disclosure, a sweetening agent, preservative, dye/colorant, flavor enhancer, or any combination thereof. Exemplary compositions intended for administration by injection may further contain a surfactant, preservative, wetting agent, dispersing agent, suspending agent, buffer, stabilizer, isotonic agent, or any combination thereof.

Liquid pharmaceutical compositions of this disclosure, whether they are solutions, suspensions or other like forms, may further comprise adjuvants, including sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A pharmaceutical composition of this disclosure may be intended for topical administration, in which case the carrier may comprise a suitable solution, emulsion, ointment, gel base, or any combination thereof. The base, for example, may comprise petrolatum, lanolin, polyethylene glycols, bee wax, mineral oil, diluents such as water and alcohol, emulsifiers, stabilizers, or any combination thereof. Thickening agents may be present in a pharmaceutical composition of this disclosure for topical administration. If intended for transdermal administration, the composition may include a transdermal patch or iontophoresis device.

A pharmaceutical composition of this disclosure may be intended for rectal administration, in the form, for example, of a suppository, which will melt in the rectum and release the active compound(s). A composition for rectal administration may contain an oleaginous base as a suitable nonirritating excipient. Exemplary bases include lanolin, cocoa butter, polyethylene glycol, or any combination thereof.

A pharmaceutical composition of this disclosure may include various materials that modify the physical form of a solid or liquid dosage unit. For example, a composition may include materials that form a coating shell around the active ingredient(s). Exemplary materials for forming a coating shell may be inert, such as sugar, shellac, or other enteric coating agents. Alternatively, active ingredient(s) may be encased in a gelatin capsule.

In certain embodiments, compounds and compositions of this disclosure may be in the form of a solid or liquid. Exemplary solid or liquid formulations include semi solid, semi liquid, suspension, and gel forms. A pharmaceutical composition of this disclosure in solid or liquid form may further include an agent that binds to the compound of this disclosure and thereby assists in the delivery of the compound. Suitable agents that may act in this capacity include a monoclonal or polyclonal antibody, a protein, or a liposome.

A pharmaceutical composition of this disclosure may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of this disclosure may be delivered in single phase, bi phasic, or tri phasic systems in order to deliver the active ingredient(s). Delivery of the aerosol includes the necessary container, activators, valves, subcontainers, and the like, which together may form a kit.

Pharmaceutical compositions of this disclosure may be prepared by methodology well known in the pharmaceutical art. For example, a pharmaceutical composition intended to be administered by injection can be prepared by combining a compound of this disclosure with sterile, distilled water to form a solution. A surfactant may be added to facilitate the formation of a homogeneous solution or suspension. Surfactants are compounds that non covalently interact with the compound of this disclosure to facilitate dissolution or homogeneous suspension of a compound in an aqueous delivery system.

Compounds of this disclosure, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Following administration of therapies according to the formulations and methods of this disclosure, test subjects will exhibit about a 10% up to about a 99% reduction in one or more symptoms associated with the disease or disorder being treated, as compared to placebo-treated or other suitable control subjects.

Compounds of this disclosure, or pharmaceutically acceptable derivatives thereof, may also be administered simultaneously with, prior to, or after administration of one or more other therapeutic agents. Such combination therapy includes administration of a single pharmaceutical dosage formulation which contains a compound of this disclosure and one or more additional active agents, as well as administration of the compound of this disclosure and each active agent in its own separate pharmaceutical dosage formulation. For example, a compound of this disclosure and the other active agent can be administered to the patient together in a single oral dosage composition such as a tablet or capsule, or each agent administered in separate oral dosage formulations. Where separate dosage formulations are used, the compounds of this disclosure and one or more additional active agents can be administered at essentially the same time, i.e., concurrently, or at separately staggered times, i.e., sequentially; combination therapy is understood to include all these regimens.

It will also be appreciated by those skilled in the art that in the process described herein the functional groups of intermediate compounds may need to be protected by suitable protecting groups. Such functional groups include hydroxy, amino, mercapto, and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, or the like. Suitable protecting groups for mercapto include C(O) R" (where R" is alkyl, aryl or arylalkyl), p methoxybenzyl, trityl or the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those of skill in the art, although such protected derivatives of compounds of this disclosure may not possess pharmacological activity as such, they may be administered to a mammal and thereafter metabolized in the body to form compounds of this disclosure which are pharmacologically active. Such derivatives may, therefore, be described as "prodrugs". In certain embodiments, compounds of this disclosure are in the form of a prodrug.

Furthermore, all compounds of this disclosure that exist in free base or acid form can be converted to their pharmaceutically acceptable salts by treatment with the appropriate inorganic or organic base or acid by methods known to those skilled in the art. Salts of the compounds of this disclosure can be converted to their free base or acid form by standard techniques.

In the case of transformed host cells expressing a fusion protein according to this disclosure, administration may be performed using individual aliquots of the cells. In certain embodiments, transformed host cells comprise T cells, which may comprise $CD4^+$ T cells, $CD8^+$ T cells, or both. In certain embodiments, T cells comprise a heterologous nucleic acid encoding a chimeric antigen receptor (CAR). In certain embodiments, T cells are sorted to provide for a 1:1 ratio of $CD4^+$ and $CD8^+$ CD20 CAR T cells for administration to the subject. Cells may be administered intravenously over approximately 20-30 minutes at the specified cell dose for each subject. Specified cell doses may be determined by the expression level of a transduction marker that is expressed coordinately with the fusion protein in the vector. For example, in certain embodiments, a T cell is transformed using one or more vectors that coordinately express a truncated CD19 transduction marker and a CAR. Exemplary CD20 CAR T cell dosage levels for use in various embodiments of the present disclosure are set forth in Table 1 below.

TABLE 1

| CD20 CAR T cell formulation and infusion | | |
|---|---|---|
| Dose Level | $tCD19^+$ $CD4^+$/ $tCD19^+$ $CD8^+$ ratio | Total $tCD19^+$ T cell dose*,** |
| 0 | 1:1 | $1 \times 10^5$/kg |
| 1 | 1:1 | $3.3 \times 10^5$/kg |
| 2 | 1:1 | $1 \times 10^6$/kg |
| 3 | 1:1 | $3.3 \times 10^6$/kg |
| 4 | 1:1 | $1 \times 10^7$/kg |

*per kg recipient weight;
**upper limit per dosing level ±15%

In certain embodiments, cells are manufactured from an autologous peripheral blood mononuclear cell (PBMC) product obtained by standard non-mobilized leukapheresis from the subject. Immunomagnetic selection may be performed to enrich $CD8^+$ cells or $CD4^+$ T cells. In certain embodiments, $CD8^+$ cells and $CD4^+$ T cells are enriched separately, and each subset is separately stimulated with, e.g., anti-CD3/CD28 paramagnetic beads, followed by transduction with a vector (e.g., a lentiviral vector) encoding the fusion protein and, optionally, a transduction marker such as, for example, a tCD19 transduction marker. The transduced T cells may be expanded, then re-stimulated with a CD20-expressing target cell line to boost growth, further expanded ex vivo, and then formulated to achieve the specified cell dose for infusion. For example, in certain embodiments, anti-CD20 CART cells (e.g., 1.5.3-NQ-28-BB-z) according to the present disclosure may be manufactured in accordance with a method comprising:

1. Enrichment of $CD4^+$ T cells from a fraction of leukapheresis product or peripheral blood mononuclear cells (PBMC) from whole blood.
2. In parallel with $CD4^+$ T cell enrichment, enrichment of $CD8^+$ T cells from the remaining leukapheresis product or PBMC.
3. Stimulation of the enriched $CD4^+$ and $CD8^+$ cells in separate cultures with clinical grade anti-CD3 and anti-CD28 coated paramagnetic beads (anti-CD3/CD28 beads) in RPMI 1640 medium supplemented with glutamine, β mercaptoethanol, and fetal bovine serum (CTL Media+10% FBS), 50 IU/mL IL-2.
4. Transduction of the $CD4^+$ and $CD8^+$ cells with 1.5.3-NQ-28-BB-z CAR lentiviral vector on day 1 after anti-CD3/CD28 bead stimulation.
5. Expansion of transduced $CD4^+$ and $CD8^+$ T cells in CTL Media+10% FBS and 50 IU/mL IL-2.
6. 2× removal of the anti-CD3/CD28 beads by magnetic depletion on day 4 after CD3/CD28 stimulation.
7. Stimulation with an irradiated, clinically qualified, transformed CD20+ B cell line (TM-LCL) on day 7 after anti-CD3/CD28 stimulation. This step may be omitted if in-process cell counts on day 7 predict sufficient cell expansion without the TM-LCL stimulation.
8. Expansion of $CD4^+$ and $CD8^+$ cells in G-Rex flasks with CTL Media+10% FBS and 50 IU/mL IL-2.
9. Cell harvest of each subset on day 15 (range 13-17) after anti-CD3/CD28 stimulation, and formulation of a combined $CD4^+$/$CD8^+$ T cell product for cryopreservation or infusion.

10. Sample collection at appropriate points during the manufacturing procedure from each of the CD8+ and CD4+ T cells for in-process and final release testing.
11. Administration to the patient by intravenous infusion at the indicated dose in 1:1 ratio of tCD19+ CD4+ and tCD19+ CD8+ T cells. Subjects will be pre-treated with lymphodepletion chemotherapy and receive the T cell infusions at least 36 hours after completing chemotherapy.

In certain embodiments, cells generated for a subject may be given as fresh cells immediately after manufacture, or may be first cryopreserved and stored in a liquid nitrogen freezer, and then the thawed cells washed to remove residual cryoprotectant and then formulated for infusion. The total number of cells will be sufficient to account for cell loss during recovery from thaw and to achieve the cell dose level specified in the clinical protocol. In certain embodiments comprising both CD4+ and CD8+ T cells, the total ratio of CD4+ and CD8+ T cells may differ from 1:1 due to differences in transduction of the individual subsets in individual subjects. For this reason, the subsets may be transduced separately to achieve a desired formulation of the transduced T cells. CD4 and CD8 CAR T cells have demonstrated synergistic effects in animal models (Sommermeyer et al., *Leukemia* 2015).

Transformed cells may be suspended in an appropriate cryopreservation medium (e.g., CryoStor CS10®) for cryopreservation in a controlled rate freezer. Cryopreserved cells may be stored in the vapor phase of a liquid nitrogen freezer. The fresh or thawed cells may then be resuspended in Normosol+1% HSA and transferred to a transfer pack at the total cell dose level specified in the clinical protocol. The formulated product may be stored at 2-8° C. and then transferred under appropriate conditions to the clinical site for administration.

Following leukapharesis, subjects may receive cytoreductive chemotherapy to control disease during production of the transformed cells. For example, in certain embodiments, a subject may receive may receive low-intensity chemotherapy (e.g. lenalidomide, ibrutinib) after leukapheresis. Prior to administering transformed cells according to the present disclosure, chemotherapy or immune modulatory therapy may be appropriate in order to provide lymphodepletion to facilitate survival of transferred T cells, and to reduce the tumor burden prior to infusion of the cells. For example, subjects may receive lymphodepleting chemotherapy for a predetermined time prior to (e.g., 36-96 hours) the infusion of the cells. In certain embodiments, a subject may initially be treated with a single dose of a chemotherapy agent such as cyclophosphamide (CY) i.v. (e.g., at 1 g/m$^2$) initially. However, if the subject response rate is determined to be inadequate, the lymphodepletion regimen may be changed so that subsequent patients receive a second, further chemotherapeutic or immunomodulatory agent (e.g., CY+fludarabine). Additionally, a subject may, but need not, receive a premedication prior to administration of the cells.

One or more intravenous infusions of the cells described herein may be administered to the subject following completion of lymphodepleting chemotherapy (e.g., 36-96 hours thereafter). The dose of cells administered to the subject may be determined according to the dose levels shown in Table 1, and may be adjusted thereafter to increase, decrease, or otherwise change the amount, composition, ratio, or rate of the cells administered. In certain embodiments, a single infusion is administered to the subject. In further embodiments, a second infusion may be given if the first infusion does not produce a complete response (CR), or if the disease relapses after a CR. In still further embodiments, a third, fourth, fifth, sixth, seventh, eighth, ninth, tenth, or further infusion may be given. In certain embodiments, a cell infusion may be administered intravenously over a selected period of time (e.g., approximately 20-30 minutes), adjusted as needed to comply with guidelines for endotoxin limits for parenteral drugs (£ 5 EU/kg/hour). The infusion rate may also be adjusted if subjects experience mild infusion-related adverse events (grade 2 or lower).

EXAMPLES

Example 1

Materials and Methods

Cell Lines

Raji, Daudi, and Ramos (Burkitt lymphoma), Rec-1 (mantle cell lymphoma), and K562 (CD20-negative erythroid leukemia) tumor cell lines were obtained from ATCC. Granta-519 (mantle cell lymphoma) was obtained from DSMZ, and FL-18 (transformed follicular lymphoma) was obtained from Dr. David Maloney (Fred Hutchinson Cancer Research Center). CD20 expression was authenticated by flow cytometry on all cell lines prior to experiments. Cell lines were cultured in RPMI 1640 with 25 mM HEPES, 10% fetal bovine serum (FBS), 1% penicillin/streptomycin, and 1% L-glutamine and incubated at 37° C. in 5% $CO_2$. K562 cells were transduced with a retroviral vector to express CD20, and some cells were again transduced with a lentiviral vector to express human CD80. Low, medium, and high CD20-expressing K562-CD80 cell lines were obtained by selection after limiting dilution cloning. Raji-ffLuc cells were produced by transduction of Raji cells with retrovirus encoding firefly luciferase-Thy1.1-Neo and selected with G418 as previously described (James et al., *Blood* 2009; 114(27):5454-63). Rituximab-refractory Raji-ffLuc cells were generated with repeated, intermittent cycles of escalating rituximab concentrations as previously described (Czuczman et al., *Clin Cancer Res* 2008; 14(5):1561-70).

Flow Cytometry

Ramos cell lines were incubated with rituximab concentrations ranging from 0 to 200 µg/ml at room temperature for 30 minutes. Following CD20 blocking, anti-CD20-PE antibody (clone L27 [Leu16], BD Biosciences) was added, and cells were incubated at either 4° C. or 37° C. for 30 minutes. Cells were washed with cold FACS buffer (0.5% fetal bovine serum and 2.5 mM EDTA in PBS) and analyzed on a BD Canto 2 flow cytometer. Data were analyzed using FlowJo version 7.6.1 (TreeStar). In a separate experiment, FL-18 cells were blocked with varying concentrations of rituximab, washed once with FACS buffer, and then anti-CD20-FITC antibody (clone 1F5, produced in-house from a hybridoma; Press et al., *Blood* 1987; 69(2):584-91) was added and incubated with blocked cells for 15 minutes at 4° C. Cells were then washed and analyzed as described above. Similar experiments were also conducted using ofatumumab instead of rituximab.

Vector Constructs

The CD20-specific Leu16-28-BB-z-tEGFR construct (SEQ ID NO.:57) was generated by amplifying the Leu16 scFv (Wang et al., *Hum Gene Ther* 2007; 18(8):712-25; Wang et al., *Mol Ther* 2004; 9(4):577-86) by PCR and cloning into NheI and RsrII sites of an epHIV7 lentiviral vector encoding an IgG4-Fc, CD28, and 41BB domains, and CD3ζ domain (Hudecek et al., *Clin Cancer Res* 2013; 19(12):3153-64). The Leu16-28-z construct (SEQ ID NO.:

49 or 58) was generated by splice overlap PCR of the Leu16-28-BB-z-tEGFR vector to remove the 41BB domain and truncated EGFR. The lentiviral vector encoding the CD20-specific 1F5-28-BB-z CAR has been previously described (Budde et al., *PLoS One* 2013; 8(12):e82742), but was transferred to the HIV-1-based RRL.sin-.cPPT.PGK.GFP.wpre self-inactivating $3^{rd}$ generation lentiviral vector backbone (Becker et al., *Gene Ther* 2010; 17(10):1244-52; from Dr. Hans-Peter Kiem, FHCRC). The Fc spacer region of this construct was modified to abrogate binding to Fcγ receptors by substituting the IgG1 junction amino acids with the IgG2 junction amino acids (SEQ ID NO.:9) and adding an N297Q mutation (SEQ ID NO.:10) as previously described (Hudecek et al., *Cancer immunology research* 2014; 3(2):125-35; Hombach et al., *Gene Ther* 2010; 17(10):1206-13), to create the 1F5-NQ-28-BB-z construct (SEQ ID NO.:50 or 59). To generate the 1.5.3-NQ-28-BB-z CAR construct (SEQ ID NO.:44 or 53), a novel scFv sequence was produced by synthesizing the $V_L$ and $V_H$ sequences from the 1.5.3 fully human anti-CD20 antibody (see, e.g., Bornstein et al., *Invest New Drugs* 2010; 28(5): 561-74; PCT Publication No. WO 2006/130458) using a codon optimization algorithm (GenScript), separated by a 15 amino acid glycine-serine linker (SEQ ID NO.:20), preceded by the GM-CSF signal peptide (SEQ ID NO.:18). An overlapping fragment produced by splice overlap PCR was used to replace the scFv domain of the 1F5-NQ-28-BB-z construct, cloning it into AgeI/SacII restriction sites. The inducible caspase 9 suicide gene and downstream 2A sequence (SEQ ID NO.:22 or 23) were removed from this construct by splice overlap PCR. The 1.5.3-NQ-28-z construct (SEQ ID NO.:27) was generated by removing the 41BB domain from 1.5.3-NQ-28-BB-z by splice overlap PCR. All constructs were confirmed by Sanger sequencing. Lentivirus was produced using 293T cells transiently transfected with the described backbone vectors as well as the packaging vectors pCGHP-2, pCMV-Rev2, and pCMV-G, and supernatants containing packaged lentivirus were concentrated 100-fold by centrifugation.

T Cell Isolation and Transduction

Peripheral blood mononuclear cells (PBMC) were obtained either by apheresis from healthy donors consented under Institutional Review Board (IRB)-approved research protocols at the FHCRC or from used Pall leukocyte filters purchased from the Puget Sound Blood Center. PBMC isolated by centrifugation with Ficoll-Paque density gradient medium underwent red blood cell lysis with ammonium-chloride-potassium (ACK) buffer and were cryopreserved in 10% DMSO and 90% FBS. For in vitro experiments, T cells were negatively selected from thawed PMBC by MACS using a Pan T cell Isolation Kit II (Miltenyi Biotec). For cytotoxicity experiments, $CD8^+$ T cells were positively selected from healthy donor apheresis PBMC by MACS using anti-CD8 antibody coated beads (Miltenyi Biotec) prior to cryopreservation. For some experiments, central memory T cells ($T_{CM}$) were isolated from healthy donor apheresis PBMC prior to cryopreservation by negative selection using an AutoMACS device after incubation with CliniMACS anti-CD14 and anti-CD45RA beads (Miltenyi Biotec), followed by positive selection with CliniMACS CD62L beads. In other experiments, CD4 and CD8 cells were enriched by positive immunomagnetic selection using anti-CD4 or anti-CD8 beads (Miltenyi Biotec). Selected T cells were stimulated with αCD3/αCD28 Ab-coated Human T-Expander Beads (Invitrogen) at a 3:1 bead:T-cell ratio. Activated T cells were spin-transduced (2100 rpm for 60 minutes at 32° C.) the next day with lentiviral vector encoding one of the CD20 CAR constructs (multiplicity of infection of 2-6) plus 4-8 μg/ml polybrene. Transduced T cells were cultured in media containing 50 IU/ml recombinant human interleukin 2 (rhIL-2) with or without 10 ng/ml rhIL-15 (Miltenyi Biotec), incubated for 4-5 days after stimulation before magnetic removal of αCD3/αCD28 beads, and analyzed by flow cytometry to confirm CAR expression. $CAR^+$ T cells were used in functional assays.

For in vivo mouse experiments, $T_{CM}$ or CD4 and CD8-enriched T cells were thawed, activated, and transduced the next day with concentrated lentiviral supernatant encoding the construct indicated in each experiment. CD3/CD28 beads were removed on day 5, cells were expanded in 50 IU/mL rhIL-2, restimulated on day 7-10 with irradiated $CD20^+$ LCL at a 1:1 responder:stimulator ratio, and injected into mice 8-11 days after restimulation with LCL.

Proliferation and Cytokine Secretion Assays

T cells ($2\times10^5$ total cells) stained with 5 μM carboxyfluorescein succinimidyl ester (CFSE) were then co-cultured at 1:1 ratios with tumor target lines that had been irradiated with 8000-10000 cGy. In rituximab blocking experiments, irradiated target cells were incubated for 30 minutes at room temperature with various rituximab concentrations prior to co-incubation with T cells. Supernatant was collected 24 hours after plating and stored at −20° C. until subsequent cytokine analysis by Luminex assay as previously described (Till et al., *Blood* 2012; 119(17):3940-50) to quantify interferon-gamma (IFN-γ), interleukin-2 (IL-2), and TNF-α. After 4-5 days, cells were stained with anti-CD3-APC (BioLegend), and CFSE dilution of CD3-gated lymphocytes as a measure of proliferation was determined by flow cytometry. Cell size as another measure of activation was determined by flow cytometry using the geometric mean of the forward scatter (FSC-A) parameter, and subtracting the cell size of resting T cells. Flow cytometry data were analyzed using FlowJo software (v7.6.1; Treestar, Ashland, OR). In some experiments, ofatumumab was substituted for rituximab.

Assessment of cytokine secretion was also determined by intracellular staining of IFN-γ. CD20 $CAR^+$ $CD4^+$ or $CD8^+$ T cells were co-cultured with irradiated K562 or K562-CD20 cells for 24 hours. For intracellular staining, cells were fixed, permeabilized with BD Cytofix/Cytoperm kit (BD Biosciences) for 15 minutes on ice. Cells were then stained with anti-IFN-γ (Biolegend) for 1 hour on ice after fixation and permeabilization. Data were analyzed on BD FACSCanto (BD Biosciences). FlowJo Software was used to analyze the data.

Cytotoxicity Assays

Standard $^{51}Cr$-release assays were performed by co-incubating CD20 CAR $CD8^+$ T cells with $^{51}Cr$-labeled target cell lines for 4-5 hours as previously described. (See, Wang, et al. Hum Gene Ther. 2007; 18:712-725). Maximal $^{51}Cr$ release was determined by directly measuring the $^{51}Cr$ content of supernatants of labeled cells lysed with 5% IGEPAL CA-630. Supernatants were harvested into 96-well Lumaplates, air-dried overnight, and counts were assayed with a TopCount (PerkinElmer). Percent cytotoxicity was calculated by the equation: $[Sample-Min_{avg}]/[Max_{avg}-Min_{avg}]*100$.

For rituximab blocking experiments, $^{51}Cr$-labeled target cell lines were incubated at various rituximab concentrations (ranging from 0 to 200 μg/mL) for 30 minutes (at double the final concentration during the initial incubation to yield final concentrations of 10, 25, 50, 100, and 200 μg/ml) before addition of $CAR^+CD8^+$ T cells at various effector to target (E:T) ratios. Cells were cultured in duplicate at 37° C. for 5 hours in medium containing heat-inactivated FBS, with $^{51}Cr$-labeled rituximab-blocked target cells in U-bottom 96-well plates. Control wells contained target cells incubated in rituximab-containing medium without T cells (denoted in figures as "0:1" E:T ratio) to exclude the possibility of rituximab-induced CDC. In some experiments ofatumumab was used in place of rituximab.

In Vivo Assessment of Rituximab Effect on CAR T Cell Efficacy

Groups of 5-10 NOD.Cg-Prkdc$^{scid}$Il2rg$^{tw1Wjl}$/SzJ (NOD/SCID/$\gamma^{-/-}$ [NSG]) mice 6-10 weeks of age (Jackson Laboratory) were inoculated with $5\times10^5$ rituximab-resistant Raji-ffLuc or Granta-519 lymphoma cells 2-7 days by tail vein. 2-7 days later (as indicated in each experiment), $10^7$ CD20 CAR T cells (tCD19$^+$) or empty vector T cells were injected by tail vein. In the rituximab blocking experiment, 25 or 200 μg of rituximab was administered intraperitoneally (i.p.) 5 days after tumor inoculation and 1 day before administration of CAR T cells. Bioluminescence imaging to determine tumor growth was performed using known methods (see, James et al., *Blood* 2009; 114(27):5454-63; Rufener et al., *Cancer Immunol Res.* 2016; 4:509-519). Binning and exposure were adjusted to achieve maximum sensitivity without leading to image saturation. Survival curves were generated using the Kaplan-Meier method with GraphPad Prism 6 software.

To test for persistence of adoptively transferred T cells, whole blood collected at various timepoints by retro-orbital bleeding was lysed by ACK lysing buffer (Quality Biological). Mouse serum was obtained by centrifugation of clotted blood specimens from the retro-orbital plexus on days 6 and 13 after tumor inoculation, and serum rituximab levels were measured using an ELISA assay to determine rituximab concentrations as previously described (see, Gopal A K, et al., *Blood* 2008; 112(3):830-5; Maloney D G, et al., *Blood* 1997; 90(6):2188-95). Fc receptors of isolated cells were blocked with intravenous immunoglobulin (IVIG), and cells were stained with monoclonal antibodies (mAbs) to mCD45 (30-F11, Biolegend), hCD3 (HTT3a, Biolegend), and hCD19 (HIB19, BD Bioscience). Data were collected with a BD Canto 2 and analyzed on FlowJo Software (Treestar). Mouse studies were approved by the FHCRC Institutional Animal Care and Use Committee.

Patient Serum Samples

Human serum samples were provided by B-cell lymphoma patients following IRB approval and informed consent obtained in accordance with the Declaration of Helsinki. Serum samples were collected within 4 months after rituximab-containing salvage chemoimmunotherapy. Serum rituximab concentrations were determined as previously published (Maloney et al., *Blood* 1997; 90(6):2188-95).

Example 2

Effect of Rituximab on CD20 Binding by CAR Containing Anti-CD20 scFv

CD20-directed CARs using scFvs derived from two different murine monoclonal antibodies, either the Leu16 (L27; see, Till et al., *Blood* 2008; 112(6):2261-71; Till et al., *Blood* 2012; 119(17):3940-50) or 1F5 antibodies (see, Wang J, et al., *Hum Gene Ther* 2007; 18(8):712-25; Budde et al., *PLoS One* 2013; 8(12):e82742), each of which bind to epitopes on the large extracellular loop of the CD20 molecule, were previously tested (see, Polyak et al., *Blood* 2002; 99(9):3256-62). These CD20 epitopes overlap with the rituximab epitope (see, Polyak et al., *Blood* 2002; 99(9):3256-62) and, thus, rituximab would be expected to block the binding of these CARs. Using flow cytometry, the ability of varying concentrations of rituximab to block binding of the Leu16 anti-CD20 antibody to CD20 expressed on Ramos lymphoma cells was assessed by pre-incubating these cells with rituximab prior to incubation with the Leu16 Ab. A dose-dependent blockade of CD20 was observed, with near complete blockade at 50 μg/ml rituximab at 4° C. But, when anti-CD20-PE (Leu16) was incubated at the physiologically relevant temperature of 37° C., low-level CD20 binding occurred even at 200 μg/ml of rituximab (FIGS. 2A-2F). Similar findings were observed in experiments using the 1F5 anti-CD20 antibody on FL-18 cells (data not shown). Thus, rituximab binds to overlapping epitopes with the anti-CD20 CARs of this disclosure and has the potential to interfere with CAR T cell activity against CD20$^+$ target cells.

Example 3

Effect of Rituximab on In Vitro Function of CAR T Cells

The impact of CD20 blocking by rituximab on the function of CD20 CAR T cells was assessed by measuring proliferation, cytokine secretion, and cytotoxicity using five different CD20 CAR lentiviral constructs after incubation with a variety of CD20$^+$ B cell NHL cell lines. The CAR constructs (FIGS. 1A and 1B) were the 3$^{rd}$-generation Leu16-28-BB-z-tEGFR and 1F5-28-BBz constructs (see, Budde et al., *PLoS One* 2013; 8(12):e82742), the 2$^{nd}$-generation Leu16-28-z construct, and two CD20 CARs (1.5.3-NQ-28-BB-z and 1.5.3-NQ-28-z) derived from the fully human 1.5.3 anti-CD20 Ab, which also binds to an overlapping epitope with rituximab (see, Bornstein et al., *Invest New Drugs* 2010; 28(5):561-74). CAR expression was typically achieved in 40-80% of the T cells (data not shown).

Figure 3A:
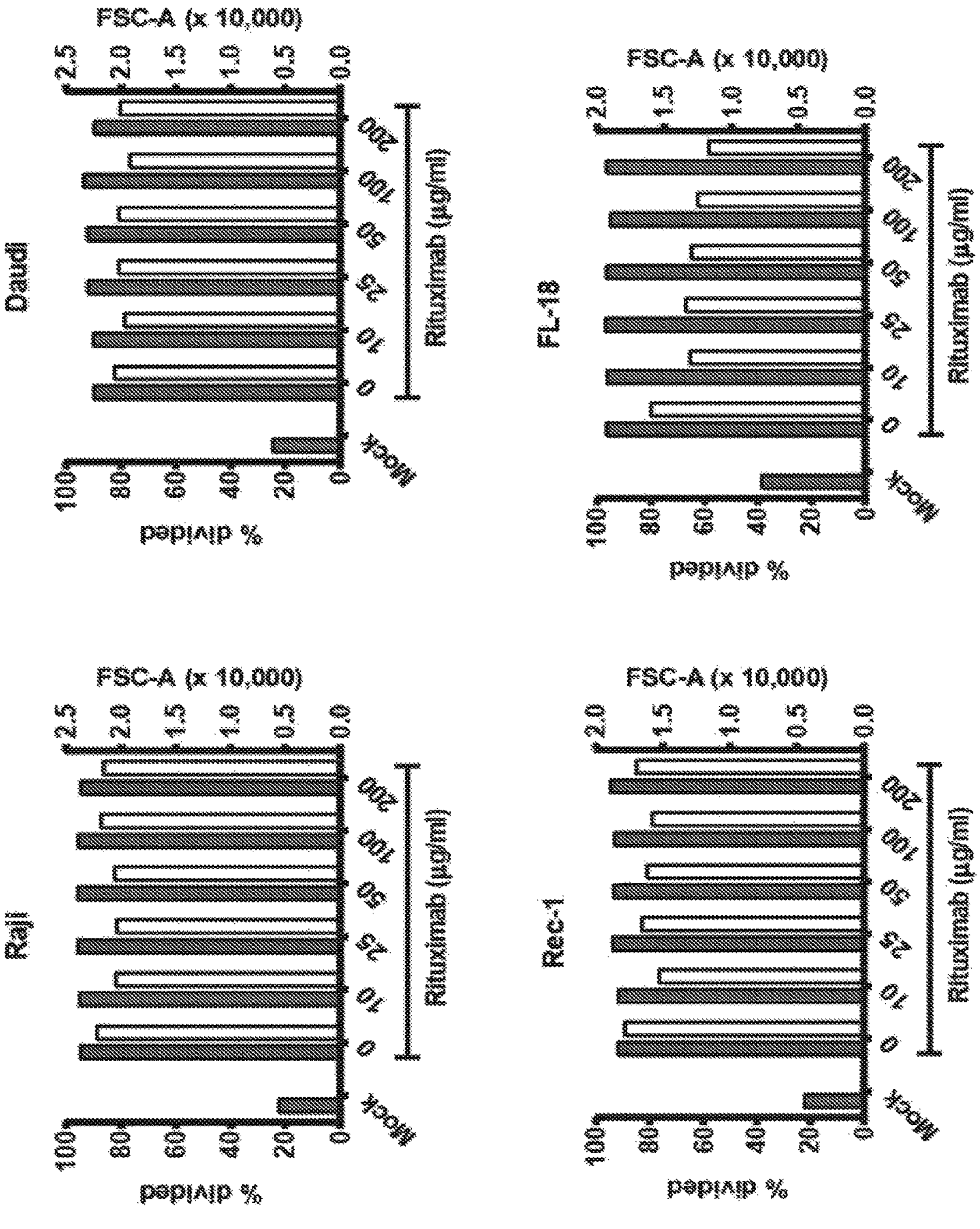
FIGS. 3A and 3B show the effect of rituximab on CAR T cell function in vitro. The indicated B-cell NHL cell lines were irradiated and incubated for 30 minutes at room temperature with varying rituximab concentrations (at 2× the concentrations during incubation to yield the indicated final concentrations after addition of T cells). CFSE-stained T cells expressing the Leu16-28-BB-z-tEGFR CD20-specific CAR were added to the target cells at a 1:1 volume and ratio. (A) Proliferation of the T cells was analyzed 4 days later by flow cytometry for CFSE dilution. The percent divided $CD3^+$ T cells relative to unstimulated T cells are shown on the left axis (filled bars). Cell size of $CD3^+$ T cells as determined by geometric mean of forward scatter (subtracting size of cells in media only) is shown on the right axis (open bars). (B) Cytokine secretion of these T cells was measured by Luminex assay using supernatants from 24 hours after restimulation. Interleukin (IL)-2 concentrations are shown on the left y-axis and Interferon (IFN)-γ and tumor necrosis factor (TNF)-α on the right y-axis. The data shown are representative of 3 independent experiments.

Proliferation of CFSE-labeled CAR T cells was largely unimpaired when cultured with various NHL target cell lines (Raji, Daudi, Rec-1, and FL-18) in the presence of rituximab. CAR T cells stimulated with target cells in the presence of rituximab at concentrations up to 200 μg/ml exhibited >96% of the proliferation observed after stimulation in the absence of rituximab (FIG. 3A). Cell size is another measure of T cell activation (see, Grumont et al., *Immunity* 2004; 21(1):19-30). CAR$^+$ T cells were analyzed by flow cytometry for forward scatter as an estimate of cell size and found that following stimulation with Raji, Daudi, or Rec-1 tumor cells pre-incubated with rituximab, CART cells exhibited a median size >85% of the size of control cells not exposed to rituximab (FIG. 3A). T cells incubated with FL-18 cells exhibited a slightly more pronounced, but still modest, reduction in cell size following incubation with rituximab (73% of control cell size at 200 μg/ml).

Figure 3B:
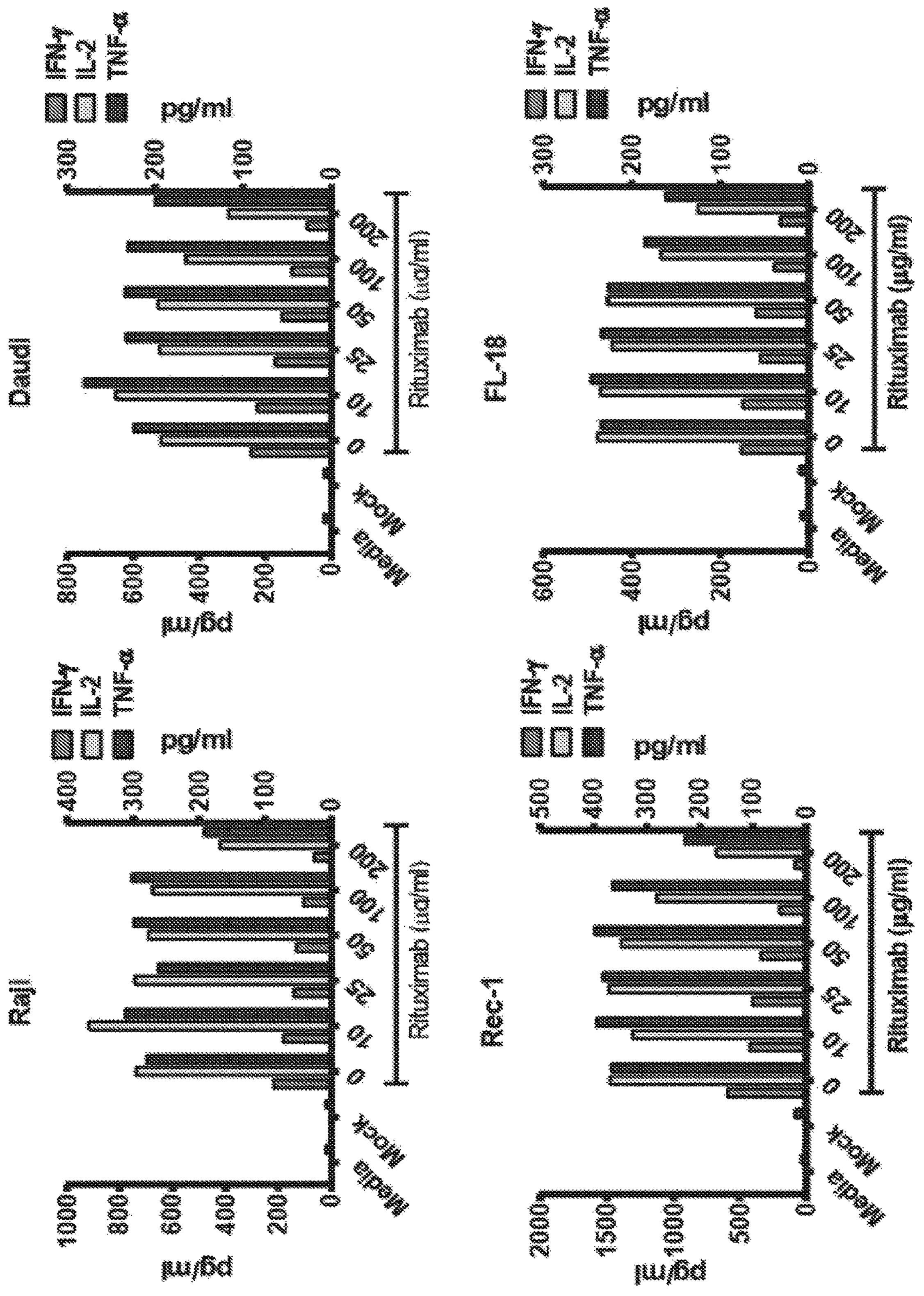
Figure 6A:
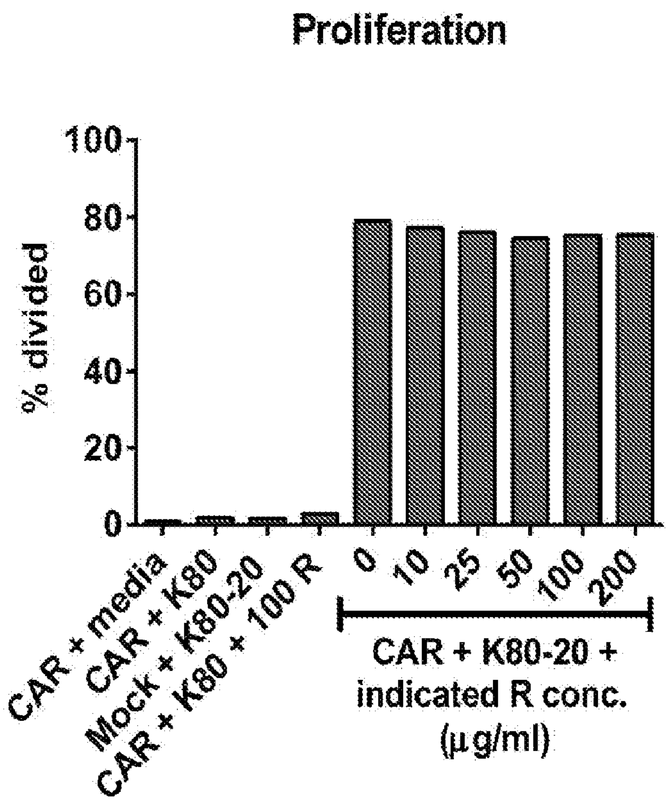
FIGS. 6A and 6B show proliferation and cytokine secretion by T cells expressing an anti-CD20 CAR. Healthy donor T cells were sorted and stimulated using anti-CD3/28 beads, followed by transduction with lentiviral vector encoding the 1F5-28-BB-z CAR construct. (A) At day 9 after stimulation, CAR T cells were labeled with CFSE, restimulated with either K562-CD80-CD20 ("K80-20") or K562-CD80 ("K80") target cells that had been irradiated, and CFSE dilution was measured by flow cytometry 4 days later to measure T cell proliferation. The percent divided $CD3^+$ T cells relative to unstimulated T cells are shown. Mock-transduced T cells were used as a negative control. (B) Cytokine secretion by the T cells was determined by harvesting supernatant samples from the above cultures at 24 hours after restimulation and analyzing the indicated cytokine concentration by Luminex assay.
Figure 6B:
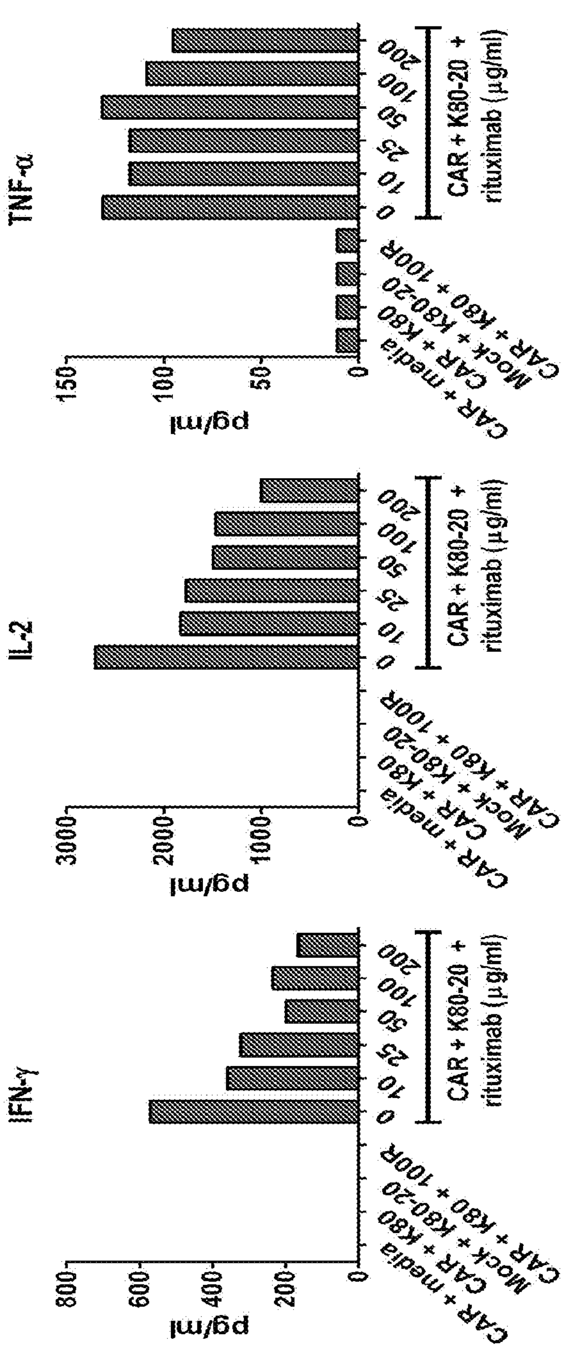

In contrast to proliferation, cytokine secretion by CAR T cells was found to be decreased in the presence of increasing rituximab levels (FIG. 3B). However, even at 100 μg/ml of rituximab, the cytokines IFN-γ, IL-2, and TNF-α were produced at 34-51%, 70-92%, and 79-108% of baseline levels, respectively. Similar findings were observed using K562 cells genetically modified to express CD80 and CD20 as targets, with CD20-negative K562-CD80 cells as a control to demonstrate antigen specificity of CD20 CAR T cell activity (FIGS. 6A and 6B).

The impact of rituximab on the cytolytic activity of CAR$^+$ T cells against various CD20$^+$ NHL target cell lines was also examined. Using standard $^{51}Cr$-release assays with CAR$^+$/

Figure 4:
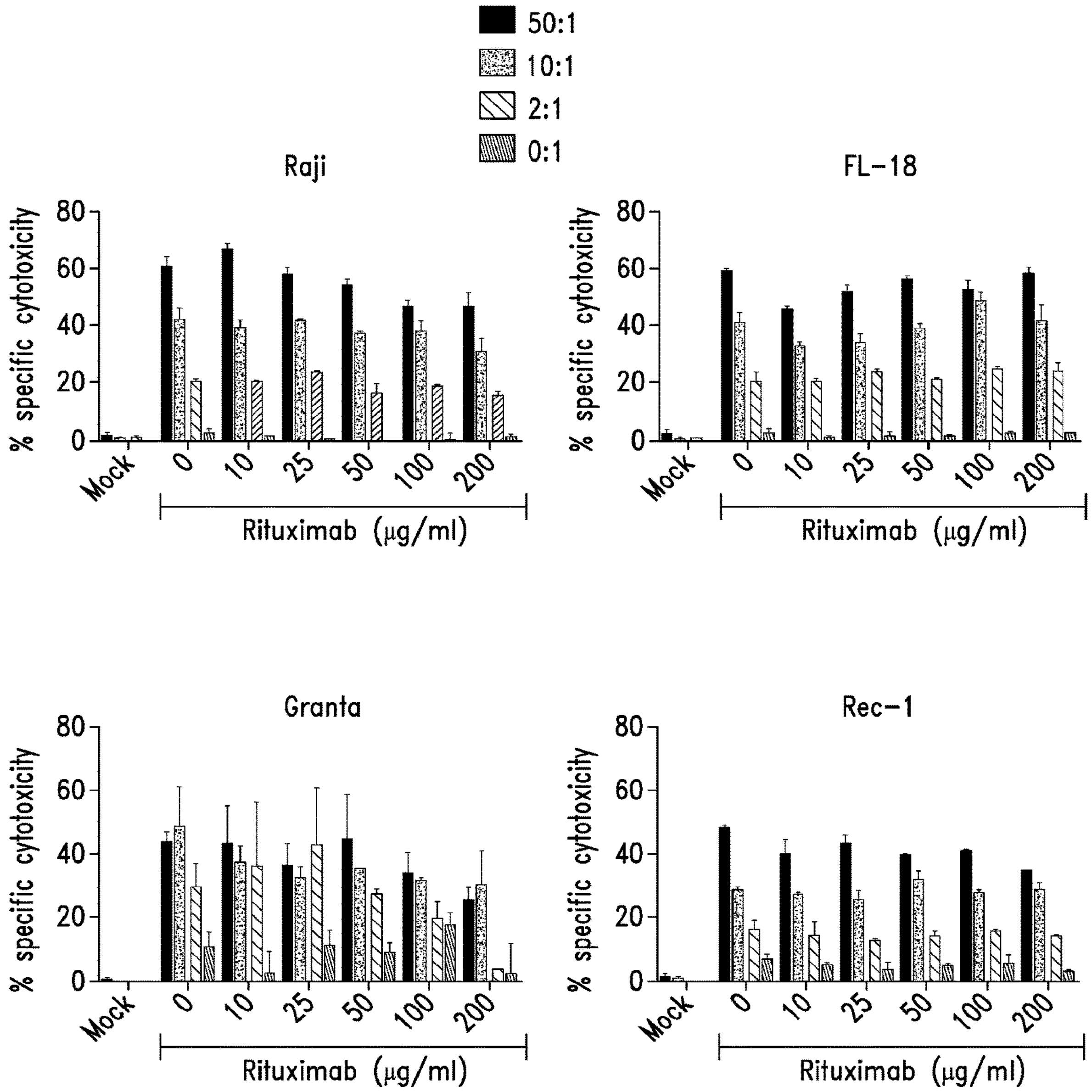
FIG. 4 shows the effect of rituximab on CAR T cell-mediated cytotoxicity. The indicated $^{51}$Cr-labeled target cells were pre-incubated for 30 minutes with rituximab (at 2× the concentrations during incubation to yield the indicated final concentrations after addition of T cells), and then $CD8^+$ T cells expressing the Leu16-28-z CAR were added at the E:T ratios shown in a standard 5-hour $^{51}$chromium-release assay. Mock-transduced T cells, and samples with rituximab and target cells only ("0:1") were used as negative controls. The average value of duplicate wells is shown, with error bars representing standard deviation. The data are representative of results from 4 independent experiments.

$CD8^+$ T cells as effectors and Raji, FL-18, Granta, or Rec-1 as targets, cytotoxicity was found to be minimally impaired at rituximab concentrations up to 50 μg/ml (FIG. 4), and >65% of baseline cytolytic activity was retained in rituximab concentrations of 100 μg/ml against all target cell lines tested.

The in vitro functionality of the fully human 1.5.3-NQ-28-z and 1.5.3-NQ-28-BB-z CAR T cells were tested in the presence of rituximab. As with the Leu16 and 1F5 CARs, a modest dose-dependent decrease in cytokine secretion and cytotoxicity against rituximab pre-treated target cells was observed, but not proliferation.

Example 4

Effect of Expression Levels of CD20 on CAR T Cell Sensitivity to Anti-CD20

Figure 5A:
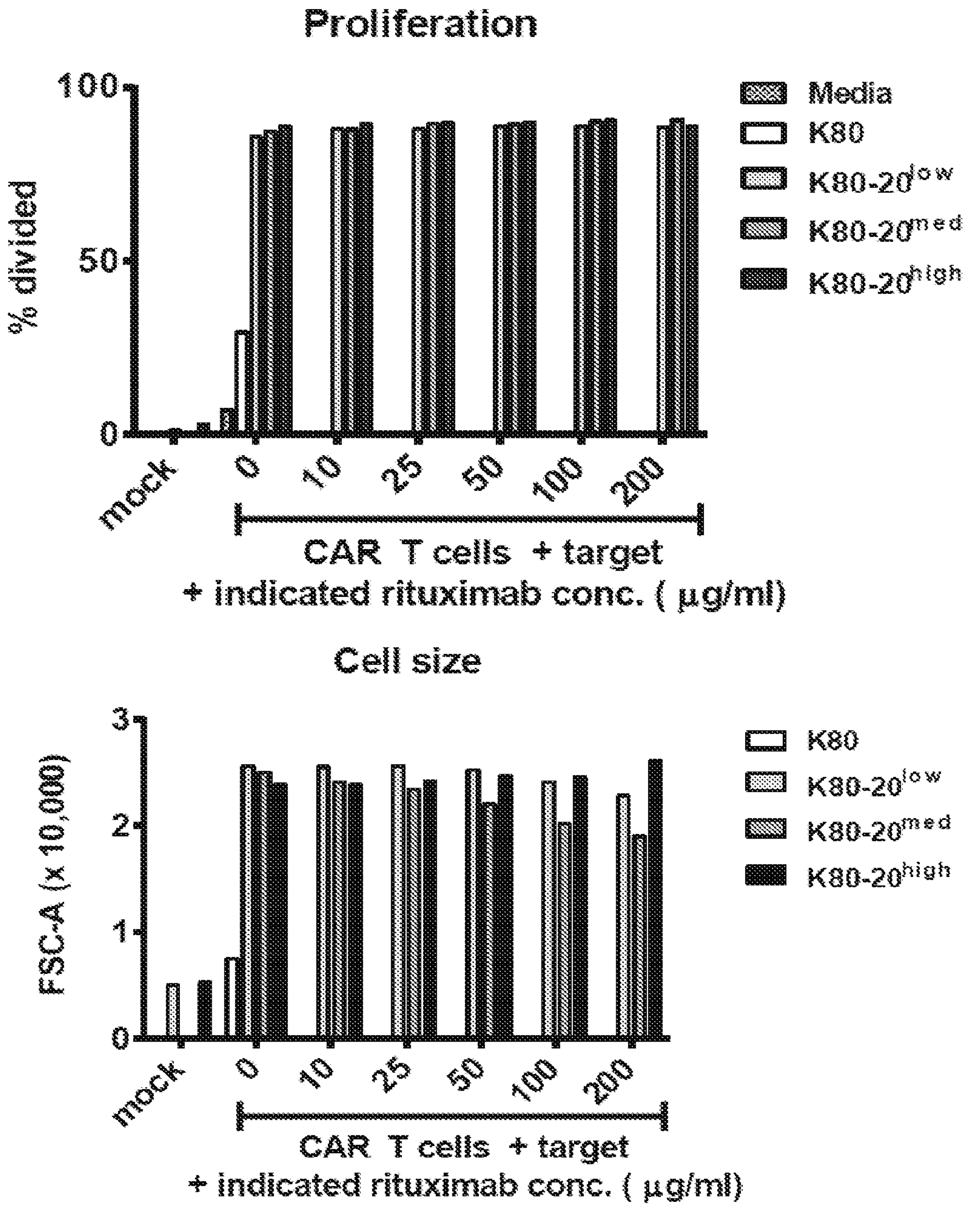
FIGS. 5A-5C show that sensitivity to rituximab blockade is dependent on CD20 antigen density on target cells. K562 cells transduced with CD80 and CD20 ("K80-20") were cloned by limiting dilution, selected for high, medium, or low levels of CD20 expression (FIG. 10), and used as target cells in assays for (FIG. 5A) proliferation and cell size (geometric mean forward scatter of gated $CD3^+$ cells minus the size of cells in media only) using CFSE-labeled Leu16-28-z CAR-transduced T cells as described in FIG. 3.
Figure 5B:
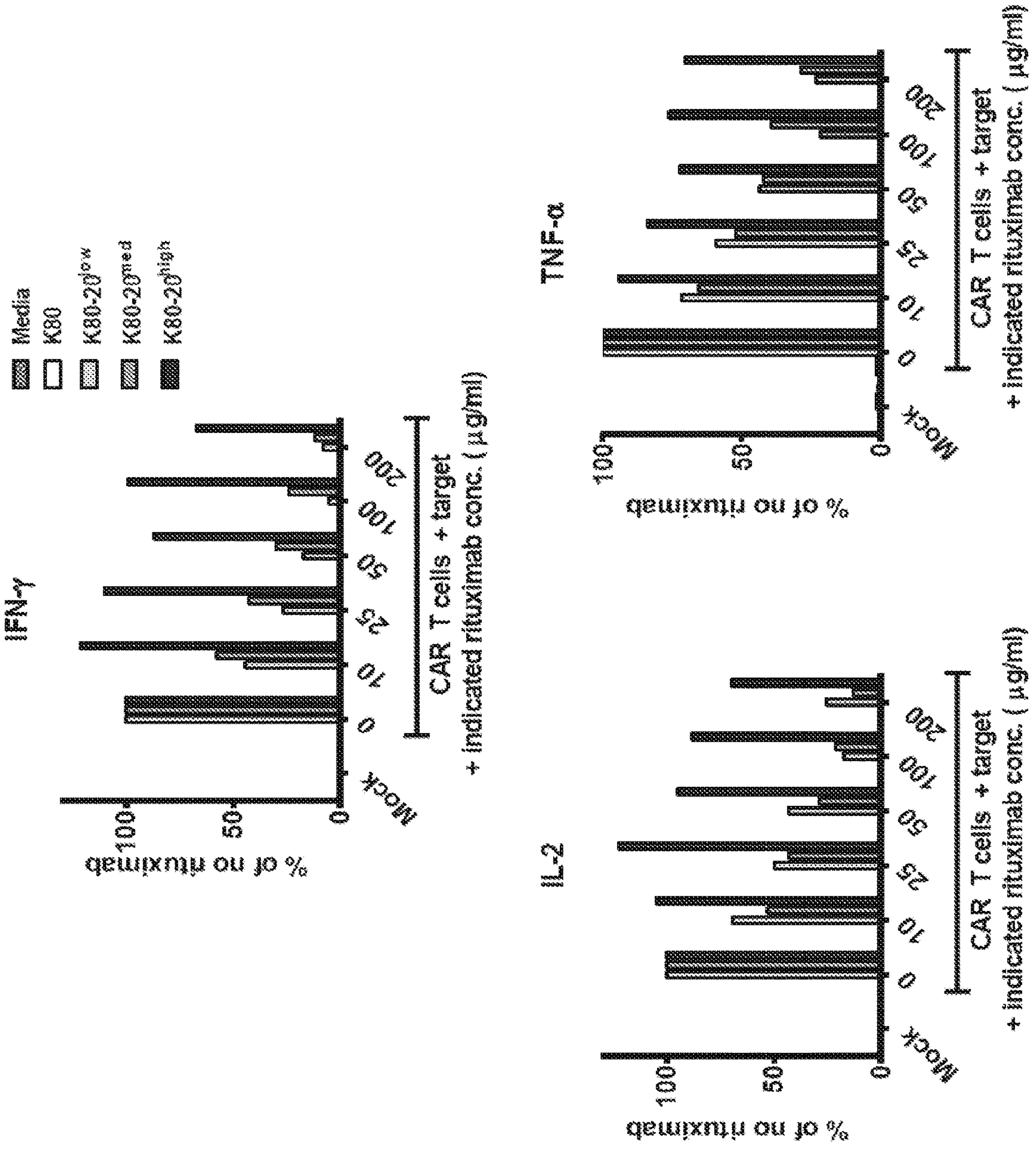
Figure 10:
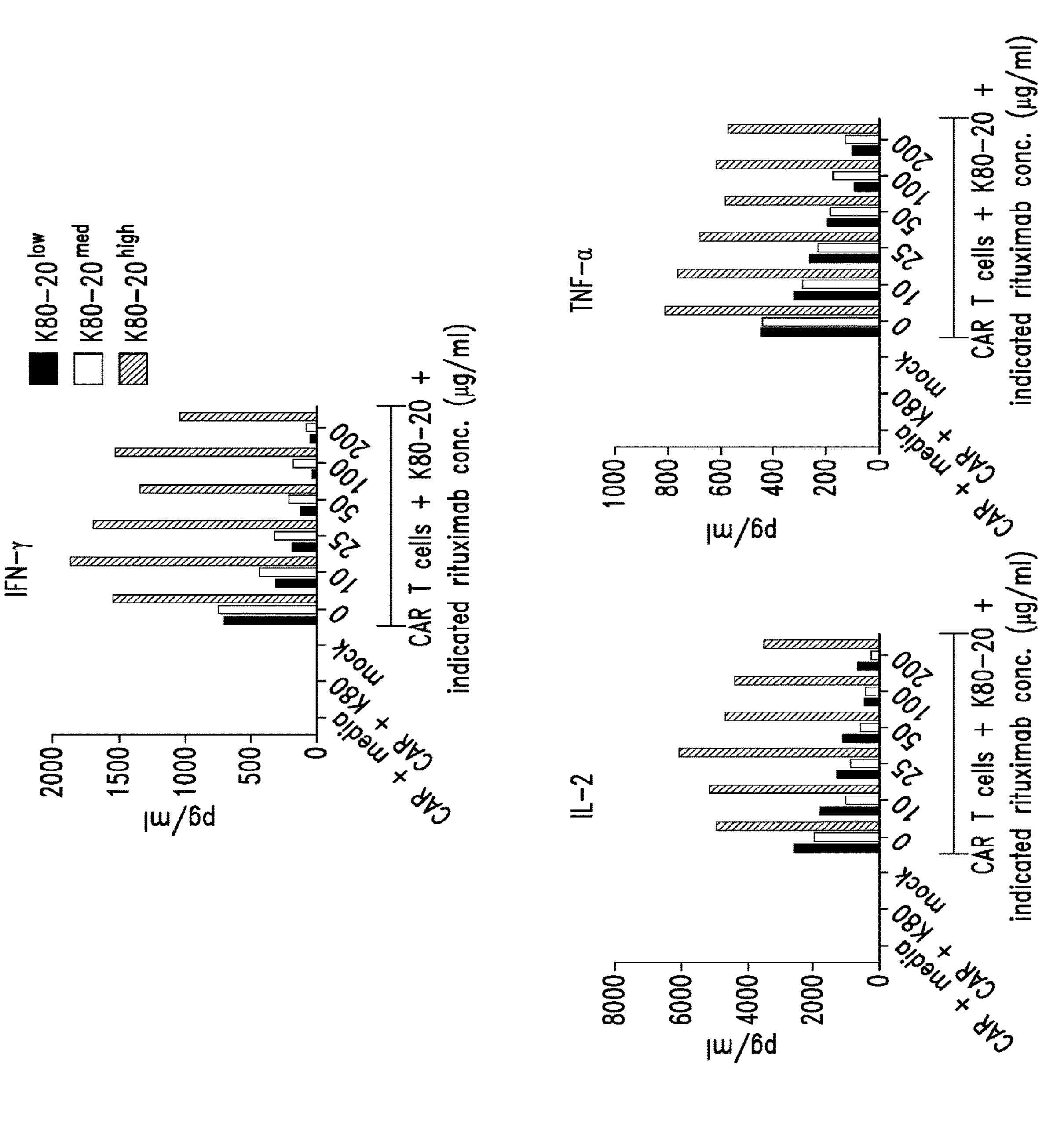
FIG. 10 shows the absolute cytokine concentrations from T cell supernatants from the experiment in FIG. 5 are shown.
Figure 11A:
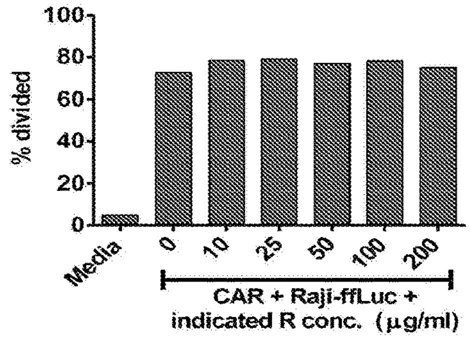
FIGS. 11A-11E show proliferation, cytokine secretion, and cytotoxicity of CAR T cells with fully human anti-CD20 scFv. Healthy donor $CD14^-CD45RA^-CD62L^+$ central memory T cells were stimulated using anti-CD3/28 beads, followed by transduction with lentiviral vector encoding either the 1.5.3-NQ-28-z or 1.5.3-NQ-28-BB-z CAR. CAR T cells were labeled with CFSE and restimulated with irradiated Raji-ffLuc, rituximab-refractory Raji-ffLuc (RR-Raji), or Rec-1 target cells. (A) Proliferation of 1.5.3-NQ-28-z T cells was assessed by analyzing the cells 4 days later by flow cytometry for CFSE dilution. The percent divided $CD3^+$ T cells relative to unstimulated T cells are shown. (B) Cytokine secretion by 1.5.3-NQ-28-z T cells was determined by harvesting supernatant samples from the above cultures at 24 hours after restimulation and analyzing the indicated cytokine concentrations by Luminex assay. IL-2 and TNF-α concentrations are shown on the left y-axis and IFN-γ concentrations are plotted on the right y-axis. (C) Cytokine secretion by 1.5.3-NQ-28-BB-z T cells determined as in part B above. (D) Cytotoxicity of 1.5.3-NQ-28-BB-z CART cells was determined using a standard 5-hour Chromium$^{51}$-release assay with the indicated target cell lines. (E) Cytokine secretion by 1.5.3-NQ-28-BB-z T cells as in part (A) above and stimulated with Granta, Rec-1, FL-18, or K80-20 cells.
Figure 11B:
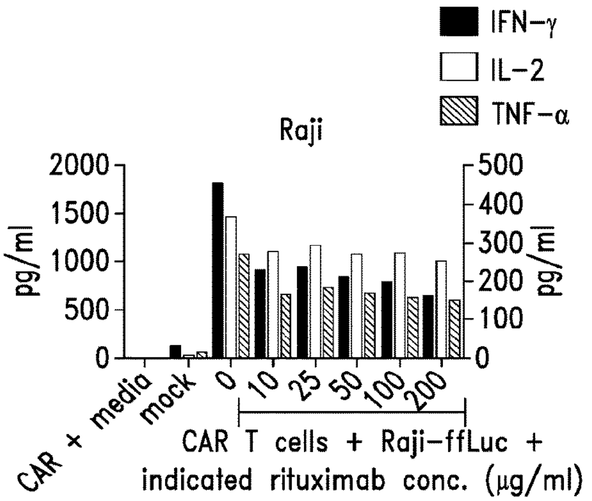
Figure 11C:
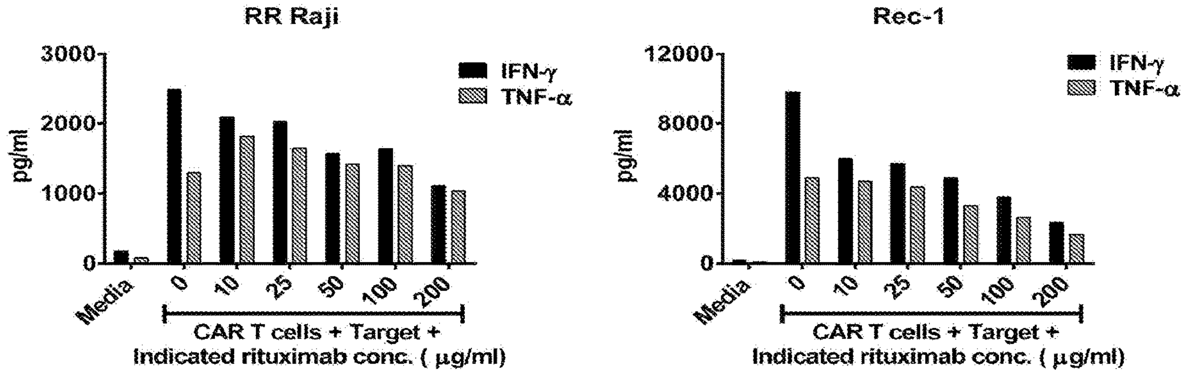
Figure 11D:
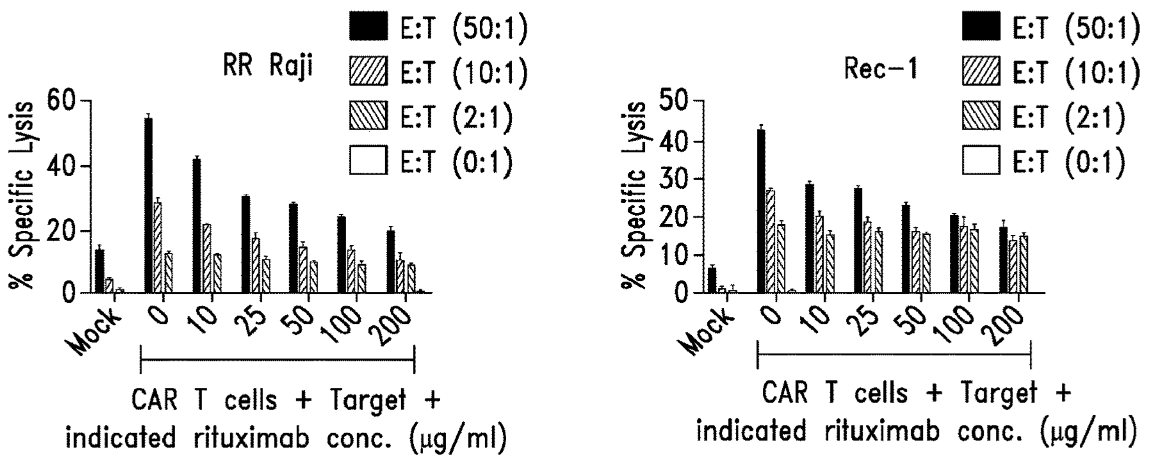
Figure 11E:
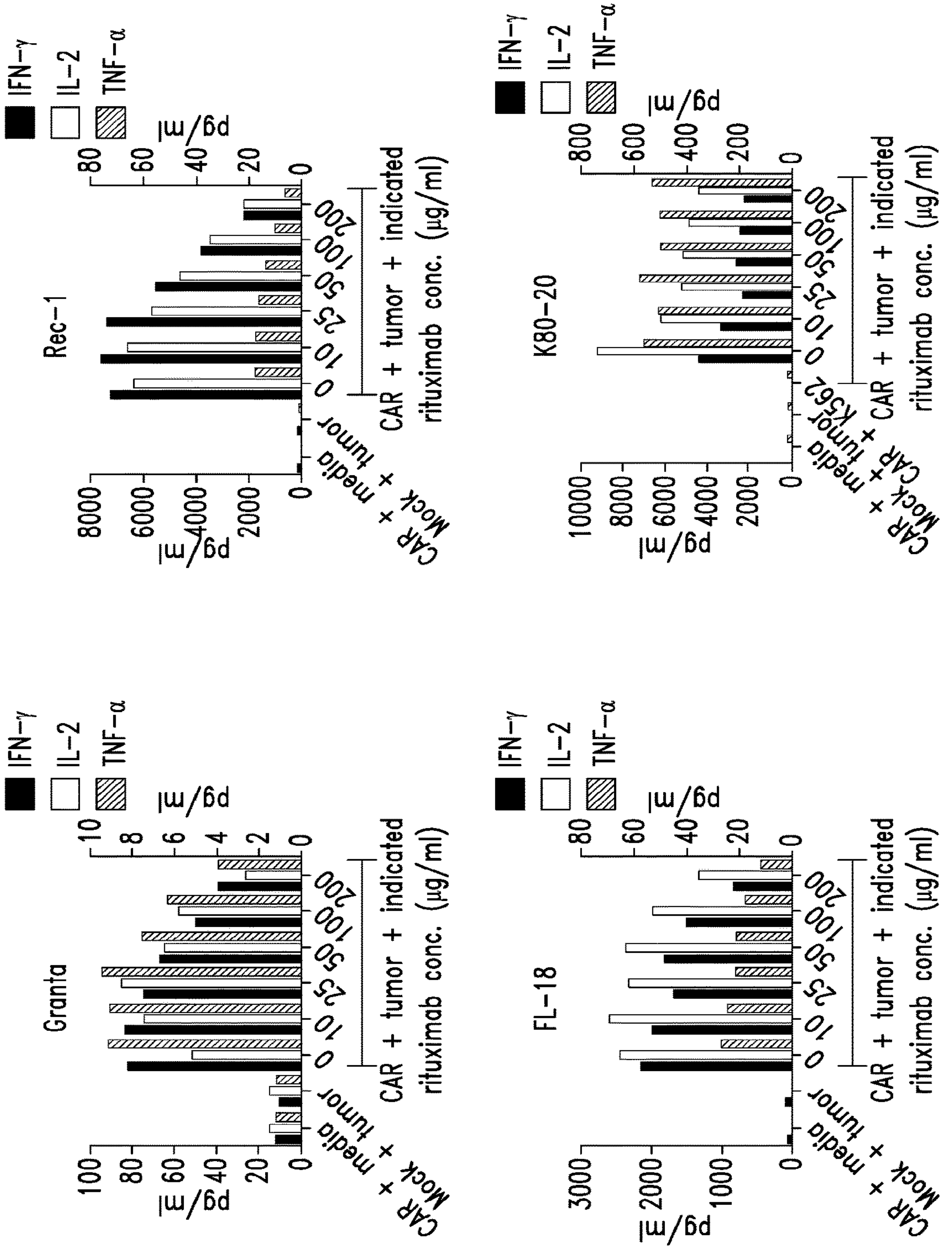

To examine whether the level of CD20 expression on tumor cells might impact sensitivity to rituximab blockade, K562-CD80 cell lines with low, medium, and high levels of CD20 expression after limiting dilution cloning (FIG. 10) were selected for testing. The in vitro CAR T cell function was again assessed in the presence of varying concentrations of rituximab. As with the NHL cell lines, proliferation of CAR T cells was completely intact regardless of the expression level of CD20 on target cells (FIG. 5A). Cell size was undiminished when $CD20^{high}$ cells were used as targets, although a modest reduction in cell size was found for cells expressing lower levels of CD20. In contrast to proliferation and cell size, cytokine secretion was significantly impaired upon stimulation with $CD20^{low}$ target cells, with IFN-γ, IL-2, and TNF-α levels as low as 5%, 17%, and 22% of baseline values, respectively, at 100-200 μg/ml of rituximab (FIG. 5B; FIG. 11A-11E), whereas T cells stimulated with $CD20^{high}$ targets retained >75% of baseline activity at rituximab concentrations of 100 μg/ml.

Figure 5C:
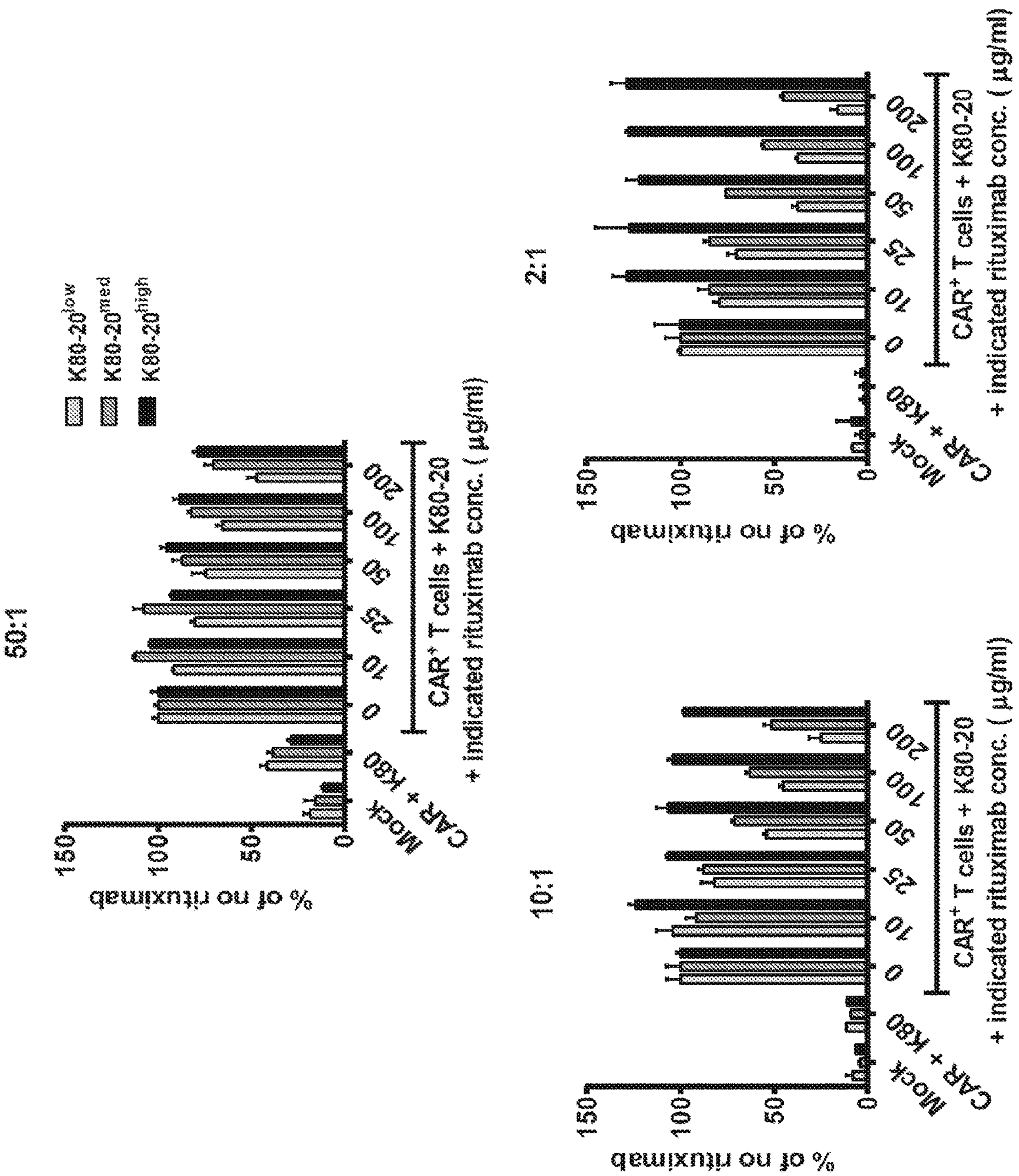

The impact of CD20 antigen density on the rituximab-mediated inhibition of CAR T cell cytolytic activity is shown in FIG. 5C. T cell killing of target cells expressing high levels of CD20 was minimally impacted by rituximab, even at low E:T ratios. However, there was a dose-dependent decrease in T cell cytotoxicity against $CD20^{low}$ and $CD20^{medium}$ K562-CD80 targets, which was most pronounced at lower effector to target (E:T) ratios. Cytolytic activity against $CD20^{low}$ targets was retained at 47% of baseline at a 50:1 E:T ratio at 200 μm/ml rituximab, but was only 16% of baseline at a 2:1 E:T ratio.

Example 5

In Vivo Anti-Tumor Activity of CD20 CAR T Cells in the Presence of Residual Rituximab The in vitro experiments above indicated that CD20 CAR T cells retain significant functionality against $CD20^+$ tumors despite the presence of moderate levels of rituximab. To evaluate how these observations would translate to the in vivo setting, the impact of residual rituximab on CAR T cell activity in a mouse lymphoma model was examined.

Figure 12:
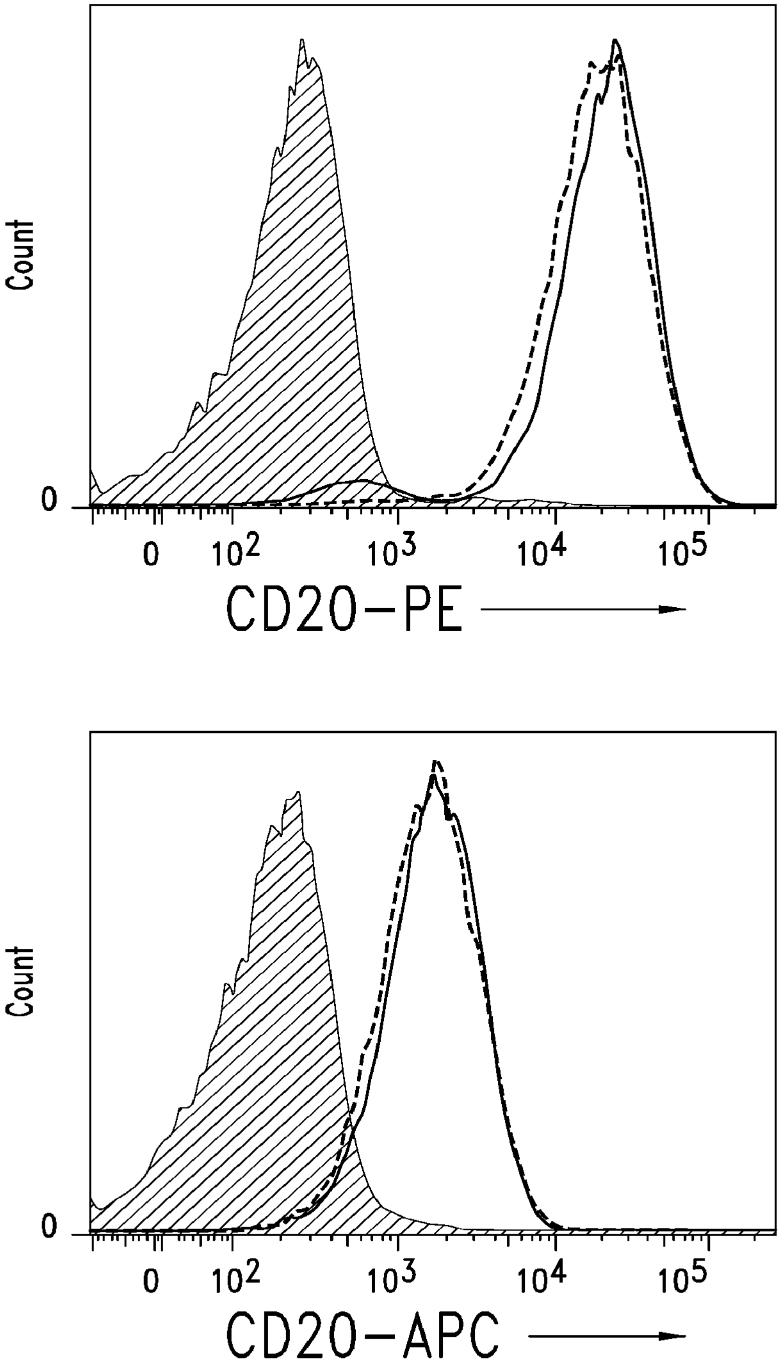
FIG. 12 shows that rituximab-refractory Raji-ffLuc have the same CD20 expression as parental Raji-ffLuc cells. Raji-ffLuc (solid-line histogram) or rituximab-refractory Raji-ffLuc (dashed-line histogram) cells were stained with anti-CD20-PE or anti-CD20-APC antibodies and then analyzed by flow cytometry. CD20 expression relative to isotype control antibody (filled histogram) is shown for each cell line.

By way of background, rituximab as a single agent has significant anti-tumor activity against Raji cells in immunocompromised mouse xenograft models (see, Hernandez-Ilizaliturri F J, et al., *Clin Cancer Res* 2003; 9(16 Pt 1):5866-73). To overcome a potential confounding therapeutic effect from rituximab in combination therapy experiments, a rituximab-refractory Raji cell line (RR-Raji) was generated using previously described methods (see, Czuczman M S, et al., *Clin Cancer Res* 2008; 14(5):1561-70), and CD20 expression was found to be retained in this cell line (FIG. 12).

Figure 7A:
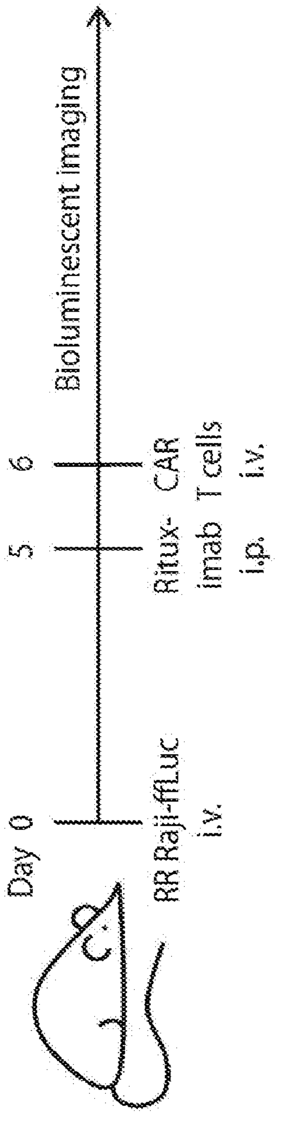
FIGS. 7A-7E show the in vivo effect of rituximab on CD20 CAR T cell function. Nod-SCID-$\gamma^{-/-}$ (NSG) mice were injected intravenously (i.v.) with $5\times10^5$ rituximab-refractory Raji-ffLuc lymphoma cells, followed by one of the following treatments: no treatment, rituximab only (25 μg or 200 μg) intraperitoneally (i.p.) 5 days later, $10^7$ 1.5.3-NQ-28-BBz CART cells only 6 days after tumor, or rituximab (25 μg or 200 μg) i.p. at 5 days followed by $10^7$ CAR T cells at 6 days after tumor. Mice were imaged twice weekly for bioluminescence. (A) Schema of mouse experiment. (B) Average tumor burden per group over time as measured by total body bioluminescence. The geometric mean luminescence values with 95% confidence intervals are shown, and to prevent misleading fluctuations in tumor volume graphs, the last bioluminescence level of each mouse was carried forward after it was killed until no mice in that group remained. Individual bioluminescence traces are shown in FIG. 13. (C) Kaplan-Meier plot showing overall survival of each treatment group. (D) Serum rituximab levels on the day of T cell infusion (day 6) and 1 week post T cell infusion (day 13). The horizontal bars denote the median values. (E) Serum rituximab levels from lymphoma patients who underwent rituximab-containing salvage chemotherapy within the 4 preceding months. The gray horizontal bar line indicates the median, and black horizontal bar lines indicate the interquartile range (25-75%).
Figure 7B:
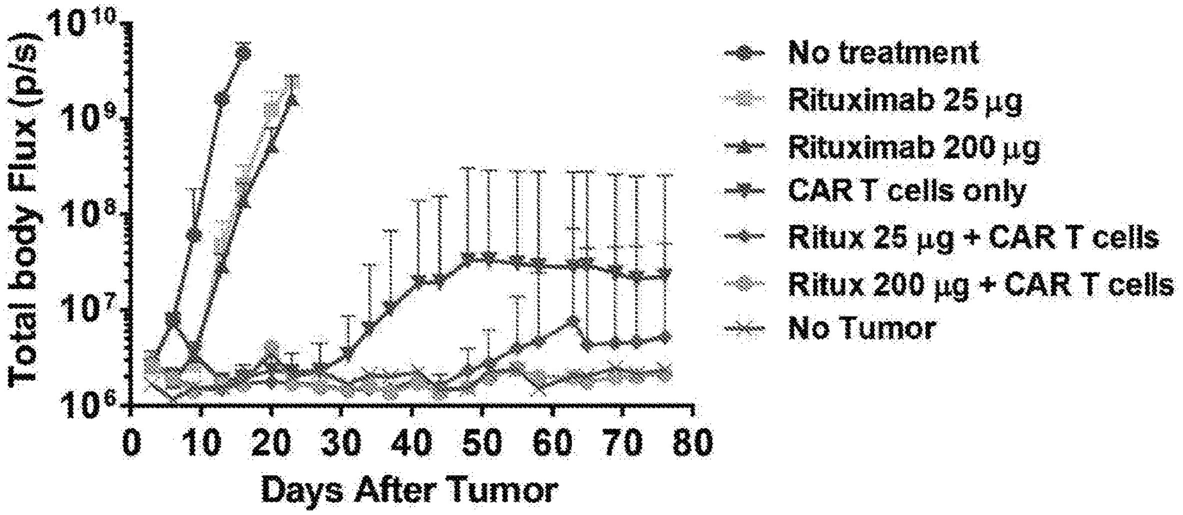
Figure 7C:
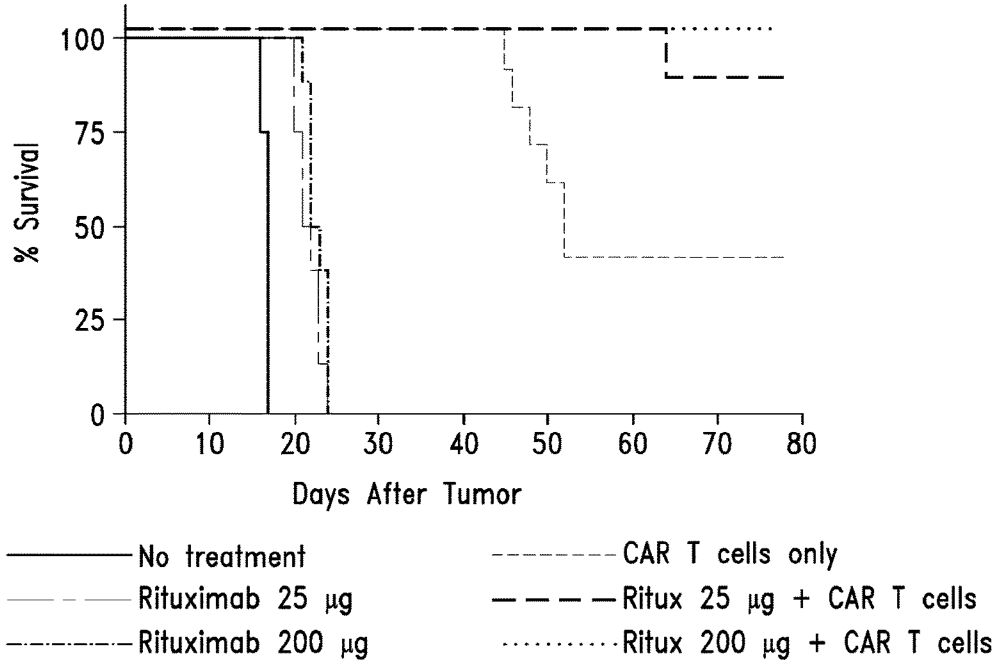
Figure 13A:
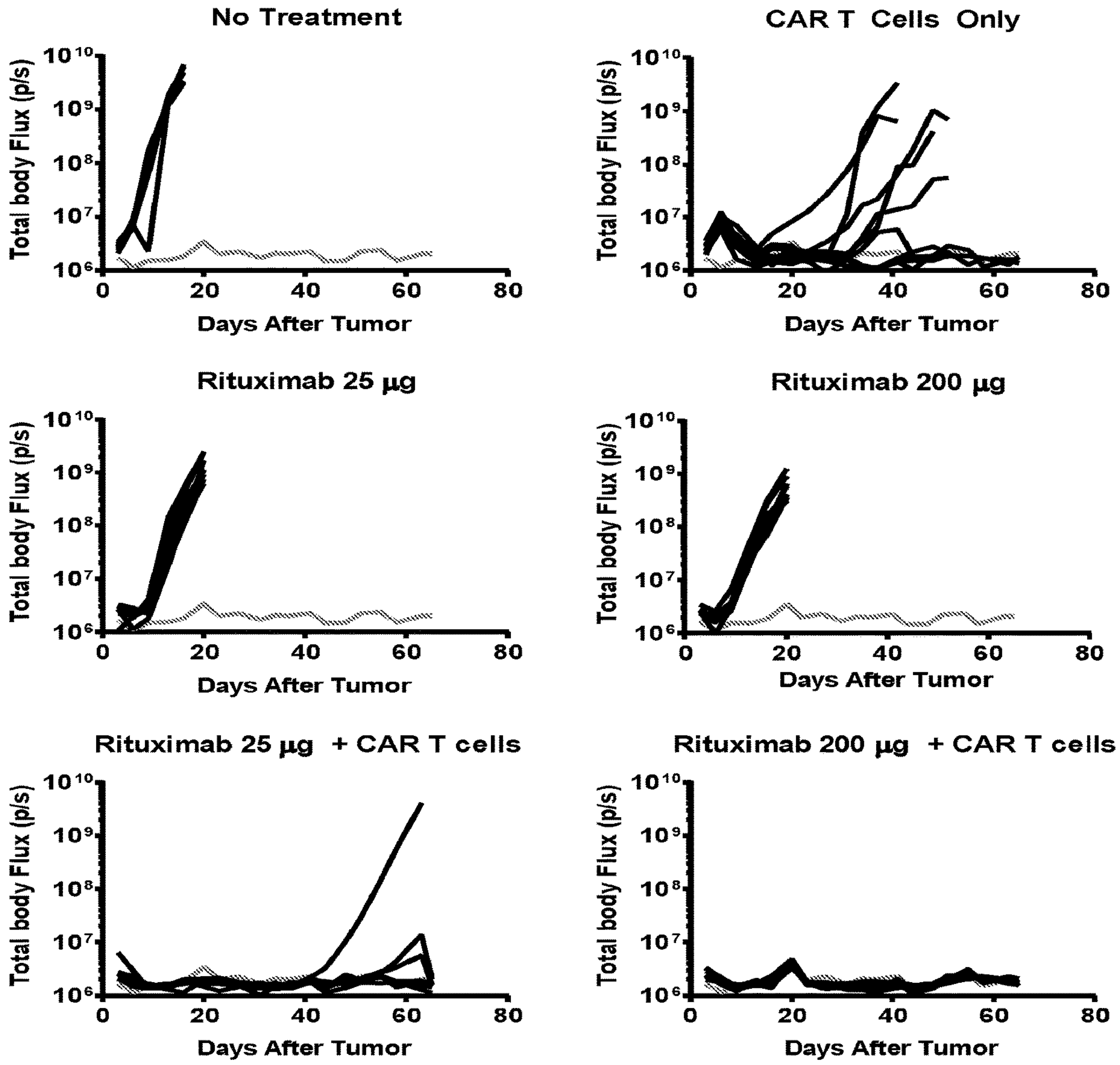
FIGS. 13A and 13B show bioluminescent traces and images from a xenograft tumor mouse model from FIG. 7 treated with anti-CD20 CAR T cells. (A) Individual mouse bioluminescent tumor burden traces over time. Each line represents an individual mouse. The grey line represents a mouse with no tumor, which defines the baseline autofluorescence. (B) Representative mouse bioluminescence images.
Figure 13B:
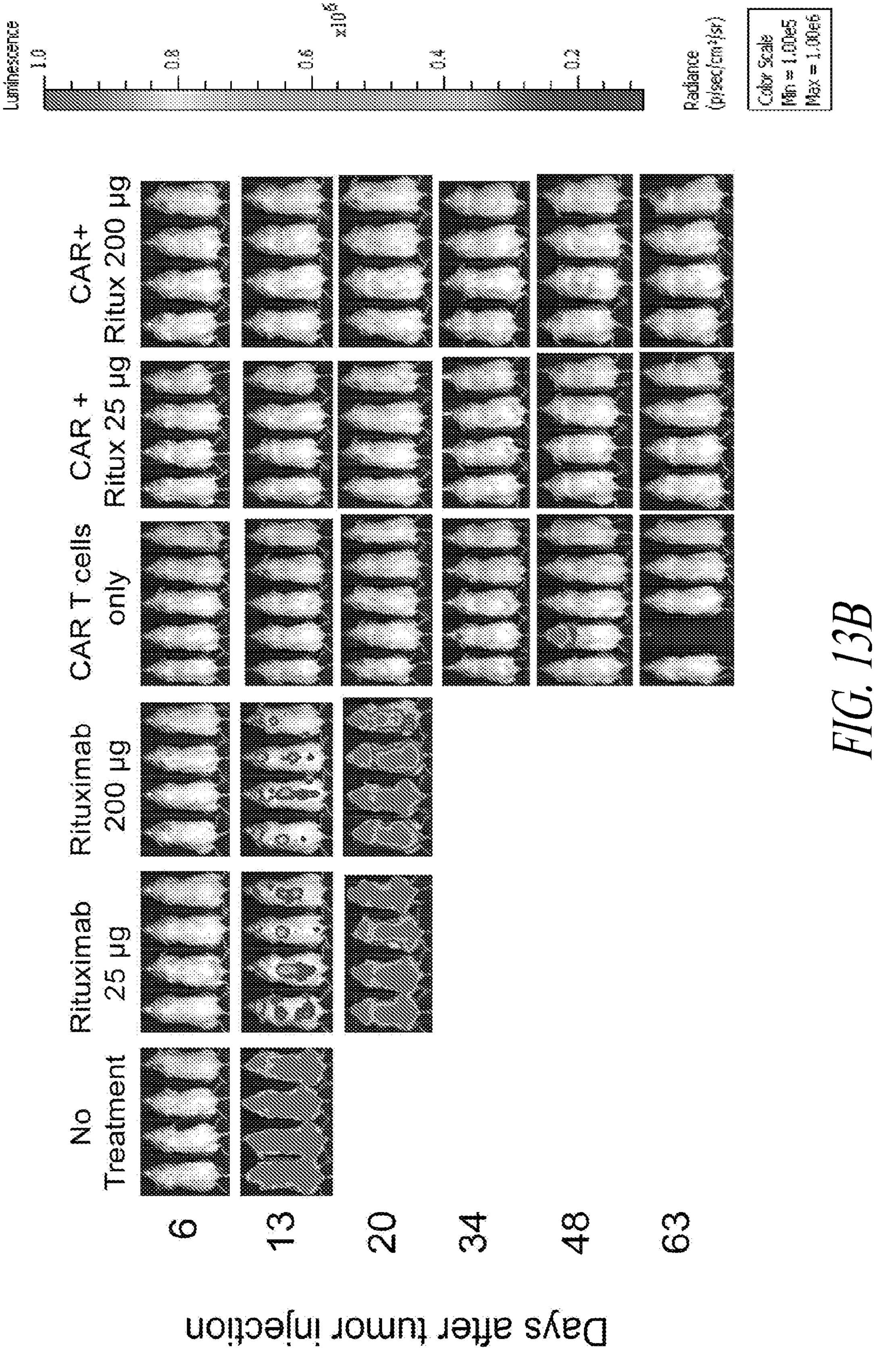

NSG mice were inoculated i.v. with RR-Raji cells and some groups were treated with high or low-dose rituximab once tumors were established 5 days after inoculation, and then CD20 $CAR^+$ T cells were administered i.v. the following day (FIG. 7A). Mice that received rituximab alone demonstrated a modest, transient anti-tumor effect, but all died of tumor progression by day 24, whereas mice treated with CAR T cells alone had significant tumor regression, with tumor eradication in 40% of mice and a doubling of median survival (52 days). Mice that received rituximab the day prior to T cell infusion did not have impaired in vivo CAR T cell activity as compared to mice receiving CAR T cells alone; all but one mouse in the 25 μg/ml rituximab group and all mice in the 200 μg/ml rituximab group demonstrated tumor eradication (FIGS. 7B and 7C; FIGS. 13A and 13B).

Figure 7D:
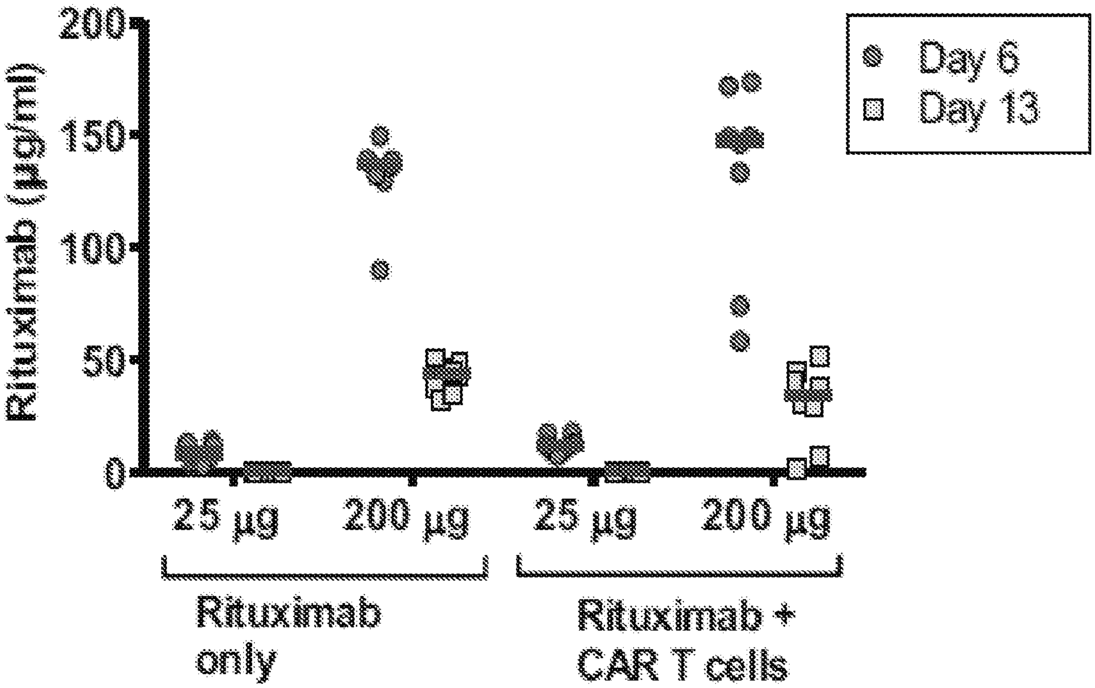

To confirm that these tumor remissions occurred in the presence of physiologically relevant serum levels of rituximab, serum from rituximab-treated mice was collected on the day of T cell infusion and one week later and serum rituximab levels were measured. Mice receiving 200 μg/ml rituximab had an initial median serum rituximab concentration of 138.5 μg/ml (range 54.5-173.6) and 39.7 μg/ml (range 1.6-51.9) a week later, and mice receiving 25 μg/ml rituximab had a median concentration of 11.7 μg/ml (range 2.8-17.8) at baseline and 0 μg/ml at 1 week after T cell infusion (FIG. 7D).

Figure 14A:
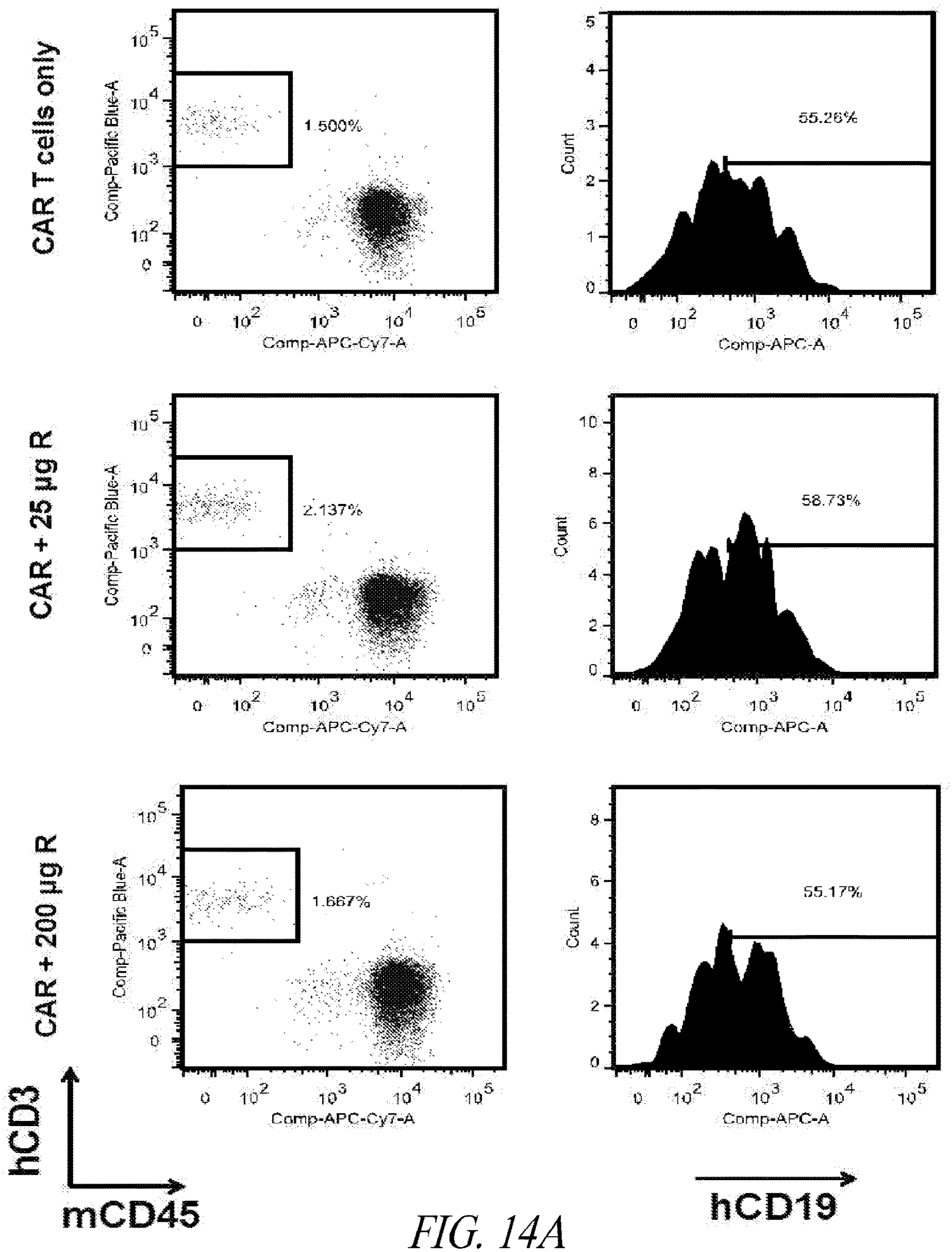
FIGS. 14A-14C show presence of circulating T cells in mice. Peripheral blood mononuclear cells (PBMC) were isolated from retroorbital blood samples taken at day 28 after tumor injection and analyzed by flow cytometry for human CD3, mouse CD45, and human CD19 (as a marker of transduced T cells). (A) Representative dot plots of circulating human T cells (gated on viable lymphocytes) are shown in left panels and CAR$^+$ cells (based on CD19 expression), gated on human CD3$^+$ T cells are shown in right panels. (B) Summary of T cell persistence at day 28. (C) Summary CAR expression on persisting T cells. For both FIG. 14B and FIG. 14C, the difference between CAR only and CAR+rituximab groups were not statistically significant, based on unpaired two-tailed t test.
Figure 14B:
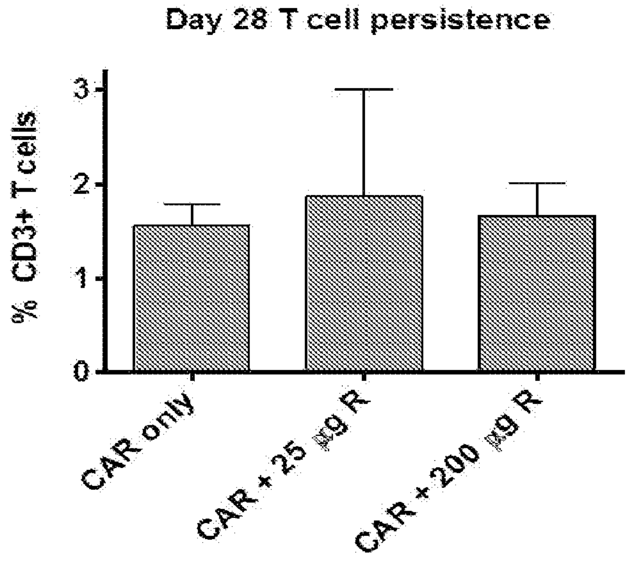
Figure 14C:
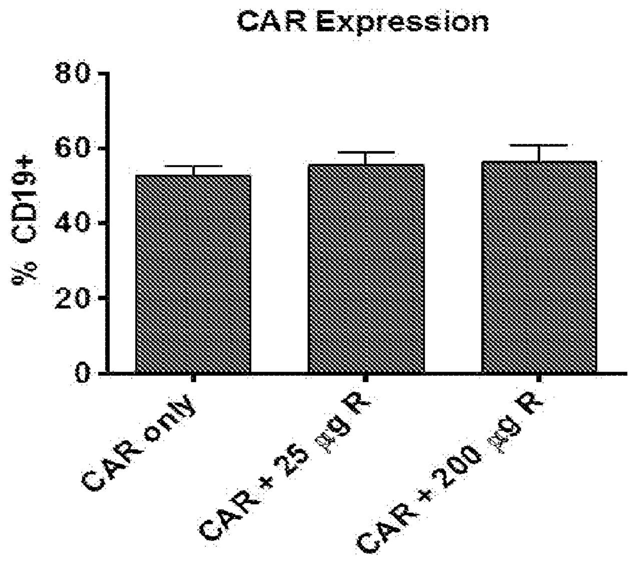

In addition, circulating CAR T cell levels were quantified by flow cytometry 28 days after tumor injection. There was no significant difference CAR T cell levels between mice receiving CAR T cells alone or rituximab plus CAR T cells, indicating that the presence of rituximab did not impair the in vivo persistence of CAR T cells (FIGS. 14A-14C).

Example 6

Figure 7E:
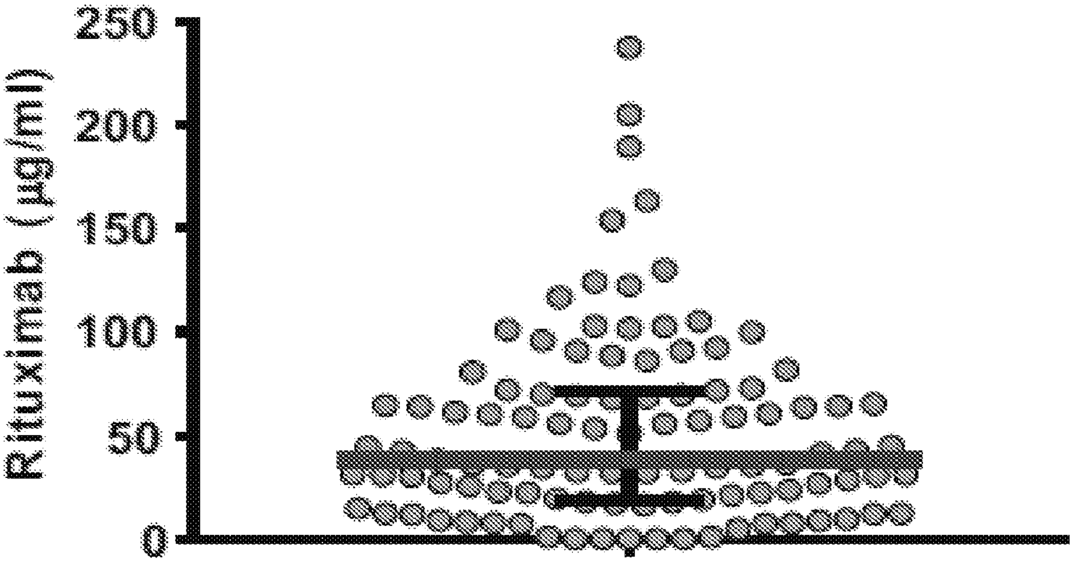

Serum Rituximab Concentrations of Patients Treated with Salvage Rituximab-Containing Regimens To place the above-noted results into a clinical context, a clinically relevant range of residual serum rituximab levels in the intended patient population was queried in a database of patients with B-cell NHL who underwent autologous stem cell transplantation on investigational protocols and had a pre-transplant serum rituximab measurement available (see, Gopal et al., *Blood* 2008; 112(3):830-5). A total of 103 patients who received a rituximab-containing chemotherapy regimen within 4 months of the serum blood draw (range 0.5-3.8 months, median 1.8) were identified, and the median rituximab concentration in these patients was 38.3 μg/ml, with an interquartile range of 19.1-71.7 μg/ml (FIG. 7E). The rituximab concentration was 100 μg/ml or lower in 86% of patients.

Example 7

Effect of Ofatumumab on CD20 CAR T Cell Function

Figure 2A:
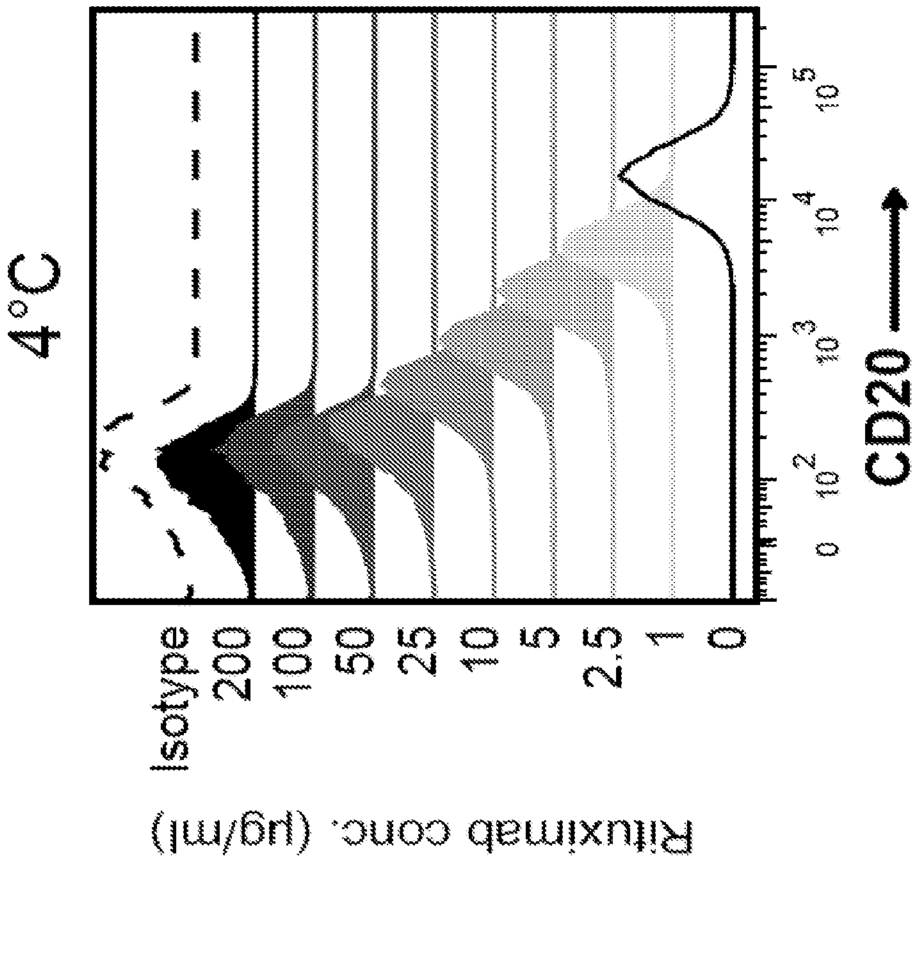
FIGS. 2A-2F show rituximab and ofatumumab block antigen binding of antibody used to generate a CAR scFv. Ramos cells ($CD20^+$) were incubated with the indicated rituximab (A-C) or ofatumumab (D-F) concentrations for 30 minutes, followed by incubation with PE-labeled anti-CD20 antibody (clone Leu16) or isotype control at either 4° C. (A and D) or 37° C. (B and E) for 30 minutes. Cells were washed and analyzed by flow cytometry to determine available CD20 binding sites as measured by PE fluorescence intensity. The graphs depicted in FIG. 2C and FIG. 2F summarize the geometric mean fluorescence intensity (MFI) at either 4° C. or 37° C. as a function of rituximab or ofatumumab concentration, respectively. The data are representative of three independent experiments.
Figure 2B:
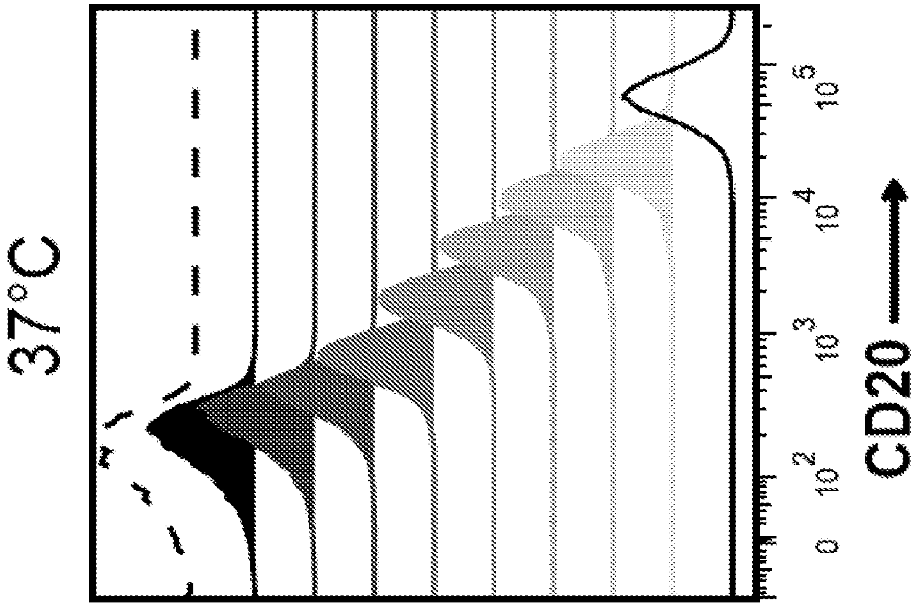
Figure 2C:
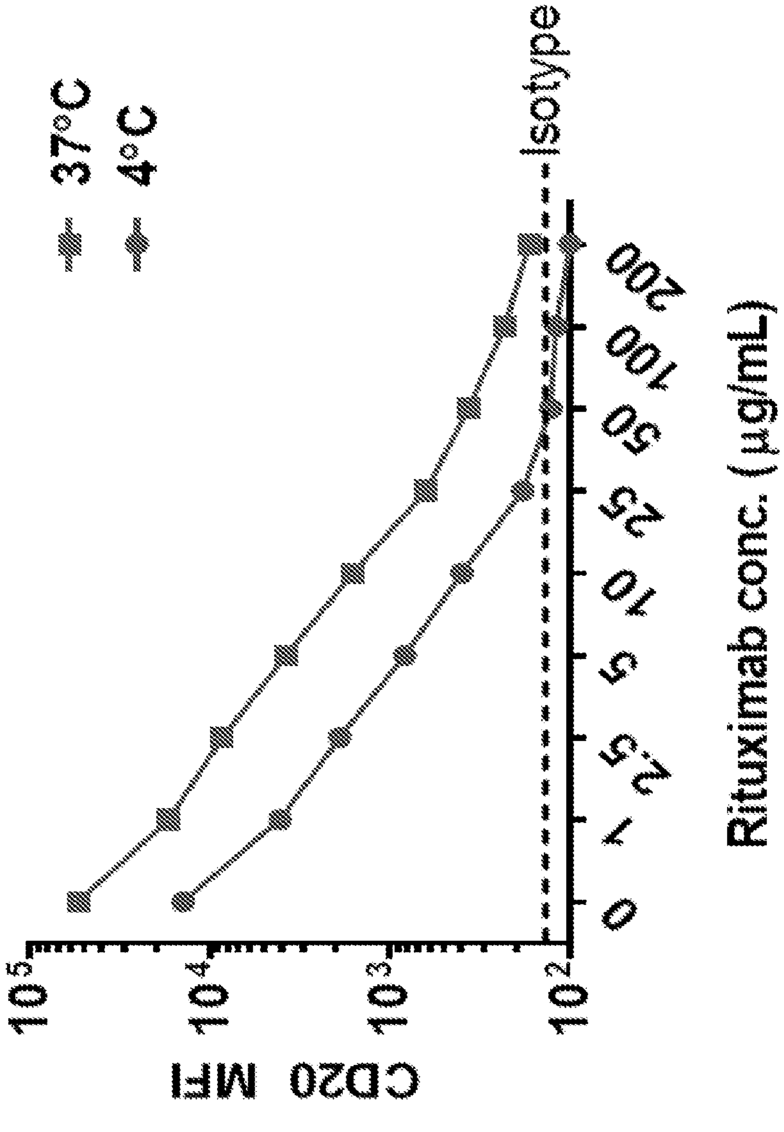
Figure 2E:
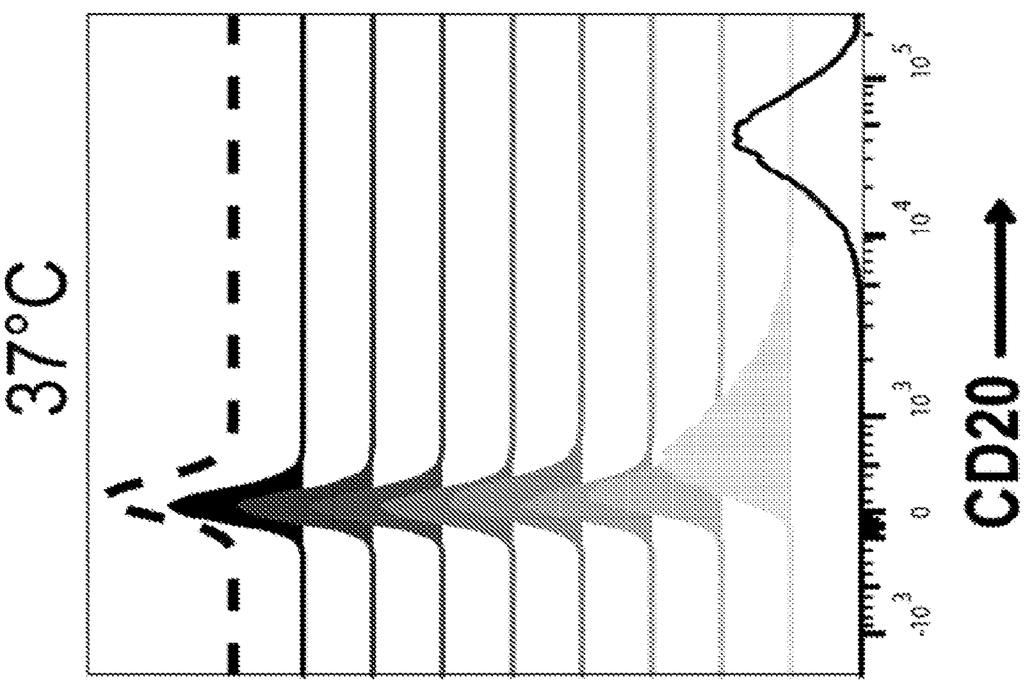
Figure 2D:
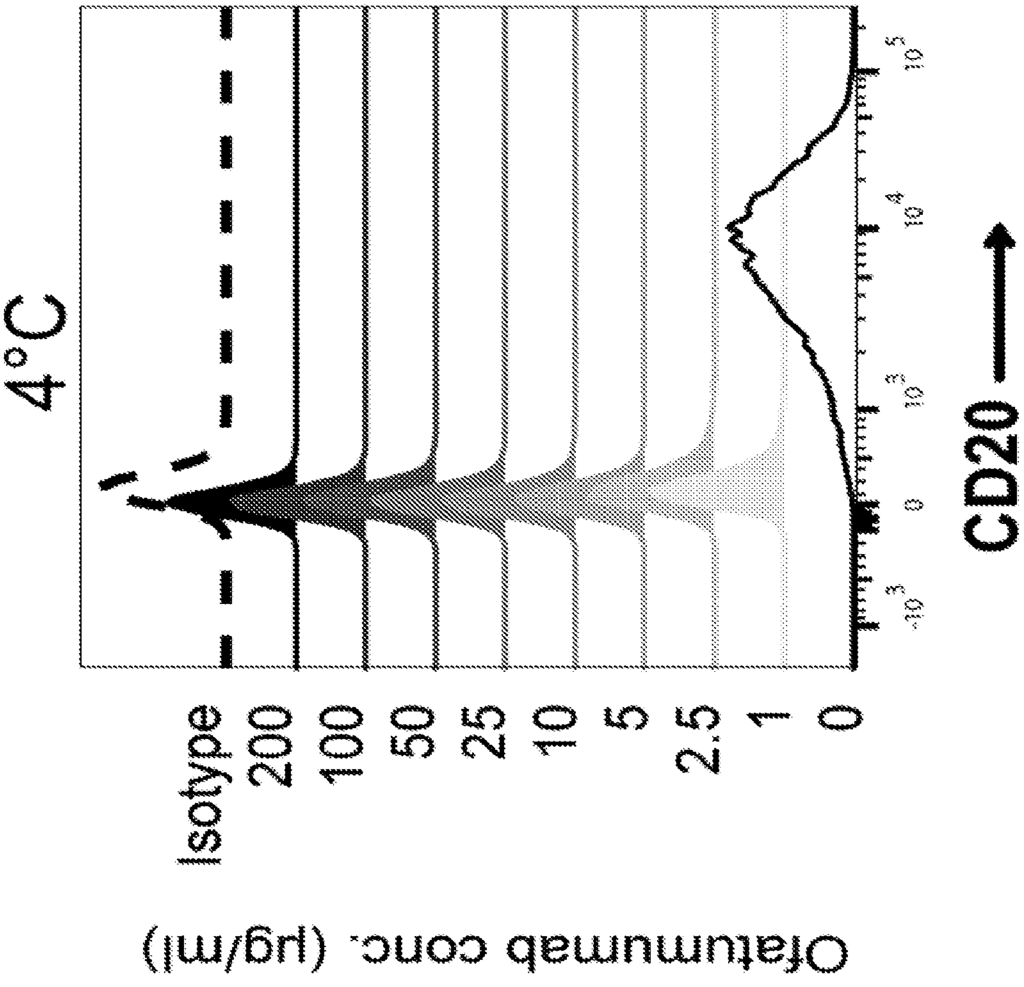
Figure 2F:
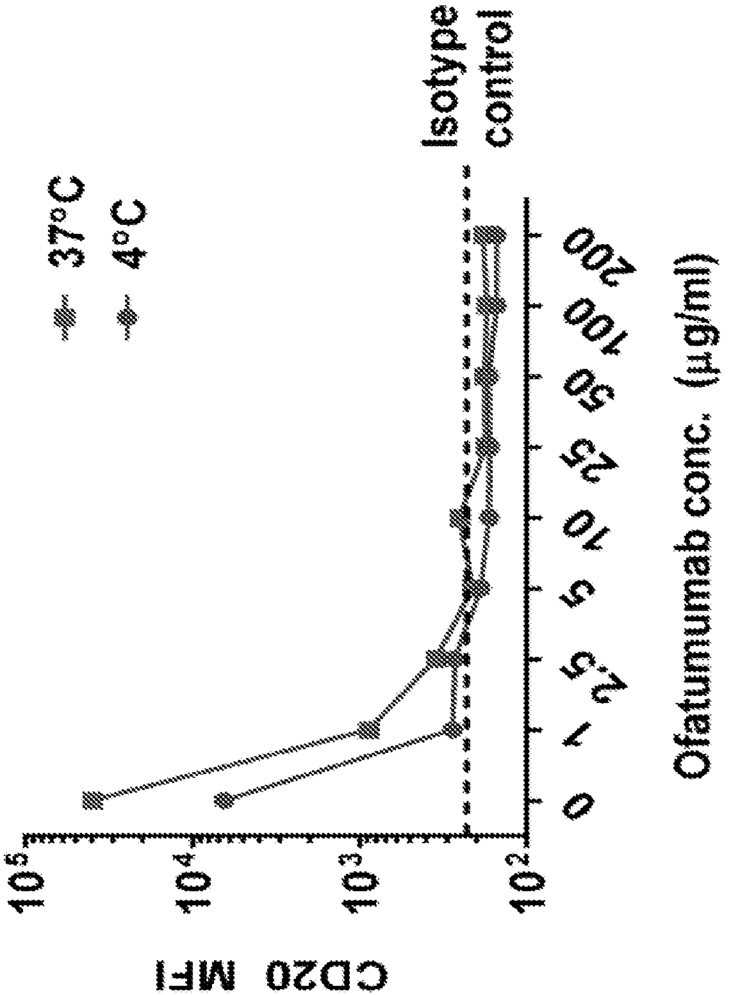
Figure 8A:
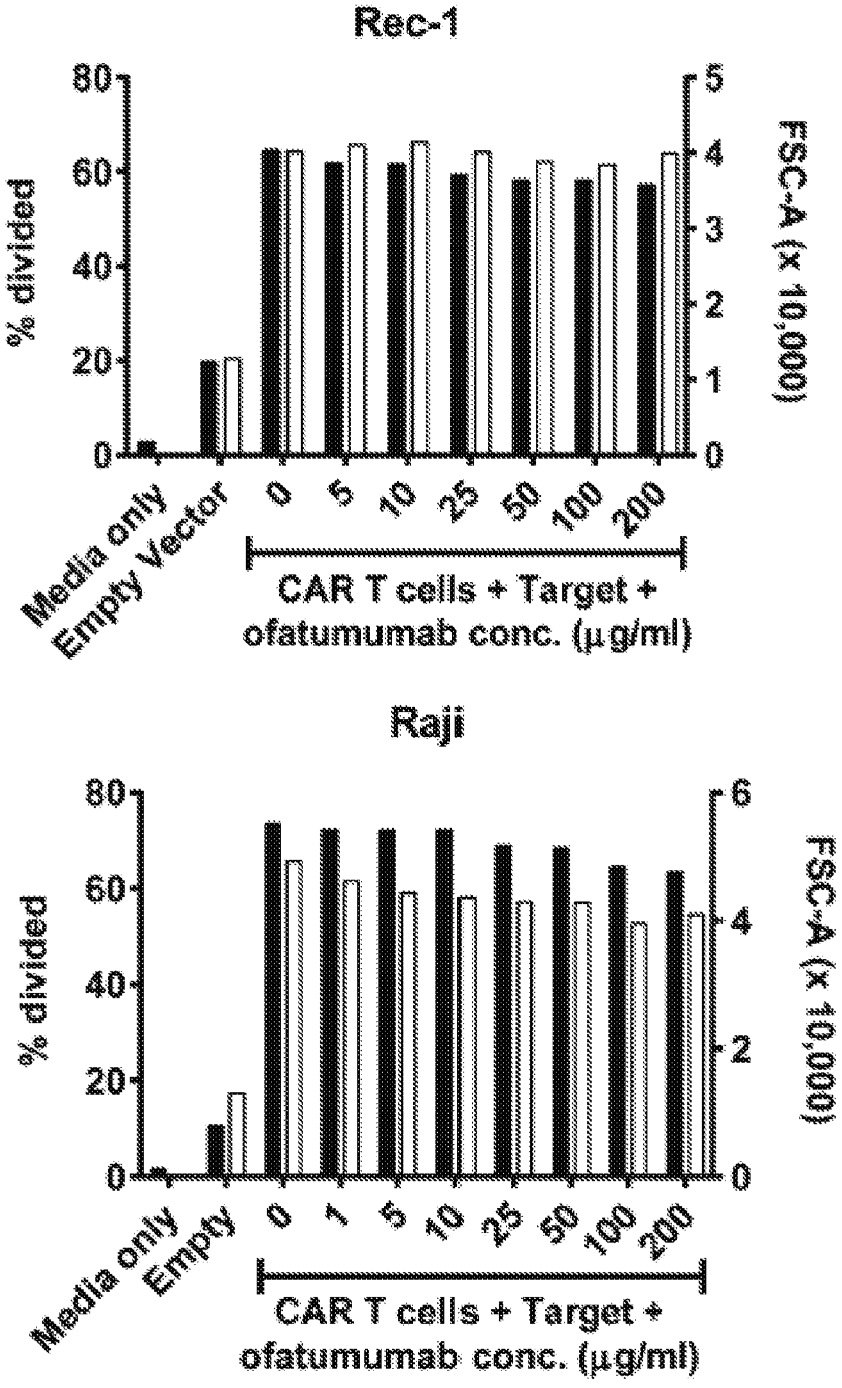
FIGS. 8A-8C show the effect of ofatumumab on CD20 CAR T cell function in vitro. Irradiated Rec-1 or Raji-ffLuc cells or non-irradiated $^{51}$Cr-labeled Rec-1 cells were pre-incubated for 30 minutes with 2× the indicated concentrations of ofatumumab, followed by experiments to determine function of T cells expressing the 1.5.3-NQ-28-BB-z CAR, using the methodologies described in the legend of FIGS. 3 and 4. (A) The percent divided $CD3^+$ T cells relative to unstimulated T cells are shown on the left axis (filled bars). Cell size of $CD3^+$ T cells as determined by geometric mean of forward scatter (subtracting size of cells in media only) is shown on the right axis (open bars). (B) Cytokine secretion of these T cells was measured by Luminex assay using supernatants from 24 hours after restimulation. IL-2 concentrations are shown on the left y-axis and IFN-γ on the right y-axis. (C) Cytotoxicity of 1.5.3-NQ-28-BB-z CART cells was determined using a standard 4-hour $^{51}$Cr-release assay with Rec-1 target cells. The average value of duplicate wells is shown, with error bars representing standard deviation.
Figure 8B:
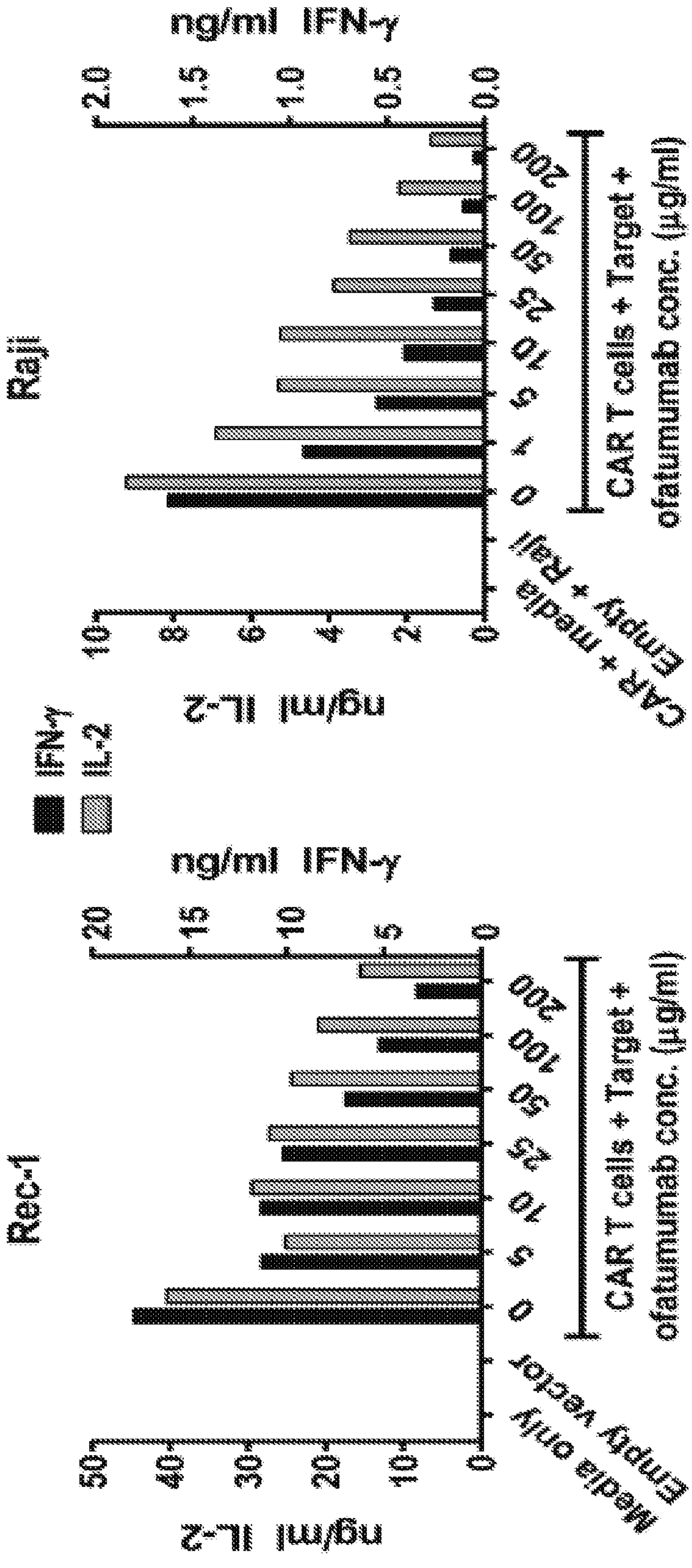
Figure 8C:
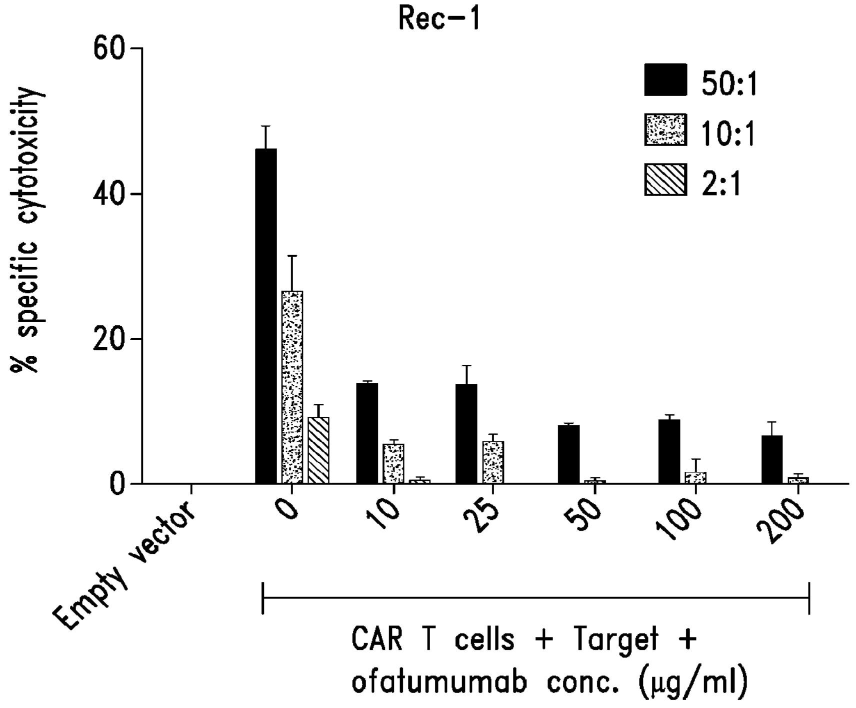
Figure 9:
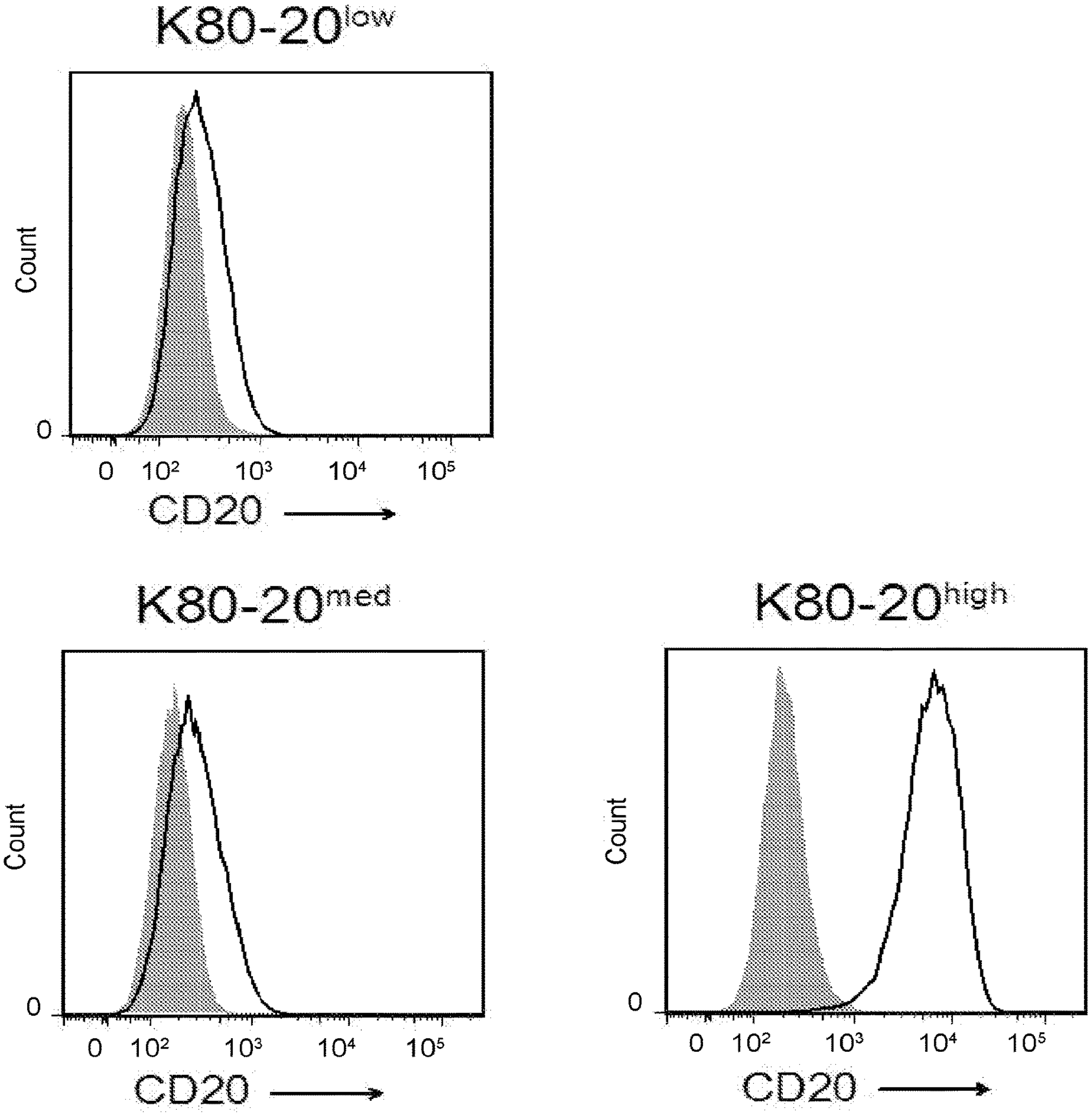
FIG. 9 shows CD20 expression of K80-$20^{low}$, K80-$20^{med}$, K80-$20^{high}$ as determined by flow cytometry. Open histograms represent cells stained with FITC-conjugated 1F5 antibody (anti-CD20), and filled histograms represent cells stained with an isotype control antibody Ab.

To determine the importance of epitope location on the effect of anti-CD20 antibodies on CAR function, the in vitro assays were repeated with ofatumumab, an anti-CD20 antibody that binds to a distinct epitope from rituximab, which involves a smaller extracellular loop of CD20 as well as a different area of the large loop (see, Du et al., *Mol Immunol* 2009; 46(11-12):2419-23; Teeling et al., *J Immunol* 2006; 177(1):362-71). The ability of ofatumumab to block binding of the Leu16 anti-CD20 antibody was first evaluated by flow cytometry, which showed that despite the different epitope, binding of the second antibody was profoundly blocked by ofatumumab. Moreover, the blocking of binding was at even lower concentrations than rituximab (FIGS. 2D-F). Then in vitro functional assays were performed on Rec-1 and Raji-ffLuc lymphoma cells that had been pre-incubated with varying concentrations of ofatumumab (FIGS. 8A-8C). The results were similar to those with rituximab, in that proliferation and cell size were minimally affected, but cytokine production was more impacted, in a dose-dependent manner. Compared with rituximab, cytotoxicity was more profoundly impaired in the presence of ofatumumab. These findings indicated that the inhibitory effect of anti-CD20 antibody is due to steric inhibition and not to direct blocking of the CAR binding epitope. Hence, the stronger inhibitory effect of ofatumumab resulted from a slower off-rate compared with rituximab. This was supported by competitive cell-binding flow cytometry studies at 4° C. or 37° C. (FIGS. 2D-F), which confirmed a much lower dissociation of ofatumumab, consistent with previously reported data (see, Teeling et al., *Blood* 2004; 104(6):1793-800).

Example 8

Cytokine Secretion by Various CAR Constructs In Vitro

Figure 15A:
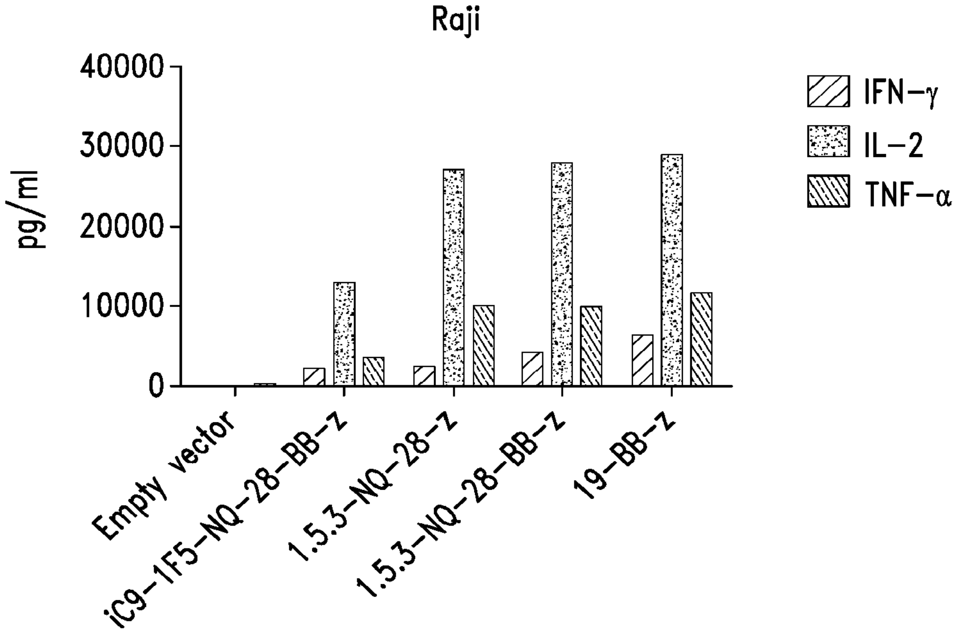
FIGS. 15A-15D show cytokine secretion by various CAR constructs in vitro. Central memory (CD14$^-$CD45RA$^-$CD62L$^+$) T cells were stimulated with anti-CD3/CD28 antibody coated beads, transduced 24 hours later with lentiviral vectors encoding the indicated CAR constructs, and expanded in vivo. At day 14, the cells were re-stimulated with either irradiated Raji-ffLuc cells (FIG. 15A and FIG. 15C), Granta-519 cells (FIG. 15B), and Jeko cells (FIG. 15D). The "19-BB-z" construct is a clinical-grade CD19-targeted CAR being used in clinical trials and is provided as a positive control. Supernatants were harvested 24 hours later and analyzed by Luminex assay for interferon (IFN)-γ, IL-2, and tumor necrosis factor-α levels.
Figure 15B:
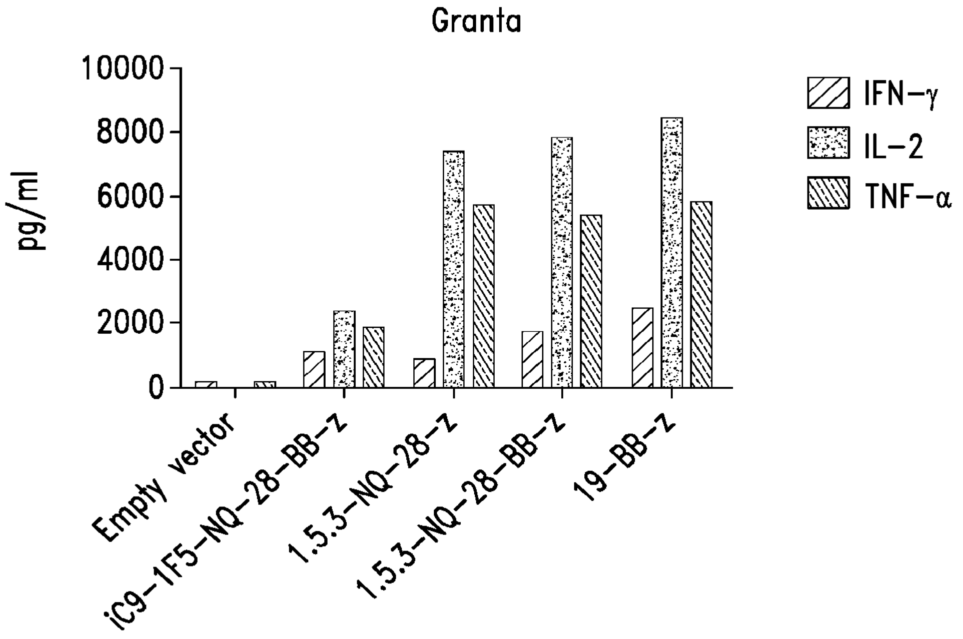
Figure 15C:
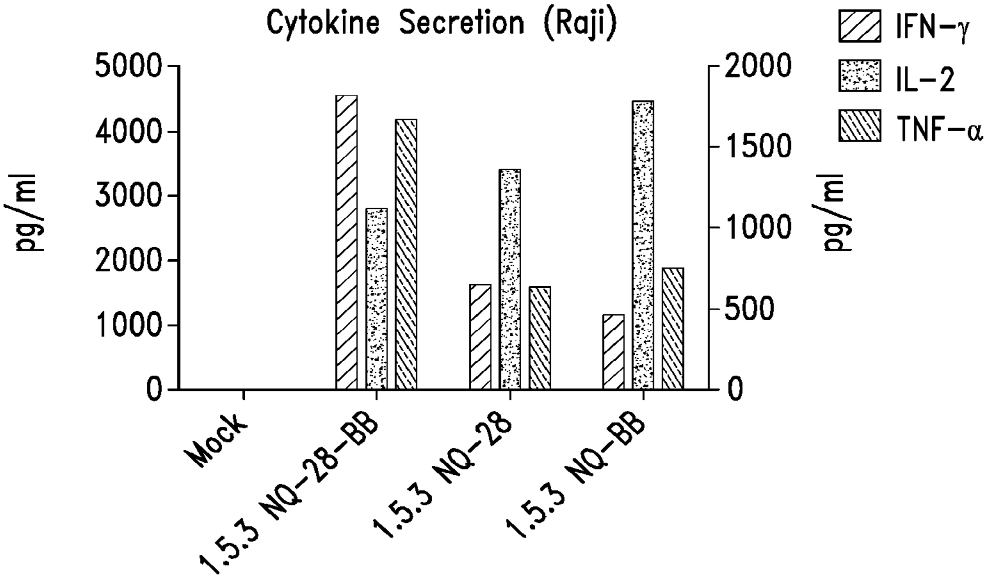
Figure 15D:
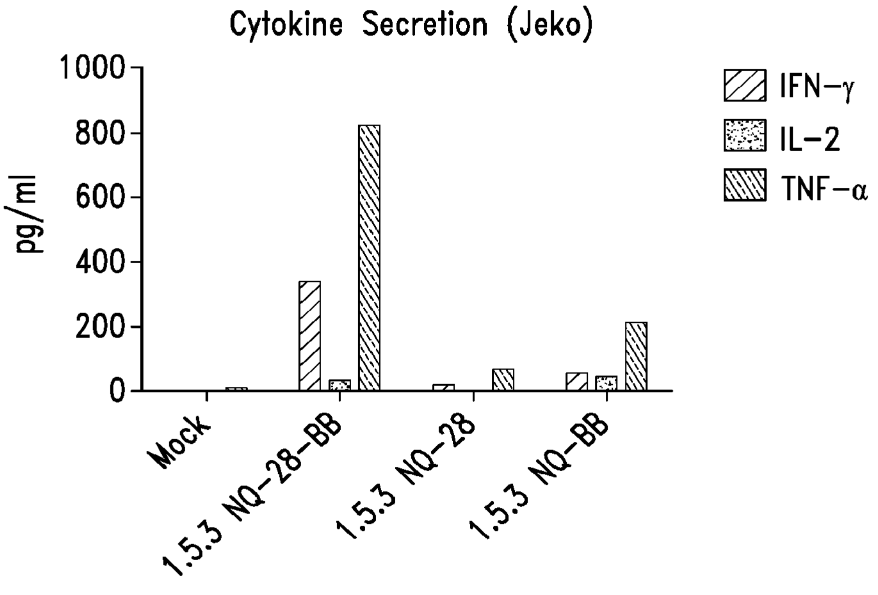

Central memory ($CD14^-CD45RA^-CD62L^+$) T cells were stimulated with anti-CD3/CD28 antibody coated beads, transduced 24 hours later with lentiviral vectors encoding the indicated CAR constructs, and expanded in vivo. At day 14, the cells were re-stimulated with either irradiated Raji-ffLuc cells (FIG. 15A and FIG. 15C), Granta-519 cells (FIG. 15B), and Jeko cells (FIG. 15D). The "19-BB-z" construct is a clinical-grade CD19-targeted CAR being used in clinical trials and is provided as a positive control. Supernatants were harvested 24 hours later and analyzed by Luminex assay for interferon (IFN)-γ, IL-2, and tumor necrosis factor-α levels.

Example 9

Figure 16A:
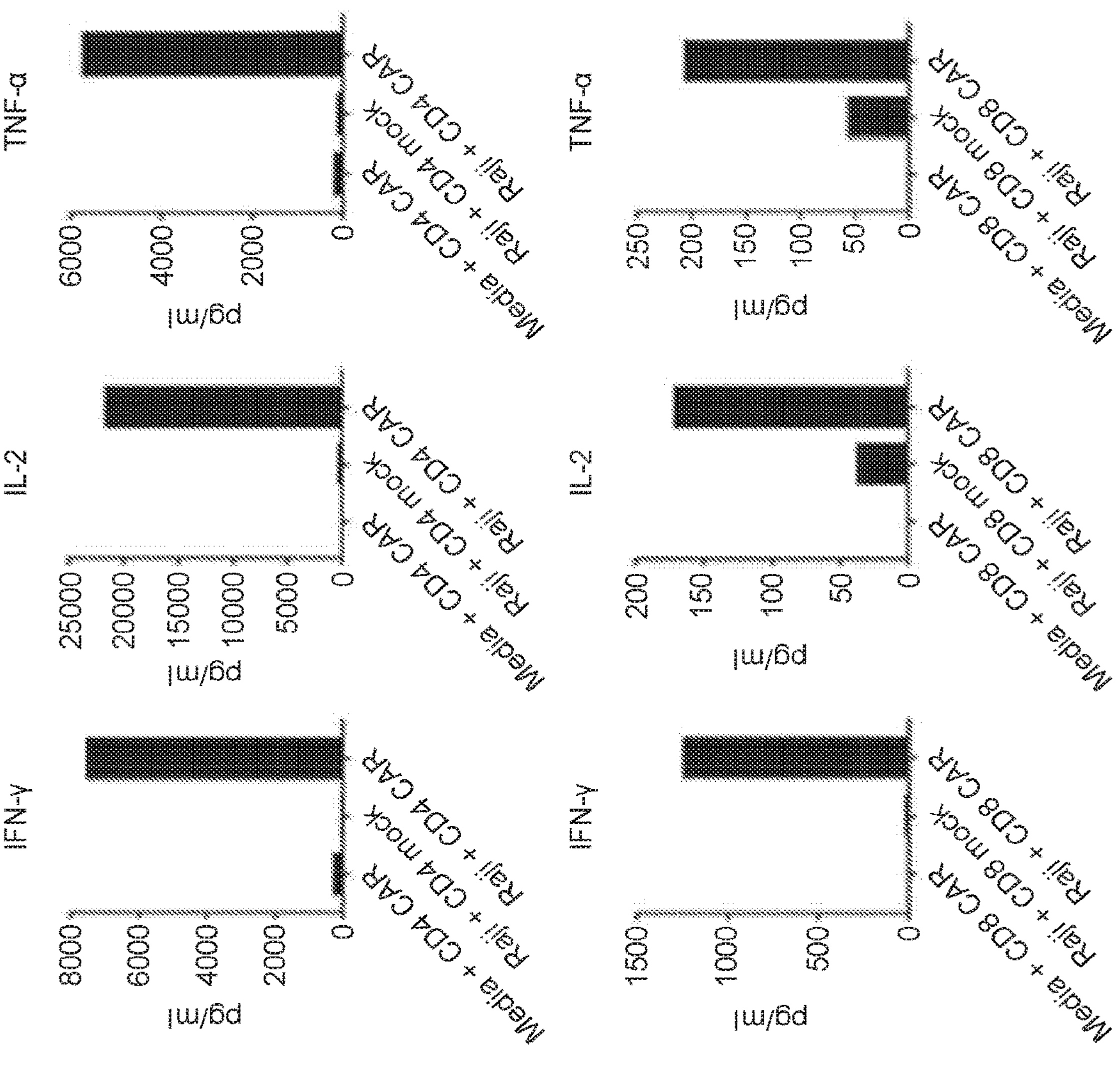
FIGS. 16A and 16B show cytokine secretion by CD20 CAR T cells. (A) CD4$^+$ and CD8$^+$ T cells transduced with the 1.5.3-NQ-28-BB-z lentiviral vector and expanded ex vivo were restimulated with irradiated Raji-ffLuc CD20$^+$ lymphoma cells. Secretion of the indicated cytokines was measured in cell supernatants after 24 hours by Luminex assay. (B) Cryopreserved CD4$^+$ and CD8$^+$ CD20 CAR T cells were thawed and restimulated with K562 cells or K562 cells expressing CD20 and at 24 hours were analyzed by intracellular staining for IFN-γ by flow cytometry.
Figure 16B:
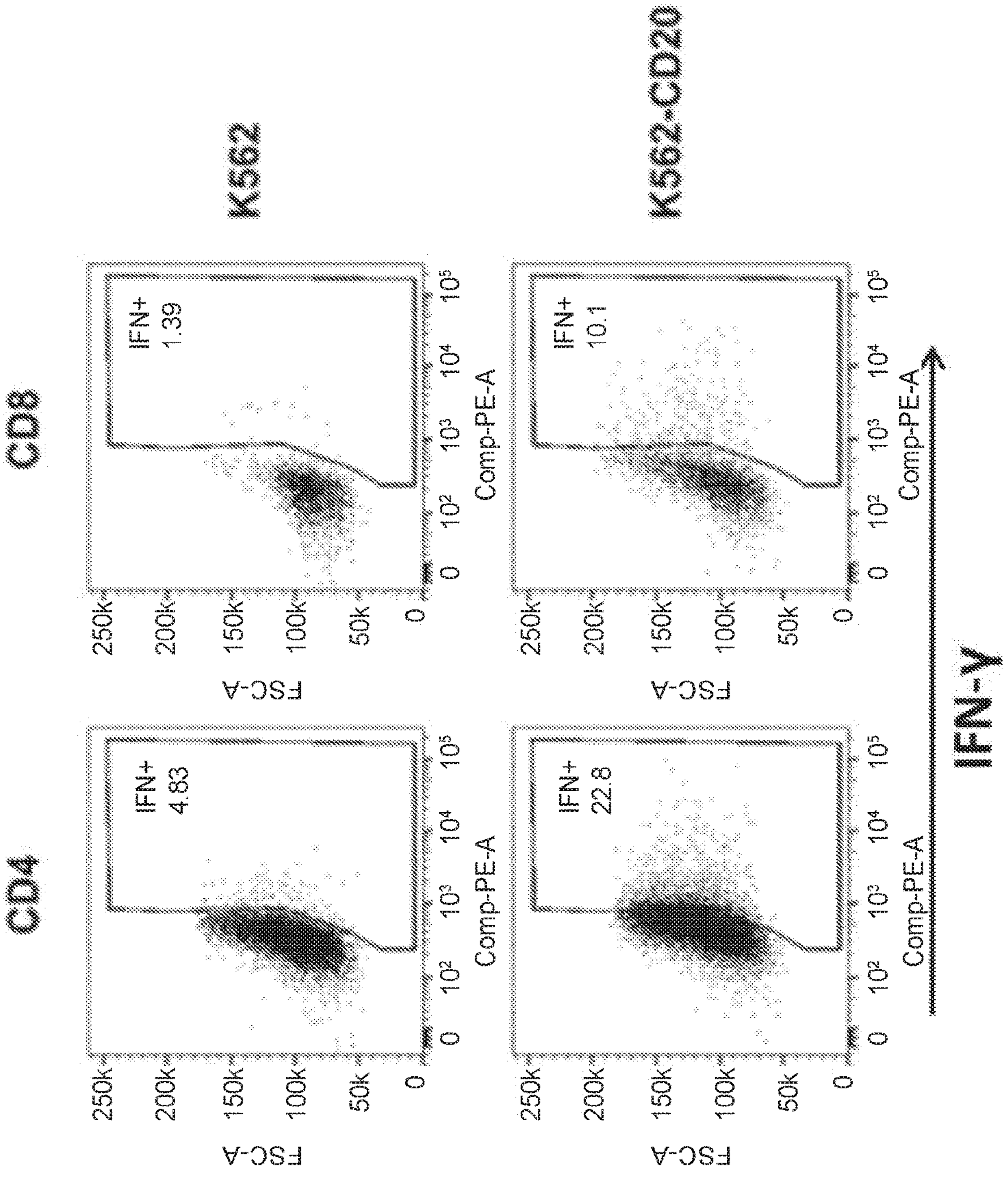

Cytokine Secretion by CD20 CAR T Cells $CD4^+$ and $CD8^+$ T cells transduced with the 1.5.3-NQ-28-BB-z lentiviral vector and expanded ex vivo were restimulated with irradiated Raji-ffLuc $CD20^+$ lymphoma cells. Secretion of the indicated cytokines was measured in cell supernatants after 24 hours by Luminex assay. (FIG. 16A). Cryopreserved $CD4^+$ and $CD8^+$ CD20 CAR T cells were thawed and restimulated with K562 cells or K562 cells expressing CD20 and at 24 hours were analyzed by intracellular staining for IFN-γ by flow cytometry. (FIG. 16B).

Example 10

In Vitro Cytotoxicity of Various CAR Constructs

Figure 17A:
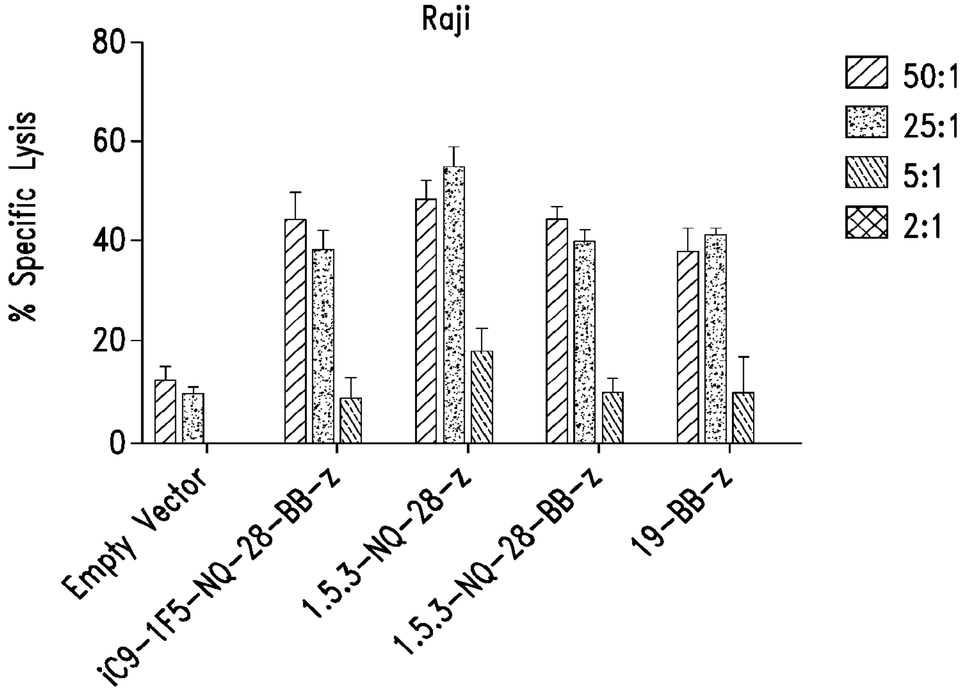
FIGS. 17A and 17B shows in vitro cytotoxicity of various CAR constructs. Central memory (CD14$^-$CD45RA$^-$CD62L$^+$) T cells were stimulated with anti-CD3/CD28 antibody coated beads, transduced 24 hours later with lentiviral vectors encoding the indicated CAR constructs, and expanded in vivo. At day 14, the cells were used as effectors in a standard 4-hour $^{51}$Cr-release assay, using (FIGS. 17A and 17B) Raji-ffLuc, and (FIG. 17B) Jeko cells as targets. The "19-BB-z" construct is a clinical-grade CD19-targeted CAR being used in clinical trials and is provided as a positive control. The specific target cell lysis of each CART cell population is shown.
Figure 17B:
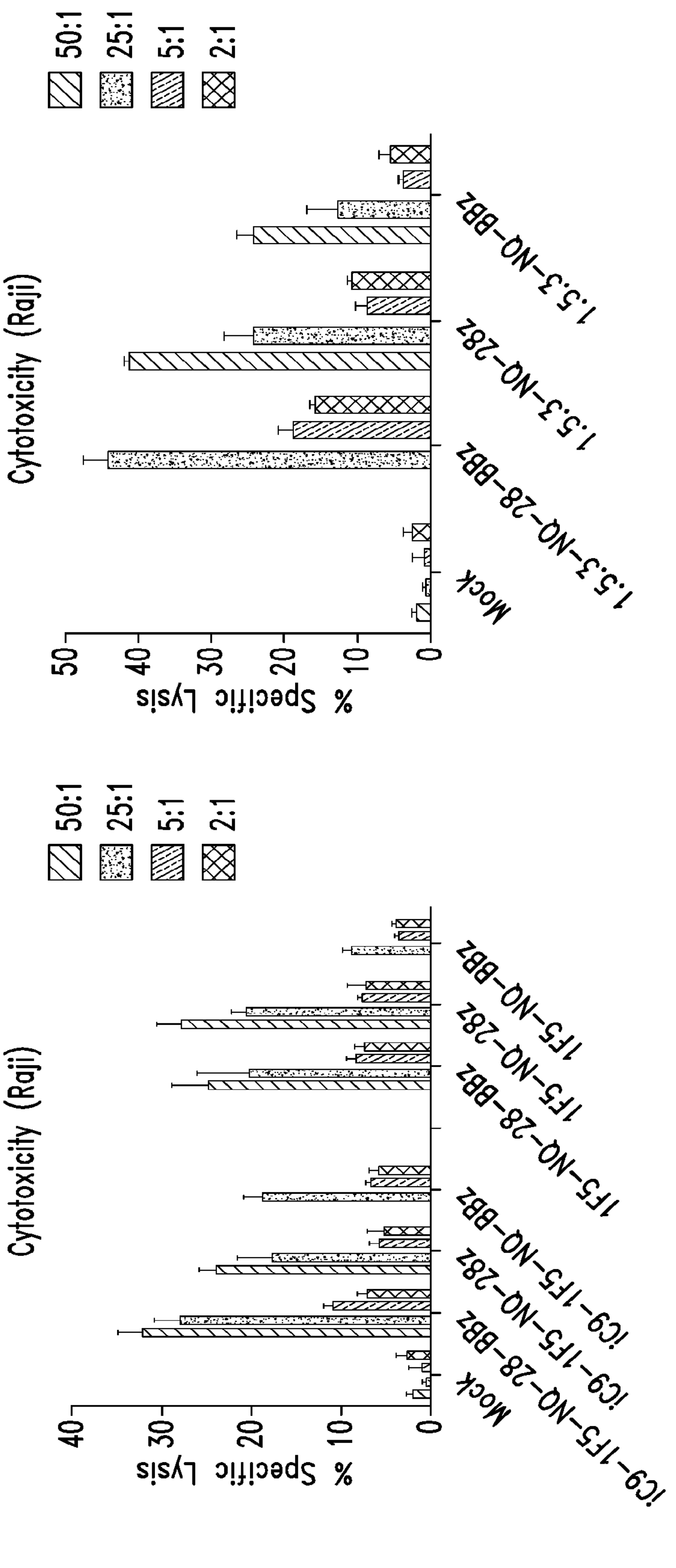
Figure 17B:
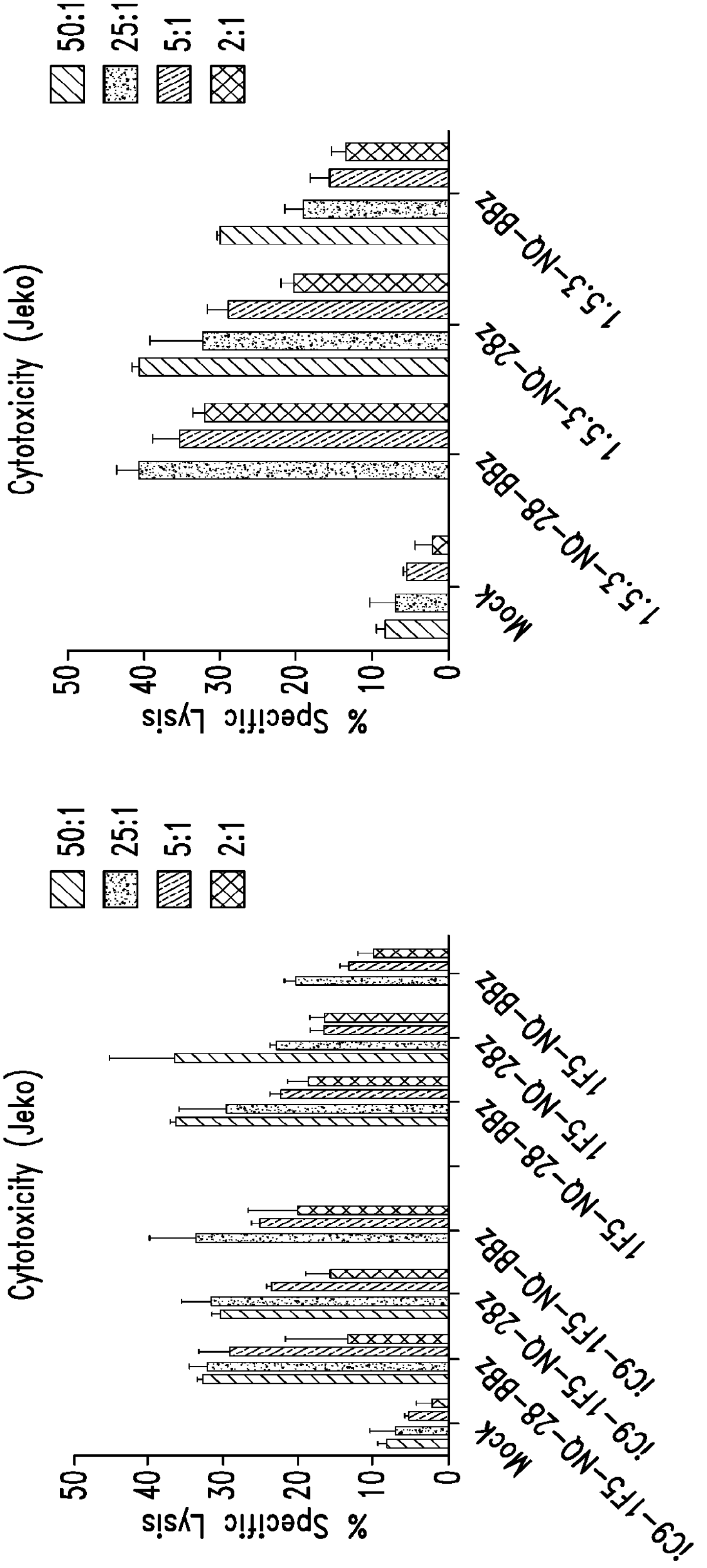

Central memory ($CD14^-CD45RA^-CD62L^+$) T cells were stimulated with anti-CD3/CD28 antibody coated beads, transduced 24 hours later with lentiviral vectors encoding the indicated CAR constructs, and expanded in vivo. At day 14, the cells were used as effectors in a standard 4-hour $^{51}Cr$-release assay, using (FIGS. 17A and 17B) Raji-ffLuc, and (FIG. 17B) Jeko cells as targets. The "19-BB-z" construct is a clinical-grade CD19-targeted CAR being used in clinical trials and is provided as a positive control. The specific target cell lysis of each CAR T cell population is shown.

Example 11

Figure 18A:
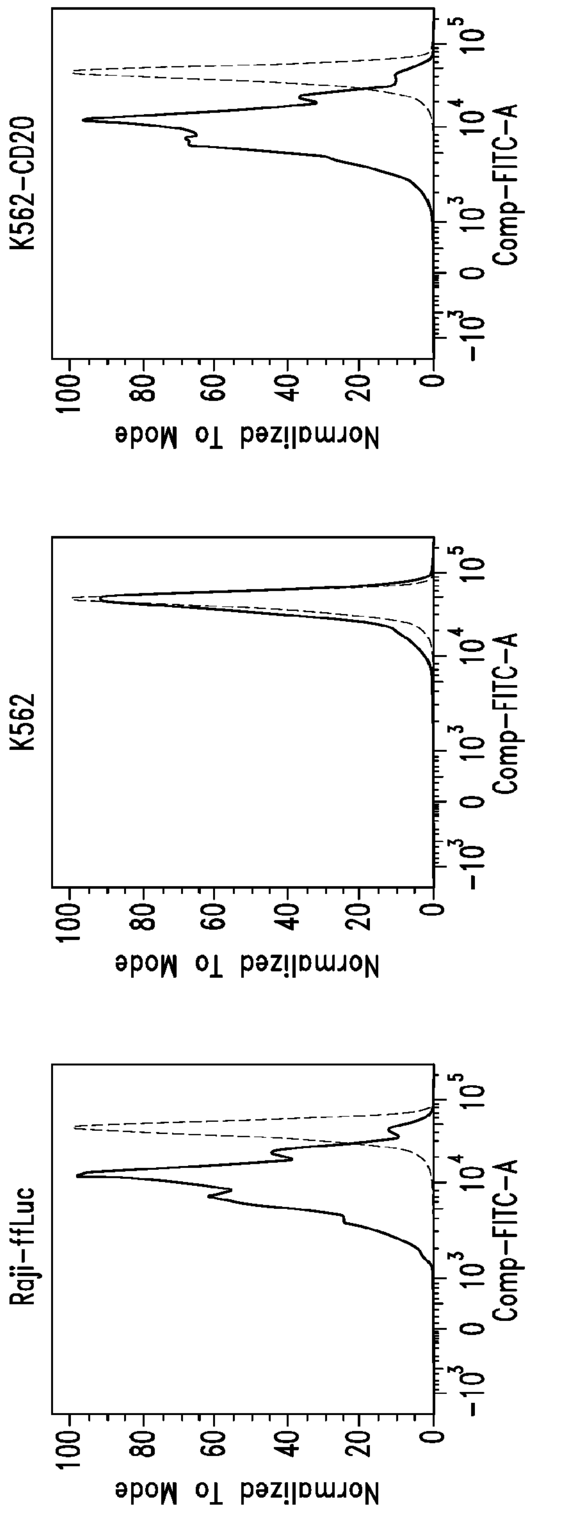
FIGS. 18A and 18B show proliferation of CD20 CAR T cells. CD8$^+$ T cells were transduced with the 1.5.3-NQ-28-BB-z lentiviral vector (or were mock-transduced) and expanded ex vivo, and then cryopreserved. The cells were then thawed, stained with carboxyfluorescein succinamidyl ester (CFSE), and restimulated with irradiated CD20$^+$ Raji-ffLuc lymphoma cells, K562 cells, or K562 cells expressing CD20. Cells were analyzed by flow cytometry 4 days later. (A) CFSE dilution of CAR$^-$ cells (gated on CD3$^+$/tCD19$^+$) is shown. The dashed-line histogram shows CFSE fluorescence of T cells in culture medium only, and solid-line histograms are T cells co-incubated with target cells. (B) The percentage of divided cells is shown for each group.
Figure 18B:
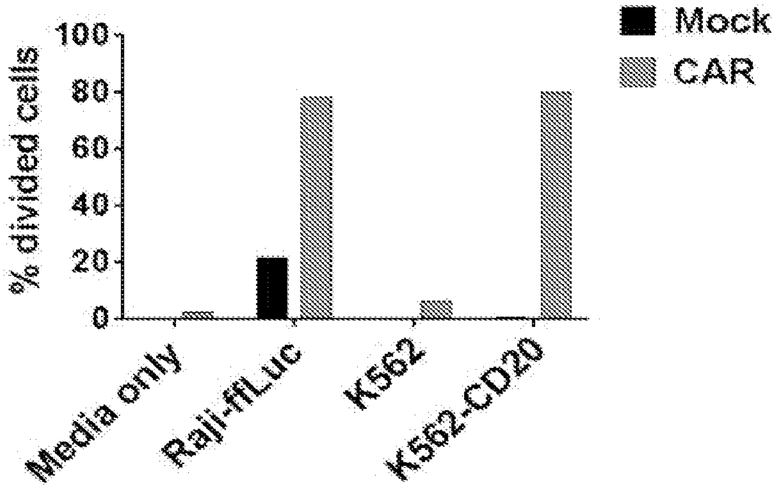

Proliferation of CD20 CAR T Cells $CD8^+$ T cells were transduced with the 1.5.3-NQ-28-BB-z lentiviral vector (or were mock-transduced) and expanded ex vivo, and then cryopreserved. The cells were then thawed, stained with carboxyfluorescein succinamidyl ester (CFSE), and restimulated with irradiated $CD20^+$ Raji-ffLuc lymphoma cells, K562 cells, or K562 cells expressing CD20. Cells were analyzed by flow cytometry 4 days later. (FIG. 18A) CFSE dilution of $CAR^+$ cells (gated on $CD3^+$/$tCD19^+$) is shown. The dashed-line histogram shows CFSE fluorescence of T cells in culture medium only, and solid line-histograms are T cells co-incubated with target cells. (FIG. 18B) The percentage of divided cells is shown for each group.

Example 12

In Vivo Anti-Tumor Activity of Various CAR Constructs

Figure 19A:
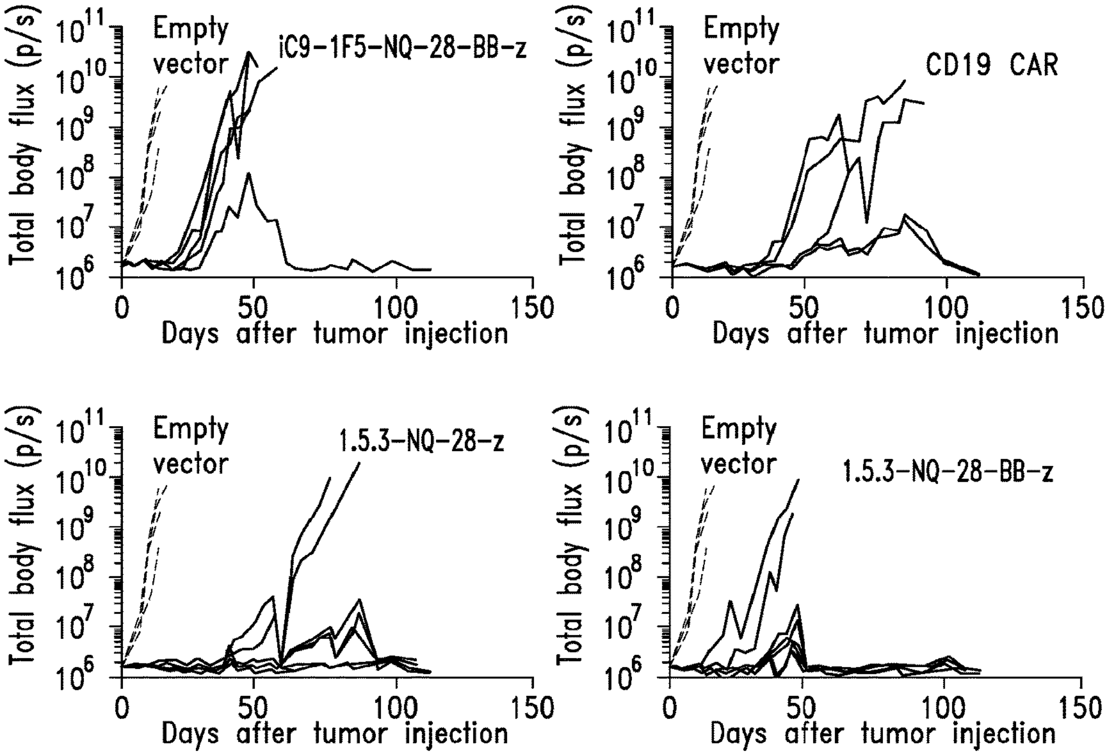
FIGS. 19A and 19B show in vivo anti-tumor activity of various CAR constructs. Central memory (CD14$^-$CD45RA$^-$CD62L$^+$) T cells were stimulated with anti-CD3/CD28 antibody coated beads, transduced 24 hours later with lentiviral vectors encoding the indicated CAR constructs, and expanded in vitro. The "19-BB-z" construct is a clinical-grade CD19-targeted CAR being used in clinical trials at our center and provided as a benchmark control. NSG mice were injected i.v. with Raji-ffLuc tumor cells, followed 2 days later by i.v. injection of expanded central memory (CD14$^-$CD45RA$^-$CD62L$^+$) T cells transduced with the 1.5.3-NQ-28-BB-z CAR, 1.5.3-NQ-28-z CAR, JCAR-014 (anti-CD19-41BB-ζ) or an empty vector. (A) Tumor burden over time as assessed by bioluminescence imaging; and (B) Kaplan-Meier plot of overall survival.
Figure 19B:
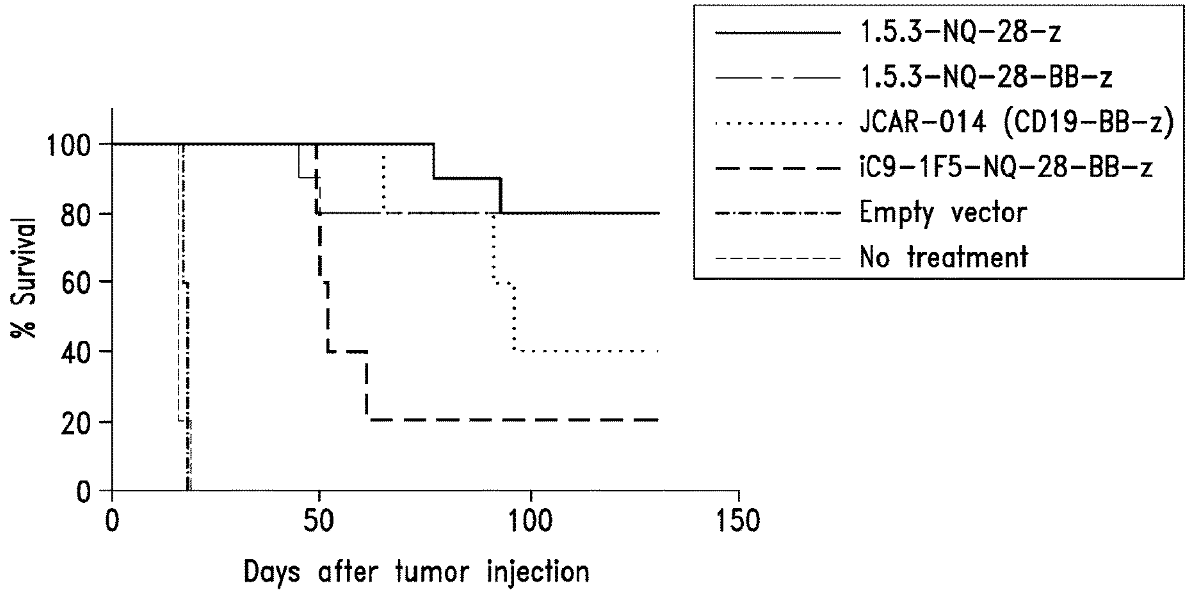

Central memory ($CD14^-CD45RA^-CD62L^+$) T cells were stimulated with anti-CD3/CD28 antibody coated beads, transduced 24 hours later with lentiviral vectors encoding the indicated CAR constructs, and expanded in vivo. The "19-BB-z" construct is a clinical-grade CD19-targeted CAR being used in clinical trials at our center and provided as a benchmark control. NSG mice were injected i.v. with Raji-ffLuc tumor cells, followed 2 days later by i.v. injection of expanded central memory ($CD14^-CD45RA^-CD62L^+$) T cells transduced with the 1.5.3-NQ-28-BB-z CAR, 1.5.3-NQ-28-z CAR, JCAR-014 (anti-CD19-41BB-ζ), or an empty vector. (FIG. 19A) Tumor burden over time as assessed by bioluminescence imaging; and (FIG. 19B) Kaplan-Meier plot of overall survival.

Example 13

Figure 20:
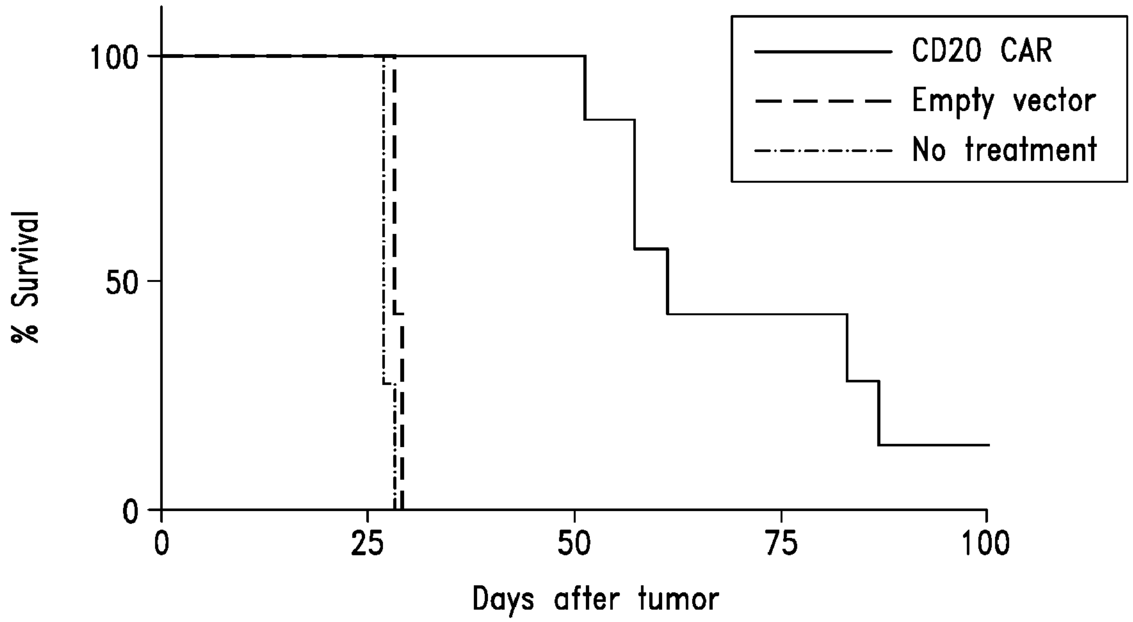
FIG. 20 shows in vivo activity of CD20 CAR T cells against mantle cell lymphoma. CD4$^+$ and CD8$^+$ CD20 CART cells were transduced with the 1.5.3-NQ-28-BBz CAR and used to treat NSG mice that had been inoculated 7 days earlier with Granta-ffLuc mantle cell lymphoma cells by tail vein. Kaplan-Meier plot of overall survival.

In Vivo Activity of CD20 CAR T Cells Against Mantle Cell Lymphoma $CD4^+$ and $CD8^+$ CD20 CART cells were transduced with the 1.5.3-NQ-28-BBz CAR and used to treat NSG mice that had been inoculated 7 days earlier with Granta-ffLuc mantle cell lymphoma cells by tail vein. A Kaplan-Meier plot of overall survival is shown in FIG. 20.

Example 14

In Vivo CAR T Cell Persistence and Related Physiological Effects

Figure 21A:
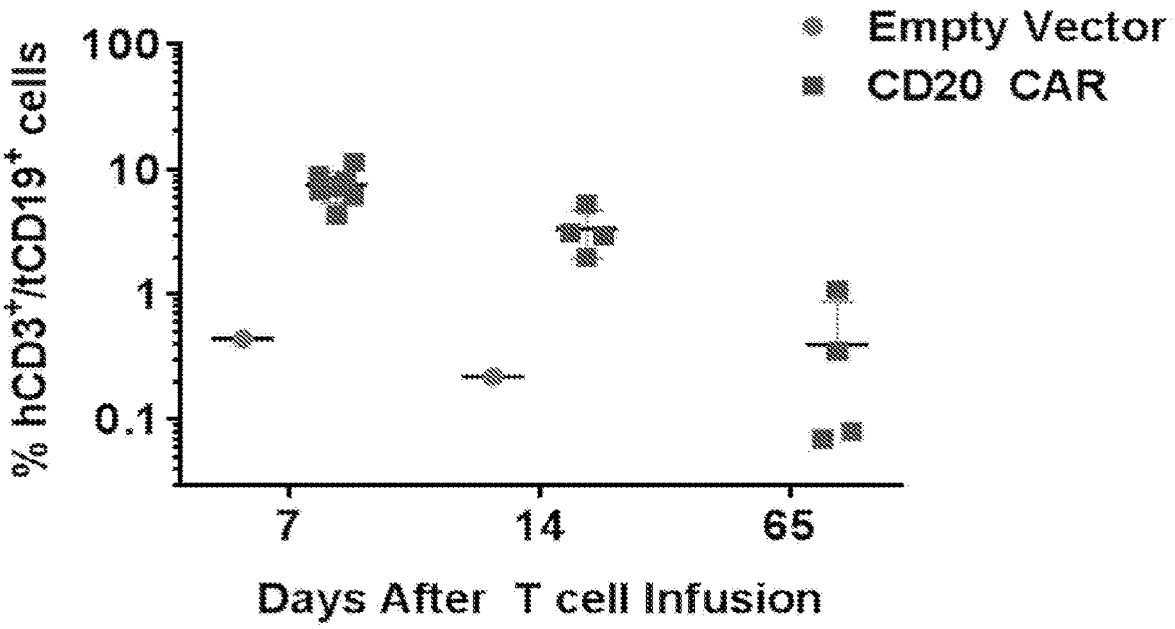
FIGS. 21A and 21B show in vivo CAR T cell persistence. Retroorbital blood samples were obtained at serial time points after infusion of either CD20 CAR T cells or empty vector tCD19-expressing T cells in NSG mice bearing Raji-ffLuc disseminated tumors. CD20 CAR T cells expressing the tCD19 transduction marker were quantified by flow cytometry at each time point as human CD3$^+$/mouse CD45-negative/human CD19$^+$ cells.
Figure 21B:
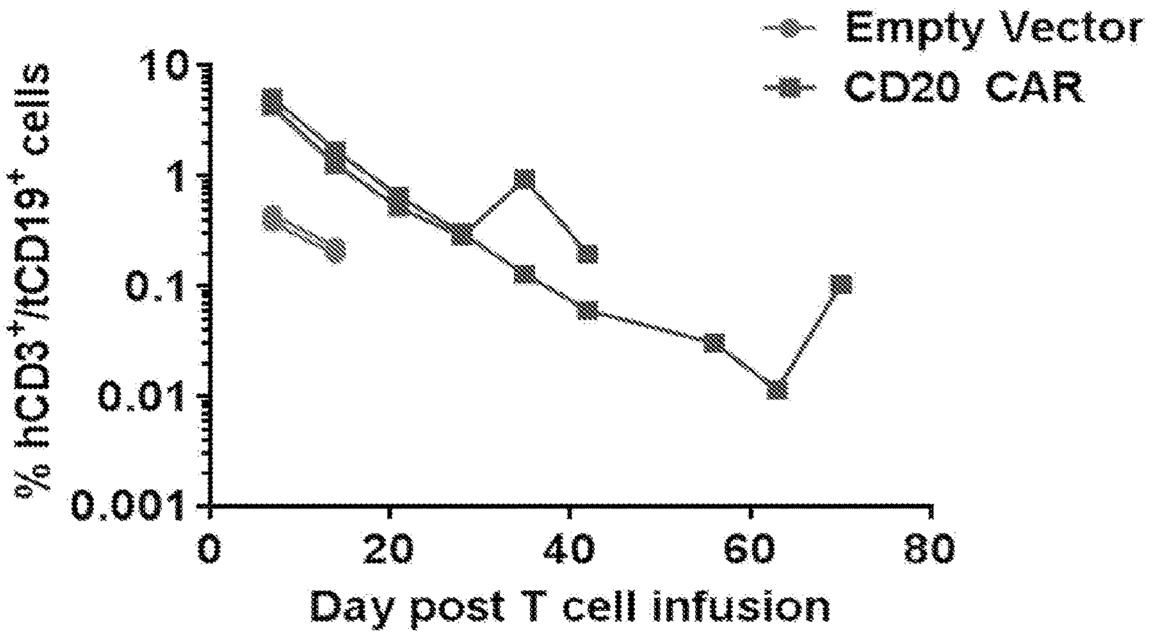
Figure 22B:
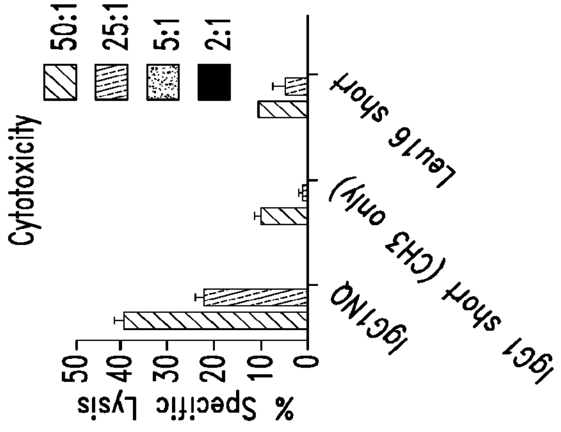
FIGS. 22A and 22B show comparative data for various constructs having spacers of varying lengths. Central memory (CD14$^-$CD45RA$^-$CD62L$^+$) T cells were stimulated with anti-CD3/CD28 antibody coated beads, transduced 24 hours later with lentiviral vectors encoding the indicated CAR constructs, and expanded in vitro. The 1F5-28-BB-z, IgG1mut have full-length spacers. The No Linker is nearly full length but missing a 6 amino acid linker (junction amino acid), and the CH3 has a truncated spacer, missing the junction amino acids and CH2 domain. (A) On day 20, the cells were re-stimulated with Granta or Rec-1 lymphoma cells, and 24 hours later supernatants were harvested and analyzed by Luminex assay for IL-2 (right) and IFN-γ (left) concentrations. (B) Central memory T cells (CD14$^-$CD45RA$^-$CD62L$^+$) were stimulated with anti-CD3/anti- CD28 antibody coated beads, transduced 24 hours later with lentiviral vectors encoding the indicated CAR constructs, and expanded in vitro. The "IgG1mut NQ" has a full length CH2CH3 spacer, CH3 only is intermediate length as discussed above, and Leu16 short lacks both CH2 and CH3 domains. On day 20, cells were used as effector cells in a standard 4-hour $^{51}$Cr-release assay, using Raji cells as targets.
Figure 22A:
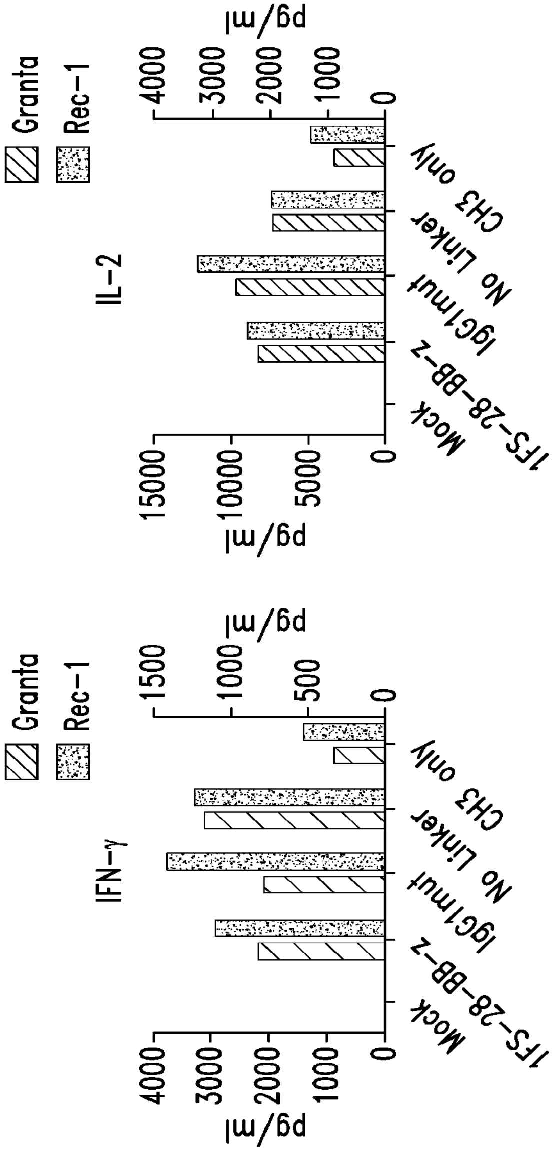
Figure 23A:
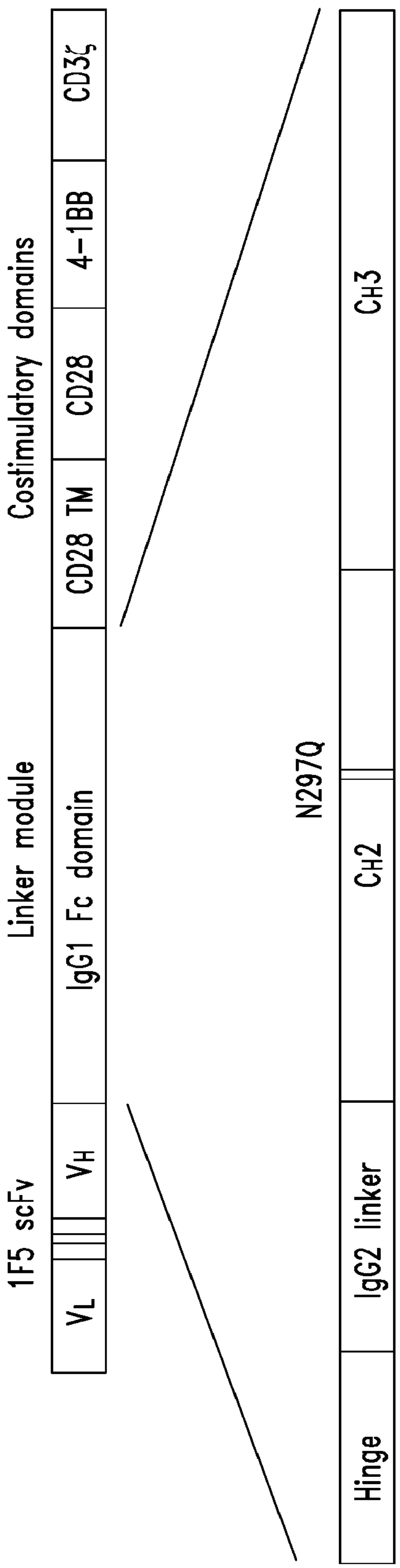
FIGS. 23A-23F show comparative data for various constructs having spacers with various modifications. A schematic diagram of a CAR with IgG2 junction amino acids (denoted "IgG1mut") and N297Q (denoted "NQ") mutations is shown (FIG. 23A). T cells expressing CARs with a wild-type IgG1 spacer, IgG1 mutant spacer (IgG1 junction amino acids replaced with IgG2 junction amino acids), or no junction amino acids (IgG1 junction amino acids deleted) were stained with biotinylated soluble CD64 (FcγRI) followed by streptavidin-PE and then analyzed by flow cytometry, demonstrating Fc receptor binding to wild-type but not modified spacers (FIG. 23B). T cells expressing the indicated CAR constructs were co-incubated with K562 cells expressing CD64 (FcγRI) or parental K562 lacking Fc receptors. At 24 hours after co-incubation the T cells were evaluated for CD25 and CD69 expression by flow cytometry as an indication of activation. Dot plots represent $CD3^+$ $CD19^+$ cells ($CAR^+$ T cells). Binding of wild type spacers to Fc receptors led to T cell activation whereas modified spacers did not (FIG. 23C). Central memory ($CD14^-$ $CD45RA^-CD62L^+$) T cells were stimulated with anti-CD3/CD28 antibody coated beads, transduced 24 hours later with lentiviral vectors encoding the indicated CAR constructs, expanded in vitro, and injected into NSG mice 2 days after i.v. administration of Raji-ffLuc cells. (D and E) Tumor burden data by bioluminescence for two different experiments. (F) Kaplan-Meier survival curve from experiment in part (E) above.
Figure 23B:
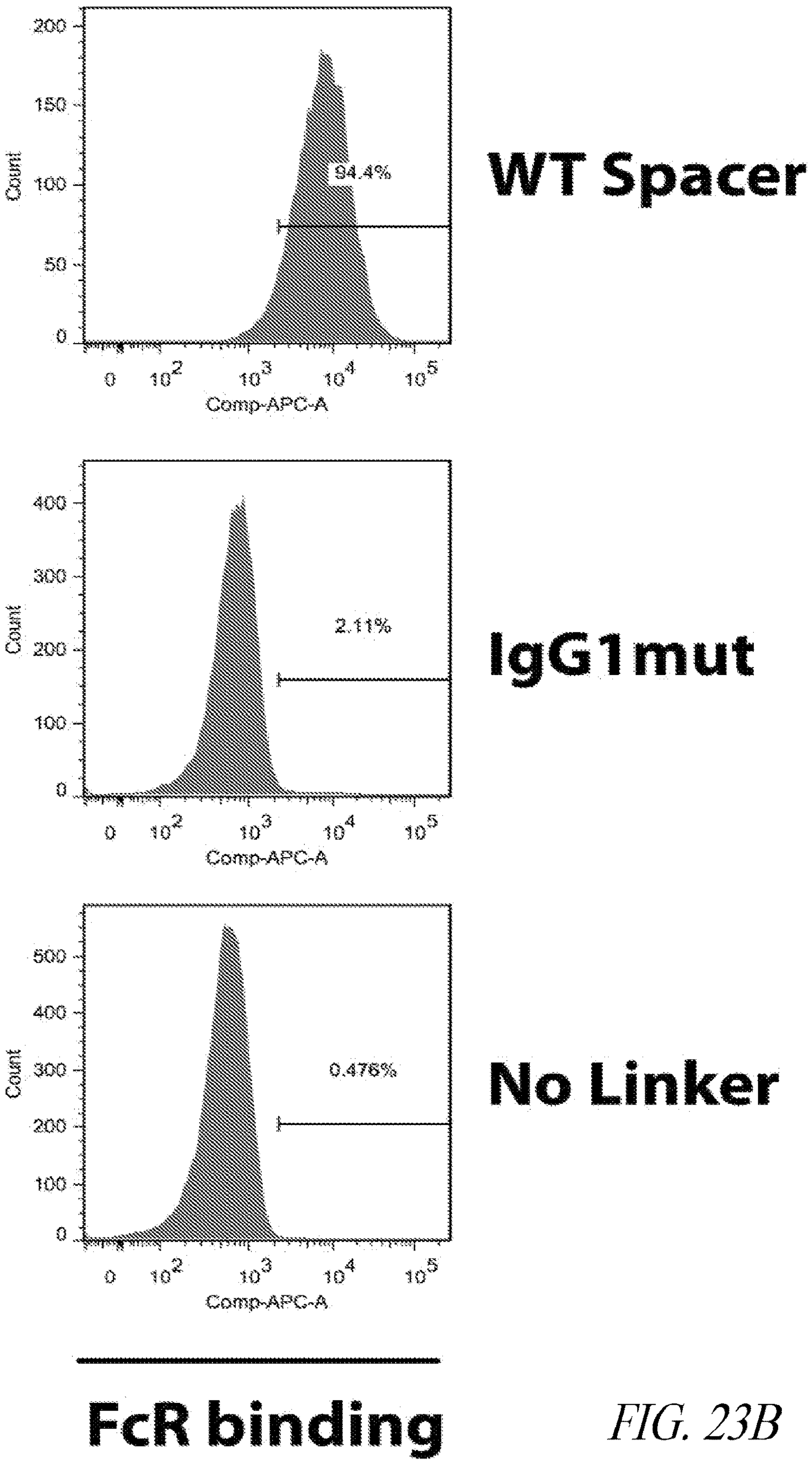
Figure 23C:
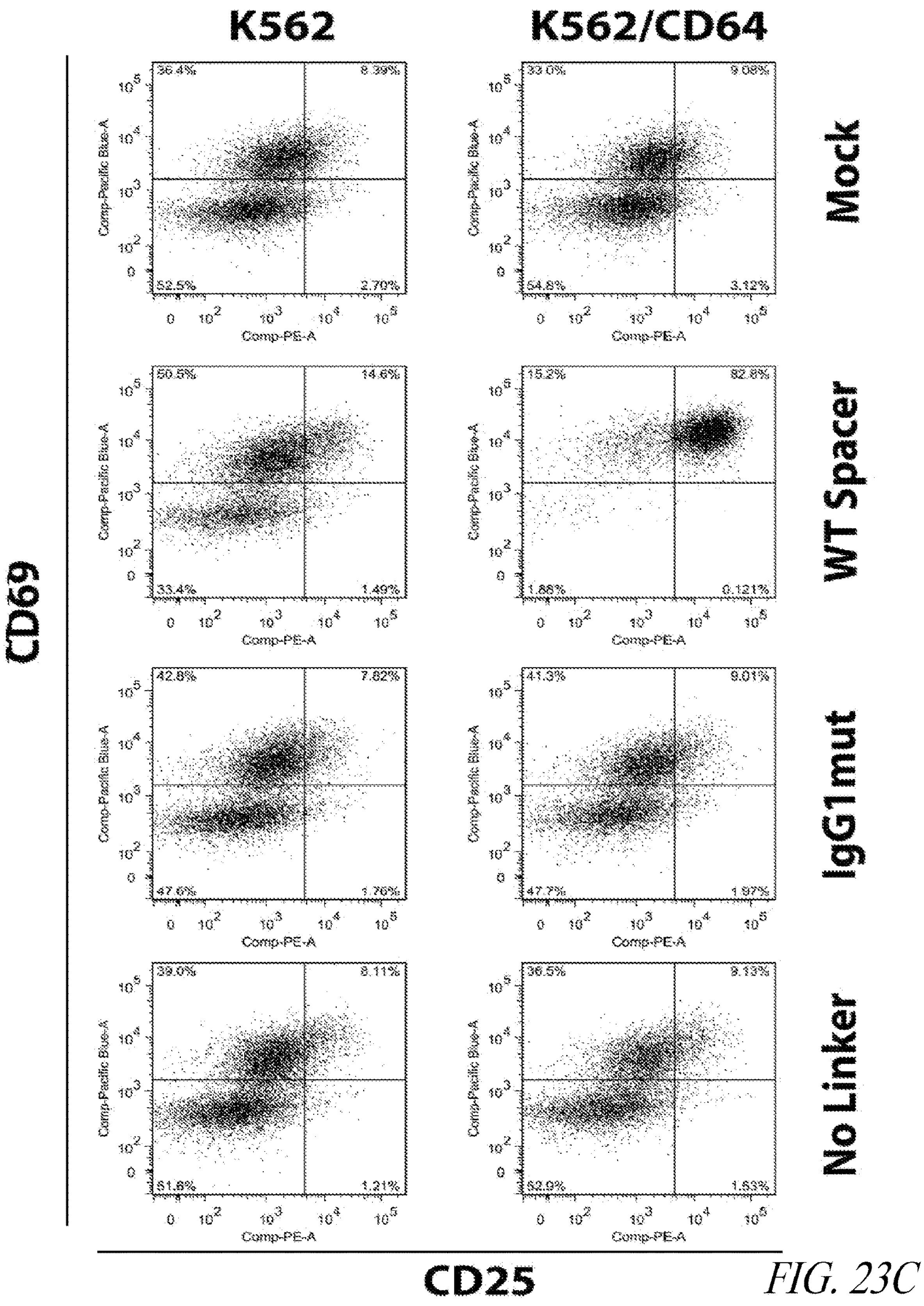
Figure 23D:
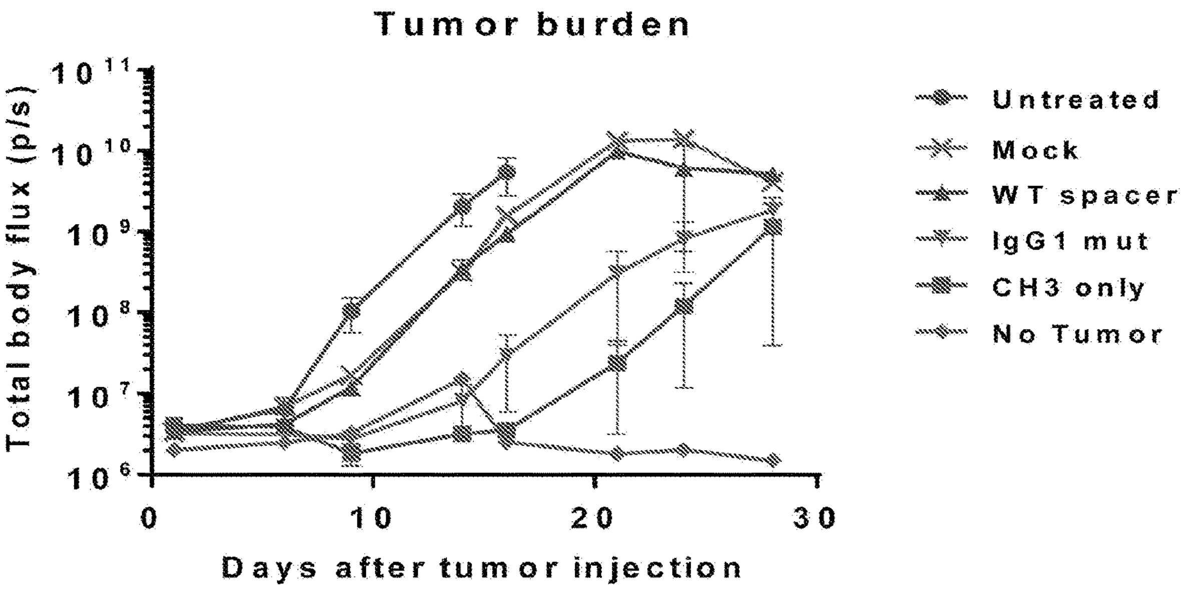
Figure 23E:
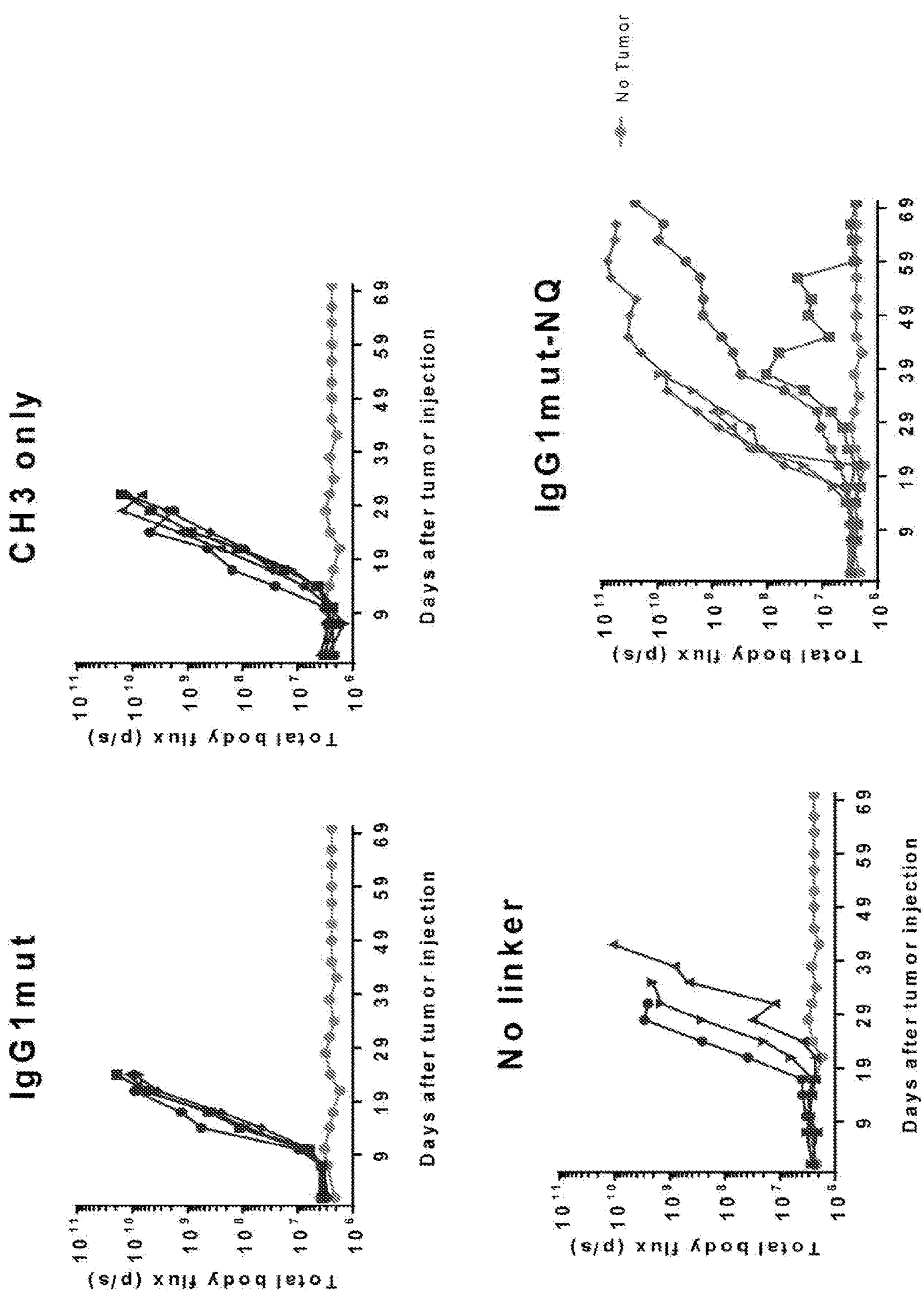
Figure 23F:
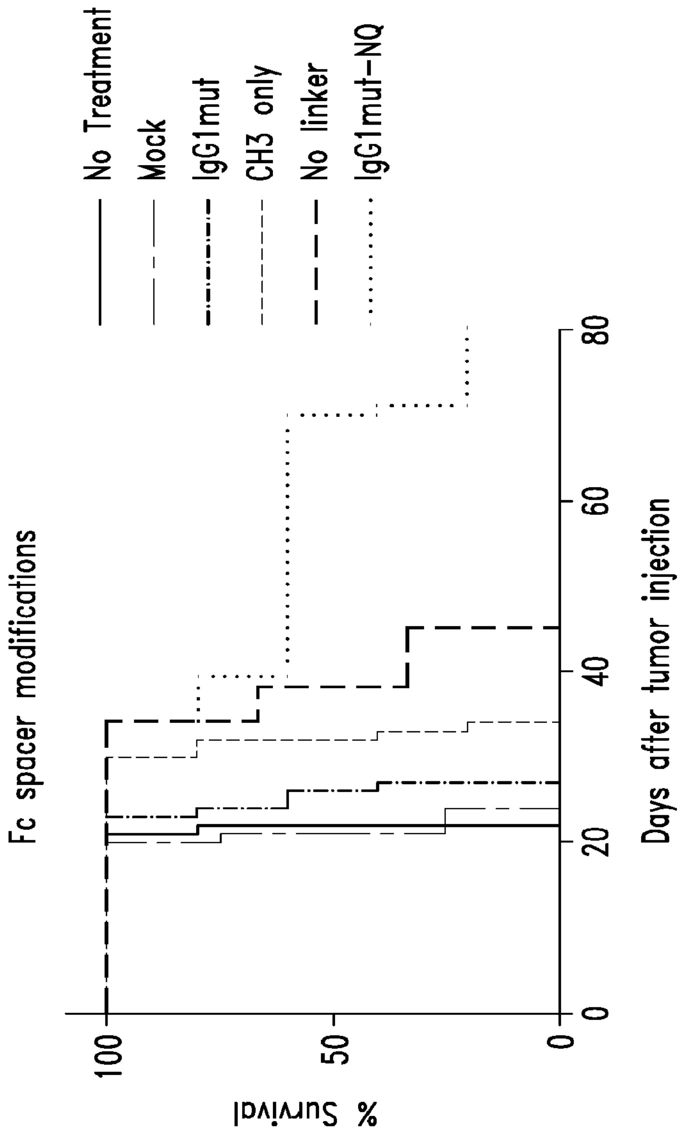

Retroorbital blood samples were obtained at serial time points after infusion of either CD20 CAR T cells or empty vector tCD19-expressing T cells in NSG mice bearing Raji-ffLuc disseminated tumors. CD20 CAR T cells expressing the tCD19 transduction marker were quantified by flow cytometry at each time point as human $CD3^+$/mouse CD45-negative/human $CD19^+$ cells. (FIG. 21A) $tCD19^+$ T cells at 3 post-infusion time points as a percentage of total nucleated cells in the blood are shown (n=9 initially in CAR T cell group). Truncated $CD19^+$ cells from an empty vector mouse are shown for reference. (FIG. 21B) In a separate experiment, the $tCD19^+$ cells from 2 mice in each group (empty vector vs CAR T cells) are shown longitudinally with weekly measurements.

Additionally, mice treated with CD20 CAR T cells were monitored for signs of toxicity based on weight, general behavior and appearance, physical activity, posture, grooming habits, skin color, presence of diarrhea, signs of eye, mouth, or skin inflammation, lethargy, or signs of severe anemia (pale ear pinnae or feet or mucous membranes). No signs of T-cell-related toxicity were observed in any mice over 11 experiments using CD20 CAR T cells, with the exception of the finding of xenogeneic graft-versus-host disease that developed in some mice at late time-points. This finding occurred both in mice receiving CD20 CAR T cells as well as in mice receiving empty vector cells and, thus, is not associated with the CAR vector but rather is a known consequence of xenogeneic T cell transfer. In each experiment, the weight of each mouse was recorded at least 3 times per week, and was generally stable except in mice that experienced terminal tumor progression, in which weight loss occurred over the last few days of life (data not shown).

Finally, blood samples were taken from a subset of mice in two experiments to determine physiological function of the animals. In the first experiment, mice bearing Granta mantle cell lymphoma tumors were treated with either untransduced T cells, CD20 CAR T cells that had not been restimulated with $CD20^+$ TM-LCL cells, or CD20 CAR T cells that had been restimulated with TM-LCL cells (either freshly infused or first cryopreserved, then thawed and infused). Renal function was measured using blood urea nitrogen (BUN) and creatinine, hepatic function was measured using alanine and aspartate aminotransferases (ALT and AST), and marrow function was measured by white blood cell count (WBC), hemoglobin, and platelet count in retroorbital blood samples in treated mice (data not shown). Compared with untreated mice, no increases in BUN or creatinine or significant changes in hepatic function were seen in mice treated with CAR T cells. Mice treated with CAR T cells that had not been restimulated with TM-LCL cells had a drop in WBC compared with untreated mice, but this was not observed in mice treated with T cells that had been restimulated with TM-LCLs. A small drop in hematocrit, but not hemoglobin, was observed in mice treated with TM-LCL-restimulated CAR T cells, though this was not seen in mice receiving non-restimulated CAR T cells. The platelet count increased in mice receiving non-restimulated CAR T cells, but no significant changes were seen in mice receiving restimulated CAR T cells.

In the second experiment, mice bearing Raji-ffLuc tumors were treated with either low-dose ($1\times10^6$ CAR+ cells/mouse) or high dose ($5\times10^6$ CAR+ cells/mouse), and renal and hepatic function was assessed. A trend towards higher BUN was seen in the mice receiving T cells, but there was no change in serum creatinine (data not shown). No elevation of hepatic transaminases was observed.

Example 15

Clinical Study of Anti-CD20 CAR Therapy

Figure 1B:
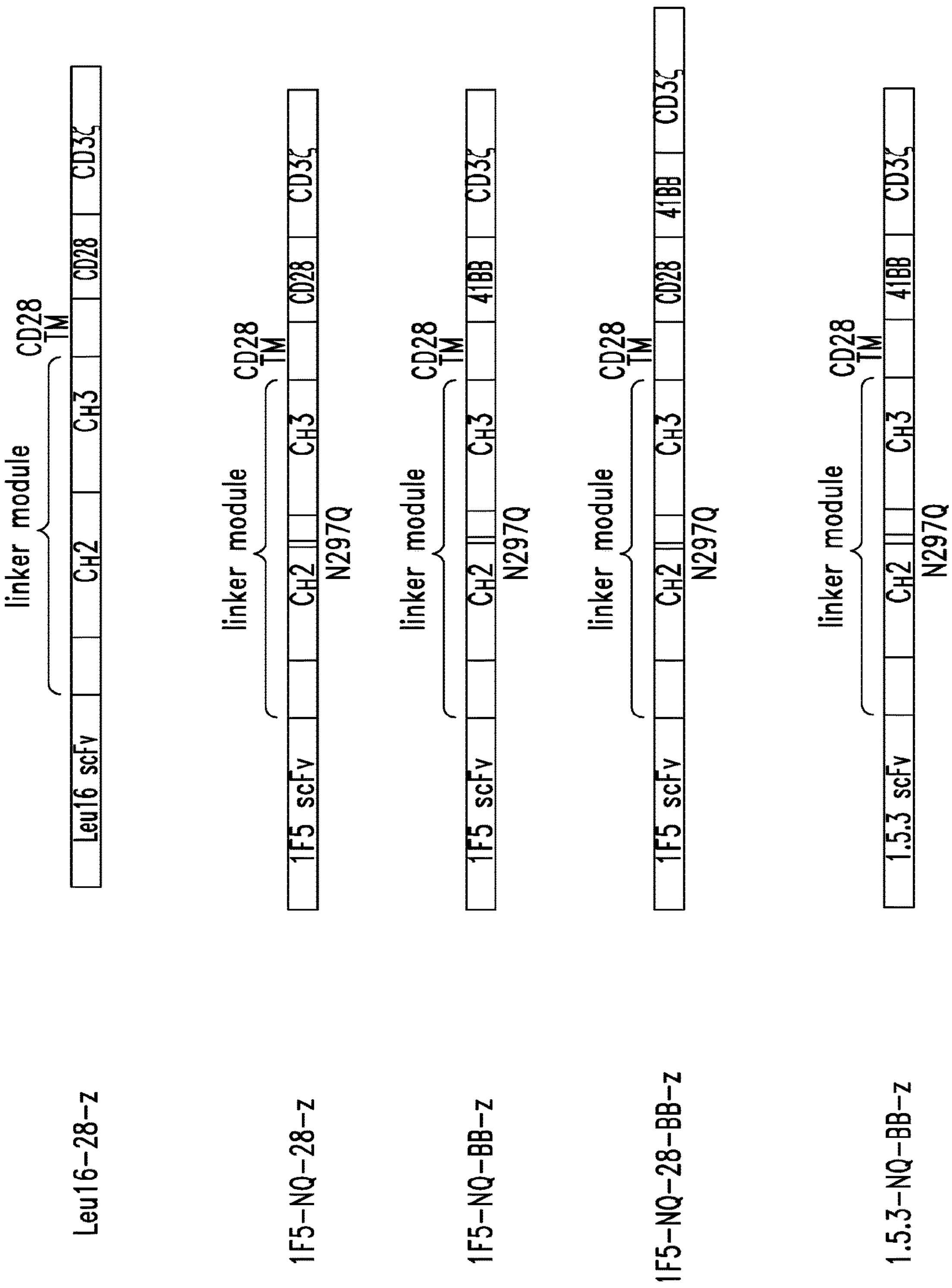

A phase I/II study was designed to assess the safety and maximum tolerated dose (MTD) of adoptive T cell therapy with a 1:1 mixture of autologous CD4+ and CD8+ T cells transduced to express a CD20-specific CAR, 1.5.3-NQ-28-BB-z. The self-inactivating (SIN) lentiviral vector carrying this construct used to transduce T cells in this study is a $3^{rd}$-generation HIV-1-derived lentivirus, which encodes an scFv from the 1.5.3 fully human monoclonal antibody that recognizes an epitope in the large extracellular loop of human CD20, and which is linked to a modified human IgG1 hinge/spacer region, human CD28 transmembrane and intracellular domains, and the human 4-1BB and CD3ζ signaling domains (FIG. 1A). The vector also encodes a non-functional, truncated cell surface human CD19 (tCD19) separated from the CAR cassette by a self-cleavable E2A element, which facilitates tracking of the CAR T cells in vivo. The truncation of CD19 shortens the intracellular domain to 19 amino acids, removing all tyrosine residues that serve as phosphorylation sites, but retains the extracellular epitopes recognized by anti-CD19 antibodies. The tCD19 can also be used as a target for CD19-targeted antibodies or antibody-drug conjugates to eliminate the CAR T cells, for example, in the case of prolonged B cell aplasia.

Previous efforts investigating anti-CD20 CAR T therapies showed some success, but low transfection efficiency (<0.1%) required antibiotic selection and prolonged ex vivo growth, resulting in low CAR expression and T cell exhaustion (see, e.g., Till et al., *Blood* 119(17):3940-3950, 2012; see also Till et al., *Blood* 112(6):2261-2271, 2008; Wang et al., *J. Clin. Immunol.* 155(2):160-75, 2014; da Silva et al., Blood ASH Annual Meeting Abstracts: Abstract #1851, 2016).

The clinical trial will enroll 30 subjects with B-cell non-Hodgkin lymphoma, including mantle cell, follicular, lymphoplasmacytic, marginal zone, transformed indolent B cell lymphoma (including transformed CLL), or diffuse large B cell lymphoma that has relapsed after a response to at least one prior therapy regimen or is refractory to prior therapy. Critical eligibility criteria include: age 18 years or older (of any gender, race, or ethnicity); measurable disease with evidence of CD20 expression; female participants may not be pregnant or breastfeeding; adequate hepatic, renal, pulmonary, cardiac, and hematologic function as defined in clinical protocol; no active central nervous system metastases or past/current clinically relevant central nervous system pathology; no HIV, active uncontrolled infection, or active autoimmune disease requiring systemic immunosuppressive therapy.

Figure 24:
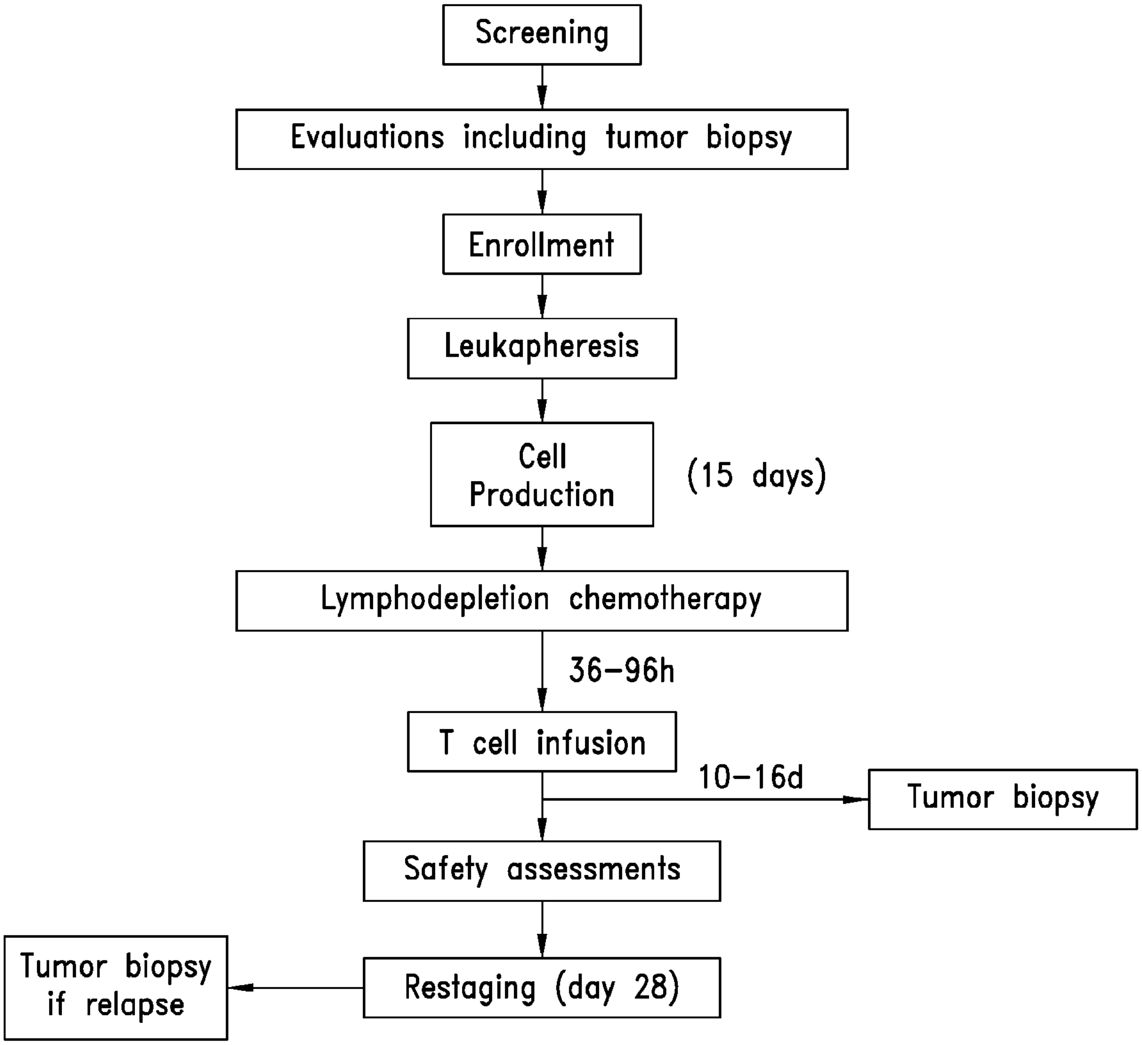
FIG. 24 shows a diagram of a treatment schema for a clinical trial involving immunotherapy methods and compositions of the present disclosure.
Figure 25A:
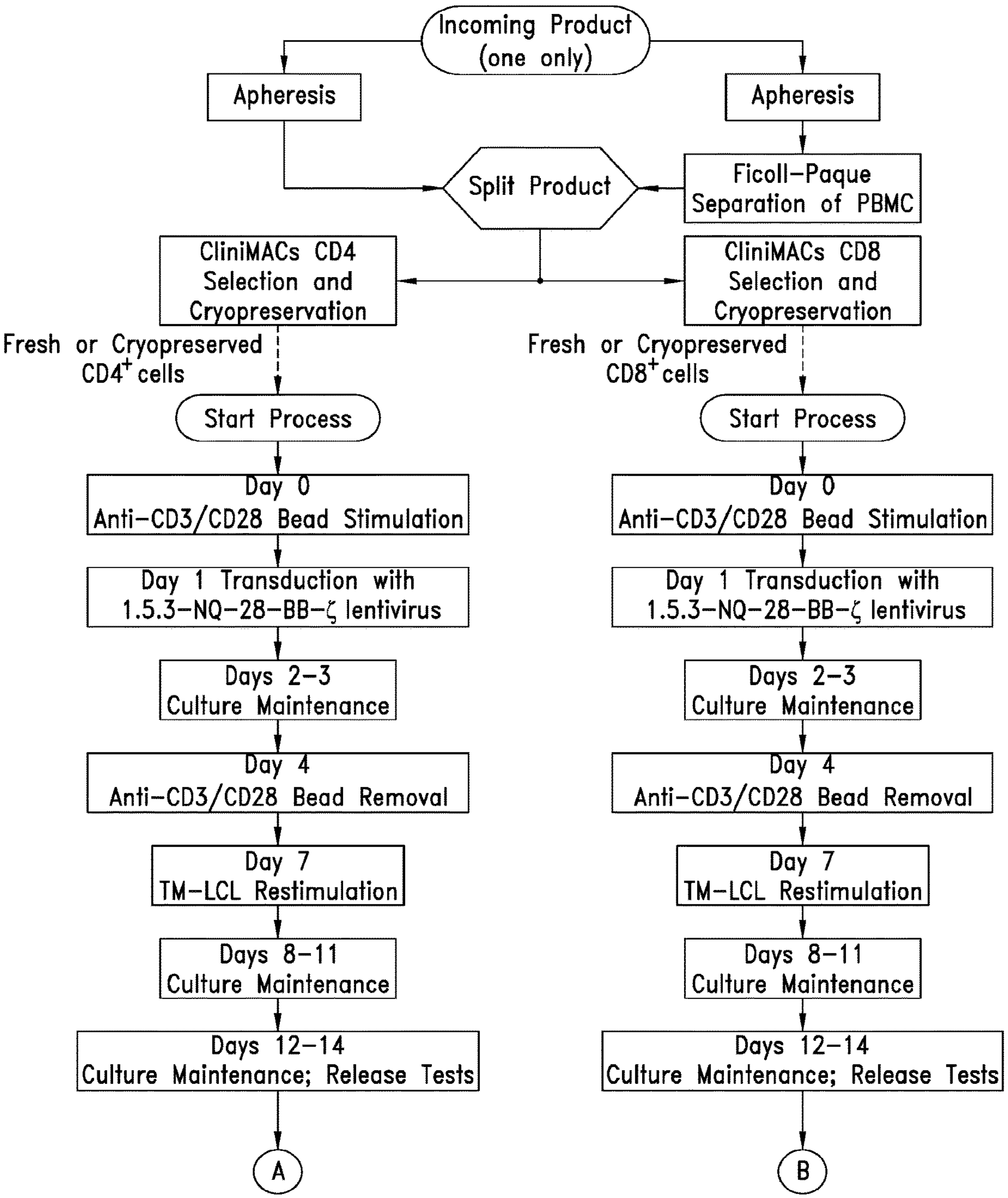
FIGS. 25A and 25B show a diagram of a method of formulation and model of administration of anti-CD20 CAR T cells in a clinical trial.
Figure 25B:
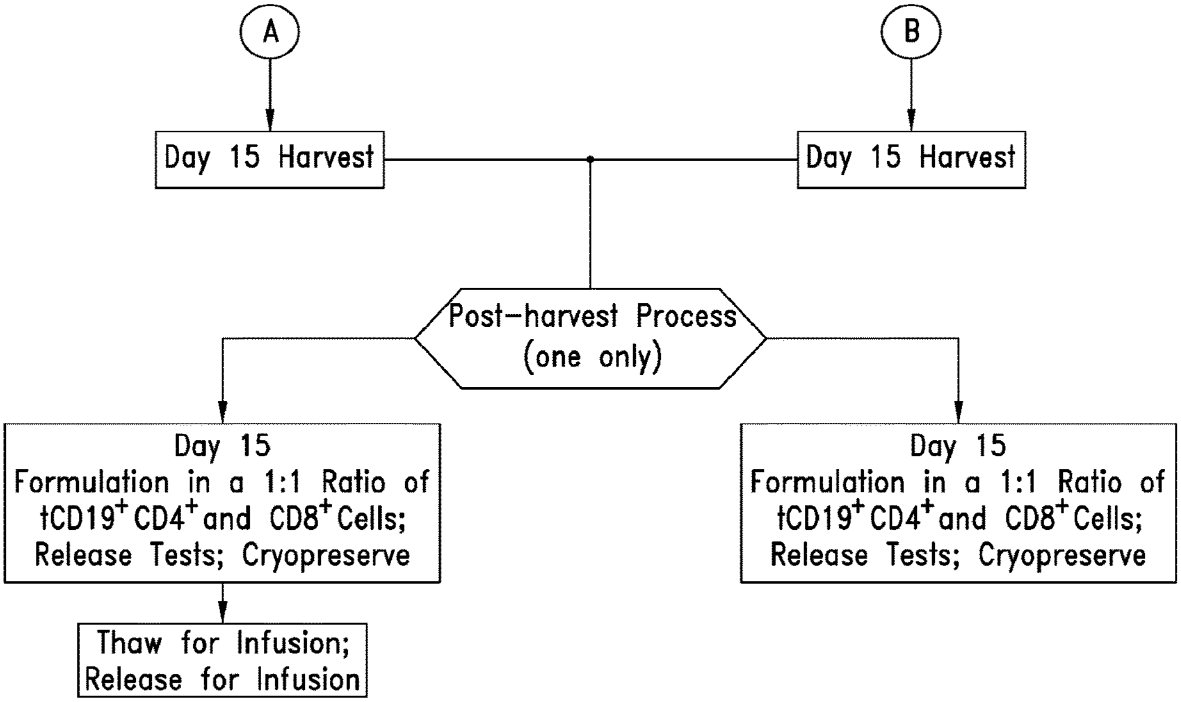

Patients with de novo DLBCL must meet one of the following criteria:

- Biopsy-proven refractory disease after a frontline regimen containing both an anthracycline and rituximab or other anti-CD20 antibody (i.e. "primary refractory"), where any disease recurring within 3 months of completion of the regimen is considered refractory.
- Relapsed or refractory disease after at least one of the following:
  - At least 2 lines of therapy (including at least one with an anthracycline and anti-CD20 antibody) Autologous stem cell transplant
  - Allogeneic stem cell transplant A diagram of the general treatment schema is provided in FIG. 24, and diagrammatic representation of the formulation and model of administration of the CAR T cells is provided in FIGS. 25A and 25 B.

Leukapheresis will be performed on each patient to obtain peripheral blood mononuclear cells. Patients ineligible for a vein-to-vein apheresis may elect to have a percutaneous central venous catheter placed to permit this collection.

Patients ineligible for apheresis who have a hematocrit of at least 38% and a total non-malignant (normal) lymphocyte count of >2000/mcl may undergo phlebotomy of 400 ml of blood to obtain PBMCs necessary for generation of the CAR T cells. This approach would only be taken in patients that would be enrolled at dose levels 0 ($1\times10^5$ tCD19+ cells/kg), 1 ($3.3\times10^5$ $tCD19^+$ cells/kg) and 2 ($1\times10^6$ $tCD19^+$ cells/kg). Participants will undergo tumor biopsy prior to leukapheresis. PET CT may be performed before or after tumor biopsy and leukapheresis, depending on accessibility of lymph node.

CAR T cells are manufactured from an autologous peripheral blood mononuclear cell (PBMC) product obtained by standard non-mobilized leukapheresis for each patient. PBMC undergo immunomagnetic selection to enrich CD8+ and CD4+ T cells separately, and each subset is separately stimulated with anti-CD3/CD28 paramagnetic beads, followed by transduction with the 1.5.3-NQ-28-BB-t lentiviral vector encoding the fully human 3rd-generation CD20-specific CAR and tCD19 transduction marker. The transduced T cells are expanded, then re-stimulated with a CD20-expressing target cell line to boost growth, further expanded ex vivo, and then formulated in a 1:1 CD4/CD8 ratio to achieve the specified cell dose for infusion. Cell products may either be infused fresh, or cryopreserved and then thawed, washed, and infused.

The CD20 CAR T cell product will consist of a 1:1 ratio of tCD19+ $CD4^+$ and $tCD19^+$ $CD8^+$ T cells, where tCD19 is a transduction marker that is co-expressed with the CAR and identifies $CAR^+$ cells. The CD20 CAR T-cell product generated for each patient may be given either as fresh cells immediately after manufacture, or may be first cryopreserved and stored in a liquid nitrogen freezer, and then the thawed cells washed to remove residual cryoprotectant and then formulated for infusion. The total number of cells will be sufficient to account for cell loss during recovery from thaw and to achieve the cell dose level specified in the clinical protocol. The total ratio of $CD4^+$ and $CD8^+$ T cells may differ from 1:1, because transduction of the individual subsets is similar but not identical in individual patients. For this reason, the subsets are transduced separately enabling precise formulation of transduced T cells. The rationale for this ratio is based on published work demonstrating synergy between CD4 and CD8 CAR T cells in animal models (Sommermeyer et al., *Leukemia* 2015) and on our objective of providing a uniform cell product to all patients to assist in evaluating toxicity and efficacy, which is difficult if every patient receives a different composition.

The CD20 CAR T cells will be suspended in CryoStor CS10® or other appropriate cryopreservation medium for cryopreservation in a controlled rate freezer. Cryopreserved cells will be stored in the vapor phase of a liquid nitrogen freezer. The fresh or thawed CD20 CAR T cells will be resuspended in Normosol+1% HSA and transferred to a transfer pack at the total cell dose level specified in the clinical protocol. The formulated product will be stored at 2-8° C. and then transferred on refrigerated gel packs to the clinical site at either the University of Washington or Seattle Cancer Care Alliance for administration. The product will be released by the FHCRC Cell Processing Facility. The cell product should be infused into the research participant within 6 hours of formulation. The FHCRC Cell Processing Facility will be responsible for documenting the dispensation and return (when applicable) of the investigational product.

Patients will receive lymphodepleting chemotherapy 36-96 hours prior to the infusion of CD20 CAR T cells. There must be at least a 36-hour interval between the last dose of chemotherapy and the T cell infusion. The goals of administering chemotherapy are to provide lymphodepletion to facilitate survival of transferred T cells, and to reduce the tumor burden prior to infusion of CD20 CAR T cells. As outlined in the statistical considerations of the protocol, patients will initially be treated with a single dose of cyclophosphamide (CY) i.v. 1 $g/m^2$ initially. However, if the response rate is inadequate, the lymphodepletion regimen will be changed so that subsequent patients receive CY+ fludarabine.

Prior to receiving CD20 CAR T cells, participants will be assessed to ensure they have not developed any pulmonary, cardiovascular, hepatic, renal, or neurologic toxicities prohibited by the protocol; have not developed uncontrolled, active, and serious infection; and have not received treatment with other investigational agents within 30 days of T cell infusion.

Premedications are not required prior to the administration of the CD20 CAR T cell product. Standard premedications may be used at the discretion of investigator.

Each patient will receive a single intravenous infusion of CD20 CAR T cells 36-96 hours following completion of lymphodepleting chemotherapy. The dose of CD20 CAR T cells administered to each patient will be determined according to the statistical design described in the clinical protocol. The dose levels are shown in Table 2 below. A second infusion of CD20 CART cells may be given if the first infusion does not produce a CR, or if the disease relapses after a CR. For this purpose, patients must meet criteria specified in the clinical protocol below.

Cell administration: A single cell product, combined from individual aliquots of CD4+ and CD8+ CD20 CAR T cells in a 1:1 ratio, will be administered intravenously over approximately 20-30 minutes at the specified cell dose for each subject. The specified T cell dose refers to CAR+ T cells determined by the expression of the truncated CD19 transduction marker, which is expressed coordinately with the CAR in the vector. Dose levels planned for administration under the proposed protocol are as follows:

TABLE 2

CD20 CAR T Cell Formulation and Infusion

| Dose Level | $tCD19^+$ $CD4^+$/ $tCD19^+$ $CD8^+$ ratio | Total $tCD19^+$ T cell dose*,** |
|---|---|---|
| 0 | 1:1 | $1\times10^5$/kg |
| 1 | 1:1 | $3.3\times10^5$/kg |
| 2 | 1:1 | $1\times10^6$/kg |
| 3 | 1:1 | $3.3\times10^6$/kg |
| 4 | 1:1 | $1\times10^7$/kg |

*per kg recipient weight
**upper limit per dosing level, ±15%; Dose level 1 is the starting dose level All patients will be monitored during each T cell infusion. Vital signs (including oxygen saturation) should be recorded before and during the infusion and approximately hourly for 2 hours after the infusion. Oxygen saturation should be monitored with continuous pulse oximetry during the T cell infusion and for 2 hours following T cell infusion. Subjects will remain on the cell infusion unit for a minimum of 2 hours following infusion, or until resolution of any infusion-related toxicity deemed to pose a significant risk to the study subject as an outpatient.

Infusion Rate: Each cell infusion should be administered intravenously over approximately 20-30 minutes, adjusted as needed to comply with guidelines for endotoxin limits for parenteral drugs (£ 5 EU/kg/hour). The infusion rate can also be adjusted if subjects experience mild infusion-related adverse events (grade 2 or lower).

The primary objective of this study is to estimate the maximum tolerated dose (MTD) of CAR T cells. The MTD for these purposes will be defined as a true dose limiting toxicity rate of 25%, where DLT is defined as Grade 3 or higher non-hematologic toxicity attributable to the CAR T cell infusion occurring within 28 days of the infusion, lasting at least 4 days, and not responsive to tociluzimab, dexamethasone, or other anti-inflammatory drugs. A modification of the continual reassessment method (CRM) will be used to estimate the MTD. The modifications include treating patients in groups of two (rather than one), and allowing a maximum increase of one dose level between groups. Patients will receive a single intravenous infusion of CD20 CAR T cells at one of four escalating dose levels beginning with dose level 1 for the first group of two patients. Dose escalation or de-escalation is determined by the CRM algorithm, taking into account the number of patients experiencing a serious toxicity at each dose level (see above).

Treatment of patients in the dose-escalation/de-escalation groups will be staggered such that a minimum of a 28-day interval following infusion is required between each set of 2 patients before escalating to the next dose level. These dose levels will be initially evaluated in combination with CY alone, evaluating the CR rate to determine if CY alone has sufficient activity or if fludarabine will be added (CY/flu). If any criteria are met to switch to CY/flu, the CRM will be reinitiated starting at one dose level below the interim recommended dose (with CY alone) in combination with CY/flu. The interim recommended dose will be defined as lower of either the maximum dose evaluated to date or the next dose that would have been selected based on the mCRM following the 8th, 16th, or 20th patient for the $1^{st}$, $2^{nd}$ and $3^{rd}$ interim analyses. This evaluation will continue to a total of 30 patients. If none of these criteria are met, the CRM approach will continue with CY alone in an additional 10 patients (to reach a total of 30 patients). For patients who receive a second infusion, DLT and efficacy outcomes will be evaluated based on the dose of their primary infusion.

Patients receiving CD20 CAR T cells may develop serious toxicity due to T cell activation, proliferation, and cytokine secretion after encounter with tumor antigen. Cytokine release syndrome, macrophage activation, and neurotoxicity may occur and require intensive care support, and will not be considered DLTs if they are considered due to T cell recognition of the tumor unless these toxicities are not reversible after 4 consecutive days of treatment with corticosteroids and/or tocilizumab.

If there ever exists sufficient evidence to suggest that the true probability of treatment-related death by day 100 exceeds 20% (regardless of dose), enrollment of patients will be suspended pending a detailed review by the PI, study monitor, statistician, and DSMB. Sufficient evidence for this purpose will be defined as any observed outcome whose lower 80% confidence limit exceeds 20%.

Evaluations will also be performed to provide a preliminary assessment of efficacy. Secondary objectives of the study include an examination of efficacy (in terms of rate of remissions, progression-free survival, and in vivo persistence of T cells). These analyses will be performed using patients treated with all doses combined with the final lymphodepletion regimen (either CY alone or CY/fludarabine), modeling outcomes as a function of dose. A logistic regression model will be used to evaluate binary outcomes (CR and CR/PR). A Cox proportional hazards model will be used to evaluate time-to-event outcomes (PFS, OS). No formal statistical hypotheses will be tested with respect to these endpoints; rather, estimates and associated confidence intervals will be provided descriptively.

Additional secondary objectives are to evaluate of the duration of persistence of adoptively transferred CD20 CAR T cells and the migration of adoptively transferred CD20 CAR T cells. To evaluate the persistence of the CAR T cells, the patient-level area under the curve (AUC) will be estimated and the summary statistics of the AUCs will be evaluated. Migration (if CAR T cells are present post treatment), is defined as the presence of CART cells in the tumor at day 10-16 and, if applicable, the BM at day 28. The association between AUC and migration with clinical outcomes will mostly descriptive in nature including graphical presentation.

To evaluate the secondary objectives associated with evaluating biological causes of treatment resistance, the following analyses will be performed. A paired t-test will be used to compare the biomarker profiles between baseline tumors and post-treatment tumors with appropriate transformation if needed. A logistic regression model will be used to evaluate the association between baseline biomarker values and response. A landmark analysis among patients achieving a CR or PR at 1 month, measuring survival times (PFS and OS) from the landmark time, using a Cox proportional hazard regression model to evaluate the association of correlates measured at the time of CR/PR for patients in whom a biopsy is acquired at that time. Models will include values for all patients/dose levels and include a variable for dose level.

The development of endogenous anti-tumor responses and epitope spreading will also be assessed in a largely exploratory fashion. Data at each time point will be summarized, and with sufficient data, a mixed effect model will be used to model time-varying outcomes. Differential gene expression analysis will be conducted between patients with and without demonstrated epitope spreading to identify the biomarker associated with immune response.

Patients in the study who failed to achieve a CR, or who achieve a complete response (CR) but later relapse, who wish to receive a second infusion of CD20 CAR T cells may be eligible to do so, provided that a sufficient number of CD20 CART cells can be produced and the criteria listed below are met:

a. There is evidence of persistent disease after the first T cell infusion, or the tumor relapses after a CR.
b. There were no toxicities attributed to the first infusion that were dose-limiting or required dose de-escalation
c. The patient is ≥30 days from the first T cell infusion.
d. There are no clinical and/or laboratory exclusion criteria (Patients who achieved a CR and later relapsed must have a post-relapse biopsy demonstrating ongoing CD20 expression on the tumor cells.

Participants will undergo evaluations at screening, prior to lymphodepleting chemotherapy, during T cell infusions, and at intervals following each T cell infusion. The following data will be obtained for safety and toxicity assessment, according to the clinical protocol:

History and physical exam before and at intervals after T cell infusions.
Pulse oximetry before and during the infusion
Hematologic, hepatic, renal, and electrolyte blood tests before and at intervals after the T cell infusion
Lab tests evaluating for tumor lysis syndrome, coagulopathy, and cytokine release syndrome before and at intervals after the T cell infusion.

Toxicity grading according to NCI CTCAE Version 4.0
Serum cytokine levels
B cell reconstitution
Serum immunoglobulin levels
Replication competent lentivirus testing
Persistence of genetically modified T cells
Adverse event reporting The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An isolated polynucleotide that encodes a CD20-specific fusion protein, wherein the encoded fusion protein comprises the amino acid sequence of SEQ ID NO.:26.

2. The isolated polynucleotide of claim 1, wherein the encoded fusion protein consists of the amino acid sequence of SEQ ID NO.:26.

3. The isolated polynucleotide of claim 1, wherein a nucleotide sequence encoding SEQ ID NO.:26 is comprised in a nucleotide sequence encoding SEQ ID NO.:35.

4. The isolated polynucleotide of claim 1, wherein the polynucleotide comprises or consists of the nucleotide sequence of SEQ ID NO.:44 or SEQ ID NO.:53.

5. A vector comprising the polynucleotide of claim 1.

6. The vector of claim 5, wherein the vector is a lentiviral vector or a retroviral vector.

7. A vector comprising the polynucleotide of claim 2.

8. The vector of claim 7, wherein the vector is a lentiviral vector or a retroviral vector.

9. A host cell comprising the polynucleotide of claim 1 and capable of expressing the encoded fusion protein.

10. The host cell of claim 9, wherein the host cell is a T cell or a T cell autologous to a subject.

11. The host cell of claim 10, wherein the T cell is a CD8+ T cell, a CD4+ T cell, a bulk population of T cells, a subpopulation of T cells, a naïve T cell, a memory stem T cell, a central memory T cell, an effector memory T cell, or any combination thereof.

12. A host cell comprising the polynucleotide of claim 2 and capable of expressing the encoded fusion protein.

13. The host cell of claim 12, wherein the host cell is a T cell or a T cell autologous to a subject.

14. The host cell of claim 13, wherein the T cell is a CD8+ T cell, a CD4+ T cell, a bulk population of T cells, a subpopulation of T cells, a naïve T cell, a memory stem T cell, a central memory T cell, an effector memory T cell, or any combination thereof.

15. A method of treating a disease or disorder associated with CD20 expression in a subject having or suspected of having a disease or disorder associated with CD20 expression, comprising administering a therapeutically effective amount of a host cell of claim 10.

16. The method of claim 15, wherein the host cell is a CD8+ T cell, a CD4+ T cell, a CD8+ T cell and a CD4+ T cell, a bulk population of T cells, a subpopulation of T cells, a naïve T cell, a memory stem T cell, a central memory T cell, an effector memory T cell, or any combination thereof.

17. The method of claim 15, wherein the disorder or disease associated with CD20 expression is a B-cell lymphoma or leukemia such as B-cell non-Hodgkins lymphoma (NHL) (including Burkitt's lymphoma, chronic lymphocytic leukemia (CLL), small lymphocytic lymphoma (SLL), diffuse large B-cell lymphoma, follicular lymphoma, immunoblastic large cell lymphoma, precursor B-lymphoblastic lymphoma, and mantle cell lymphoma), hairy cell leukemia, Waldenström's macroglobulinemia, B-cell pro-lymphocytic leukemia, CD37+ dendritic cell lymphoma, lymphoplasmacytic lymphoma, splenic marginal zone lymphoma, extranodal marginal zone B-cell lymphoma of mucosa-associated (MALT) lymphoid tissue, nodal marginal zone B-cell lymphoma, mediastinal (thymic) large B-cell lymphoma, intravascular large B-cell lymphoma, and primary effusion lymphoma, a disease characterized by autoantibody production such as idiopathic inflammatory myopathy, rheumatoid arthritis, juvenile rheumatoid arthritis, myasthenia gravis, Grave's disease, type I diabetes mellitus, anti-glomerular basement membrane disease, rapidly progressive glomerulonephritis, Berger's disease (IgA nephropathy), systemic lupus erythematosus (SLE), Crohn's disease, ulcerative colitis, idiopathic thrombocytopenic purpura (ITP), anti-phospholipid antibody syndrome, neuromyelitis optica, multiple sclerosis, an autoimmune disease, dermatomyositis, polymyositis, a disease characterized by inappropriate T-cell stimulation associated with a B-cell pathway, multiple myeloma, or melanoma.

18. The method of claim 15, wherein the disease or disorder associated with CD20 expression is:

(i) a cancer;

(ii) a cancer associated with aberrant B cell activity;

(iii) Non-Hodgkins lymphoma (NHL);

(iv) chronic lymphocytic leukemia (CLL);

(v) a leukemia; or (vi) any combination thereof.

19. A method of treating a disease or disorder associated with CD20 expression in a subject having or suspected of having a disease or disorder associated with CD20 expression, comprising administering a therapeutically effective amount of a host cell of claim 13.

20. The method of claim 19, wherein the host cell is a CD8+ T cell, a CD4+ T cell, a CD8+ T cell and a CD4+ T cell, a bulk population of T cells, a subpopulation of T cells, a naïve T cell, a memory stem T cell, a central memory T cell, an effector memory T cell, or any combination thereof.

21. The method of claim 19, wherein the disorder or disease associated with CD20 expression is a B-cell lymphoma or leukemia such as B-cell non-Hodgkins lymphoma (NHL) (including Burkitt's lymphoma, chronic lymphocytic leukemia (CLL), small lymphocytic lymphoma (SLL), diffuse large B-cell lymphoma, follicular lymphoma, immunoblastic large cell lymphoma, precursor B-lymphoblastic lymphoma, and mantle cell lymphoma), hairy cell leukemia, Waldenström's macroglobulinemia, B-cell pro-lymphocytic leukemia, CD37+ dendritic cell lymphoma, lymphoplasmacytic lymphoma, splenic marginal zone lymphoma, extranodal marginal zone B-cell lymphoma of mucosa-associated (MALT) lymphoid tissue, nodal marginal zone B-cell lymphoma, mediastinal (thymic) large B-cell lymphoma, intravascular large B-cell lymphoma, and primary effusion lymphoma, a disease characterized by autoantibody production such as idiopathic inflammatory myopathy, rheumatoid arthritis, juvenile rheumatoid arthritis, myasthenia gravis, Grave's disease, type I diabetes mellitus, anti-glomerular basement membrane disease, rapidly progressive glomerulonephritis, Berger's disease (IgA nephropathy), systemic lupus erythematosus (SLE), Crohn's disease, ulcerative colitis, idiopathic thrombocytopenic purpura (ITP), anti-phospholipid antibody syndrome, neuromyelitis optica, multiple sclerosis, an autoimmune disease, dermatomyositis, polymyositis, a disease characterized by inappropriate T-cell stimulation associated with a B-cell pathway, multiple myeloma, or melanoma.

22. The method of claim 19, wherein the disease or disorder associated with CD20 expression is:

(i) a cancer;

(ii) a cancer associated with aberrant B cell activity;

(iii) Non-Hodgkins lymphoma (NHL);

(iv) chronic lymphocytic leukemia (CLL);

(v) a leukemia; or (vi) any combination thereof.

* * * * *